(12) United States Patent
Martinborough et al.

(10) Patent No.: US 8,357,706 B2
(45) Date of Patent: Jan. 22, 2013

(54) SPHINGOSINE 1 PHOSPHATE RECEPTOR MODULATORS AND METHODS OF CHIRAL SYNTHESIS

(75) Inventors: Esther Martinborough, San Diego, CA (US); Marcus F. Boehm, San Diego, CA (US); Adam Richard Yeager, San Diego, CA (US); Junko Tamiya, Carlsbad, CA (US); Liming Huang, San Diego, CA (US); Enugurthi Brahmachary, San Diego, CA (US); Manisha Moorjani, San Diego, CA (US)

(73) Assignee: Receptos, Inc., San Diego, CA (US)

( * ) Notice: Subject to any disclaimer, the term of this patent is extended or adjusted under 35 U.S.C. 154(b) by 0 days.

(21) Appl. No.: 12/946,800

(22) Filed: Nov. 15, 2010

(65) Prior Publication Data
US 2011/0178056 A1    Jul. 21, 2011

Related U.S. Application Data

(60) Provisional application No. 61/262,474, filed on Nov. 18, 2009, provisional application No. 61/261,282, filed on Nov. 13, 2009.

(51) Int. Cl.
*A61K 31/4245* (2006.01)
*A61K 31/5377* (2006.01)
*A61K 31/454* (2006.01)
*C07D 271/06* (2006.01)
*C07D 413/12* (2006.01)

(52) U.S. Cl. ............. 514/364; 514/210.18; 514/236.2; 514/326; 544/138; 546/209; 548/131

(58) Field of Classification Search ............ 514/364, 514/210.18, 236.2, 326; 544/138; 546/209; 548/131
See application file for complete search history.

(56) References Cited

U.S. PATENT DOCUMENTS

| 6,511,975 B1 | 1/2003 | Nishi et al. |
|---|---|---|
| 2006/0161005 A1 | 7/2006 | Doherty et al. |
| 2007/0293545 A1 | 12/2007 | Edwards et al. |
| 2008/0009534 A1 | 1/2008 | Cheng et al. |
| 2008/0249093 A1* | 10/2008 | Colandrea et al. ......... 514/236.2 |
| 2008/0280876 A1 | 11/2008 | Hobson et al. |
| 2011/0172202 A1 | 7/2011 | Martinborough et al. |
| 2011/0183953 A1 | 7/2011 | Boehm et al. |

FOREIGN PATENT DOCUMENTS

| WO | WO 2005/032465 A2 | 4/2005 |
|---|---|---|
| WO | WO 2006/120577 A1 | 11/2006 |
| WO | WO 2008/076356 A1 | 6/2008 |

OTHER PUBLICATIONS

Wu and Farrelly, Toxicology 236:1-6, 2007.*
Zanotti-Gerosa et al., Ruthenium-Catalysed Asymmetric Reduction of Ketones, Platinum Metals Rev, 2005, vol. 49(4), pp. 158-165.
Fujiwara et al., Identification of the Hydrophobic Ligand Binding Pocket of the S1P1 Receptor, The Journal of Biological chemistry, 2007, vol. 282(4), pp. 2374-2385.
International Search Report for PCT/US10/56757, PCT/ISA/210, Jan. 14, 2011, pp. 1-3.
International Search Report for PCT/US10/56760, PCT/ISA/210, Jan. 19, 2011, pp. 1-3.
International Search Report for PCT/US10/56759, PCT/ISA/210, Jan. 12, 2011, pp. 1-3.

* cited by examiner

*Primary Examiner* — Yong Chu
(74) *Attorney, Agent, or Firm* — Seed IP Law Group PLLC

(57) ABSTRACT

Compounds that selectively modulate the sphingosine 1 phosphate receptor are provided including compounds which modulate subtype 1 of the S1P receptor. Methods of chiral synthesis of such compounds is provided. Uses, methods of treatment or prevention and methods of preparing inventive compositions including inventive compounds are provided in connection with the treatment or prevention of diseases, mal-conditions, and disorders for which modulation of the sphingosine 1 phosphate receptor is medically indicated.

31 Claims, No Drawings

SPHINGOSINE 1 PHOSPHATE RECEPTOR MODULATORS AND METHODS OF CHIRAL SYNTHESIS

CROSS-REFERENCE TO RELATED APPLICATIONS

This application claims the priority of U.S. Ser. No. 61/261,282, filed Nov. 13, 2009 and U.S. Ser. No. 61/262,474, filed Nov. 18, 2009, the disclosures of which are incorporated herein in their entireties.

FIELD OF THE INVENTION

The invention relates to compounds which are agonists of the sphingosine 1-phosphate receptor subtype 1, methods of their synthesis and methods of their therapeutic and/or prophylactic use.

BACKGROUND

The $S1P_1/EDG_1$ receptor is a G-protein coupled receptor (GPCR) and is a member of the endothelial cell differentiation gene (EDG) receptor family. Endogenous ligands for EDG receptors include lysophospholipids, such as sphingosine-1-phosphate (S1P). Like all GPCRs, ligation of the receptor propagates second messenger signals via activation of G-proteins (alpha, beta and gamma).

Development of small molecule $S1P_1$ agonists and antagonists has provided insight into some physiological roles of the $S1P_1/S1P$-receptor signaling system. Agonism of the $S1P_1$ receptor perturbs lymphocyte trafficking, sequestering them in lymph nodes and other secondary lymphoid tissue. This leads to rapid and reversible lymphopenia, and is probably due to receptor ligation on both lymphatic endothelial cells and lymphocytes themselves (Rosen et al, *Immunol. Rev.*, 195:160-177, 2003). A clinically valuable consequence of lymphocyte sequestration is exclusion of them from sights of inflammation and/or auto-immune reactivity in peripheral tissues.

Agonism of $S1P_1$ has also been reported to promote survival of oligodendrocyte progenitors (Miron et al, *Ann. Neurol.*, 63:61-71, 2008). This activity, in conjunction with lymphocyte sequestration would be useful in treating inflammatory and autoimmune conditions of the central nervous system.

SUMMARY OF THE INVENTION

The present invention is directed to heterocyclic compounds adapted to act as agonists of S1P receptor subtype 1, $S1P_1$; methods of preparation and methods of use, such as in treatment of a malcondition mediated by $S1P_1$ activation, or when activation of $S1P_1$ is medically indicated.

Certain embodiments of the present invention comprise a compound having the structure of Formula I-R or I-S or a pharmaceutically acceptable salt, ester, prodrug, homolog, hydrate or solvate thereof:

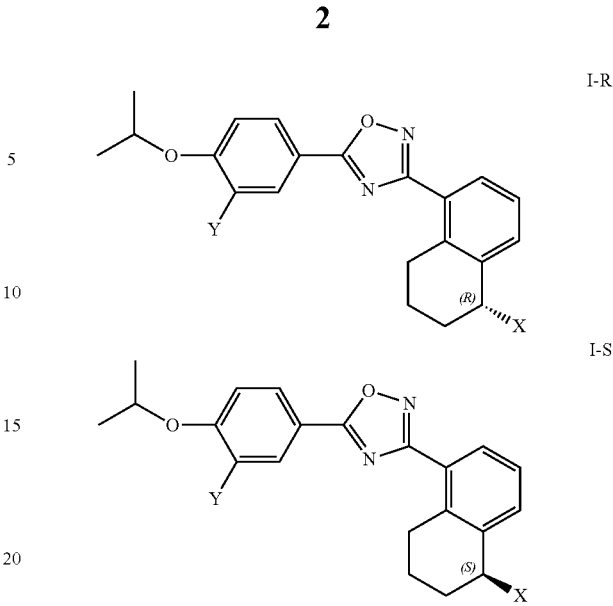

X can be —NR'R" or —OR''' and Y can be —CN, —Cl, or —$CF_3$.

R' can be H, $C_{1-4}$ alkyl, n-hydroxy $C_{1-4}$ alkyl, —$SO_2$—$R^1$, or —CO—$R^1$. R" can be H, —$SO_2$—$R^3$, $C_{1-4}$ alkyl optionally substituted with 1 or more $R^2$, or a ring moiety optionally substituted with $R^4$ wherein such ring moiety is piperidinyl, cyclohexyl, morpholinyl, pyrrolidinyl, imidazolyl, or phenyl. R''' can be H, $C_{1-4}$ alkyl, or —CO—$R^1$. Alternatively, R' and R" taken together with the nitrogen atom to which they are bound form a 4, 5, or 6 membered saturated heterocyclic ring containing 0 or 1 additional heteroatoms where such additional heteroatom is O or N wherein such heterocycle isoptionally singly or multiply substituted with substituents independently selected from —OH, oxo, —$NH_2$, n-hydroxy-$C_{1-4}$ alkyl, —COOH, —$(CH_2)_m$—COOH, —$(CH_2)_m$—$COOR^1$, —$N(R^1R^1)$, and —$(CH_2)_m$—CO—$N(R^5R^5)$.

Each $R^1$ can be independently $C_{1-4}$ alkyl or H and each $R^2$ can be independently H, halo, OH, oxo, =NH, $NH_2$, —COOH, F, —$NHR^1$, —$N(R^5R^5)$, —$SO_2$—$R^1$, —$SO_2$—$N(R^5R^5)$, —$N(R^1)$—$SO_2$—$R^1$, —$COOR^1$, —OCO—$R^1$, —CO—$N(R^5R^5)$, —$N(R^1)$—$COR^1$, $C_{1-3}$ alkyl, $C_{1-3}$ alkoxy, and a ring moiety optionally substituted with $R^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl.

Each $R^3$ can be independently $R^2$, $C_{1-4}$ alkyl, $C_{3-6}$ cycloalkyl, or $C_{1-4}$ alkyl optionally substituted with 1 or more $R^2$; and each $R^4$ can be independently halo, OH, —$NH_2$, —$NHR^1$, —$N(R^1R^1)$, —COOH, —$COOR^1$, —NHCO—$R^1$. Each $R^5$ can be independently $C_{1-4}$ alkyl or H, or alternatively two $R^5$ taken together with the nitrogen atom to which they are bound can form a 4, 5, or 6 membered saturated heterocyclic ring containing 0 or 1 additional heteroatoms where such additional heteroatom is O or N wherein such heterocycle isoptionally substituted with —OH, —$NH_2$, —$N(R^1R^1)$, n-hydroxy $C_{1-4}$ alkyl, —$(CH_2)_m$—COOH, —$(CH_2)_m$—$COOR^1$. Each m is independently 0, 1, 2, or 3.

In certain embodiments, a pharmaceutical composition comprising a compound of the invention and a suitable excipient is provided.

In certain embodiments, a method of use of an inventive compound comprising preparation of a medicament is provided.

In certain combinations, a pharmaceutical combination comprising a compound of the invention and a second medicament is provided. In various embodiments the second medicament is medically indicated for the treatment of multiple sclerosis, transplant rejection, acute respiratory distress syndrome or adult respiratory distress syndrome.

In certain embodiments, a method of activation or agonism of a sphingosine-1-phosphate receptor subtype 1 comprising contacting the receptor subtype 1 with a compound of claim 1 is provided. In various embodiments, the compound of claim 1 activates or agonizes the sphingosine-1-phosphate receptor subtype 1 to a greater degree than the compound activates or agonizes a sphingosin-1-phosphate receptor subtype 3.

In certain embodiments a method of treatment of a malcondition in a patient for which activation or agonism of an $S1P_1$ receptor is medically indicated, is provided. In various embodiment, selective activation or agonism of an $S1P_1$ receptor, such as with respect to an $S1P_3$ receptor, is medically indicated. In various embodiments, the malcondition comprises multiple sclerosis, transplant rejection, or acute respiratory distress syndrome.

In certain embodiments, a method is provided for chiral synthesis of certain compounds including compounds of the invention. In certain other embodiments the invention provides certain intermediate compounds associated with such methods of chiral synthesis.

DETAILED DESCRIPTION OF THE INVENTION

Certain embodiments of the present invention comprise a compound having the structure of Formula I-R or I-S or a pharmaceutically acceptable salt, ester, prodrug, homolog, hydrate or solvate thereof:

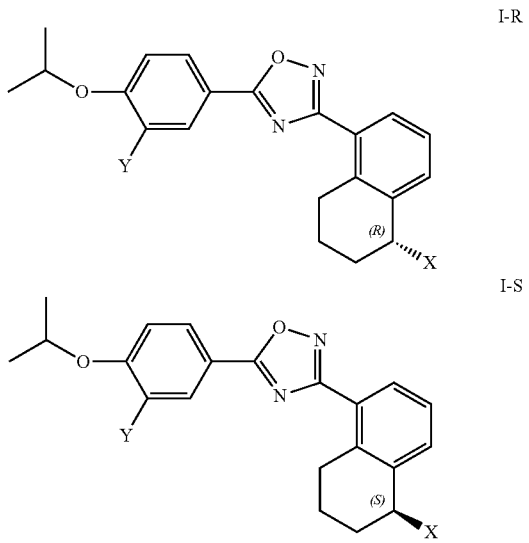

X can be —NR'R" or —OR''' and Y can be —CN, —Cl, or —CF$_3$. R' can be H, $C_{1-4}$ alkyl, n-hydroxy $C_{1-4}$ alkyl, —SO$_2$—R$^1$, or —CO—R$^1$. R" can be H, —SO$_2$—R$^3$, $C_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl. R''' can be H, $C_{1-4}$ alkyl, or —CO—R$^1$. Alternatively, R' and R" taken together with the nitrogen atom to which they are bound form a 4, 5, or 6 membered saturated heterocyclic ring containing 0 or 1 additional heteroatoms where such additional heteroatom is O or N wherein such heterocycle isoptionally singly or multiply substituted with substituents independently selected from —OH, oxo, —NH$_2$, n-hydroxy-$C_{1-4}$ alkyl, —COOH, —(CH$_2$)$_m$—COOH, —(CH$_2$)$_m$—COOR$^1$, —N(R$^1$R$^1$), and —(CH$_2$)$_m$—CO—N(R$^5$R$^5$).

Each R$^1$ can be independently $C_{1-4}$ alkyl or H and each R$^2$ can be independently H, halo, OH, oxo, =NH, NH$_2$, —COOH, F, —NHR$^1$, —N(R$^5$R$^5$), —SO$_2$—R$^1$, —SO$_2$—N(R$^5$R$^5$), —N(R$^1$)—SO$_2$—R$^1$, —COOR$^1$, —OCO—R$^1$, —CO—N(R$^5$R$^5$), —N(R$^1$)—COR$^1$, $C_{1-3}$ alkyl, $C_{1-3}$ alkoxy, and a ring moiety optionally substituted with R$^4$ wherein such ring moiety is piperazinyl, piperidinyl, morpholinyl, pyrrolidinyl, pyrazolyl, thiazolyl, imidazolyl, benzimidazolyl, azetidinyl, cyclobutinyl, or phenyl.

Each R$^3$ can be independently R$^2$, $C_{1-4}$ alkyl, $C_{3-6}$ cycloalkyl, or $C_{1-4}$ alkyl optionally substituted with 1 or more R$^2$; and each R$^4$ can be independently halo, OH, —NH$_2$, —NHR$^1$, —N(R$^1$R$^1$), —COOH, —COOR$^1$, —NHCO—R$^1$. Each R$^5$ can be independently $C_{1-4}$ alkyl or H, or alternatively two R$^5$ taken together with the nitrogen atom to which they are bound can form a 4, 5, or 6 membered saturated heterocyclic ring containing 0 or 1 additional heteroatoms where such additional heteroatom is O or N wherein such heterocycle isoptionally substituted with —OH, —NH$_2$, —N(R$^1$R$^1$), n-hydroxy $C_{1-4}$ alkyl, —(CH$_2$)$_m$—COOH, —(CH$_2$)$_m$—COOR$^1$. Each m is independently 0, 1, 2, or 3.

In certain embodiments, the compounds of the invention have the structure of Formula I-R or a pharmaceutically acceptable salt, ester, prodrug, homolog, hydrate or solvate thereof. In other embodiments, the compounds of the invention have the structure of Formula I-S or a pharmaceutically acceptable salt, ester, prodrug, homolog, hydrate or solvate thereof.

In certain embodiments the invention provides compounds which are substantially enantiomerically pure.

In certain embodiments the invention provides compounds which have an EC$_{50}$ as an agonist of the wild type SIP receptor subtype 1 which is at least ten times smaller than the EC$_{50}$ of such compound as an agonist of a mutant S1P receptor subtype 1 having a single mutation with respect to wild type S1P receptor subtype 1 such that the 101$^{st}$ amino acid residue is changed from asparagine to alanine.

In certain embodiments the invention provides compounds which have an EC$_{50}$ as an agonist of the wild type S1P receptor subtype 1 which is at least twenty times smaller than the EC$_{50}$ of such compound as an agonist of a mutant S1P receptor subtype 1 having a single mutation with respect to wild type S1P receptor subtype 1 such that the 101$^{st}$ amino acid residue is changed from asparagine to alanine.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is at least five times greater than the therapeutic index for the enantiomer of such compound.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is greater than the therapeutic index for the enantiomer of such compound. In certain embodiments, the therapeutic index for a compound is at least 150% of the therapeutic index for the enantiomer of such compound.

In certain embodiments the invention provides compounds where Y is Cl, in other embodiments the invention provides compounds where Y is $CF_3$ and in other embodiments the invention provides compounds where Y is CN.

In certain embodiments the invention provides compounds where X is —NR'R", in other embodiments the invention provides compounds where X is —OR'". In certain embodiments the invention provides compounds where X is —OR'". In certain embodiments the invention provides compounds where X is —OH and in other embodiments the invention provides compounds where X is —OCO—$R^1$.

In certain embodiments the invention provides compounds where $R_1$ is $C_{1-3}$ alkyl; in other embodiments the invention provides compounds where R' is H.

In certain embodiments the invention provides compounds where R' is —$COR^1$; in other embodiments the invention provides compounds where R' is $SO_2$—$R^1$. In certain embodiments the invention provides compounds where R" is H.

In certain embodiments the invention provides compounds where R" is —$SO_2$—$R^3$; in other embodiments the invention provides compounds where R" is $C_{1-4}$ alkyl where the $C_{1-4}$ alkyl is optionally substituted with 1 or more substituents defined by $R^2$. In certain embodiments the invention provides compounds where R" is —$(CR^aR^b)_n$—$R^2$ and each $R^a$ and each $R^b$ can be independently any of H, hydroxyl and methyl or where $R^a$ and $R^b$ are bound to the same carbon they can be taken together to form oxo (i.e. with the carbon to which they are bound forming a carbonyl moiety). In certain such embodiments n can be 0, 1, 2, or 3 and in certain embodiments n is 2. In certain such embodiments $R_2$ can be —OH, —$NH_2$, —$NHR^1$, —$N(R^5R^5)$, or —COOH.

In certain embodiments the invention provides compounds where $R^3$ is $C_{1-4}$ alkyl optionally substituted with 1 or more $R^2$. In certain embodiments the invention provides compounds where $R^2$ is OH; in other embodiments the invention provides compounds where $R^2$ is $C_{1-3}$ alkoxy. In certain embodiments the invention provides compounds where $R^3$ is $(CH_2)_2$—$OR^1$.

In certain embodiments the invention provides compounds where Y is CN and X is —NH—$SO_2$—$R^3$. In certain embodiments the invention provides compounds where $R^3$ is —$C_2H_5$—$N((R^5R^5)$ or —$CH_2$—CO—$N(R^5R^5)$. In certain embodiments the invention provides compounds where Y is CN and X is —NH—CO—$N(R^5R^5)$.

In certain embodiments X is —$NH_2$ and in certain of such embodiments Y is CN.

In certain embodiments the invention provides one or more of compounds 1-55:

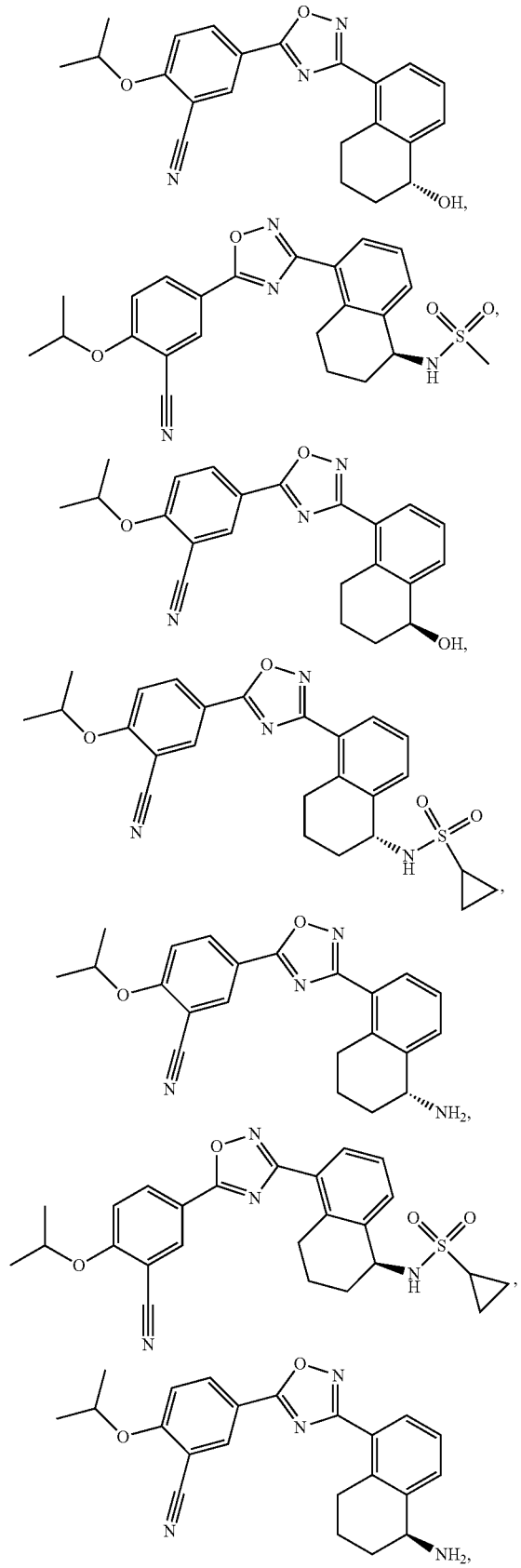

7
-continued
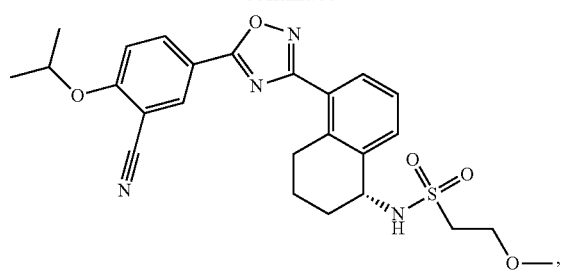
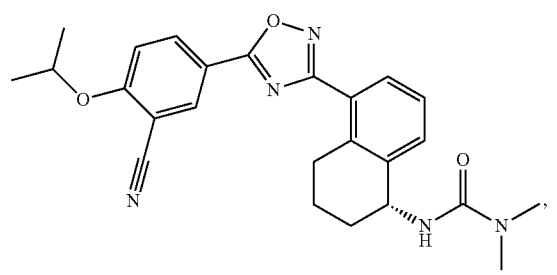
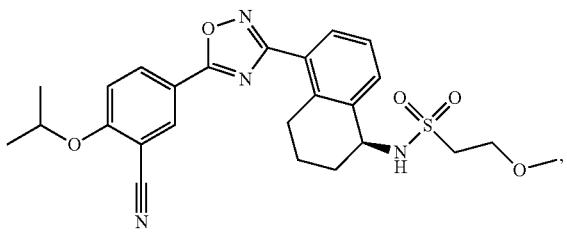
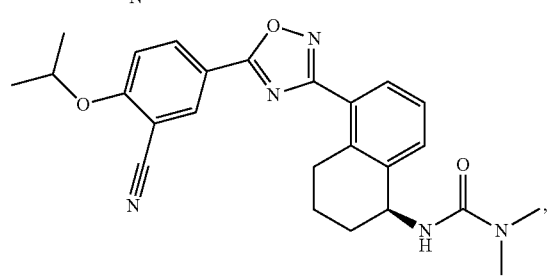
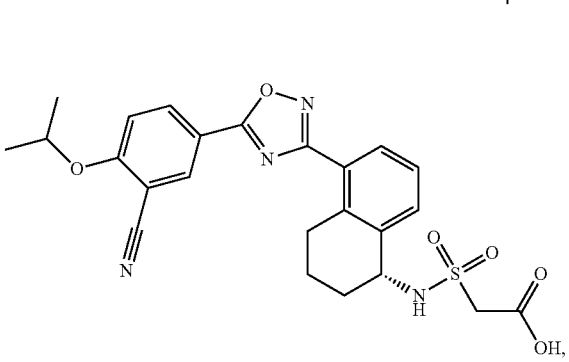
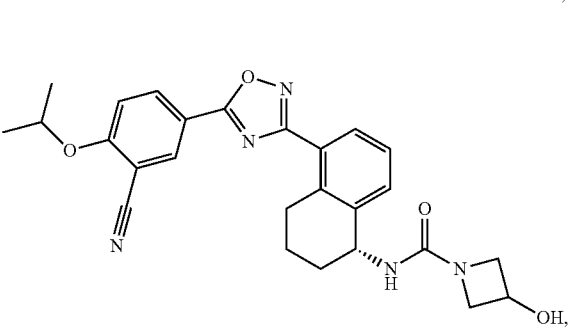
8
-continued
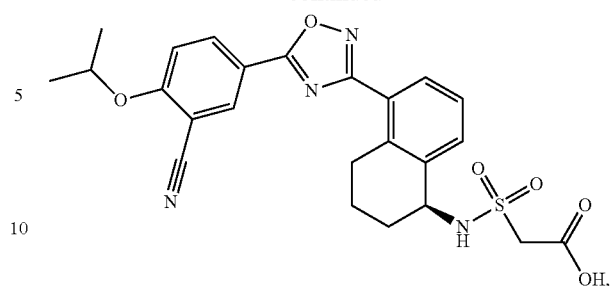
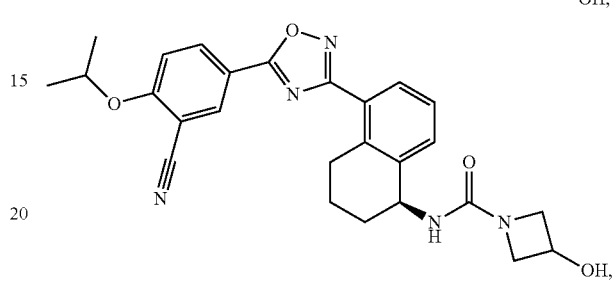
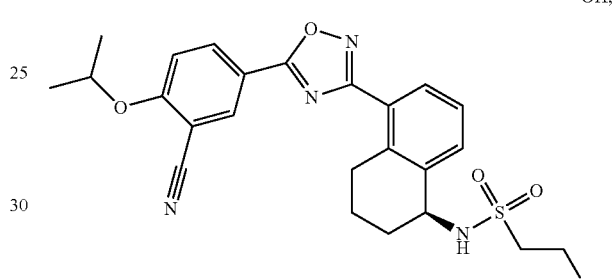
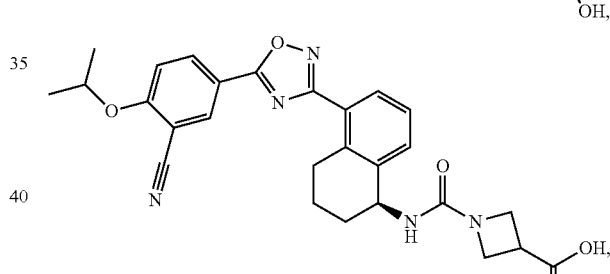
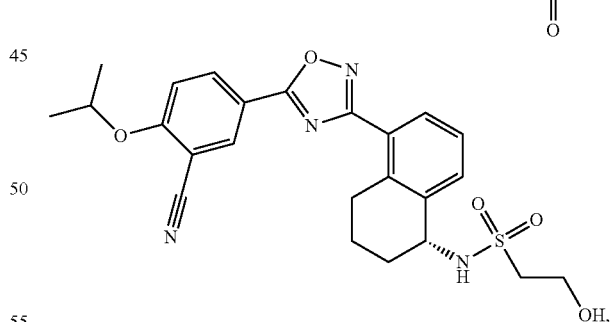
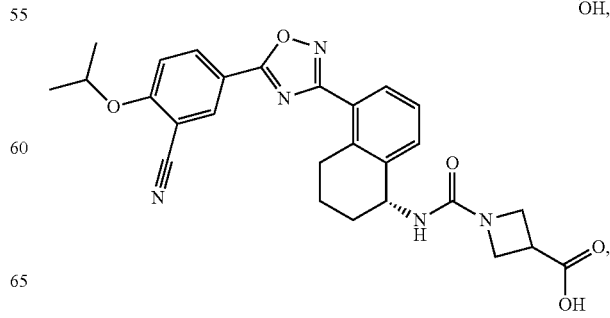

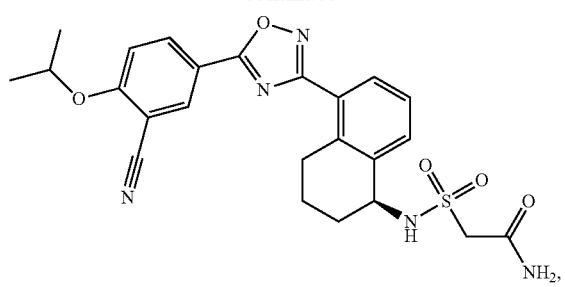
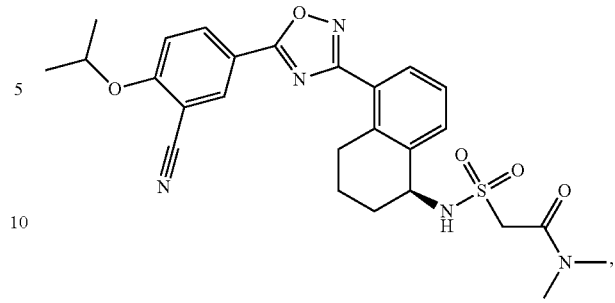
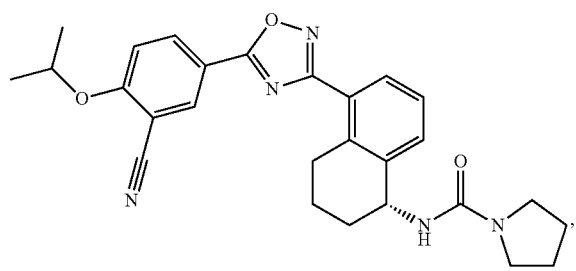
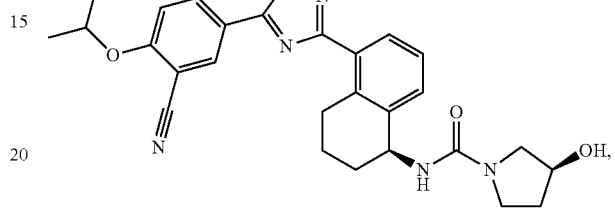
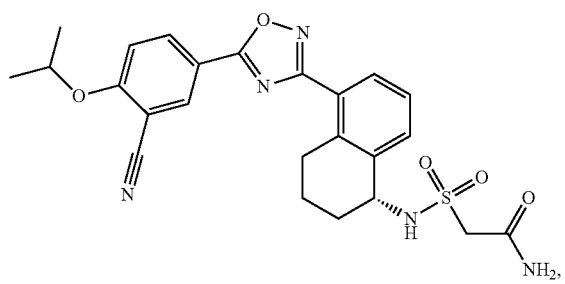
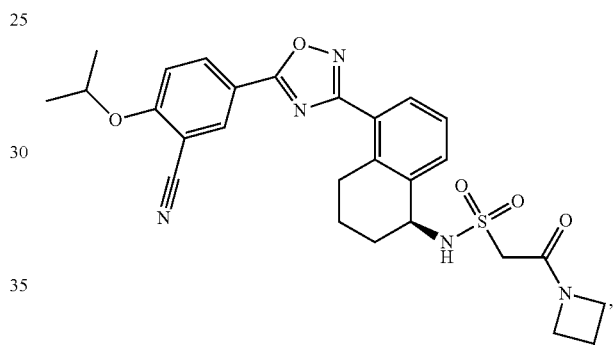
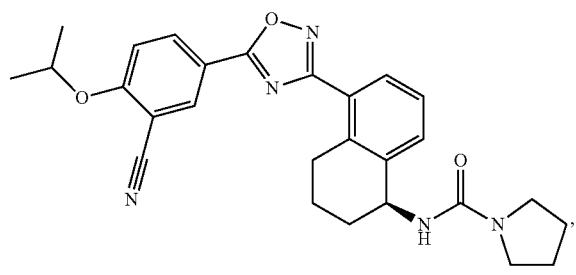
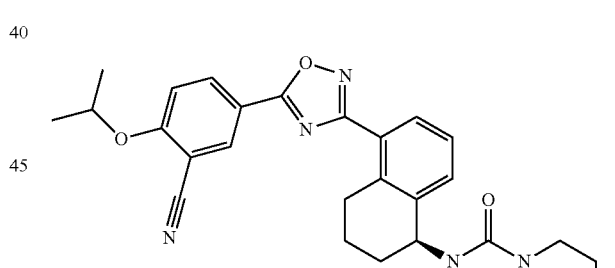
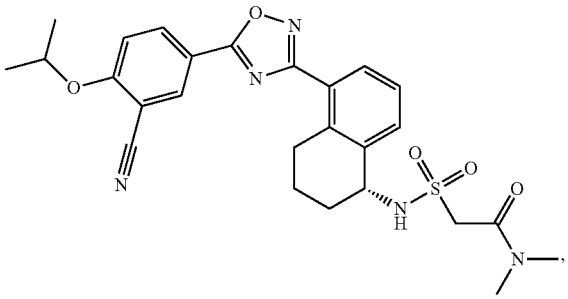
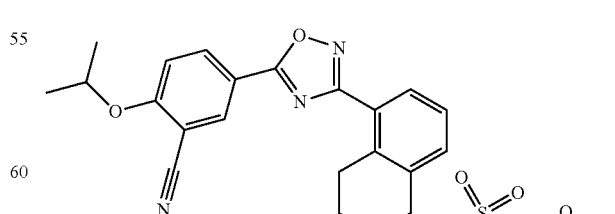
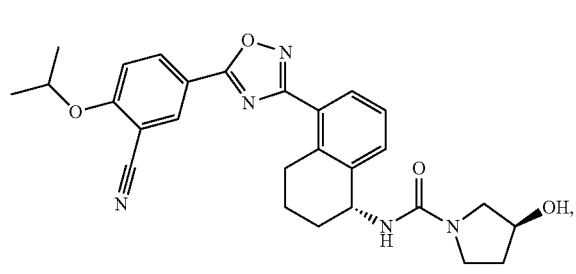
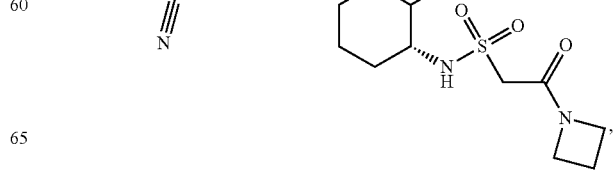

11
-continued
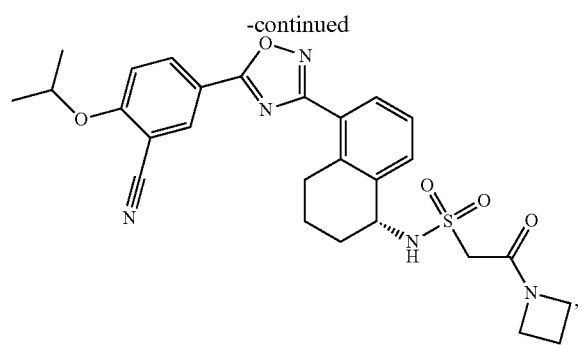
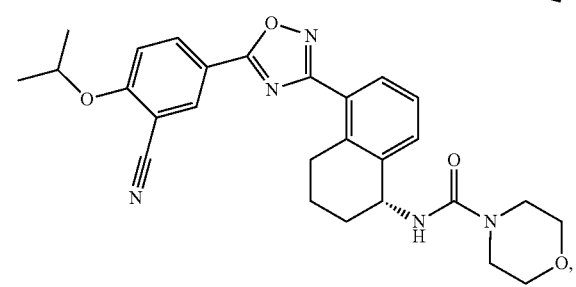
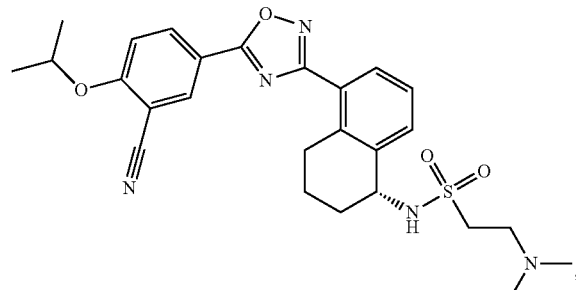
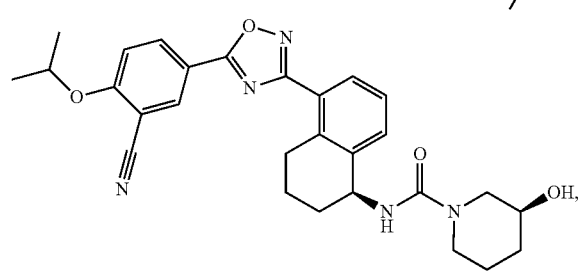
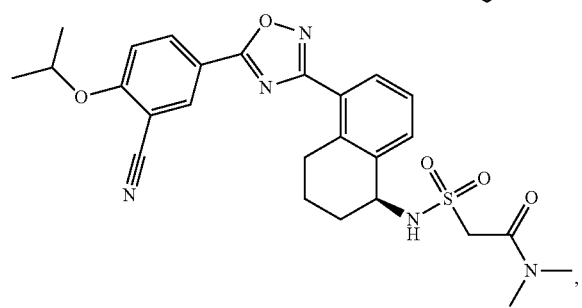
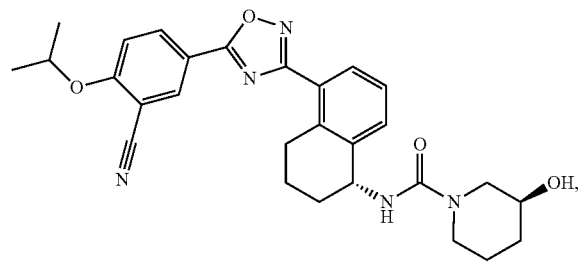
12
-continued
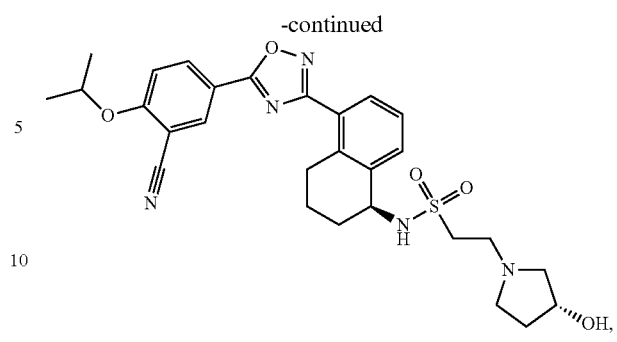
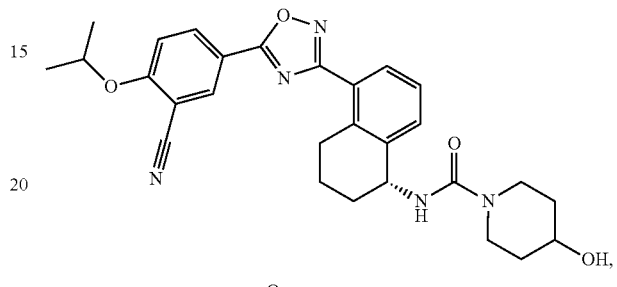
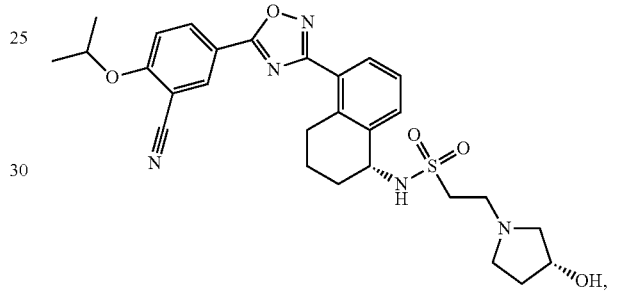
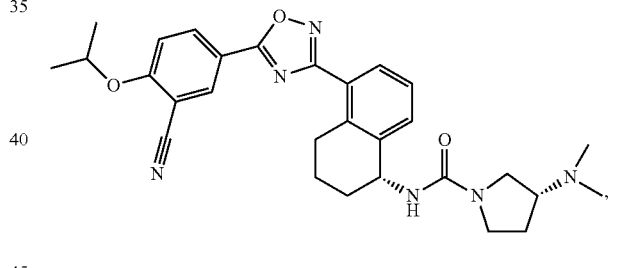
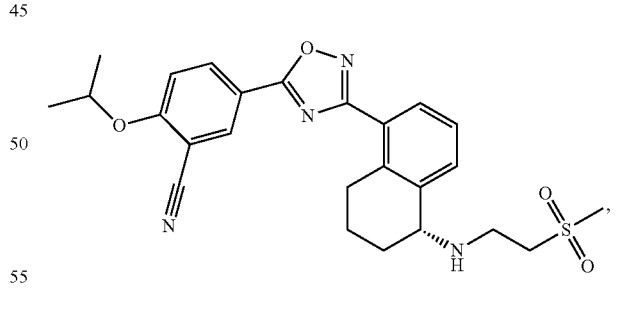
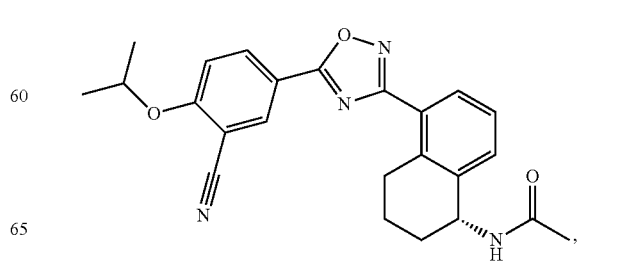

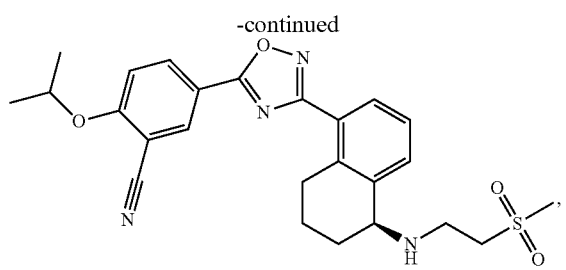
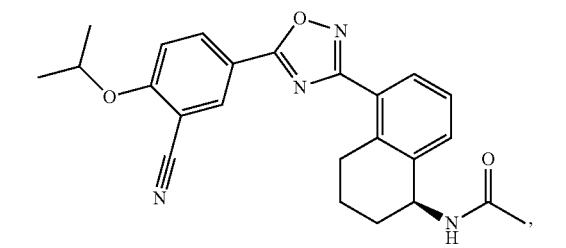
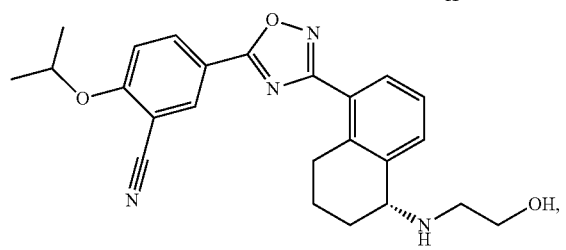
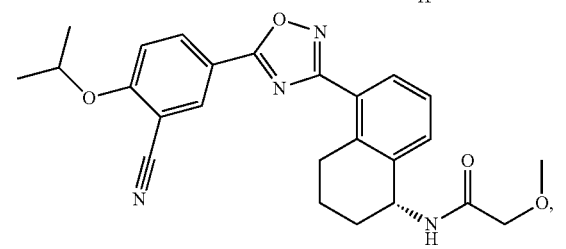
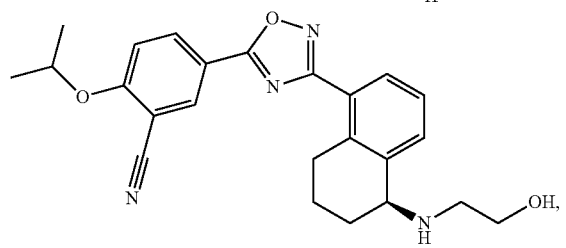
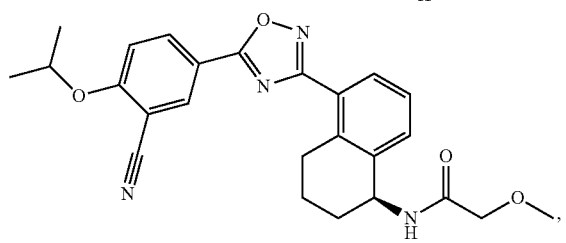
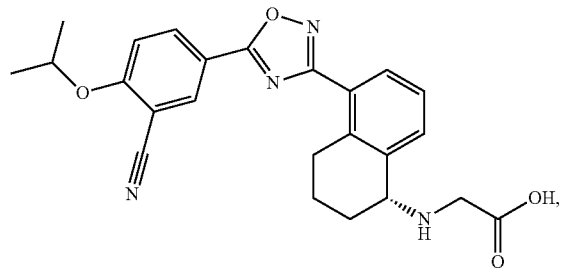
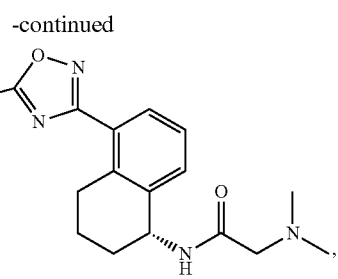
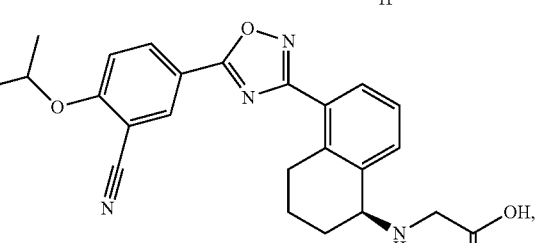
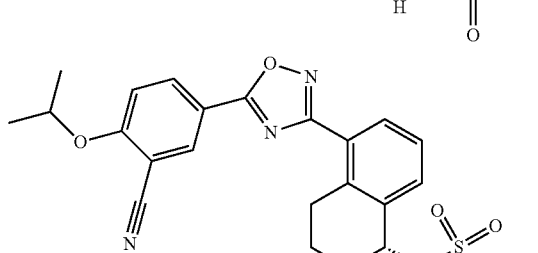
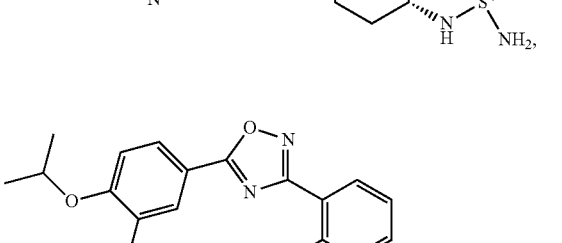
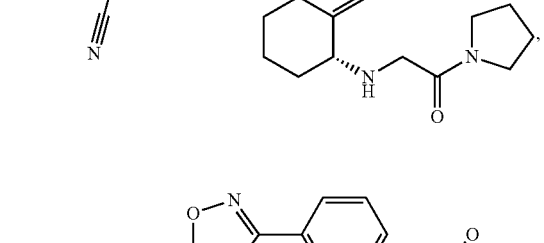
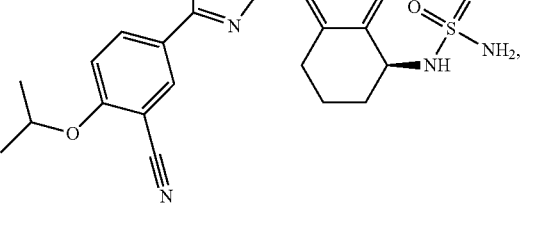
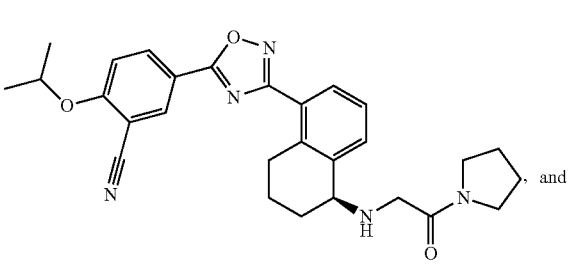

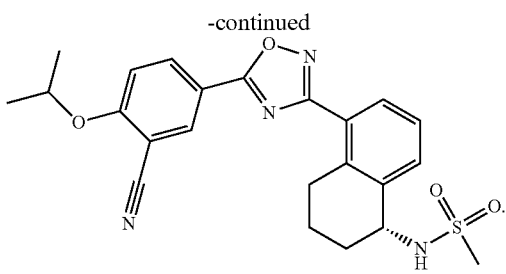

or any pharmaceutically acceptable salt, tautomer, stereoisomer, solvate, hydrate, or prodrug thereof. In certain of such embodiments, the invention provides a compound selected from compounds 8, 13, 29, 33, 37, and 49 or any pharmaceutically acceptable salt, ester, tautomer, stereoisomer, solvate, hydrate, homolog, or prodrug thereof.

In certain embodiments, an invention compound of Formula I is provided wherein the compound has at least one chiral center and is substantially enantiomerically pure.

In other embodiments, a pharmaceutical composition comprising an invention compound of Formula I and a suitable excipient is provided.

In other embodiments, a pharmaceutical combination comprising an invention compound and a second medicament is provided. In still other embodiments, a pharmaceutical combination comprising an invention compound and a second medicament is provided wherein the second medicament is medically indicated for the treatment of multiple sclerosis, transplant rejection, or adult respiratory distress syndrome.

In certain embodiments, a method of use of an invention compound for preparation of a medicament is provided.

In certain embodiments a method of activation or agonism of a sphingosine-1-phosphate receptor subtype 1 by contacting the receptor subtype 1 with an effective amount of an invention compound. In further embodiments, a method of activation or agonism of a sphingosine-1-phosphate receptor subtype 1 by contacting the receptor subtype 1 with an effective amount of an invention compound is provided, wherein the compound activates or agonizes the sphingosine-1-phosphate receptor subtype 1 to a greater extent than the compound activates or agonizes a sphingosine-1-phosphate receptor subtype 3. In further embodiments, a method of activation or agonism of a sphingosine-1-phosphate receptor subtype 1 by contacting the receptor subtype 1 with an effective amount of an invention compound is provided, wherein the sphingosine-1-phosphate receptor subtype 1 is disposed within a living mammal.

In certain embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient. In further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein selective activation or agonism of an S1P subtype 1 receptor with respect to other subtypes of S1P receptor is medically indicated. In yet further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein the malcondition comprises rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicIous anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; siderosis; retinitis pigmentosa; senile macular degeneration; vitreal scarring; inflammatory eye disease; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. In yet further embodiments, the malcondition is one or more of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma. In yet further embodiments the malcondition is one of influenza, ulcerative colitis, multiple sclerosis, transplant rejection, acute respiratory distress syndrome or adult respiratory distress syndrome.

In certain embodiments, methods are provided for use of an invention compound for preparation of a medicament adapted for treatment of a disorder or a malcondition wherein activation or inhibition of a sphingosine-1-phosphate receptor subtype 1 is medically indicated.

In certain embodiments the invention provides a method for the chiral synthesis of a compound comprising a tetrahydronaphthalene moiety having a chiral carbon in the six-membered saturated ring of the tetrahydronaphthalene moiety where the compound is enantiomerically enriched with respect to the chiral carbon. In such embodiments, the method of the invention provides the steps of (i) providing a compound comprising a tetrahydronaphthalene moiety where the ring carbon of the six-membered saturated ring of the tetrahydronaphthalene moiety where chiral substitution is desired is oxo substituted at such carbon; and (ii) reacting such compound with a chiral reagent to form a chiral center at the tetrahydronaphthalene moiety carbon previously bound to the oxo group. In certain of such embodiments, the chiral reagent is RuCl(p-cymene)[(R,R)-Ts-DPEN] or RuCl(p-cymene)[(S,S)-Ts-DPEN].

In certain of such embodiments the compound comprising a tetrahydronaphthalene moiety provided in step (i) is contacted with the chiral reagent to form in step (ii) an intermediate of Formula VI-R or VI-S:

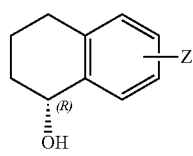

VI-R

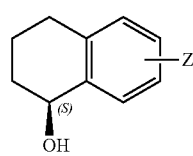

VI-S wherein Z is —CN, —Cl, or —CF$_3$. In certain of such embodiments Z is —CN.

In certain embodiments the invention provides the method comprising the step of reversing the chiral configuration of the chiral carbon in the six-membered saturated ring of the tetrahydronaphthalene moiety that was previously bound to the oxo group by treating the intermediate of Formula VI-R or VI-S with diphenylphosphoryl azide (DPPA) to form an azido tetrahydronaphthalene of Formula VII-S or VII-R:

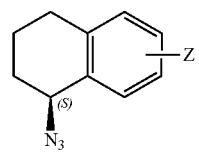

VII-S

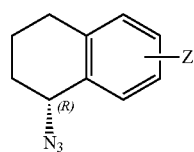

VII-R where the azido substituent in the six-membered saturated ring of the tetrahydronaphthalene moiety replaces the hydroxy substituent of Formula VI-R or VI-S and the resulting chiral carbon that is bound to the azido substituent has a reverse chiral configuration of the chiral carbon when it was previously bound to the hydroxy substituent.

In certain embodiments the invention provides the method where Z is —CN and the method further comprises the additional steps of (a) forming a substituted 1,2,4-oxadiazole on the tetrahydronaphthalene moiety by (a) reacting the intermediate of VII-R or VII-S with a protecting agent and then reacting the resulting protected form of the intermediate of VII-R or VII-S with a hydroxylamine or a hydroxylamine hydrochloride to form a hydroxyamidine at the phenyl carbon to which Z had been attached, the resulting compound of such reaction having the Formula VIII-R or VIII-S:

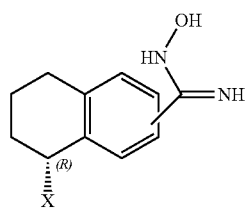

VIII-R

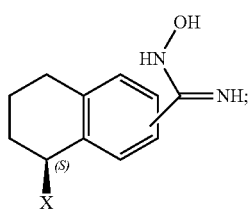

VIII-S and (b) contacting the intermediate of Formula VIII-R or VIII-S with substituted benzoic acid and a coupling reagent to form a compound of Formula IX-R or XI-S:

IX-R

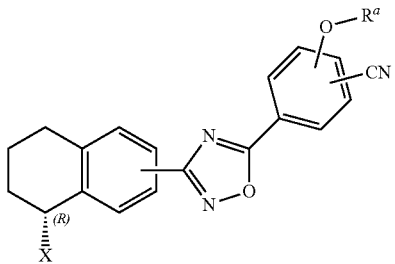

XI-S

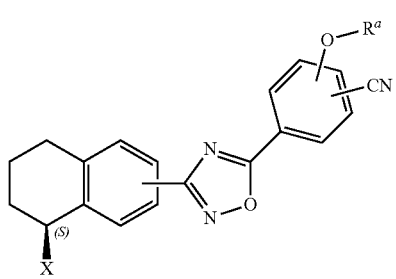

where X is as defined above or in certain embodiments OH, $N_3$, NH-PG, $NH_2$ or NR'R"; PG can be a protecting group; R' can be H, $C_{1-4}$ alkyl, n-hydroxy $C_{1-4}$ alkyl, —$SO_2$—$R^1$, or —CO—$R^1$; R" can be H, —$SO_2$—$R^3$, $C_{1-4}$ alkyl optionally substituted with 1 or more $R^2$, or a ring moiety optionally substituted with $R^4$ wherein such ring moiety is piperidinyl, cyclohexyl, morpholinyl, thiazolyl, pyrazolyl, pyrrolidinyl, imidazolyl, or phenyl; $R^a$ is lower alkyl and $R^1$, $R^2$, $R^3$, and $R^4$ are as defined above. In certain of such embodiments the compounds of Formula IX-R or IX-S have the structures below:

IX-R

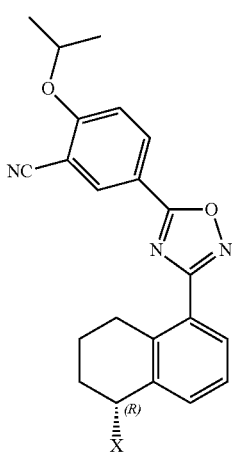

XI-S

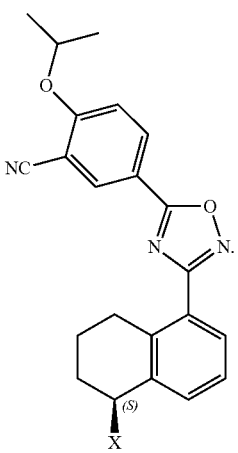

In certain of such embodiments, the coupling reagent can be a mixture comprising hydroxybenzotriazole (HOBt) and 1-ethyl-3-(3-dimethylaminopropyl)-carbodiimide (EDC).

Protecting groups can render chemical functionality inert to specific reaction conditions and can be appended to and removed from such functionality in a molecule without substantially damaging the remainder of the molecule. Practitioners in the art would be familiar with suitable protecting groups for use in the synthetic methods of the invention. See, e.g., Greene and Wuts, *Protective Groups in Organic Synthesis*, $2^{nd}$ ed., John Wiley & Sons, New York, 1991.

In certain embodiments the invention provides the method where the compound provided in step (i) is

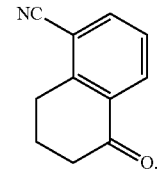 [SMILES: N#Cc1cccc2c1CCCC2=O]

In certain embodiments the invention provides the method where the resulting compound comprising a tetrahydronaphthalene moiety having a chiral carbon in the six-membered saturated ring of the tetrahydronaphthalene moiety is enantiomerically enriched at least 90%. In certain such embodiments the resulting compound is enantiomerically enriched at least 95%. In certain such embodiments the resulting compound is enantiomerically enriched at least 98%. In certain such embodiments the resulting compound is enantiomerically enriched at least 99%.

In certain of such embodiments, the invention provides a method for chiral synthesis of a chiral compound comprising a tetrahydronaphthalene moiety having a chiral carbon in the six-membered saturated ring of the tetrahydronaphthalene moiety or a chiral compound comprising an oxadiazole-tetrahydronaphthalene moiety having a chiral carbon in the six-membered saturated ring of the tetrahydronaphthalene moiety where the chiral compound has an enantiomeric enrichment of at least 75%, 85%, 90%, 95%, 98%, or 99%.

In certain of such embodiments, the invention provides a method for synthesis of a chiral compound of the invention having an enantiomeric enrichment of at least 75%, 85%, 90%, 95%, 98%, or 99%.

In certain embodiments, the invention provides compounds which can be intermediates in the herein described methods for chiral syntheses. In certain such embodiments, the invention provides one or more of the following intermediate compounds:

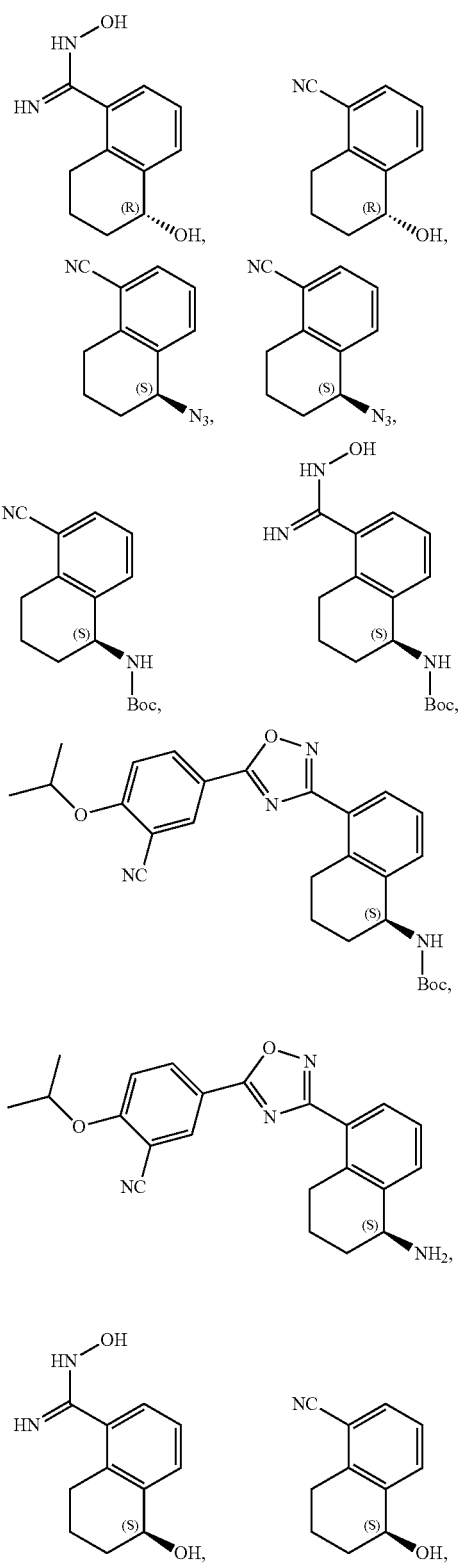

-continued

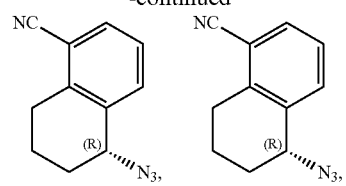

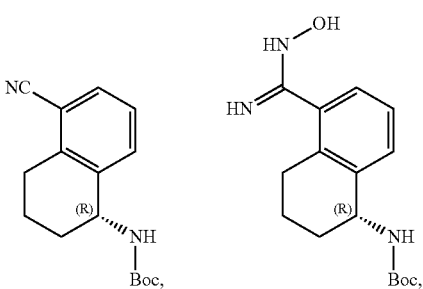

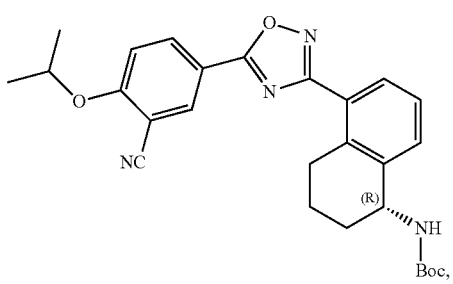

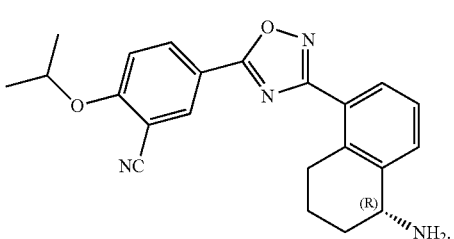

In certain of such embodiments, the invention provides a method for the synthesis of a compound comprising a tetrahydronaphthalene moiety having a chiral carbon in the six-membered saturated ring of the tetrahydronaphthalene moiety, where the compound is enantiomerically enriched with respect to such chiral carbon, with the method comprising a step of providing one of such intermediate compounds.

In certain embodiments, a method for the synthesis of a compound comprising a tetrahydronaphthalene moiety having a chiral carbon in the six-membered saturated ring of the tetrahydronaphthalene moiety where the compound is enantiomerically enriched with respect to the chiral carbon is provided. In certain embodiments, a method comprising a step of providing a compound of the structures described herein is provided.

In certain embodiments, the invention provides a method for the synthesis of a compound of the Formula IX-R or XI-S:

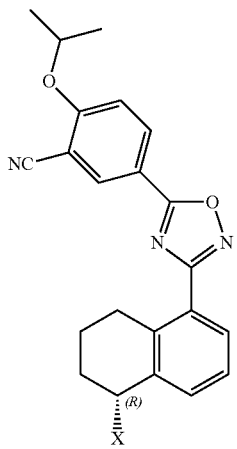

IX-R

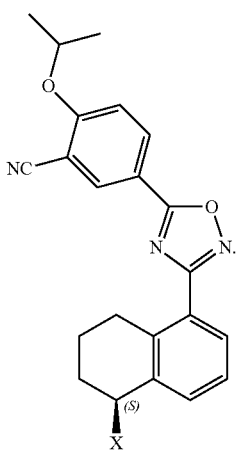

XI-S wherein X is as defined herein, with the method comprising a step of providing one of the intermediate compounds described above. In certain of such embodiments the invention provides a method for the synthesis of a compound of the invention.

In certain embodiments the invention provides a method for the chiral synthesis of the structure of Formula IX-R or IX-S or a pharmaceutically acceptable salt, ester, prodrug, homolog, hydrate or solvate thereof:

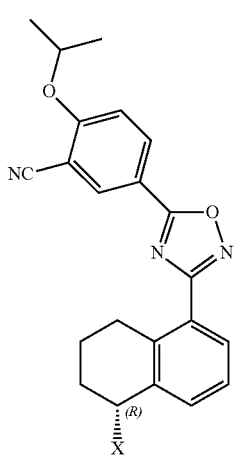

IX-R

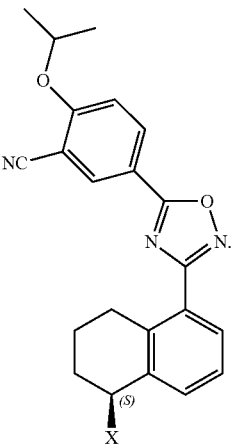

XI-S where X is defined as above and where the compound is enantiomerically enriched with respect to the chiral carbon. In such embodiments, the method of the invention provides the steps of (i) providing the compound

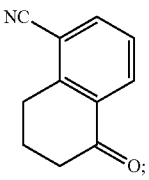

and (ii) reacting such compound with a chiral reagent RuCl(p-cymene)[(R,R)-Ts-DPEN] or RuCl(p-cymene)[(S,S)-Ts-DPEN]; and (iii) forming a chiral center at the tetrahydronaphthalene moiety carbon previously bound to the oxo group.

Additional steps for the preparation of such compounds can be adapted from the synthetic methods disclosed herein including recrystallization and other processes for purification.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The term "S1P$_1$" as used herein refers to subtype 1 of a sphingosine-1-phosphate receptor, while other sphingosine-1-phosphate receptor subtypes are referred to in a corresponding manner, for example, sphingosine-1-phosphate receptor subtype 3 is referred to as "S1P$_3$".

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "$S1P_1$ compound" or "$S1P_1$ agonist" or "$S1P_1$ activator" or "$S1P_1$ inhibitor" or "$S1P_1$ antagonist" as the terms are used herein refer to compounds that interact in some way with the S1P receptor subtype 1. They can be agonist or activators, or they can be antagonists or inhibitors. An "$S1P_1$ compound" of the invention can be selective for action on subtype 1 of the S1P receptor family; for example a compound of the invention can act at a lower concentration on subtype 1 of the S1P receptor family than on other subtypes of the S1P receptor family; more specifically, an "$S1P_1$ compound" of the invention can selectively act on subtype 1 receptors compared to its action on subtype 3, or "$S1P_3$" receptors.

In certain embodiments, compounds of the invention are orthostatic agonists. In certain other embodiments, compounds of the invention are allosteric agonists. Receptor agonists may be classified as either orthosteric or allosteric. An orthosteric agonist binds to a site in the receptor that significantly overlaps with the binding of the natural ligand and replicates the key interactions of the natural ligand with the receptor. An orthosteric agonist will activate the receptor by a molecular mechanism similar to that of the natural ligand, will be competitive for the natural ligand, and will be competitively antagonized by pharmacological agents that are competitive antagonists for the natural ligand. An allosteric agonist binds to a site in the receptor that makes some significant interactions that are partly or wholly non-overlapping with the natural ligand. Allosteric agonists are true agonists and not allosteric potentiators. Consequently, they activate receptor signaling alone and without a requirement for a sub-maximal concentration of the natural ligand. Allosteric agonists may be identified when an antagonist known to be competitive for the orthosteric ligand shows non-competitive antagonism. The allosteric agonist site can also be mapped by receptor mutagenesis. The introduction of single point mutations in receptors that retain receptor activation by allosteric agonist, while diminishing or abolishing signaling induced by orthosteric agonist or vice versa provide formal evidence for differences in binding interactions. Orthosteric agonists may destabilize GPCR structure and conformation, while allosteric agonists may either stabilize or destabilize GPCR structure and conformation. Allosteric agonists, by virtue of their different interactions with receptor, may be pharmaceutically useful because the allosteric site may confer additional opportunities for agonist potency and selectivity within a related family of receptor subtypes that share a similar orthosteric ligand. In addition, the allosteric site may require very different physical and chemical properties of an agonist compared to the orthosteric ligand. These chemico-physical properties, which include hydrophobicity, aromaticity, charge distribution and solubility may also provide advantages in generating agonists of varying pharmacokinetic, oral bioavailability, distributional and metabolism profiles that facilitate the development of effective pharmaceutical substances.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by a sphingosine-1-phosphate receptor of subtype 1 refers to the amount of a compound of the invention that is effective to bind to as an agonist or as an antagonist a $S1P_1$ receptor in the individual's tissues, wherein the $S1P_1$ is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of sphingosine-1-phosphate receptor subtype 1 ($S1P_1$) activity. A therapeutically effective amount is also one in which any toxic or detrimental effects of compounds of the invention are outweighed by the therapeutically beneficial effects. For example, in the context of treating a malcondition mediated by activation of $S1P_1$, a therapeutically effective amount of an $S1P_1$ agonist of the invention is an amount sufficient to control the malcondition, to mitigate the progress of the malcondition, or to relieve the symptoms of the malcondition. Examples of malconditions that can be so treated include multiple sclerosis, transplant rejection, adult respiratory distress syndrome.

Diseases, disorders and conditions which may be treated by compounds of the invention include rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicIous anemia; megaloblastic anemia; aneryth-roplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; siderosis; retinitis pigmentosa; senile macular degeneration; vitreal scarring; inflammatory eye disease; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. Particularly preferred diseases and conditions which may be treated with compounds of the invention comprise the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

Furthermore, compounds of Formula I-R or I-S are also useful, in combination with one or several immunosuppressant agents, for the treatment of diseases, disorders and conditions associated with an activated immune system and selected from the list as above-mentioned. According to a preferred embodiment of the invention, said immunosuppressant agent is selected from the group comprising or consisting of cyclosporin, daclizumab, basiliximab, everolimus, tacrolimus (FK506), azathiopirene, leflunomide, 15-deoxyspergualin, or other immunosuppressant drugs All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the examples, the Cahn-Ingold-Prelog ranking is A>B>C>D. The lowest ranking atom, D is oriented away from the viewer.

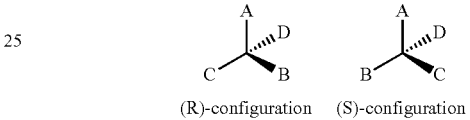

(R)-configuration    (S)-configuration

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the ex tent that a compound may be isolated as, and exist indefinitely, as a single stable rotamer. The present invention therefore includes any possible stable rotamers of compounds of the invention which are biologically active in the treatment of a disease, disorder or condition for which a compound of the invention may be effective as described herein.

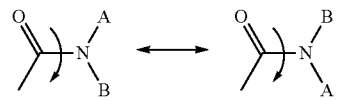

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

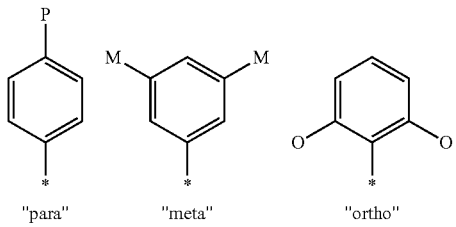

All structures encompassed within a claim are "chemically feasible", by which is meant that the structure depicted by any combination or subcombination of optional substituents meant to be recited by the claim 1s physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboy/date esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles. The substituents of the substituted groups can further be substituted with alkyl, alkenyl, cycloalkyl, aryl, heteroaryl, and alkynyl groups as defined herein, which can themselves be further substituted. For example, an C$_{1-4}$ alkyl group can be substituted with an amide, and the amide can further be substituted with another C$_{1-4}$ alkyl, which can further be substituted.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms (C$_{1-20}$ alkyl), and typically from 1 to 12 carbons (C$_{1-12}$ alkyl) or, in some embodiments, from 1 to 8 carbon atoms (C$_{1-8}$ alkyl) or, in some embodiments, from 1 to 4 carbon atoms (C$_{1-4}$ alkyl) or, in some embodiments, from 1 to 3 carbon atoms (C$_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups. The group "n-hydroxy C$_{1-4}$ alkyl" represents an C$_{1-4}$ alkyl substituted with a terminal hydroxy group.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-, 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds (heterocyclic rings) containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C$_2$-heterocyclyl can be a 5-membered ring with two carbon atoms and three heteroatoms, a 6-membered ring with two carbon atoms and four heteroatoms and so forth. Likewise a C$_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring hetero atom. Heterocyclyl groups include, but are not limited to, pyrrolidinyl, fuxanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a C$_2$-heteroaryl can be a 5-membered ring with two carbon atoms and three heteroatoms, a 6-membered ring with two carbon atoms and four heteroatoms and so forth. Likewise a C$_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl; 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo thiophenyl), 2,3-dihydro-benzo[b]thiophenyl, (2-(2,3-dihydro-benzo[b] thiophenyl), 3-(2,3-dihydro-benzo[b]thiophenyl), 4-(2,3-dihydro-benzo[b]thiophenyl), 5-(2,3-dihydro-benzo[b] thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "mono cyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or Spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amities having, e.g., the formula N(group)$_3$ wherein each group can independently be H or non-H, such as alkyl, aryl, and the like. Amines include but are not limited to RNH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR'R", and —NR'C(O)R" groups, respectively. The R' and R" of the C-amide may join together to form a heterocyclic ring with the nitrogen atom. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium and alkyl ammonium salts such as tromethamine salts, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein Nonlimiting examples of potential salts of this invention include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandelate, napsylate, napadisylate, oxalate, oleate, sebacate, stearate, succinate, thiocyanate, undecylenate, and xinafoate.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "homolog" of a compound of the invention is a compound having one or more atoms of the compound replaced by an isotope of such atom. For example, homologs include compounds with deuterium in place of some hydrogen atoms of the compound such as compounds of the invention in which the methyl groups of the isopropoxy moiety of Formulas I-R and I-S are fully or partially deuterated (e.g., (D$_3$C)$_2$C—O—). Isotopic substitutions which may be made in the formation of homologs of the invention include non-radioactive (stable) atoms such as deuterium and carbon 13, as well as radioactive (unstable) atoms such as tritium, carbon 14, iodine 123, iodine 125, etc.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

Any compound which can be converted in vivo to the active drug by chemical or biochemical transformations functions as a prodrug. Prodrugs of claimed compounds are covered under this invention.

Some examples of prodrugs within the scope of this invention include:
i. If the compound contains a hydroxyl group, the hydroxyl group may be modified to form an ester, carbonate, or carbamate. Examples include acetate, pivalate, methyl and ethyl carbonates, and dimethylcarbamate. The ester may also be derived from amino acids such as glycine, serine, or lysine.
ii. If the compound contains an amine group, the amine group may be modified to form an amide. Examples include acetamide or derivatization with amino acids such as glycine, serine, or lysine.

Certain compounds of the invention and their salts may exist in more than one crystal form and the present invention includes each crystal form and mixtures thereof. In addition, the compounds of the present invention can exist in unsolvated as well as solvated forms with pharmaceutically acceptable solvents such as water to form hydrates or adducts with alcohols such as $C_{1-4}$-alkanols, and the like. Furthermore, compounds of this invention can be isolated in association with solvent molecules by crystallization from evaporation of an appropriate solvent. Such solvents include but are not limited to toluene, tetrahydrofuran, dioxane, dimethylformamide, acetonitrile, acetates such as methyl acetate, ethyl acetate, butyl acetate, isobutyl acetate, propyl- and isopropyl acetate, ethers such as diethyl ether and ethyl ether, alcohols such as methanol, ethanol, 1- or 2-butanol, 1- or 2-propanol, pentanol, and dimethylsulfoxide. In general, a depiction for the compound by structure or name is considered to embrace the compound in any form (e.g., by itself, as a hydrate, solvate, or otherwise in a mixture).

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Compositions and Combination Treatments

The $S1P_1$ compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another $S1P_1$ inhibitor or another type of therapeutic agent, or both. As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the enzymatic activity of the focal adhesion kinase to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other $S1P_1$ inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:
  a) a compound of the invention as described herein; and
  b) one or more compounds comprising:
    i) other compounds of the present invention,
    ii) other medicaments adapted for treatment of a malcondition for which activation of $S1P_1$ is medically indicated, for example multiple sclerosis, transplant rejection, or adult respiratory distress syndrome.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

In certain embodiments, the present invention encompasses orally bioavailable compounds that specifically agonize $S1P_1$ without binding ($S1P_2$, $S1P_3$ and $S1P_4$), or having significant specificity over ($S1P_5$), other EDG receptors. A selective $S1P_1$ agonist can be used to treat diseases with an autoimmune, hyperactive immune-response, angiogenesis or inflammatory components, but would not be limited to such conditions. Selective $S1P_1$ agonists have advantages over current therapies by increasing the therapeutic window because of reduced toxicity due to engagement of other EDG receptors.

In certain embodiments, the present invention encompasses compounds that bind with high affinity and specificity to the $S1P_1$ receptor in an agonist manner. Upon ligation of the $S1P_1$ receptor with agonist, signaling proceeds through $G_{\alpha i}$, inhibiting the generation of cAMP by adenylate cyclase.

In certain embodiments, the present invention provides a method for activating or agonizing (i.e., to have an agonic effect, to act as an agonist) a sphingosine-1-phosphate receptor subtype, such as $S1P_1$, with a compound of the invention. The method involves contacting the receptor with a suitable concentration of an inventive compound to bring about activation of the receptor. The contacting can take place in vitro, for example in carrying out an assay to determine the S1P receptor activation activity of an inventive compound undergoing experimentation related to a submission for regulatory approval.

In certain embodiments, the method for activating an S1P receptor, such as $S1P_1$, can also be carried out in vivo, that is, within the living body of a mammal, such as a human patient or a test animal. The inventive compound can be supplied to the living organism via one of the routes as described above, e.g., orally, or can be provided locally within the body tissues, for example by injection of a tumor within the organism. In the presence of the inventive compound, activation of the receptor takes place, and the effect thereof can be studied.

An embodiment of the present invention provides a method of treatment of a malcondition in a patient for which activation of an S1P receptor, such as $S1P_1$, is medically indicated, wherein the patient is administered the inventive compound in a dosage, at a frequency, and for a duration to produce a beneficial effect on the patient. The inventive compound can be administered by any suitable means, examples of which are described above.

Preparation of Certain Embodiments

Scheme 1:

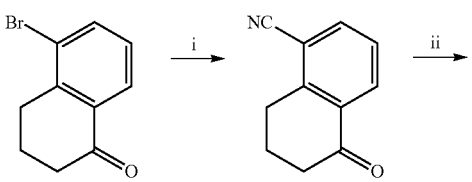

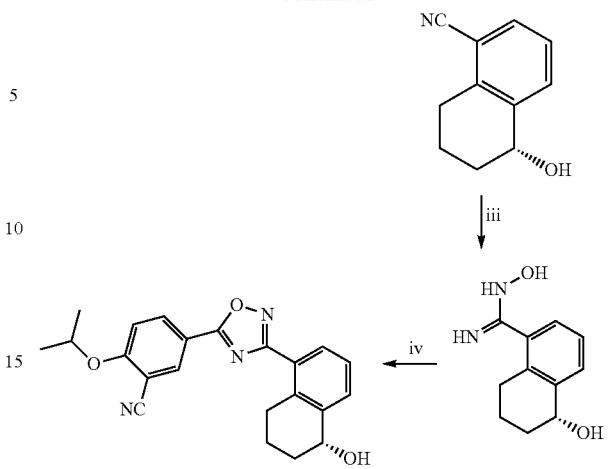

Reagents: (i) $Zn(CN)_2$, $Pd(PPh_3)_4$, NMP; (ii) RuCl(p-cymene)[(R,R)-Ts-DPEN], $HCO_2H$-TEA complex; (iii) $NH_2OH*HCl$, $Na_2CO_3$ or TEA, EtOH; (iv) HOBt, EDC, benzoic acid, DMF.

The (S)-enantiomer was prepared in the same manner outlined in Scheme 1 using RuCl(p-cymene)[(S,S)-Ts-DPEN] in step (ii). Racemic material can be prepared in the same manner outlined in Scheme 1 using $NaBH_4$ in (ii).

Scheme 2:

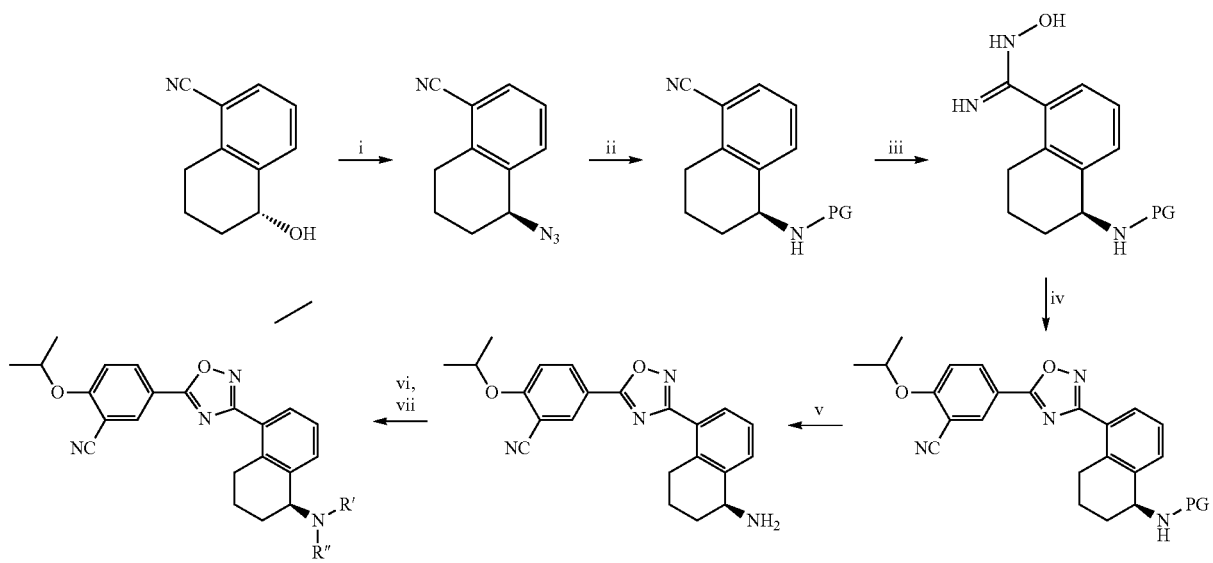

Reagents: (i) DPPA, DBU, toluene; (ii) PG = protecting group e.g. Boc: Pd/C, $H_2$, $Boc_2O$, TEA, MeOH; (iii) $NH_2OH*HCl$, $NaHCO_3$, EtOH; (iv) HOBt, EDC, benzoic acid, DMF (v) deprotection e.g. 4M HCl in dioxane; (vi) (a) R'—LG or R"—LG, where LG represents a leaving group, $K_2CO_3$, $CH_3CN$;
(b) $R^1$—$CO_2H$ or $R^2$—$CO_2H$, HOBt, EDC, DMF or $R^1$—COCl or $R^2$—COCl, TEA, DCM;
(c) $R^1$—$SO_2Cl$ or $R^3$—$SO_2Cl$, TEA, DCM (d) $R^2$—CHO, HOAc, $NaBH_4$ or $NaCNBH_3$ or $Na(OAc)_3BH$, MeOH; (e) $R^1$—OCOCl or $R^2$—OCOCl, DIEA, DMF; (f) $HN(R^5R^5)$, CDI, TEA, DCM; (g) $H_2NSO_2NH_2$, Δ, dioxane; (h) dimethyloxirane, Δ, EtOH; (vii) (a) If R' or R" = H, then reactions (vi)(a-d) can be performed;
(b) If R' or R" contains an ester then (i) hydrolysis NaOH, EtOH or (ii) reduction $NaBH_4$, MeOH can be performed; (c) If R' or R" contains an acid then coupling $HN(R^5R^5)$, HOBt, EDC, DMF can be performed;
(d) If R' or R" contains an appropriate activated alkene then Michael additions $HN(R^5R^5)$, DMF can be performed.

The (R)-enantiomer was prepared in the same manner outlined in Scheme 2 starting from (S)-5-hydroxy-5,6,7,8-tetrahydronaphthalene-1-carbonitrile.

Scheme 3:

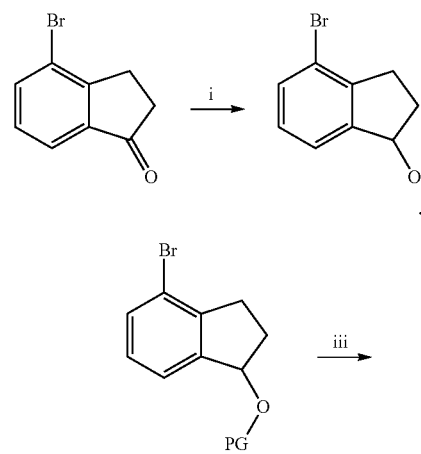

Reagents: (i) Sodium borohydride, ethanol, silica gel;
(ii) PG = protecting group e.g. TBDMS chloride, imidazole;
(iii) 4,4,4',4',5,5,5',5'-octamethyl-2,2'-bi(1,3,2-dioxaborolane), PdCl$_2$(dppf)•CH$_2$Cl$_2$, potassium acetate, dioxane.

Scheme 4:

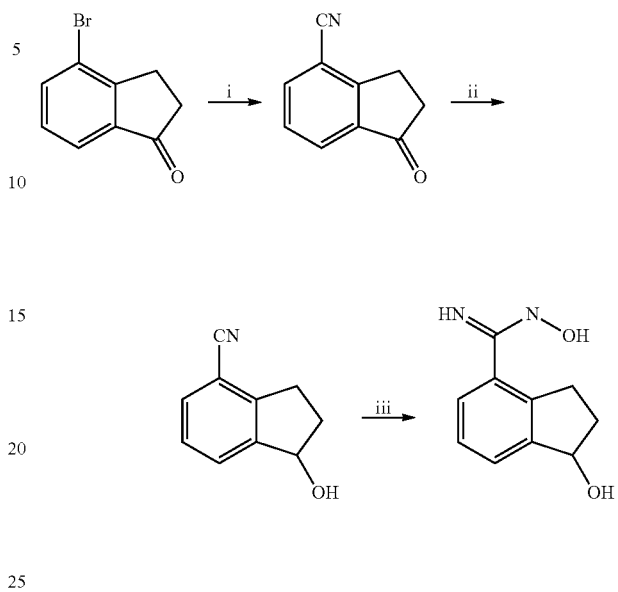

Reagents: (i) Zn(CN)$_2$, Pd(PPh$_3$)$_4$, NMP; (ii) For racemic material: Sodium borohydride, ethanol, silica gel; For (R)-indanol: (S)-(-)-2-methyl-CBS-oxazaborolidine, BH$_3$-DMS, toluene; For (S)-indanol: (R)-(+)-2-methyl-CBS-oxazaborolidine, BH$_3$-DMS, toluene;
(iii) NH$_2$OH*HCl, Na$_2$CO$_3$ or TEA, EtOH.

Scheme 5:

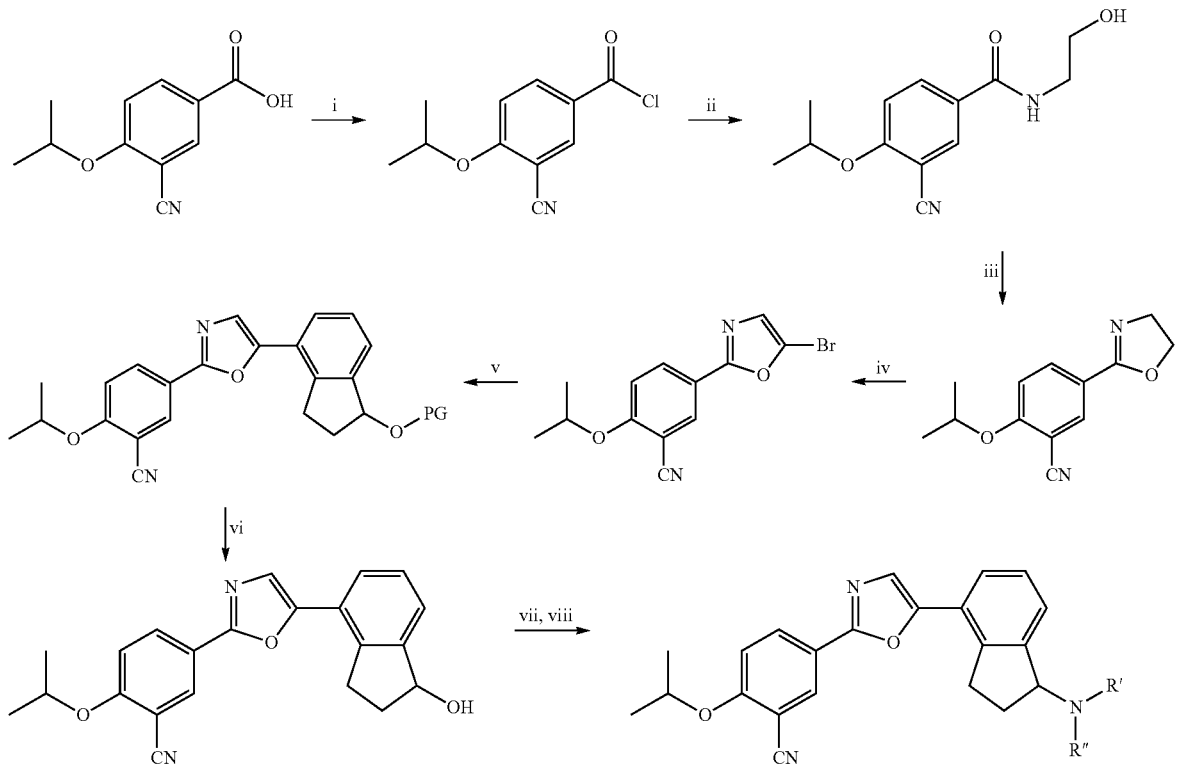

Reagents: (i) Oxalylchloride, DCM; (ii) Ethanolamine, Et$_3$N, DCM; (iii) SOCl$_2$, DCM, KOH, MeOH (iv) N-Bromosuccinimide, azoisobutyronitrile, DCM; (v) Protected (e.g. TBDMS) 4-(4,4,5,5-tetramethyl-1,3,2-dioxaborolan-2-yl)-2,3-dihydro-1H-inden-1-ol, K$_2$CO$_3$, Pd(PPh$_3$)$_4$, DME, H$_2$O; (vi) deprotection e.g. TBAF, THF; (vii) SOCl$_2$, DCM; (viii) R'—NH$_2$ or R"—NH$_2$, DIPEA, DMA.

Scheme 6:

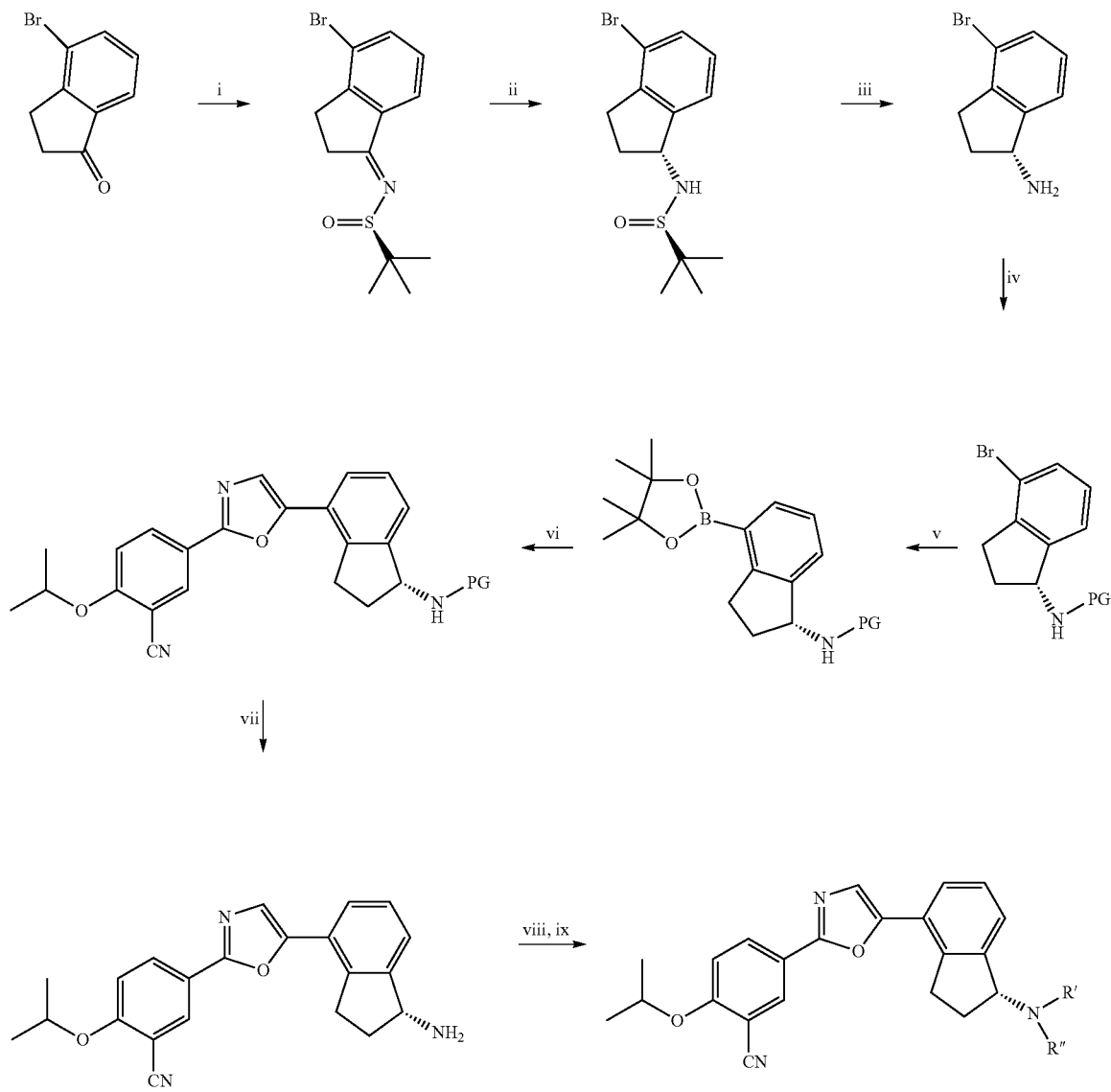

Reagents: (i) (R)-2-methylpropane-2-sulfinamide, Ti(OEt)$_4$, toluene; (ii) NaBH$_4$, THF; (iii) 4N HCl in dioxane, MeOH; (iv) Boc$_2$O, TEA, DCM; (v) 4,4,4′,4′,5,5,5′,5′-octamethyl-2,2′-bi(1,3,2-dioxaborolane), PdCl$_2$(dppf)·CH$_2$Cl$_2$, potassium acetate, dioxane; (vi) 5-(5-bromooxazol-2-yl)-2-isopropoxybenzonitrile, K$_2$CO$_3$, Pd(PPh$_3$)$_4$, DME, H$_2$O; (vii) 4N HCl in dioxane; (viii) (a) R′-LG or R″-LG, where LG represents a leaving group, K$_2$CO$_3$, CH$_3$CN; (b) R$^1$—CO$_2$H or R$^2$—CO$_2$H, HOBt, EDC, DMF or R$^1$—COCl or R$^2$—COCl, TEA, DCM; (c) R$^1$—SO$_2$Cl or R$^3$—SO$_2$Cl, TEA, DCM (d) R$^2$—CHO, HOAc, NaBH$_4$ or NaCNBH$_3$ or Na(OAc)$_3$BH, MeOH; (e) R$^1$—OCOCl or R$^2$—OCOCl, DIEA, DMF; (f) HN(R$^5$R$^5$), CDI, TEA, DCM; (g) H$_2$NSO$_2$NH$_2$, Δ, dioxane; (h) dimethyloxirane, Δ, EtOH; (ix) (a) If R′ or R″ = H, then reactions (viii)(a-d) can be performed; (b) If R′ or R″ contains an ester then (i) hydrolysis NaOH, EtOH or (ii) reduction NaBH$_4$, MeOH can be performed; (c) If R′ or R″ contains an acid then couplings HN(R$^5$R$^5$), HOBt, EDC, DMF can be performed; (d) If R′ or R″ contains an appropriate activated alkene then Micheal additions HN(R$^5$R$^5$), DMF can be performed.

The (S)-enantiomer can be prepared using (S)-2-methyl-propane-2-sulfinamide in step (i).
Scheme 7:
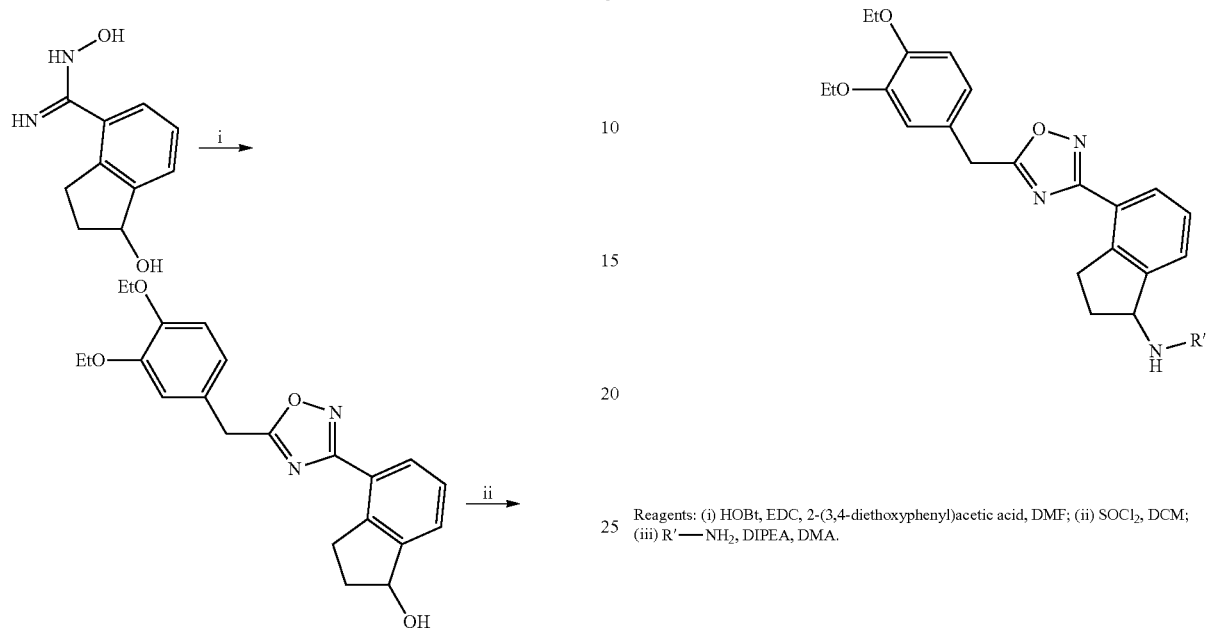
Reagents: (i) HOBt, EDC, 2-(3,4-diethoxyphenyl)acetic acid, DMF; (ii) SOCl₂, DCM; (iii) R'—NH₂, DIPEA, DMA.
Scheme 8:
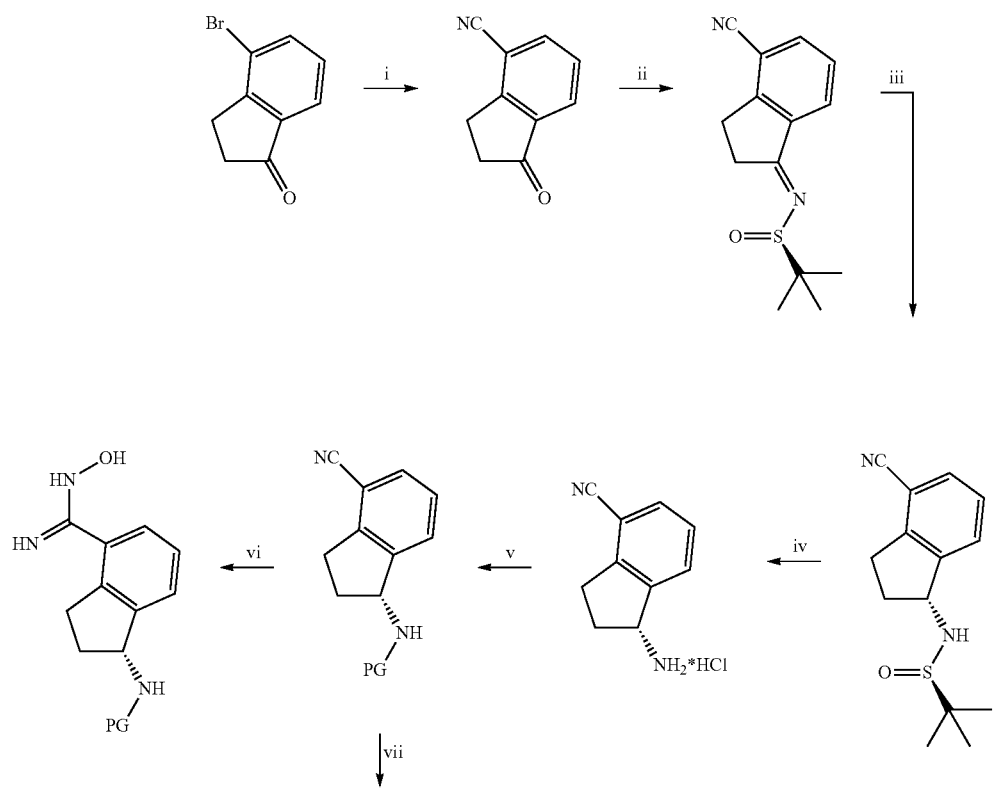

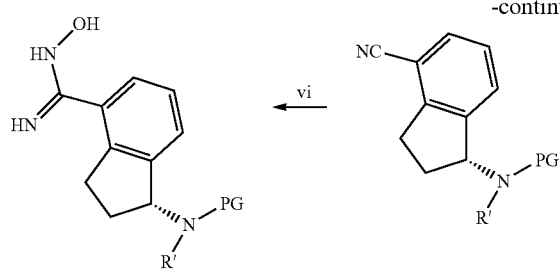

Reagents: (i) Zn(CN)$_2$, Pd(PPh$_3$)$_4$, NMP; (ii) (R)-2-methylpropane-2-sulfinamide, Ti(OEt)$_4$, toluene; (iii) NaBH$_4$, THF; (iv) 4M HCl in dioxane, MeOH; (v) PG = protecting group e.g. Boc$_2$O, TEA, DCM; (vi) NH$_2$OH*HCl, TEA, EtOH; (vii) R'-halide, NaH, DMF.

Scheme 9:

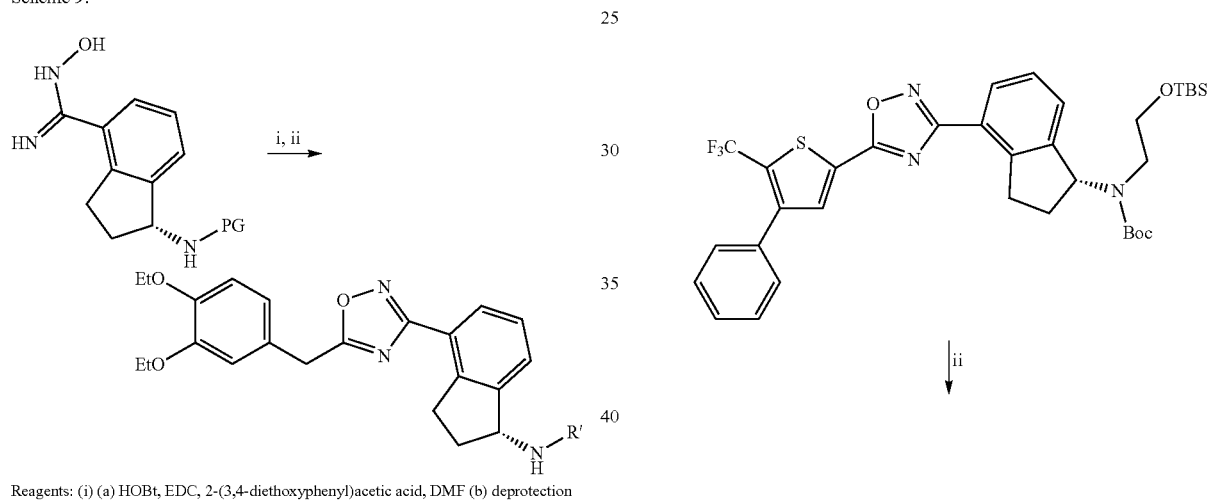

Reagents: (i) (a) HOBt, EDC, 2-(3,4-diethoxyphenyl)acetic acid, DMF (b) deprotection e.g. 4N HCl in dioxane; (ii) (a) R'—LG, where LG represents a leaving group, K$_2$CO$_3$, CH$_3$CN; (b) if R' contains an ester then (a) followed by NaOH, EtOH; (c) R'—CO$_2$H, HOBt, EDC, DMF or R'—COCl, TEA, DCM; (d) R'—SO$_2$Cl, TEA, DCM (e) R'—CHO, HOAc, NaBH$_4$ or NaCNBH$_3$ or Na(OAc)$_3$BH, MeOH.

The (S)-enantiomer can be prepared using protected (R)-1-amino-N-hydroxy-2,3-dihydro-1H-indene-4-carboximidamide in step (i).

Scheme 10:

Reagents: (i) HOBt, EDC, 4-phenyl-5-(trifluoromethyl)thiophene-2-carboxylic acid, DMF; (ii) 2N HCL in ether, DCM.

Scheme 11:
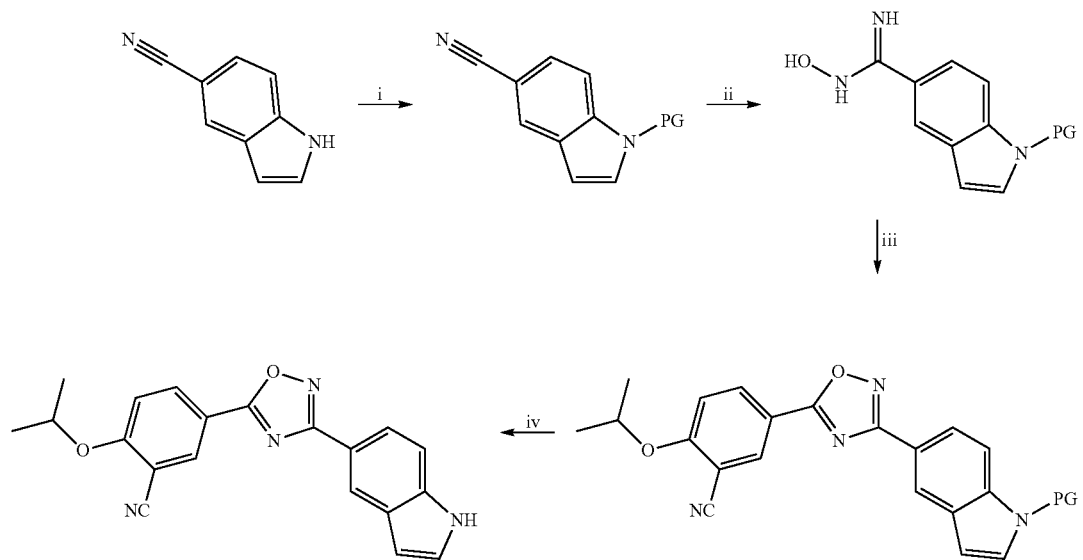
Reagents: (i) PG = protecting group e.g. Boc₂O, DMAP, ACN; (ii) NH₂OH*HCl, Na₂CO₃, EtOH; (iii) HOBt, EDC, benzoic acid, DMF; (iv) deprotection e.g. 4N HCl in dioxane.
Scheme 12:
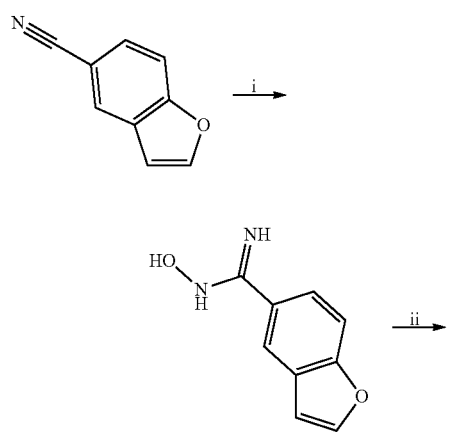
Reagents: (i) NH₂OH*HCl, Na₂CO₃, EtOH; (ii) HOBt, EDC, benzoic acid, DMF.
Scheme 13:
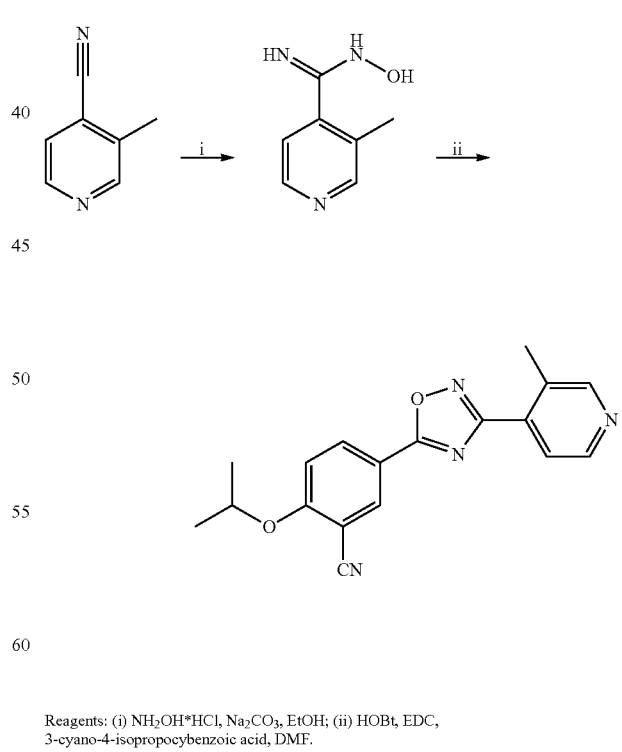
Reagents: (i) NH₂OH*HCl, Na₂CO₃, EtOH; (ii) HOBt, EDC, 3-cyano-4-isopropoxybenzoic acid, DMF.

Scheme 14:

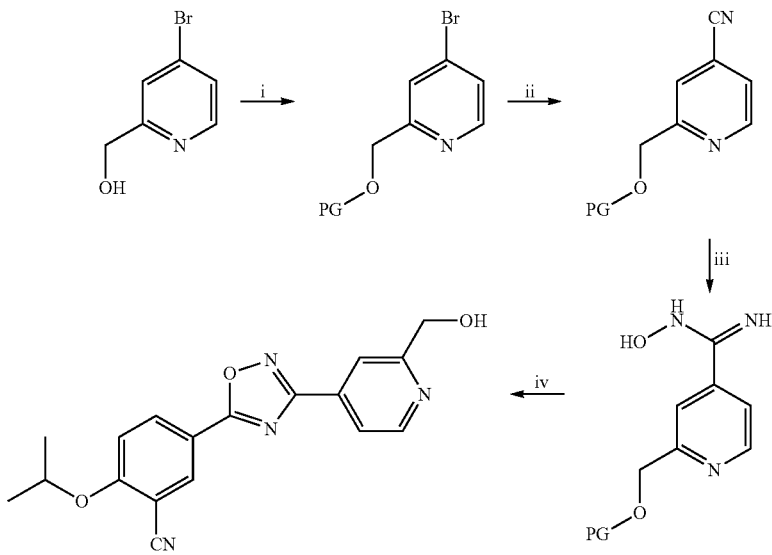

Reagents: (i) PG = protecting group e.g. tert-butylchlorodimethylsilane, TEA, DCM; (ii) Zn(CN)₂, Pd(PPh₃)₄, NMP; (iii) NH₂OH*HCl, Na₂CO₃, EtOH; (iv) HOBt, EDC, benzioc acid, DMF.

EXAMPLES

General Methods $^1$H NMR (400 MHz) and $^{13}$C NMR (100 MHz) were obtained in solution of deuteriochloroform (CDCl₃), deuteriomethanol (CD₃OD) or dimethyl sulfoxide—D₆ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100 A, 5µ (50×4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. Unless otherwise indicated, the LCMS data provided uses this method. For more hydrophobic compounds, the following gradient was used, denoted as Method 1: 40-95% over 0.5 min, hold at 95% for 8.5 min, with a flow rate of 1 mL/min. Final compounds were checked for purity using Method 2: 5% for 1 min, 5-95% over 9 min, then hold at 95% for 5 min, with a flow rate of 1 mL/min. Enantiomeric excess was determined by integration of peaks that were separated on a Chiralpak AD-H, 250×4.6 mm column at a flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column at a flow rate of 1 mL/min and an isocratic mobile phase. Chiral Method 2: Chiralcel OZ-3, 150×4.6 mm column at a flow rate of 0.75 ml/min and an isocratic mobile phase. The pyridine, dichloromethane (DCM), tetrahydrofuran (THF), and toluene used in the procedures were from Aldrich Sure-Seal bottles kept under nitrogen (N₂). All reactions were stirred magnetically and temperatures are external reaction temperatures. Chromatographies were carried out using a Combiflash Rf flash purification system (Teledyne Isco) equipped with Redisep (Teledyne Isco) silica gel (SiO₂) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Compounds with salt-able centers were presumed to be the trifluoroacetic acid (TFA) salt. Microwave heating was performed using a Biotage Initiator microwave reactor equipped with Biotage microwave vessels. The following abbreviations are used: ethyl acetate (EA), triethylamine (TEA), diethyl amine (DEA), diispropyl ethyl amine (DIEA), hydroxybenzotriazole (HOBt), 1-ethyl-3-(3-dimethylaminopropyl) carbodiimide hydrochloride (EDC), isopropanol (IPA), dimethylformamide (DMF), dimethyl acetamide (DMA). Norit is activated charcoal.

Experimental Procedures 5-oxo-5,6,7,8-tetrahydronaphthalene-1-carbonitrile (INT-1)

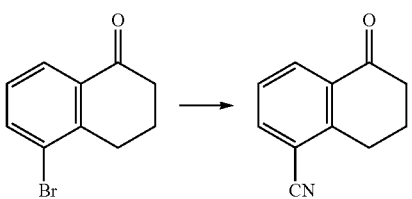 [SMILES: O=C1CCCc2c(Br)cccc21 ; N#Cc1cccc2c1CCCC2=O]

To a stirred solution of 5-bromo-3,4-dihydronaphthalen-1 (2H)-one (9.95 g, 44.2 mmol) in NMP (50 mL) was added Zn(CN)₂ (10.38 g, 88.4 mmol). The mixture was degassed twice by bubbling N₂ through the solution for 30 min then evacuated. Pd(Ph₃)₄ (0.5 g, 0.44 mmol) was added and the mixture was heated to 110° C. under N₂. After 5 h, the mixture was cooled to room temperature and poured onto ice (600 mL), using water (300 mL) to complete the transfer. After the ice had melted, the solution was filtered and the resulting solid was collected, suspended in DCM, and filtered again. The solid was collected, washed with water, and purified by column chromatography (EA/hex) to provide 6.9 g (91%) of 5-oxo-5,6,7,8-tetrahydronaphthalene-1-carbonitrile INT-1 as a white solid. LCMS-ESI (m/z) calculated for $C_{11}H_9NO$: 171.2; found 172.1 $[M+H]^+$, $t_R$=2.95 min. $^1$H NMR (400 MHz, CDCl$_3$) δ 8.26 (dd, J=7.9, 1.4 Hz, 1H), 7.82 (dd, J=7.6, 1.4 Hz, 1H), 7.44 (t, J=7.8 Hz, 1H), 3.20 (t, J=6.1 Hz, 2H), 2.72 (dd, J=7.2, 6.1 Hz, 2H), 2.30-2.17 (m, 2H). $^{13}$C NMR (101 MHz, CDCl$_3$) δ 196.22, 147.39, 137.18, 133.39, 131.59, 127.19, 116.93, 112.94, 38.48, 28.05, 22.28.

(R)-5-hydroxy-5,6,7,8-tetrahydronaphthakne-1-carbonitrile (INT-2)

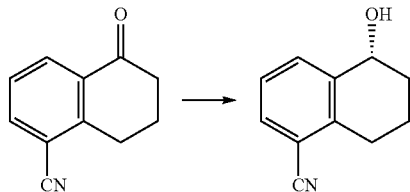 [SMILES: N#Cc1cccc2c1CCCC2=O ; N#Cc1cccc2c1CCC[C@H]2O]

To a stirred solution of 5-oxo-5,6,7,8-tetrahydronaphthalene-1-carbonitrile INT-1 (3.0 g, 17.5 mmol) in 5:1 HCO$_2$: NEt$_3$ (24 mL) was added RuCl(p-cymene)[(R,R)-Ts-DPEN] (0.13 g, 0.26 mmol). The mixture was stirred at 30° C. for 15 h then partitioned between EA and H$_2$O. The combined organic layers were dried over Na$_2$SO$_4$ and chromatographed (EA/hex) to provide 2.99 g (99%) of (R)-5-hydroxy-5,6,7,8-tetrahydronaphthalene-1-carbonitrile INT-2 as a white solid. LCMS-ESI (m/z) calculated for $C_{11}H_{11}NO$: 173.2; found 174.1 $[M+H]^+$, 156.1 $[M-NH_4]^+$, $t_R$=2.60 min. $^1$H NMR (400 MHz, CDCl$_3$) δ 7.71 (d, J=7.8 Hz, 1H), 7.54 (dt, J=8.7, 4.4 Hz, 1H), 7.34-7.26 (m, 1H), 4.85-4.71 (m, 2H), 3.48 (s, 1H), 3.13-2.96 (m, 1H), 2.90 (ddd, J=17.7, 7.8, 5.6 Hz, 1H), 2.15-1.95 (m, 2H), 1.97-1.76 (m, 2H). Chiral HPLC: (R)-5-hydroxy-5,6,7,8-tetrahydronaphthalene-1-carbonitrile was eluted with 5% IPA/hexane: 99.1% ee, $t_R$=15.3 min.

(S)-5-hydroxy-5,6,7,8-tetrahydronaphthalene-1-carbonitrile INT-3 was prepared in an analogous fashion using INT-1 and RuCl(p-cymene)[(S,S)-Ts-DPEN]. Chiral HPLC: 99.4% ee, $t_R$ for the (S)-enantiomer=17.99 min.

General Procedure 1. Preparation of Amide Oximes

To (R)- or (S)-cyanides (1 eq) in EtOH (0.56 M) was added hydroxylamine hydrochloride (3 eq) and either NaHCO$_3$ or TEA (3 eq) and the reaction mixture heated at 85° C. for 1-2 h. The organic soluble amide oximes were isolated by removal of the solvent and partitioning between water and DCM. The water soluble amide oximes were chromatographed or used directly in the cyclization. Pure amide oximes can be obtained by recrystallization from alcoholic solvents.

(R)-N,5-dihydroxy-5,6,7,8-tetrahydronaphthalene-1-carboximidamide (INT-4)

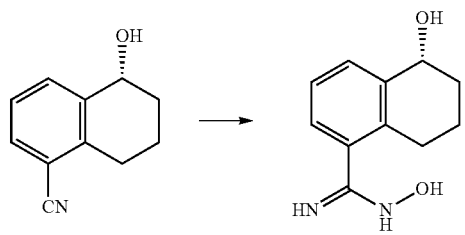 [SMILES: N#Cc1cccc2c1CCC[C@H]2O ; N=C(NO)c1cccc2c1CCC[C@H]2O]

Prepared using General Procedure 1. To a stirring solution of (R)-5-hydroxy-5,6,7,8-tetrahydronaphthalene-1-carbonitrile INT-2 (79.1 mg, 0.46 mmol) in EtOH (2 not) was added hydroxylamine hydrochloride (34.9 mg, 0.50 mmol) and sodium bicarbonate (42.2 mg, 0.50 mmol). The mixture was heated at 70° C. for 18 h. The product was purified by chromatography (MeOH/DCM) to provide 27.3 mg (29%) (R)-N,5-dihydroxy-5,6,7,8-tetrahydronaphthalene-1-carboximidamide INT-4 as a white solid. LCMS-ESI (m/z) calculated for $C_{11}H_{11}NO$: 173.2; found 174.1 $[M+H]^+$, 156.1 $[M-NH_4]^+$, $t_R$=2.60 min. (S)-N,5-dihydroxy-5,6,7,8-tetrahydronaphthalene-1-carboximidamide INT-5 was prepared in an analogous fashion from (S)-5-hydroxy-5,6,7,8-tetrahydronaphthalene-1-carbonitrile INT-3.

General Procedure 2. Cyclization to Oxadiazole Amines

A solution of the appropriate acid (1 eq), HOBt (1.3 eq), and EDC (1.3 eq) in DMF (0.08 M in acid) was stirred at room temperature under an atmosphere of N$_2$. After the complete formation of the HOBt-acid complex (1-3 h), the (R)- or (S)-amide oxime (1.1 eq) was added to the mixture. After complete formation of the coupled intermediate (ca. 0.5-2 h), the mixture was heated to 75-95° C. until the cyclization was complete (8-12 h). The reaction mixture was diluted with saturated NaHCO$_3$ and extracted with EA. The combined organic extracts were dried, concentrated, and could be purified by chromatography (EA/hexanes), preparative HPLC or recrystallization.

(R)-5-(3-(5-hydroxy-5,6,7,8-tetrahydronaphthalen-1-yl)-1,2,4-oxadiazol-5-yl)-2-isopropoxybenzonitrile (Compound 1)

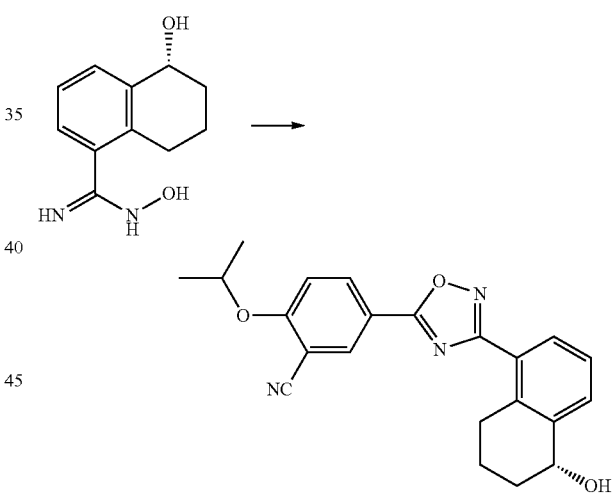

Prepared using General Procedure 2. To a stirring solution of 3-cyano-4-isopropoxybenzoic acid (16.7 mg, 0.08 mmol) in DMF (1 mL) were added HOBt (14.3 mg, 0.11 mmol) and EDCI (20.3 mg, 0.11 mmol). After stirring for 30 min, (R)-N,5-dihydroxy-5,6,7,8-tetrahydronaphthalene-1-carboximidamide INT-4 (27.3 mg, 0.09 mmol) was added as a solution in DMF (1.5 mL). After stirring at room temperature for an additional 60 min, the mixture was heated to 90° C. for 15 h. The mixture was diluted with EA and washed with NaHCO$_3$. The combined organic layers were dried, concentrated, chromatographed (EA/hexanes) to provide 12.72 mg (42.4%) (R)-5-(3-(5-hydroxy-5,6,7,8-tetrahydronaphthalen-1-yl)-1,2,4-oxadiazol-5-yl)-2-isopropoxybenzonitrile 1 as a white solid. LCMS-ESI (m/z) calculated for $C_{22}H_{21}N_3O_3$: 375.4; found 376.1 $[M+H]^+$, $t_R$=3.73 min. $^1$H NMR (400 MHz, CDCl$_3$) δ 8.42 (d, J=2.2 Hz, 1H), 8.33 (dd, J=8.9, 2.2 Hz, 1H), 7.97 (dd, J=7.7, 1.3 Hz, 1H), 7.66 (d, J=7.2 Hz, 1H), 7.38 (t, J=7.7 Hz, 1H), 7.12 (d, J=9.0 Hz, 1H), 4.91-4.83 (m, 1H), 4.79 (dq, J=12.0, 6.0 Hz, 1H), 3.20 (dt, J=17.8, 5.4 Hz, 1H), 3.01 (dt, J=13.3, 6.4 Hz, 1H), 2.13-1.81 (m, 4H), 1.79 (d, J=7.2 Hz, 1H), 1.47 (d, J=5.6 Hz, 6H). $^{13}$C NMR (101 MHz, CDCl$_3$) δ 172.70, 169.48, 162.75, 140.10, 137.4, 134.13, 133.88, 131.68, 129.96, 126.18, 125.97, 116.82, 115.26, 113.54, 103.95, 72.73, 68.47, 31.62, 28.50, 21.73, 18.57. Chiral HPLC: (R)-5-(3-(5-hydroxy-5,6,7,8-tetrahydronaphthalen-1-yl)-1,2,4-oxadiazol-5-yl)-2-isopropoxybenzonitrile was eluted with 10% IPA/hexane: 99.4% ee, $t_R$=40.85 min.

(S)-5-(3-(5-hydroxy-5,6,7,8-tetrahydronaphthalen-1-yl)-1,2,4-oxadiazol-5-yl)-2-isopropoxybenzonitrile 2 was prepared in an analogous fashion from (S)-5-hydroxy-5,6,7,8-tetrahydronaphthalene-1-carbonitrile INT-5. Chiral HPLC: 99.1% ee, $t_R$ for the (S)-enantiomer=38.19 min.

(S)-5-azido-5,6,7,8-tetrahydronaphthalene-1-carbonitrile (INT-6)

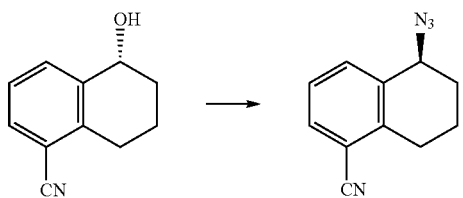 [SMILES: N#Cc1cccc2c1CCC[C@H]2O ; N#Cc1cccc2c1CCC[C@@H]2N=[N+]=[N-]]

A stirring solution of (R)-5-hydroxy-5,6,7,8-tetrahydronaphthalene-1-carbonitrile INT-2 (3.00 g, 17.32 mmol) in toluene (16 mL) under N$_2$, was cooled to 0° C. DPPA (9.53 g, 34.64 mmol) was added, followed by dropwise addition of DBU (3.16 mL, 20.78 mmol) over 20 min. The mixture was stirred at 0° C. for 4 h then slowly warmed to room temperature over 2 h and then concentrated. The resulting crude mixture was diluted with EA and washed with NaHCO$_3$. The combined organic layers were washed with brine, dried over Na$_2$SO$_4$, and chromatographed (EA/hexane) to provide 2.49 g (72.6%) of (S)-5-azido-5,6,7,8-tetrahydronaphthalene-1-carbonitrile INT-6 as a white solid. LCMS-ESI (m/z) calculated for C$_{11}$H$_{10}$N$_4$: 198.2; found 156.1 [M−N$_3$]$^+$, $t_R$=3.65 min. $^1$H NMR (400 MHz, CDCl$_3$) δ 7.60 (dd, J=7.6, 1.2 Hz, 1H), 7.56 (dd, J=7.8, 0.6 Hz, 1H), 7.33 (t, J=7.7 Hz, 1H), 4.59 (t, J=4.4 Hz, 1H), 3.08 (dt, J=18.0, 5.1 Hz, 1H), 2.99-2.83 (m, 1H), 2.15-1.96 (m, 3H), 2.00-1.81 (m, 1H). $^{13}$C NMR (101 MHz, DMSO) δ 141.05, 135.58, 133.47, 132.66, 126.58, 117.43, 113.21, 58.74, 28.28, 27.54, 18.27.

(R)-5-azido-5,6,7,8-tetrahydronaphthalene-1-carbonitrile INT-7 was prepared in an analogous fashion from (S)-5-hydroxy-5,6,7,8-tetrahydronaphthalene-1-carbonitrile INT-3.

(S)-tert-butyl (5-cyano-1,2,3,4-tetrahydronaphthalen-1-yl)carbamate (INT-8)

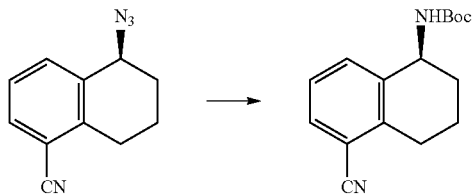 [SMILES: N#Cc1cccc2c1CCC[C@@H]2N=[N+]=[N-] ; CC(C)(C)OC(=O)N[C@H]1CCCc2c(C#N)cccc21]

To a stirring solution of (S)-5-azido-5,6,7,8-tetrahydronaphthalene-1-carbonitrile INT-6 (3.1 g, 15.63 mmol) in MeOH (50 mL) were added 10% Pd/C (500 mg), (Boc)$_2$O (6.83 g, 31.27 mmol) and Et$_3$N (3.16 g, 31.27 mmol). The reaction mixture was purged and flushed with H$_2$ (3×) and stirred under H$_2$. After 3 h the mixture was filtered through celite, rinsing with MeOH. The MeOH filtrate was concentrated, dissolved in EA and washed with NaHCO$_3$ and brine. The organic layer was dried (MgSO$_4$), concentrated and chromatographed (EA/hexanes). The resulting material was crystallized from hexanes to provide 3.45 g (81%) of (S)-tert-butyl (5-cyano-1,2,3,4-tetrahydronaphthalen-1-yl)carbamate INT-8 as a white solid. LCMS-ESI (m/z) calculated for C$_{16}$H$_{20}$N$_2$O$_2$: 272.34; found 156.1 [M−NH-Boc]$^+$, $t_R$=3.77 min. $^1$H NMR (400 MHz, CDCl$_3$) δ 7.60 (d, J=7.8 Hz, 1H), 7.53 (d, J=7.5 Hz, 1H), 7.31-7.20 (m, 1H), 4.86 (s, 1H), 4.75 (d, J=8.9 Hz, 1H), 3.06-2.85 (m, 2H), 2.07 (dt, J=11.3, 5.1 Hz, 1H), 1.91 (s, 2H), 1.86-1.71 (m, 1H), 1.48 (s, 9H). $^{13}$C NMR (101 MHz, CDCl$_3$) δ 155.38, 140.70, 139.12, 133.03, 131.63, 126.41, 117.62, 112.42, 79.62, 48.25, 29.75, 28.28, 27.77, 19.36. Chiral HPLC: (S)-tert-butyl (5-cyano-1,2,3,4-tetrahydronaphthalen-1-yl)carbamate was eluted with 2.5% EtOH/hexanes: 92.4% ee, $t_R$=14.22 min.

(R)-tert-butyl (5-cyano-1,2,3,4-tetrahydronaphthalen-1-yl)carbamate INT-9 was prepared in an analogous fashion from (R)-5-azido-5,6,7,8-tetrahydronaphthalene-1-carbonitrile INT-7. Chiral HPLC: 99.6% ee, $t_R$ for the (R)-enantiomer=11.60 min.

(S)-tert-butyl (5-(N-hydroxycarbamimidoyl)-1,2,3,4-tetrahydronaphthalen-1-yl)carbamate (INT-10)

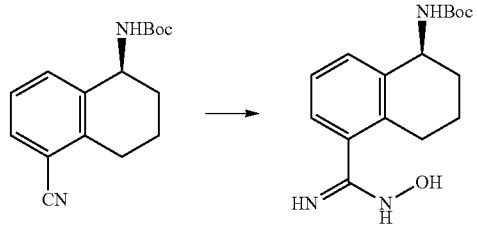 [SMILES: CC(C)(C)OC(=O)N[C@H]1CCCc2c(C#N)cccc21 ; CC(C)(C)OC(=O)N[C@H]1CCCc2c(C(=N)NO)cccc21]

Prepared using General Procedure 1. To a stirring solution of (S)-tert-butyl (5-cyano-1,2,3,4-tetrahydronaphthalen-1-yl)carbamate INT-8 (3.10 g, 11.38 mmol) in EtOH (25 mL) was added hydroxylamine hydrochloride (2.77 g, 39.84 mmol) and NEt$_3$ (3.17 mL, 22.77 mmol). After heating at 85° C. for 15 h, the mixture was concentrated, redissolved in DCM, and washed with NaHCO$_3$. The combined organic layers were dried, concentrated and chromatographed (MeOH/DCM) to provide 3.56 g crude (S)-tert-butyl (5-(N-hydroxycarbamimidoyl)-1,2,3,4-tetrahydronaphthalen-1-yl)carbamate INT-10 (58% product by UV area), which was used in the next reaction without further purification. LCMS-ESI (m/z) calculated for C$_{16}$H$_{23}$N$_3$O$_3$: 305.37; found 306.2 [M+H]$^+$, $t_R$=2.00 min.

(R)-tert-butyl (5-(N-hydroxycarbamimidoyl)-1,2,3,4-tetrahydronaphthalen-1-yl)carbamate INT-11 was prepared in an analogous fashion from (R)-tert-butyl (5-cyano-1,2,3,4-tetrahydronaphthalen-1-yl)carbamate INT-9.

(S)-tert-butyl (5-(5-(3-cyano-4-isopropoxyphenyl)-1,2,4-oxadiazol-3-yl)-1,2,3,4-tetrahydronaphthalen-1-yl)carbamate (INT-12)

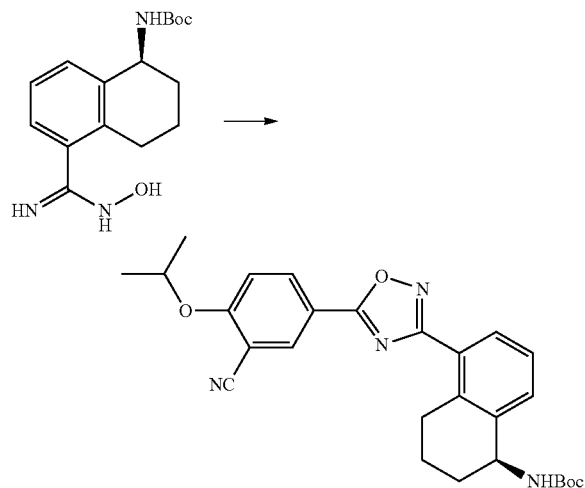

Prepared using General Procedure 2. To a stirring solution of 3-cyano-4-isopropoxybenzoic acid (556 mg, 2.72 mmol) in DMF (10 mL) was added HOBt (476.6 mg, 3.53 mmol) and EDCI (677.9 mg, 3.53 mmol). After stirring for 30 min, (S)-tert-butyl (5-(N-hydroxycarbamimidoyl)-1,2,3,4-tetrahydronaphthalen-1-yl)carbamate INT-10 (3.56 g crude, approximately 2.99 mmol) was added. After stirring at room temperature for an additional 90 min, the mixture was heated to 90° C. for 15 h. The mixture was diluted with EA and washed with NaHCO$_3$. The combined organic layers were dried, concentrated, and chromatographed (EA/hexanes) to provide 1.89 g (46%) (S)-tert-butyl (5-(5-(3-cyano-4-isopropoxyphenyl)-1,2,4-oxadiazol-3-yl)-1,2,3,4-tetrahydronaphthalen-1-yl)carbamate INT-12 as a white solid. LCMS-ESI (m/z) calculated for C$_{27}$H$_{30}$N$_4$O$_4$: 474.6; no M/Z observed, $t_R$=4.23 min. $^1$H NMR (400 MHz, CDCl$_3$) δ 8.42 (d, J=2.1 Hz, 1H), 8.33 (dd, J=8.9, 2.2 Hz, 1H), 7.92 (dd, J=7.7, 1.1 Hz, 1H), 7.56 (d, J=7.6 Hz, 1H), 7.32 (dd, J=20.3, 12.6 Hz, 1H), 7.12 (d, J=9.0 Hz, 1H), 4.94 (d, J=6.0 Hz, 1H), 4.88-4.72 (m, 1H), 3.23-3.08 (m, 1H), 3.07-2.94 (m, 1H), 2.06 (d, J=12.6 Hz, 1H), 1.97-1.78 (m, 3H), 1.53-1.43 (m, 15H). $^{13}$C NMR (101 MHz, CDCl$_3$) δ 172.64, 169.40, 162.69, 155.43, 138.65, 137.55, 134.04, 133.83, 131.68, 129.55, 126.08, 125.97, 116.74, 115.20, 113.53, 103.87, 79.44, 72.69, 48.97, 29.73, 28.40, 21.68, 19.71, 14.14.

(R)-tert-butyl (5-(5-(3-cyano-4-isopropoxyphenyl)-1,2,4-oxadiazol-3-yl-1,2,3,4-tetrahydronaphthalen-1-yl)carbamate INT-13 was prepared in an analogous fashion from (R)-tert-butyl (5-(N-hydroxycarbamimidoyl)-1,2,3,4-tetrahydronaphthalen-1-yl)carbamate INT-11.

(S)-5-(3-(5-amino-5,6,7,8-tetrahydronaphthalen-1-yl)-1,2,4-oxadiazol-5-yl)-2-isopropoxybenzonitrile (Compound 4)

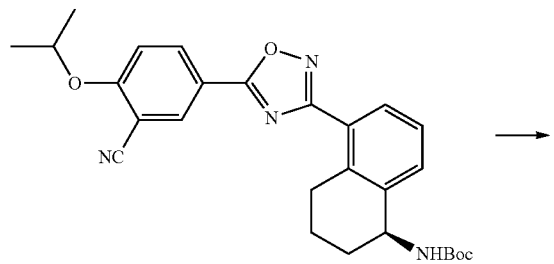

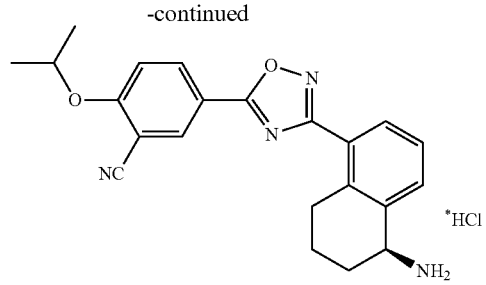

To a stirring solution of (S)-tert-butyl (5-(5-(3-cyano-4-isopropoxyphenyl)-1,2,4-oxadiazol-3-yl)-1,2,3,4-tetrahydronaphthalen-1-yl)carbamate INT-12 (0.90 g, 1.9 mmol) in dioxanes (10 mL) was added 4N HCl/dioxanes (2.5 mL). After stirring at 60° C. for 5.5 h, the mixture was concentrated to provide 0.8 g (100%) of the HCl salt of (S)-5-(3-(5-amino-5,6,7,8-tetrahydronaphthalen-1-yl)-1,2,4-oxadiazol-5-yl)-2-isopropoxybenzonitrile 4 as a white solid. An analytically pure sample was purified by preparative HPLC and the free amine was prepared by partitioning between NaHCO$_3$ and EA. LCMS-ESI (m/z) calculated for C$_{22}$H$_{22}$N$_4$O$_2$: 374.4; found 358.1 [M−NH$_2$]$^+$, $t_R$=2.45 min. NMR (400 MHz, DMSO) δ 8.63 (s, 2H), 8.50 (d, J=2.2 Hz, 1H), 8.39 (dd, J=9.0, 2.3 Hz, 1H), 7.95 (dd, J=7.7, 1.0 Hz, 1H), 7.85 (d, J=7.5 Hz, 1H), 7.56 (d, J=9.2 Hz, 1H), 7.49 (t, J=7.7 Hz, 1H), 4.98 (hept, J=6.0 Hz, 1H), 4.55 (t, J=5.3 Hz, 1H), 3.11 (dt, J=17.9, 5.5 Hz, 1H), 2.94 (dt, J=13.9, 6.1 Hz, 1H), 2.18-1.88 (m, 3H), 1.88-1.71 (m, 1H), 1.38 (d, J=6.0 Hz, 6H). $^{13}$C NMR (101 MHz, DMSO) δ 172.91, 168.60, 162.52, 137.73, 134.60, 134.09, 133.80, 132.08, 130.30, 126.29, 126.06, 115.92, 115.24, 114.93, 102.49, 72.54, 66.34, 48.02, 27.57, 26.54, 21.47, 17.68. Chiral HPLC: (S)-5-(3-(5-amino-5,6,7,8-tetrahydronaphthalen-1-yl)-1,2,4-oxadiazol-5-yl)-2-isopropoxybenzonitrile was eluted with 8% EtOH/hexanes, with 0.3% DEA (Chiral Method 1): 94.2% ee, $t_R$=42.7 min.

(R)-5-(3-(5-amino-5,6,7,8-tetrahydronaphthalen-1-yl)-1,2,4-oxadiazol-5-yl)-2-isopropoxybenzonitrile 3 was prepared in an analogous fashion from (R)-tert-butyl (5-(5-(3-cyano-4-isopropoxyphenyl)-1,2,4-oxadiazol-3-yl)-1,2,3,4-tetrahydronaphthalen-1-yl)carbamate INT-13. Chiral HPLC (Chiral Method 1): 99.9% ee, $t_R$ for the (R)-enantiomer=39.72 min.

General Procedure 3. Preparation of Tetrahydronaphthalene Ureas

To a stirring solution of CDI (1.2 eq) in DCM (0.16M) were added either the solution of (R)- or (S)-tetrahydronapthalene amine (1 eq) and Et$_3$N (3 eq) in DCM (0.01M). After stirring for 15 h, this solution was added to a second solution containing the appropriate amine (3 eq) and Et$_3$N (3 eq) in DCM (0.4M), at room temperature. The resulting mixture was stirred at room temperature for 4 h until all of starting material was consumed. The solvent was evaporated and the pure product isolated after preparative HPLC.

Compounds 5-20 were prepared using General Procedure 3.

(S)-N-(5-(5-(3-cyano-4-isopropoxyphenyl)-1,2,4-oxadiazol-3-yl)-1,2,3,4-tetrahydronaphthalen-1-yl)-3-hydroxyazetidine-1-carboxamide (Compound 8)

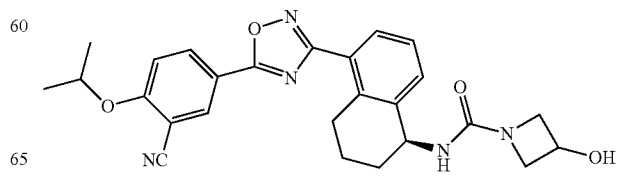

Prepared using General Procedure 3: LCMS-ESI (m/z) calculated for $C_{26}H_{27}N_5O_4$: 473.5; found 474.2 [M+H]$^+$, $t_R$=3.21 min. $^1$H NMR (400 MHz, CDCl$_3$) δ 8.41 (d, J=2.2 Hz, 1H), 8.33 (dd, J=8.9, 2.2 Hz, 1H), 7.91 (dd, J=7.7, 1.2 Hz, 1H), 7.53 (t, J=6.1 Hz, 1H), 7.32 (dd, J=20.1, 12.4 Hz, 1H), 7.12 (d, J=9.0 Hz, 1H), 5.13 (d, J=8.0 Hz, 1H), 4.79 (dt, J=12.2, 6.1 Hz, 1H), 4.68 (tt, J=6.7, 4.4 Hz, 1H), 4.35 (d, J=8.7 Hz, 1H), 4.25-4.14 (m, 2H), 3.85 (dd, J=8.8, 4.1 Hz, 2H), 3.14 (t, J=12.1 Hz, 1H), 3.10-2.92 (m, 1H), 2.16-1.96 (m, 1H), 1.99-1.64 (m, 4H), 1.48 (d, J=6.1 Hz, 6H). Chiral HPLC: (S)-N-(5-(5-(3-cyano-4-isopropoxyphenyl)-1,2,4-oxadiazol-3-yl)-1,2,3,4-tetrahydronaphthalen-1-yl)-3-hydroxyazetidine-1-carboxamide was eluted with 15% water/MeOH, (Chiral Method 2): 91.4% ee, $t_R$=15.52 min.

(R)-N-(5-(5-(3-cyano-4-isopropoxyphenyl)-1,2,4-oxadiazol-3-yl)-1,2,3,4-tetrahydronaphthalen-1-yl)-3-hydroxyazetidine-1-carboxamide 7 was prepared in an analogous fashion. Chiral HPLC: 99.94% ee, $t_R$=17.17 min (Chiral Method 2).

(S)-N-(5-(5-(3-cyano-4-isopropoxyphenyl)-1,2,4-oxadiazol-3-yl)-1,2,3,4-tetrahydronaphthalen-1-yl) pyrrolidine-1-carboxamide (Compound 12)

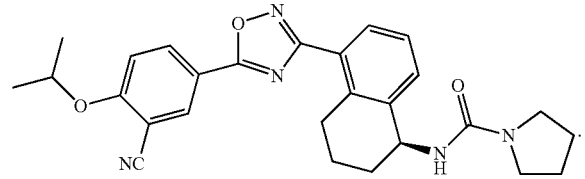 [SMILES: CC(C)Oc1ccc(-c2nc(-c3cccc4c3CCC[C@@H]4NC(=O)N3CCCC3)no2)cc1C#N]

Prepared using General Procedure 3: LCMS-ESI (m/z) calculated for $C_{27}H_{29}N_5O_3$: 471.55; found 472.2 [M+H]$^+$, $t_R$=3.78 min. $^1$H NMR (400 MHz, CDCl$_3$) δ 8.41 (d, J=2.1 Hz, 1H), 8.32 (dd, J=8.9, 2.2 Hz, 1H), 7.90 (dd, J=7.6, 1.1 Hz, 1H), 7.59 (d, J=7.6 Hz, 1H), 7.33 (t, J=7.7 Hz, 1H), 7.12 (d, J=9.0 Hz, 1H), 5.25-5.12 (m, 1H), 4.79 (hept, J=6.0 Hz, 1H), 4.45 (t, J=21.8 Hz, 1H), 3.36 (t, J=6.4 Hz, 4H), 3.23-3.09 (m, 1H), 3.02 (dt, J=18.0, 6.0 Hz, 1H), 2.16-1.99 (m, 1H), 2.01-1.79 (m, 7H), 1.47 (d, J=6.1 Hz, 6H).

(S)-N-(5-(5-(3-cyano-4-isopropoxyphenyl)-1,2,4-oxadiazol-3-A-1,2,3,4-tetrahydronaphthalen-1-yl) morpholine-4-carboxamide (Compound 15)

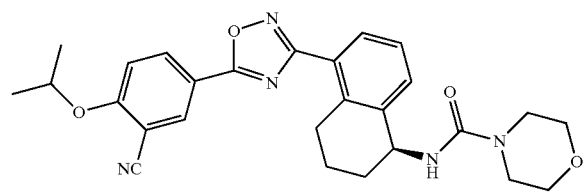 [SMILES: CC(C)Oc1ccc(-c2nc(-c3cccc4c3CCC[C@@H]4NC(=O)N3CCOCC3)no2)cc1C#N]

Prepared using General Procedure 3: LCMS-ESI (m/z) calculated for $C_{27}H_{29}N_5O_4$: 487.5; found 488.2 [M+H]$^+$, $t_R$=3.58 min. $^1$H NMR (400 MHz, CDCl$_3$) δ 8.40 (d, J=2.2 Hz, 1H), 8.32 (dd, J=8.9, 2.2 Hz, 1H), 7.91 (dd, J=7.7, 1.1 Hz, 1H), 7.55 (t, J=10.0 Hz, 1H), 7.33 (t, J=7.7 Hz, 1H), 7.12 (d, J=9.0 Hz, 1H), 5.19 (dd, J=12.9, 5.3 Hz, 1H), 4.86-4.75 (m, 1H), 4.72 (d, J=8.1 Hz, 1H), 3.76-3.63 (m, 4H), 3.36 (dd, J=11.6, 7.1 Hz, 4H), 3.16 (dt, J=16.7, 5.4 Hz, 1H), 3.02 (dt, J=12.6, 5.9 Hz, 1H), 2.14-1.98 (m, 2H), 1.94-1.81 (m, 2H), 1.47 (d, J=6.1 Hz, 6H).

(R)-N-((R)-5-(5-(3-cyano-4-isopropoxyphenyl)-1,2,4-oxadiazol-3-yl)-1,2,3,4-tetrahydronaphthalen-1-yl)-3-(dimethylamino)pyrrolidine-1-carboxamide (Compound 20)

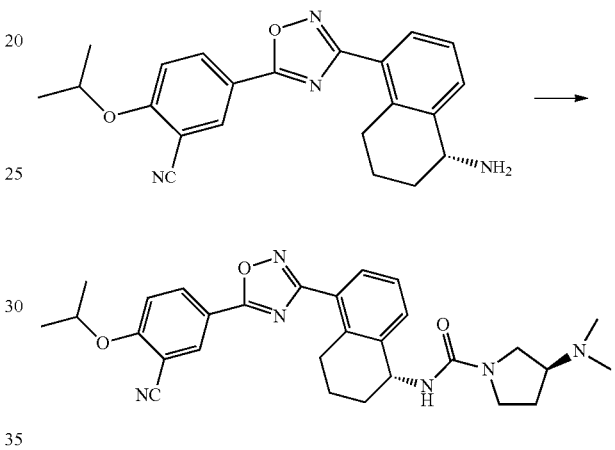

Prepared using General Procedure 3: To a stirring solution of CDI ((9.5 mg, 0.06 mmol) in DCM (1 mL) were added dropwise a solution of (R)-5-(3-(5-amino-5,6,7,8-tetrahydronaphthalen-1-yl)-1,2,4-oxadiazol-5-yl)-2-isopropoxybenzonitrile HCl salt 3 (20 mg, 0.05 mmol) and Et$_3$N (20.3 µL, 0.15 mmol) in DCM (1 mL). After stirring for 15 h at room temperature, this solution was added dropwise to another solution containing (R)-3-dimethylaminopyrrolidine (18.6 mg, 0.15 mmol)) in DCM (1 mL) at room temperature. The reaction was stirred at room temperature for 6.5 h. The solvent was evaporated and the pure product was isolated by preparative HPLC to afford 17.5 mg (70%) of (R)-N-((R)-5-(5-(3-cyano-4-isopropoxyphenyl)-1,2,4-oxadiazol-3-yl)-1,2,3,4-tetrahydronaphthalen-1-yl)-3-(dimethylamino)pyrrolidine-1-carboxamide 20. LCMS-ESI (m/z) calculated for $C_{29}H_{34}N_6O_3$: 514.6; found 515.3 [M+H]$^+$, $t_R$=2.56 min. $^1$H NMR (400 MHz, CDCl$_3$) δ 8.39 (d, J=2.2 Hz, 1H), 8.31 (dt, J=8.7, 4.3 Hz, 1H), 7.91 (d, J=7.6 Hz, 1H), 7.52 (d, J=7.6 Hz, EH), 7.34 (t, J=7.7 Hz, 1H), 7.12 (d, J=9.2 Hz, 1H), 5.13 (d, J=6.9 Hz, 1H), 4.86-4.73 (m, 1H), 4.64 (d, J=8.2 Hz, 1H), 3.91 (dd, J=10.4, 7.3 Hz, 1H), 3.80-3.56 (m, 3H), 3.41 (dd, J=17.5, 8.3 Hz, 1H), 3.15 (d, J=18.0 Hz, 1H), 3.10-2.93 (m, 1H), 2.85 (s, 6H), 2.46 (m, 2H), 2.05 (dd, J=9.2, 4.8 Hz, 1H), 1.88 (m, 3H), 1.45 (dd, J=13.9, 6.1 Hz, 6H).

General Procedure 4. Preparation of Tetrahydronapthalene Amides Via Acid Chlorides To a stirring solution of (R)- or (S)-tetrahydronapthalene amine HCl (1 eq) in DCM were added an acid chloride (2 eq) and NEt$_3$ (2 eq). The reaction was stirred at room temperature for 1 h. The solvent was evaporated and mixture was purified by preparative HPLC.

Compounds 21-25 were prepared using General Procedure 4.

63

(R)-N-(5-(5-(3-cyano-4-isopropoxyphenyl)-1,2,4-oxadiazol-3-yl)-1,2,3,4-tetrahydronaphthalen-1-yl)acetamide (Compound 21)

64

(R)-N-(5-(5-(3-cyano-4-isopropoxyphenyl)-1,2,4-oxadiazol-3-yl)-1,2,3,4-tetrahydronaphthalen-1-yl)sulfamide (Compound 26)

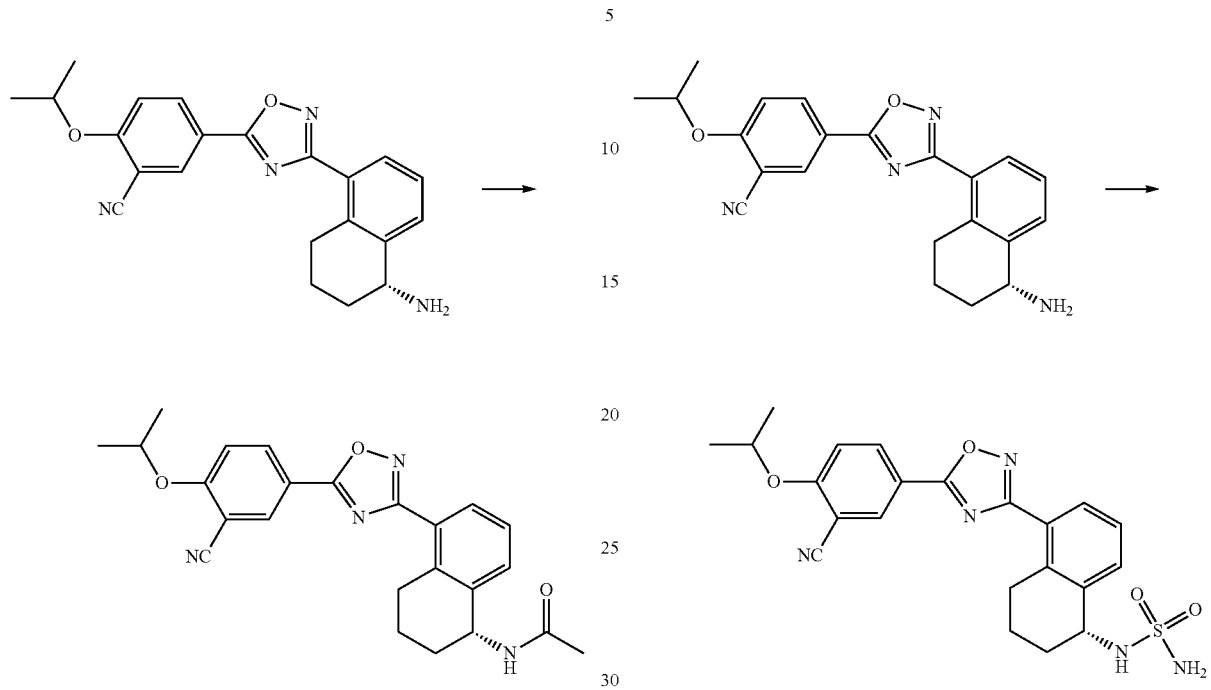

Prepared using General Procedure 4: To a stirring solution of (R)-5-(3-(5-amino-5,6,7,8-tetrahydronaphthalen-1-yl)-1,2,4-oxadiazol-5-yl)-2-isopropoxybenzonitrile HCl 3 (20 mg, 0.05 mmol) in DCM (0.5 mL) were added acetyl chloride (7 μL, 0.10 mmol) and NEt$_3$ (14 μL, 0.10 mmol). After stirring for 1 h, the solvent was evaporated and the residue was purified by preparative HPLC to provide 11.3 mg (56%) of (R)-N-(5-(5-(3-cyano-4-isopropoxyphenyl)-1,2,4-oxadiazol-3-yl)-1,2,3,4-tetrahydronaphthalen-1-yl)acetamide 21. LCMS-ESI (m/z) calculated for $C_{24}H_{24}N_4O_3$: 416.5; found 417.2 [M+H]$^+$, $t_R$=3.56 min. $^1$H NMR (400 MHz, CDCl$_3$) δ 8.40 (d, J=2.2 Hz, 1H), 8.32 (dd, J=8.9, 2.2 Hz, 1H), 7.92 (dd, J=7.7, 1.2 Hz, 1H), 7.48 (d, J=7.6 Hz, 1H), 7.33 (t, J=7.7 Hz, 1H), 7.12 (d, J=9.0 Hz, 1H), 5.83 (d, J=8.6 Hz, 1H), 5.36-5.21 (m, 1H), 4.79 (hept, J=6.0 Hz, 1H), 3.16 (dt, J=17.9, 6.0 Hz, 1H), 3.03 (dt, J=18.2, 6.3 Hz, 1H), 2.10-1.99 (m, 4H), 1.97-1.79 (m, 3H), 1.47 (d, J=6.1 Hz, 6H).

(S)-N-(5-(5-(3-cyano-4-isopropoxyphenyl)-1,2,4-oxadiazol-3-yl)-1,2,3,4-tetrahydronaphthalen-1-yl)acetamide 22 was prepared in an analogous fashion from (S)-5-(3-(5-amino-5,6,7,8-tetrahydronaphthalen-1-yl)-1,2,4-oxadiazol-5-yl)-2-isopropoxybenzonitrile HCl 4.

General Procedure 5. Preparation of Tetrahydronapthalene Sulfamides

To a solution of (R)- or (S)-tetrahydronapthalene amine HCl (1 eq) in dioxane were added sulfamide (5 eq) and DIEA (3 eq). The reaction was stirred at 110° C. for 18 h. The solvent was evaporated and mixture was purified by preparative HPLC.

Compounds 26 and 27 were prepared using General Procedure 5.

Prepared using General Procedure 5: To a stirring solution of (R)-5-(3-(5-amino-5,6,7,8-tetrahydronaphthalen-1-yl)-1,2,4-oxadiazol-5-yl)-2-isopropoxybenzonitrile HCl 3 (50 mg, 0.12 mmol) in dioxane (3 mL) were added sulfamide (58 mg, 0.61 mmol) and DIEA (47.2 μL, 0.37 mmol) and the mixture was heated to 110° C. for 14 h. The solvent was evaporated and the residue was purified by preparative HPLC to provide 22.8 mg (42%) of (R)-N-(5-(5-(3-cyano-4-isopropoxyphenyl)-1,2,4-oxadiazol-3-yl)-1,2,3,4-tetrahydronaphthalen-1-yl)sulfamide 26. LCMS-ESI (m/z) calculated for $C_{22}H_{23}N_5O_4S$: 453.5; found 454.1 [M+H]$^+$, $t_R$=3.47 min. $^1$H NMR (400 MHz, CDCl$_3$) δ 8.41 (d, J=2.2 Hz, 1H), 8.33 (dd, J=8.9, 2.2 Hz, 1H), 7.97 (dd, J=7.7, 1.2 Hz, 1H), 7.72 (d, J=7.7 Hz, 1H), 7.38 (t, J=7.8 Hz, 1H), 7.12 (d, J=9.0 Hz, 1H), 4.78 (ddd, J=13.4, 11.7, 5.7 Hz, 2H), 4.59 (d, J=19.8 Hz, 2H), 4.55 (d, J=8.2 Hz, 1H), 3.19 (dt, J=18.0, 5.6 Hz, 1H), 3.02 (dt, J=18.2, 7.2 Hz, 1H), 2.23-2.03 (m, 2H), 1.92 (dt, J=12.4, 6.3 Hz, 2H), 1.48 (d, J=6.1 Hz, 6H).

(S)-N-(5-(5-(3-cyano-4-isopropoxyphenyl)-1,2,4-oxadiazol-3-yl)-1,2,3,4-tetrahydronaphthalen-1-yl)sulfamide 27 was prepared in an analogous fashion from (S)-5-(3-(5-amino-5,6,7,8-tetrahydronaphthalen-1-yl)-1,2,4-oxadiazol-5-yl)-2-isopropoxybenzonitrile HCl 4.

General Procedure 6. Preparation of Tetrahydronaphthalene Sulfonamides Via Sulfonyl Chlorides To a solution of (R)- or (S)-tetrahydronapthalene amine HCl (1 eq) in DCM (0.05M) was added TEA (2 eq) and the appropriate sulfonyl chloride (1-2 eq.) at room temperature. The reaction mixture was stirred at room temperature for 18 h. The solvent was evaporated and the product isolated after preparative HPLC purification.

Compounds 28-33 were prepared using General Procedure 6.

65

(R)-N-(5-(5-(3-cyano-4-isopropoxyphenyl)-1,2,4-oxadiazol-3-yl)-1,2,3,4-tetrahydronaphthalen-1-yl)methanesulfonamide (Compound 28)

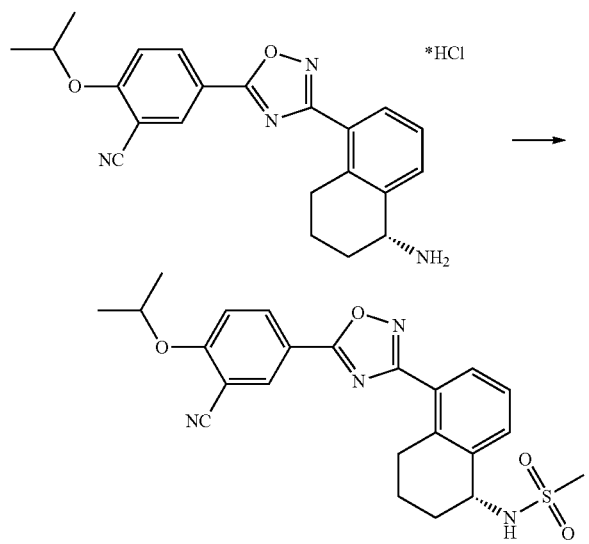

Prepared using General Procedure 6: To a stirring solution of (R)-5-(3-(5-amino-5,6,7,8-tetrahydronaphthalen-1-yl)-1,2,4-oxadiazol-5-yl)-2-isopropoxybenzonitrile hydrochloride 3 (20 mg, 0.05 mmol) in DCM (1 mL) at 0° C. was added TEA (20 µL, 0.15 mmol) and methanesulfonyl chloride (4.5 µL, 0.06 mmol). The mixture was allowed to warm to room temperature over 2 h. The solvent was evaporated and crude mixture was purified by preparative HPLC to afford 12.8 mg (58%) of (R)-N-(5-(5-(3-cyano-4-isopropoxyphenyl)-1,2,4-oxadiazol-3-yl)-1,2,3,4-tetrahydronaphthalen-1-yl)methanesulfonamide 28. LCMS-ESI (m/z) calculated for $C_{23}H_{24}N_4O_4S$: 452.5; found 453.1 [M+H]$^+$, $t_R$=3.68 min. $^1$H NMR (400 MHz, CDCl$_3$) δ 8.40 (t, J=3.5 Hz, 1H), 8.32 (dd, J=8.9, 2.2 Hz, 1H), 7.96 (dd, J=7.7, 1.1 Hz, 1H), 7.67 (d, J=7.7 Hz, 1H), 7.38 (t, J=7.7 Hz, 1H), 7.16-7.07 (m, 1H), 4.88-4.70 (m, 1H), 4.54 (d, J=8.4 Hz, 1H), 3.19 (dt, J=18.0, 5.9 Hz, 1H), 3.10 (d, J=5.0 Hz, 3H), 3.09-2.95 (m, 1H), 2.14 (qt, J=14.5, 7.3 Hz, 1H), 2.06-1.83 (m, 3H), 1.47 (t, J=5.5 Hz, 6H).

(S)-N-(5-(5-(3-cyano-4-isopropoxyphenyl)-1,2,4-oxadiazol-3-yl)-1,2,3,4-tetrahydronaphthalen-1-yl)methanesulfonamide 29 was prepared in an analogous fashion from (S)-5-(3-(5-amino-5,6,7,8-tetrahydronaphthalen-1-yl)-1,2,4-oxadiazol-5-yl)-2-isopropoxybenzonitrile hydrochloride 4.

(S)-N-(5-(5-(3-cyano-4-isopropoxyphenyl)-1,2,4-oxadiazol-3-yl)-1,2,3,4-tetrahydronaphthalen-1-A-2-methoxyethanesulfonamide (Compound 31)

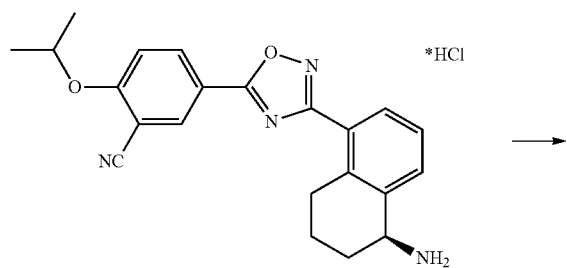

66

-continued

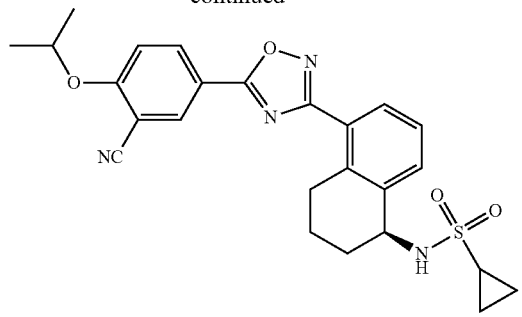

Prepared via General Procedure 6 using cyclopropanesulfonyl chloride. LCMS-ESI (m/z) calculated for $C_{25}H_{26}N_4O_4S$: 478.6; found 479.1 [M+H]$^+$, $t_R$=3.84 min.

(R)-N-(5-(5-(3-cyano-4-isopropoxyphenyl)-1,2,4-oxadiazol-3-yl)-1,2,3,4-tetrahydronaphthalen-1-yl)-2-methoxyethanesulfonamide (Compound 32)

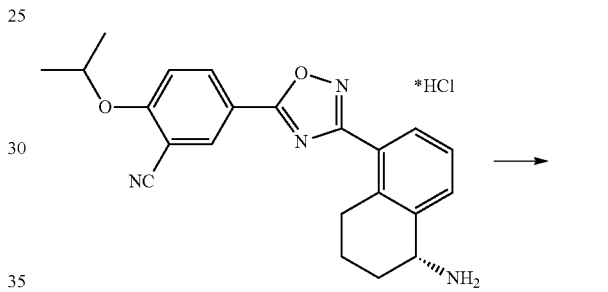

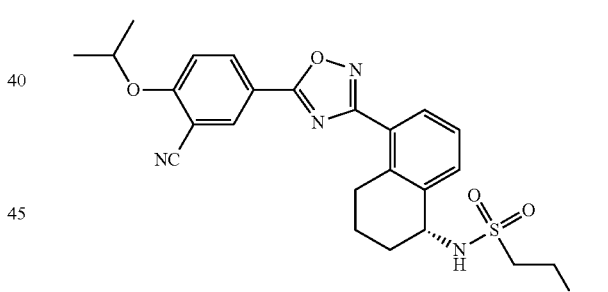

Prepared via General Procedure 6 using 2-methoxyethanesulfonyl chloride. LCMS-ESI (m/z) calculated for $C_{25}H_{28}N_4O_5S$: 496.58; found 519.1 [M+Na]$^+$, $t_R$=3.83 min. $^1$H NMR (400 MHz, CDCl$_3$) δ 8.41 (d, J=2.2 Hz, 1H), 8.33 (dd, J=8.9, 2.2 Hz, 1H), 7.99-7.92 (m, 1H), 7.74 (d, J=7.6 Hz, 1H), 7.37 (t, J=7.7 Hz, 1H), 7.12 (d, J=9.0 Hz, 1H), 4.85-4.71 (m, 2H), 4.68-4.60 (m, 1H), 3.93-3.76 (m, 2H), 3.47-3.31 (m, 5H), 3.17 (dt, J=18.0, 6.0 Hz, 1H), 3.02 (dt, J=18.1, 6.7 Hz, 1H), 2.20-1.82 (m, 4H), 1.48 (d, J=6.1 Hz, 6H). Chiral HPLC: (R)-N-(5-(5-(3-cyano-4-isopropoxyphenyl)-1,2,4-oxadiazol-3-yl)-1,2,3,4-tetrahydronaphthalen-1-yl)-2-methoxyethanesulfonamide 32 was eluted with 10% water/MeOH, (Chiral Method 2): 99.98% ee, $t_R$=21.07 min.

(S)-N-(5-(5-(3-cyano-4-isopropoxyphenyl)-1,2,4-oxadiazol-3-yl)-1,2,3,4-tetrahydro naphthalen-1-yl)-2-methoxyethanesulfonamide 33 was prepared in an analogous fashion from 4. Chiral HPLC: 99.04% ee, $t_R$=18.57 min (Chiral Method 2).

(R)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate (INT-14)

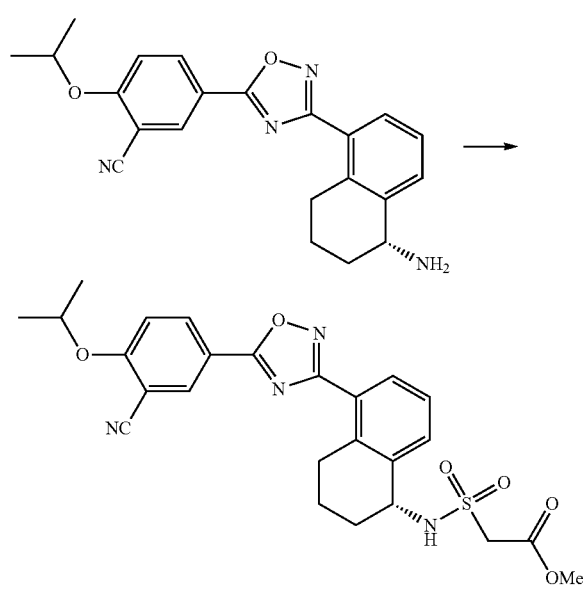

Prepared using General Procedure 6: To a stirring solution of (R)-5-(3-(5-amino-5,6,7,8-tetrahydronaphthalen-1-yl)-1,2,4-oxadiazol-5-yl)-2-isopropoxybenzonitrile hydrochloride 3 (0.15 g, 0.37 mmol) in DCM (5 mL) were added TEA (76 μL, 0.55 mmol) and methyl-2-(chlorosulfonyl)acetate (76 mg, 0.44 mmol). Additional TEA and methyl-2-(chlorosulfonyl)acetate were added to drive the reaction to completion over 24 h. The crude reaction mixture was partitioned between DCM and saturated NaHCO$_3$. The organic layer was dried over Na$_2$SO$_4$, concentrated, and purified by column chromatography (EA/hexanes) to give 0.11 g (57%) of (R)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-14. LCMS-ESI (m/z) calculated for C$_{25}$H$_{26}$N$_4$O$_6$S: 510.6; found 511.1 [M+H]$^+$, $t_R$=3.73 min. $^1$H NMR (400 MHz, CDCl$_3$) δ 8.42 (d, J=2.2 Hz, 1H), 8.33 (dd, J=8.9, 2.2 Hz, 1H), 8.01-7.93 (m, 1H), 7.74 (d, J=7.8 Hz, 1H), 7.39 (t, J=7.8 Hz, 1H), 7.12 (d, J=9.0 Hz, 1H), 5.00 (d, J=8.4 Hz, 1H), 4.81 (dq, J=18.3, 5.9 Hz, 2H), 4.25-4.00 (m, 2H), 3.83 (s, 3H), 3.20 (dt, J=18.1, 5.9 Hz, 1H), 3.12-2.97 (m, 1H), 2.22-2.01 (m, 2H), 2.02-1.83 (m, 2H), 1.48 (d, J=6.1 Hz, 6H).

(S)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-15 was prepared in an analogous fashion from (S)-5-(3-(5-amino-5,6,7,8-tetrahydronaphthalen-1-yl)-1,2,4-oxadiazol-5-yl)-2-isopropoxybenzonitrile hydrochloride 4.

General Procedure 7. Preparation of Tetrahydronapthalene Sulfonamide Acids

To a stirring solution of (R)- or (S)-tetrahydronapthalene sulfonamide ester (1 eq) in MeOH (0.2 M) was added 6N NaOH (2 eq) at room temperature. The reaction was stirred at room temperature for 6 h. The crude reaction was diluted with water, acidified with 1N HCl and extracted with DCM and EA. The organic layer was dried over Na$_2$SO$_4$, concentrated, and isolated after preparative HPLC purification.

Compounds 34 and 35 were prepared using General Procedure 7.

(R)-2-(N-(5-(5-(3-cyano-4-isopropoxyphenyl)-1,2,4-oxadiazol-3-yl)-1,2,3,4-tetrahydronaphthalen-1-yl)sulfamoyl)acetic acid (Compound 34)

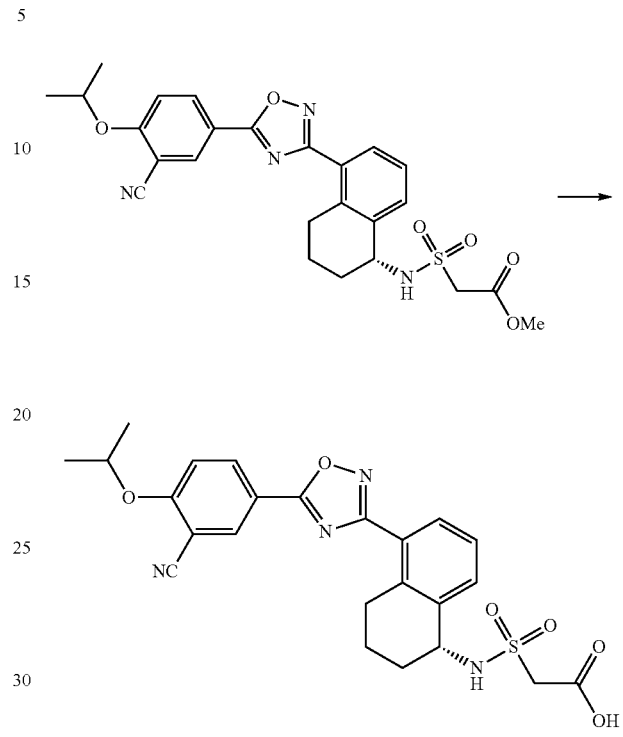

Prepared using General Procedure 7: To a stirring solution of (R)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-14 (0.082 g, 0.16 mmol) in MeOH (1.5 mL) was added 6N NaOH (0.08 mL). The reaction was stirred at room temperature for 6 h. The crude reaction was diluted with water, acidified with 1N HCl and extracted with DCM and EA. The organic layer was dried over Na$_2$SO$_4$, concentrated, and isolated after preparative HPLC purification to give 0.057 g (72%) of (R)-2-(N-(5-(5-(3-cyano-4-isopropoxyphenyl)-1,2,4-oxadiazol-3-yl)-1,2,3,4-tetrahydronaphthalen-1-yl)sulfamoyl)acetic acid 34. An analytically pure sample was prepared by preparative HPLC purification. LCMS-ESI (m/z) calculated for C$_{24}$H$_{26}$N$_4$O$_6$S: 496.5; found 520.1 [M+Na]$^+$, $t_R$=3.47 min.

(S)-2-(N-(5-(5-(3-cyano-4-isopropoxyphenyl)-1,2,4-oxadiazol-3-yl)-1,2,3,4-tetrahydronaphthalen-1-yl)sulfamoyl) acetic acid 35 was prepared in an analogous fashion from (S)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-15.

General Procedure 8. Preparation of Tetrahydronapthalene Sulfonamide Alcohols

To a stirring solution of either (R)- or (S)-tetrahydronapthalene sulfonamide ester (1 eq) in TIM (0.06 M) was added sodium borohydride (2.5 eq) at room temperature. The reaction mixture was heated to 75° C. and methanol (1 eq) was added dropwise. After 1 h, the reaction was cooled and concentrated and purified by preparative HPLC.

Compounds 36 and 37 were prepared using General Procedure 8.

(R)-N-(5-(5-(3-cyano-4-isopropoxyphenyl)-1,2,4-oxadiazol-3-yl)-1,2,3,4-, tetrahydronaphthalen-1-yl)-2-hydroxyethanesulfonamide (Compound 37)

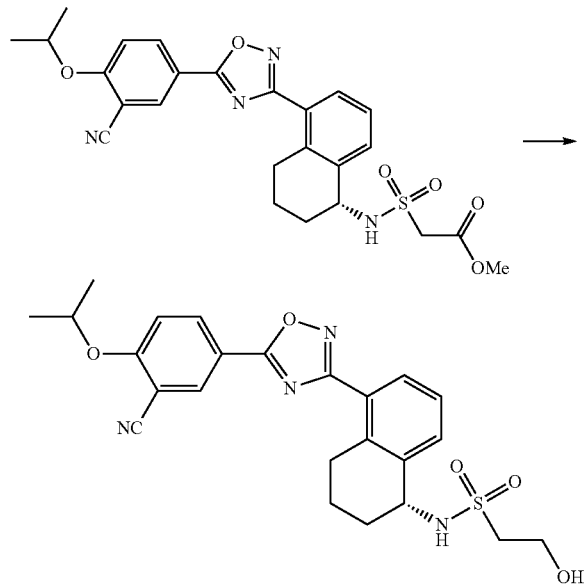

Prepared using General Procedure 8: To a stirring solution of (R)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-14 (0.025 g, 0.05 mmol) in THF (25 mL) was added sodium borohydride (0.05 g, 0.12 mmol) at room temperature. The reaction was heated to 75° C. and methanol (0.02 mL, 0.05 mmol) was added. After 1 h, the reaction was cooled and concentrated and purified by preparative HPLC to give 16.0 mg (66%) of (R)-N-(5-(5-(3-cyano-4-isopropoxyphenyl)-1,2,4-oxadiazol-3-yl)-1,2,3,4-tetrahydronaphthalen-1-yl)-2-hydroxyethanesulfonamide 37. LCMS-ESI (m/z) calculated for $C_{24}H_{26}N_4O_5S$: 482.6; found 505.1 [M+Na]$^+$, $t_R$=3.46 min. $^1$H NMR (400 MHz, CDCl$_3$) δ 8.39 (dd, J=5.4, 2.4 Hz, 1H), 8.35-8.25 (m, 1H), 7.95 (dt, J=7.7, 3.9 Hz, 1H), 7.67 (d, J=7.5 Hz, 1H), 7.43-7.32 (m, 1H), 7.12 (t, J=7.5 Hz, 1H), 4.80 (m, 3H), 4.12 (t, J=5.2 Hz, 2H), 3.46-3.28 (m, 2H), 3.17 (dt, J=18.0, 5.9 Hz, 1H), 3.02 (dt, J=18.1, 6.8 Hz, MX 2.68 (s, 1H), 2.12 (m, 1H), 2.07-1.82 (m, 3H), 1.47 (d, J=6.1 Hz, 6H). $^{13}$C NMR (101 MHz, CDCl$_3$) δ 172.82, 169.22, 162.81, 137.73, 136.90, 134.12, 133.89, 132.15, 130.28, 126.46, 126.33, 116.65, 115.22, 113.57, 103.93, 72.78, 57.32, 56.17, 52.54, 30.60, 28.06, 21.72, 19.04. Chiral HPLC: (R)-N-(5-(5-(3-cyano-4-isopropoxyphenyl)-1,2,4-oxadiazol-3-yl)-1,2,3,4-tetrahydronaphthalen-1-yl)-2-hydroxyethane sulfonamide 37 was eluted with 15% water/MeOH, (Chiral Method 2): 99.82% ee, $t_R$=22.23 min.

(S)-N-(5-(5-(3-cyano-4-isopropoxyphenyl)-1,2,4-oxadiazol-3-yl)-1,2,3,4-tetrahydronaphthalen-1-yl)-2-hydroxyethanesulfonamide 36 was prepared in an analogous fashion from (S)-methyl 2-(N-(5-(5-(3-cyano-4-isopropoxyphenyl)-1,2,4-oxadiazol-3-yl)-1,2,3,4-tetrahydronaphthalen-1-yl)sulfamoyl)acetate INT-15. Chiral HPLC: 91.7% ee, $t_R$=19.83 min (Chiral Method 2).

General Procedure 9. Preparation of Tetrahydronapthalene Sulfonamide Amides

To a stirring solution of either (R)- or (S)-tetrahydronapthalene sulfonamide acid (1 eq) in DMF (0.25 M) were added EDC and N-hydroxybenzotriazole. After 5 min, the amine was added and the reaction mixture was stirred 18 h at room temperature. The crude reaction was diluted with sat NaHCO$_3$ added extracted with EA. The combined organic layers were dried over Na$_2$SO$_4$, and purified by preparative HPLC.

Compounds 38-43 were prepared using General Procedure 9.

(R)-2-(N-(5-(5-(3-cyano-4-isopropoxyphenyl)-1,2,4-oxadiazol-3-yl)-1,2,3,4-tetrahydronaphthalen-1-yl)sulfamoyl)-N,N-dimethylacetamide (Compound 40)

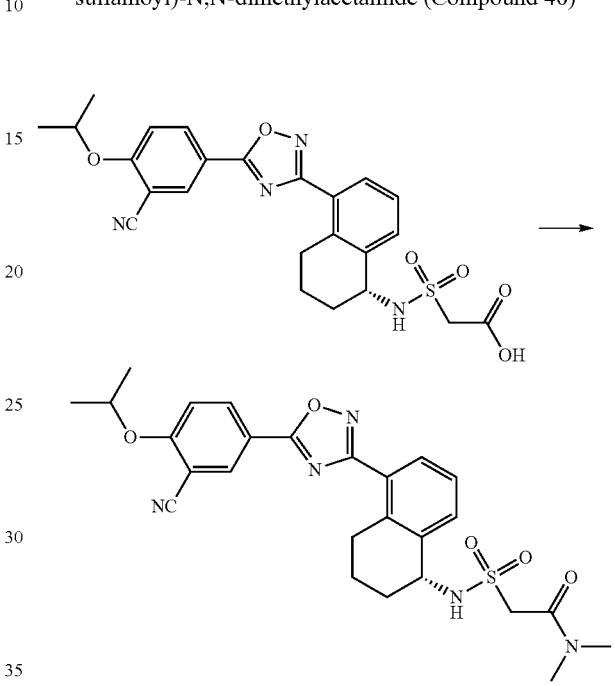

Prepared using General Procedure 9: To a stirring solution of (R)-2-(N-(5-(5-(3-cyano-4-isopropoxyphenyl)-1,2,4-oxadiazol-3-yl)-1,2,3,4-tetrahydronaphthalen-1-yl)sulfamoyl) acetic acid 34 (15 mg, 0.05 mmol) in DMF (0.5 mL) was added N-hydroxybenzotriazole (6.1 mg, 0.05 mmol) and EDC (8.7 mg, 0.05 mmol). After 5 min, dimethylamine (40 wt % solution in THF, 50 µL, 0.09 mmol) was added and the reaction mixture was stirred 18 h at room temperature. The crude reaction was diluted with sat NaHCO$_3$ and extracted with EA. The combined organic layers were dried over Na$_2$SO$_4$ and purified by preparative HPLC to give 4.41 mg (28%) of (R)-2-(N-(5-(5-(3-cyano-4-isopropoxyphenyl)-1,2,4-oxadiazol-3-yl)-1,2,3,4-tetrahydronaphthalen-1-yl)sulfamoyl)-N,N-dimethylacetamide 40. LCMS-ESI (m/z) calculated for $C_{26}H_{29}N_5O_5S$: 523.6; found 546.2 [M+Na]$^+$, $t_R$=3.58 min. $^1$H NMR (400 MHz, CDCl$_3$) δ 8.41 (d, J=2.1 Hz, 1H), 8.33 (dd, J=8.9, 2.2 Hz, 1H), 7.96 (dd, J=7.7, 1.2 Hz, 1H), 7.82 (d, J=7.5 Hz, 1H), 7.38 (t, J=7.8 Hz, 1H), 7.12 (d, J=9.0 Hz, 1H), 5.36 (t, J=17.3 Hz, 1H), 4.88-4.73 (m, 2H), 4.27 (d, J=14.6 Hz, 1H), 4.07 (d, J=14.6 Hz, 1H), 3.24-3.09 (m, 4H), 3.09-2.97 (m, 4H), 2.23-2.08 (m, 2H), 2.10-1.84 (m, 2H), 1.47 (d, J=6.1 Hz, 6H). $^{13}$C NMR (101 MHz, CDCl$_3$) δ 172.75, 169.37, 163.15, 162.77, 137.79, 136.92, 134.13, 133.90, 132.50, 130.18, 126.36, 126.17, 116.79, 115.25, 113.55, 103.96, 72.74, 55.46, 53.05, 38.22, 35.98, 29.84, 28.10, 21.73, 19.10.

((S)-2-(N-(5-(5-(3-cyano-4-isopropoxyphenyl)-1,2,4-oxadiazol-3-yl)-1,2,3,4-tetrahydronaphthalen-1-yl)sulfamoyl)-N,N-dimethylacetamide 41 was prepared in an analogous fashion from (S)-2-(N-(5-(5-(3-cyano-4-isopropoxyphenyl)-1,2,4-oxadiazol-3-yl)-1,2,3,4-tetrahydronaphthalen-1-yl)sulfamoyl)acetic acid 35.

71
(R)-N-(5-(5-(3-cyano-4-isopropoxyphenyl)-1,2,4-oxadiazol-3-yl)-1,2,3,4-tetrahydronaphthalen-1-yl)ethenesulfonamide INT-16

72
(R)-N-(5-(5-(3-cyano-4-isopropoxyphenyl)-1,2,4-oxadiazol-3-yl)-1,2,3,4-tetrahydronaphthalen-1-yl)-2-(dimethylamino)ethanesulfonamide (Compound 44)

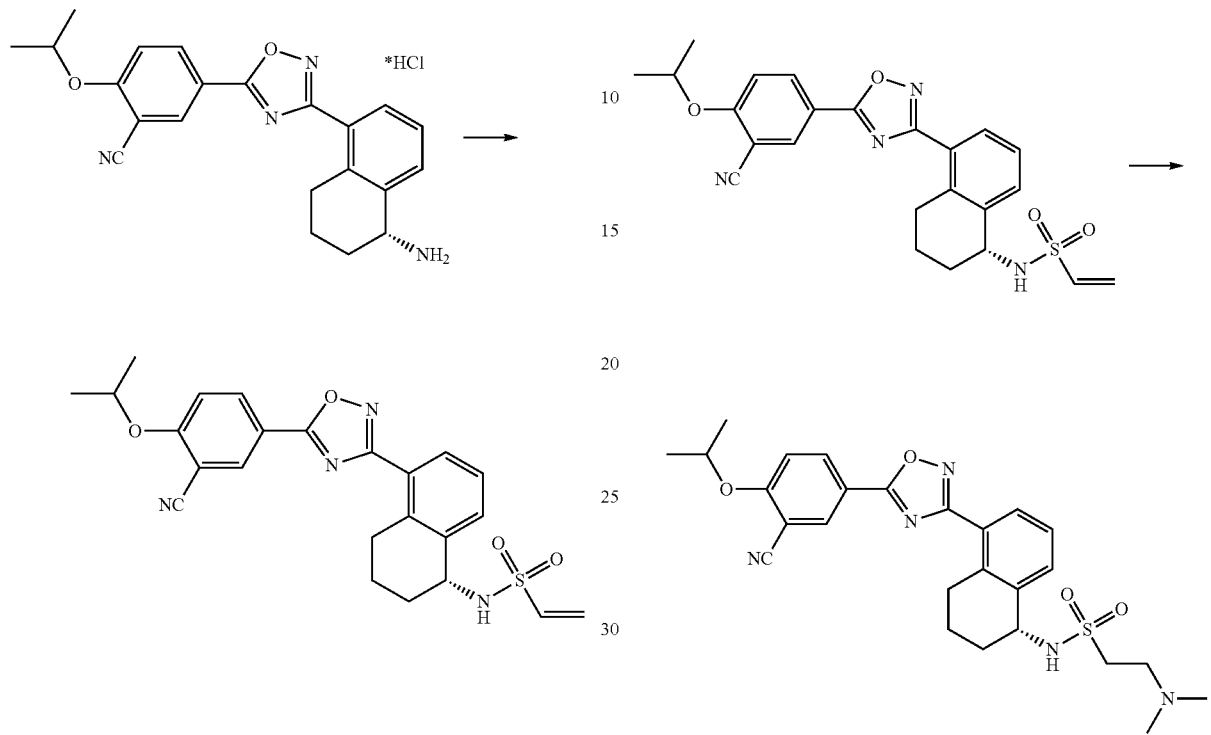

To a stirred solution of (R)-5-(3-(5-amino-5,6,7,8-tetrahydronaphthalen-1-yl)-1,2,4-oxadiazol-5-yl)-2-isopropoxybenzonitrile hydrochloride 3 (100 mg, 0.24 mmol) in DCM (5 mL) at 0° C. were added TEA (170 μL, 1.2 mmol) and 2-chloroethanesulfonyl chloride (76 μL, 0.73 mmol). The reaction mixture was warmed to room temperature and stirred for 30 min. The solvent was removed and the product was purified by chromatography (EA/hexane) to give 83.0 mg (75%) of (R)-N-(5-(5-(3-cyano-4-isopropoxyphenyl)-1,2,4-oxadiazol-3-yl)-1,2,3,4-tetrahydronaphthalen-1-yl)ethenesulfonamide INT-16 as a white solid. LCMS-ESI (m/z) calculated for $C_{24}H_{24}N_4O_4S$: 464.5; found 465.1 [M+H]$^+$, $t_R$=3.83 min. $^1$H NMR (400 MHz, CDCl$_3$) δ 8.41 (d, J=2.2 Hz, 1H), 8.32 (dd, J=8.9, 2.2 Hz, 1H), 7.96 (dd, J=7.7, 1.2 Hz, 1H), 7.62 (t, J=11.0 Hz, 1H), 7.38 (t, J=7.7 Hz, 1H), 7.12 (d, J=9.0 Hz, 1H), 6.66 (dt, J=26.0, 13.0 Hz, 1H), 6.38 (d, J=16.5 Hz, 1H), 6.03 (dd, J=10.1, 5.2 Hz, 1H), 4.86-4.73 (m, 1H), 4.68-4.57 (m, 1H), 4.50 (d, J=8.3 Hz, 1H), 3.18 (dt, J=18.1, 5.8 Hz, 1H), 3.02 (dt, J=18.1, 6.8 Hz, 1H), 2.15-1.96 (m, 2H), 1.97-1.79 (m, 2H), 1.48 (d, J=6.1 Hz, 6H).

(S)-N-(5-(5-(3-cyano-4-isopropoxyphenyl)-1,2,4-oxadiazol-3-yl)-1,2,3,4-tetrahydronaphthalen-1-yl)ethenesulfonamide INT-17 was prepared in an analogous fashion from (S)-5-(3-(5-amino-5,6,7,8-tetrahydronaphthalen-1-yl)-1,2,4-oxadiazol-5-yl)-2-isopropoxybenzonitrile hydrochloride 4.

General Procedure 10. Preparation of Tetrahydronaphthalene Sulfonamides Via Michael Addition To a stirring solution of either the (R)- or (S)-tetrahydronapthalene vinyl sulfonamide (1 eq) in DMF (0.1M) were added TEA (5 eq) and the appropriate amine (5 eq). The reaction mixture was stirred at room temperature for 18 h. The products were purified by preparative HPLC.

Compounds 44-47 were prepared using General Procedure 10.

Prepared using General Procedure 10. To a solution of ((R)-N-(5-(5-(3-cyano-4-isopropoxyphenyl)-1,2,4-oxadiazol-3-yl)-1,2,3,4-tetrahydronaphthalen-1-yl)ethenesulfonamide INT-16 (40 mg, 0.09 mmol) in DMF (1.0 mL) was added 2N methylamine in THF (0.22 mL, 0.43 mmol) and the reaction mixture was stirred at room temperature for 18 h. The crude product was purified by preparative HPLC to give 24.6 mg (54%) of the TFA salt of (R)-N-(5-(5-(3-cyano-4-isopropoxyphenyl)-1,2,4-oxadiazol-3-yl)-1,2,3,4-tetrahydronaphthalen-1-yl)-2-(dimethylamino)ethanesulfonamide 44 as a white solid. LCMS-ESI (m/z) calculated for $C_{26}H_{31}N_5O_4S$: 509.6; found 510.2 [M+H]$^+$, $t_R$=2.61 min. $^1$H NMR (400 MHz, CDCl$_3$) 8.41-8.32 (m, 1H), 8.33-8.26 (m, 1H), 7.92 (t, J=6.9 Hz, 1H), 7.61 (t, J=7.2 Hz, 1H), 7.35 (dd, J=14.5, 7.1 Hz, 1H), 7.11 (d, J=9.1 Hz, 1H), 4.86-4.64 (m, 2H), 3.61 (ddt, J=27.2, 13.7, 7.8 Hz, 4H), 3.23-3.06 (m, 1H), 3.10-2.91 (m, 1H), 2.93 (d, J=30.3 Hz, 6H), 2.09 (ddd, J=28.4, 16.5, 12.3 Hz, 1H), 1.95 (ddd, J=15.1, 8.3, 3.5 Hz, 3H), 1.46 (t, J=6.0 Hz, 6H).

(S)-N-(5-(5-(3-cyano-4-isopropoxyphenyl)-1,2,4-oxadiazol-3-yl)-1,2,3,4-tetrahydronaphthalen-1-yl)-2-(dimethylamino)ethanesulfonamide 45 was prepared in analogous fashion from ((S)-N-(5-(5-(3-cyano-4-isopropoxyphenyl)-1,2,4-oxadiazol-3-yl)-1,2,3,4-tetrahydronaphthalen-1-yl)ethenesulfonamide INT-17.

(R)-2-isopropoxy-5-(3-(5-((2-(methylsulfonyl)ethyl)
amino)-5,6,7,8-tetrahydronaphthalen-1-yl)-1,2,4-
oxadiazol-5-yl)benzonitrile (Compound 48)

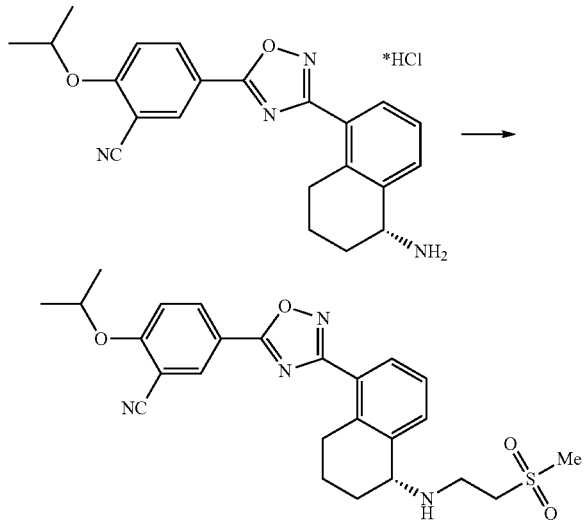

To a solution of (R)-5-(3-(5-amino-5,6,7,8-tetrahydronaphthalen-1-yl)-1,2,4-oxadiazol-5-yl)-2-isopropoxybenzonitrile hydrochloride 3 (20 mg, 0.05 mmol) in DMA (0.5 mL) was added TEA (136 μL, 0.97 mmol) and methylvinylsulfone (52 mg, 0.5 mmol). The reaction was heated to 80° C. for 24 h. The crude reaction mixture was purified by preparative HPLC to give (R)-2-isopropoxy-5-(3-(5-((2-(methylsulfonyl)ethyl)amino)-5,6,7,8-tetrahydronaphthalen-1-yl)-1,2,4-oxadiazol-5-yl)benzonitrile 48. LCMS-ESI (m/z) calculated for $C_{25}H_{28}N_4O_4S$: 480.6; found 481.2 [M+H]$^+$, $t_R$=2.58 min. $^1$H NMR (400 MHz, CDCl$_3$) δ 8.37 (t, J=9.1 Hz, 1H), 8.31 (dd, J=8.9, 2.2 Hz, 1H), 8.08 (d, J=7.1 Hz, 1H), 7.60 (d, J=7.6 Hz, 1H), 7.42 (t, J=7.7 Hz, 1H), 7.12 (d, J=9.1 Hz, 1H), 4.85-4.73 (m, 1H), 4.53 (t, J=5.0 Hz, 1H), 3.63 (dd, J=15.3, 4.0 Hz, 2H), 3.61-3.50 (m, 2H), 3.33-3.17 (m, 1H), 3.18-3.04 (m, 1H), 3.04 (d, J=8.6 Hz, 3H), 2.16 (ddd, J=29.6, 18.8, 12.2 Hz, 2H), 2.00 (dd, J=36.4, 18.4 Hz, 2H), 1.47 (d, J=6.1 Hz, 6H).

(S)-2-isopropoxy-5-(3-(5-((2-(methylsulfonyl)ethyl)amino)-5,6,7,8-tetrahydronaphthalen-1-yl)-1,2,4-oxadiazol-5-yl)benzonitrile, compound 49 was prepared in an analogous fashion from (S)-5-(3-(5-amino-5,6,7,8-tetrahydronaphthalen-1-yl)-1,2,4-oxadiazol-5-yl)-2-isopropoxybenzonitrile hydrochloride 4.

(R)-methyl 2-((5-(5-(3-cyano-4-isopropoxyphenyl)-
1,2,4-oxadiazol-3-yl)-1,2,3,4-tetrahydronaphthalen-
1-yl)amino)acetate (INT-18)

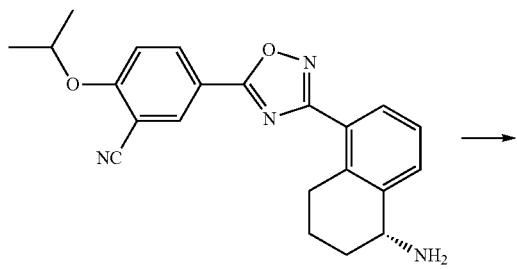

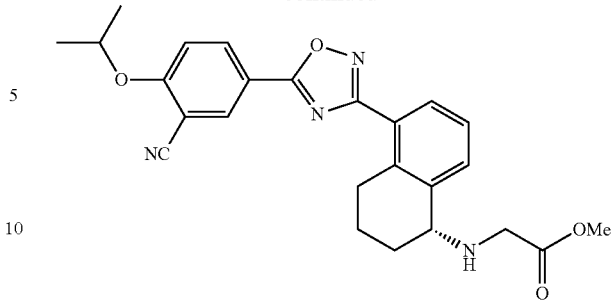

To a stirring solution of (R)-5-(3-(5-amino-5,6,7,8-tetrahydronaphthalen-1-yl)-1,2,4-oxadiazol-5-yl)-2-isopropoxybenzonitrile 3 (119 mg, 0.32 mmol) in CH$_3$CN (5.0 mL) was added methyl bromoacetate (53.5 μL, 0.35 mmol) and K$_2$CO$_3$ (138 mg, 1.27 mmol). After stirring for 18 h, the mixture was diluted with brine and washed with NaHCO$_3$. The organic layer was dried with Na$_2$SO$_4$ and concentrated. The resulting crude solid was purified by chromatography (MeOH/DCM) to provide 113.1 mg (79%) of (R)-methyl 2-((5-(5-(3-cyano-4-isopropoxyphenyl)-1,2,4-oxadiazol-3-yl)-1,2,3,4-tetrahydronaphthalen-1-yl)amino)acetate INT-18. LCMS-ESI (m/z) calculated for $C_{25}H_{26}N_4O_4$: 446.5; found 447.2 [M+H]$^+$, $t_R$=2.52 min.

(S)-methyl 2-((5-(5-(3-cyano-4-isopropoxyphenyl)-1,2,4-oxadiazol-3-yl)-1,2,3,4-tetrahydronaphthalen-1-yl)amino)acetate INT-19 was prepared in an analogous fashion from (S)-5-(3-(5-amino-5,6,7,8-tetrahydronaphthalen-1-yl)-1,2,4-oxadiazol-5-yl)-2-isopropoxybenzonitrile 4.

(S)-methyl 2-((tert-butoxycarbonyl)(5-(5-(3-cyano-
4-isopropoxyphenyl)-1,2,4-oxadiazol-3-yl)-1,2,3,4-
tetrahydronaphthalen-1-yl)amino)acetate (INT-20)

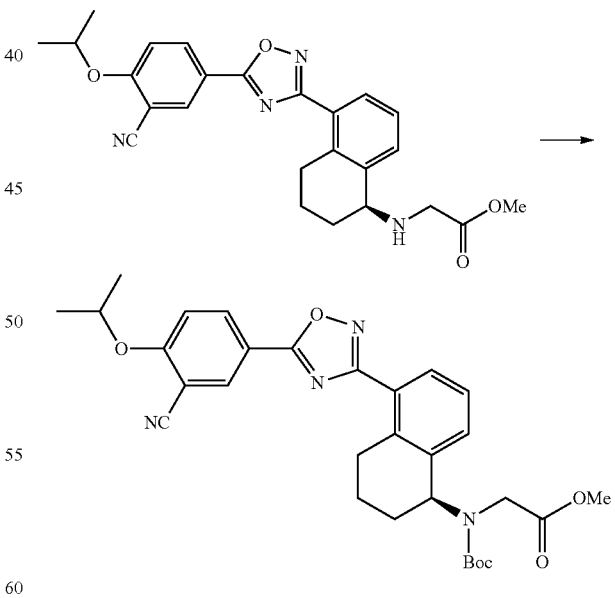

To a stirred solution of (S)-methyl 2-((5-(5-(3-cyano-4-isopropoxyphenyl)-1,2,4-oxadiazol-3-yl)-1,2,3,4-tetrahydronaphthalen-1-yl)amino)acetate INT-19 (128.0 mg, 0.29 mmol) in DCM (6.0 mL) was added Boc anhydride (125.1 mg, 0.57 mmol) and TEA (120 μL, 0.86 mmol). After stirring for 18 h, the mixture was concentrated. The resulting crude solid was purified by chromatography (EA/hexanes) to provide 119 mg (76%) of (S)-methyl 2-((tert-butoxycarbonyl) (5-(5-(3-cyano-4-isopropoxyphenyl)-1,2,4-oxadiazol-3-yl)-1,2,3,4-tetrahydronaphthalen-1-yl)amino)acetate INT-20. LCMS-ESI (m/z) calculated for $C_{30}H_{34}N_4O_6$: 546.61; no M/Z observed, $t_R$=4.32 min.

(R)-methyl 2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetate INT-21 was prepared in an analogous fashion from (R)-methyl 245-(5-(3-cyano-4-isopropoxyphenyl)-1,2,4-oxadiazol-3-yl)-1,2,3,4-tetrahydronaphthalen-1-yl)amino)acetate INT-18.

(S)-tert-butyl(5-(5-(3-cyano-4-isopropoxyphenyl)-1, 2,4-oxadiazol-3-yl)-1,2,3,4-tetrahydronaphthalen-1-yl)(2-hydroxyethyl)carbamate (INT-22)

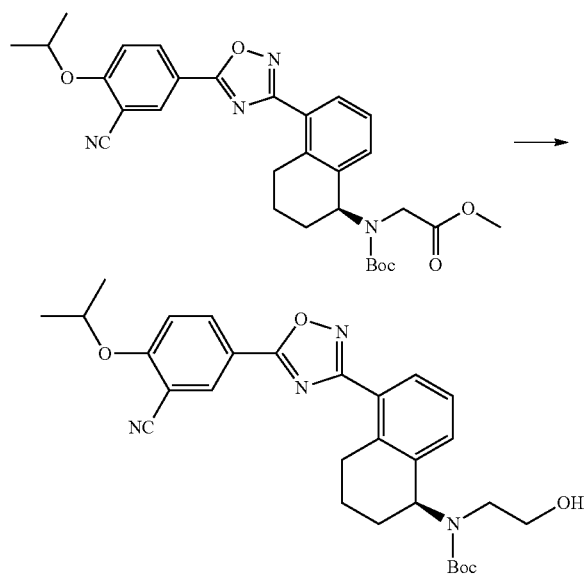

To a stirring solution of (S)-methyl 2-((5-(5-(3-cyano-4-isopropoxyphenyl)-1,2,4-oxadiazol-3-yl)-1,2,3,4-tetrahydronaphthalen-1-yl)amino)acetate INT-20 (35 mg, 0.06 mmol) in THF (6.0 mL) at 75° C. was added sodium borohydride (6 mg, 0.16 mmol). After stirring for 0.5 h, MeOH (7.7 µL, 0.19 mmol) was added and the mixture was heated for an additional 1.5 h. The mixture was concentrated and the resulting solid was purified by chromatography (EA/hexanes) to provide 16 mg (48%) of (S)-tert-butyl (5-(5-(3-cyano-4-isopropoxyphenyl)-1,2,4-oxadiazol-3-yl)-1,2,3,4-tetrahydronaphthalen-1-yl)(2-hydroxyethyl)carbamate INT-22. LCMS-ESI (m/z) calculated for $C_{29}H_{34}N_4O_5$: 518.6; found 419.2 [M−Boc+H]+, $t_R$=4.10 min.

(R)-tert-butyl (5-(5-(3-cyano-4-isopropoxyphenyl)-1,2,4-oxadiazol-3-yl)-1,2,3,4-tetrahydronaphthalen-1-yl)(2-hydroxyethyl)carbamate INT-23 was prepared in prepared in an analogous fashion from (R)-methyl 2-((tert-butoxycarbonyl) (5-(5-(3-cyano-4-isopropoxyphenyl)-1,2,4-oxadiazol-3-yl)-1,2,3,4-tetrahydronaphthalen-1-yl)amino)acetate INT-21.

General Procedure 11: Boc Deprotection of Tetrahydronaphthalene Amines

To a stirring solution of Boc protected (R)- or (S)-tetrahydronaphthalene amine in dioxane was added 4N HCl/dioxanes (4-10 eq). The reaction mixture was heated at 50° C. for 18 h. The reaction mixture was concentrated and the resulting solid was purified by preparative HPLC.

Compounds 50-53 were prepared using General Procedure 11.

(R)-5-(3-(5-((2-hydroxyethyl)amino)-5,6,7,8-tetrahydronaphthalen-1-yl)-1,2,4-oxadiazol-5-yl)-2-isopropoxybenzonitrile (Compound 50)

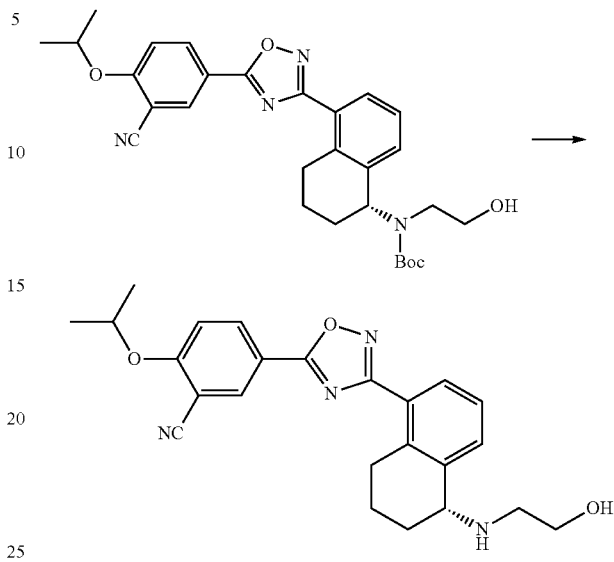

Prepared using General Procedure 11. To a stirred solution of (R)-tert-butyl (5-(5-(3-cyano-4-isopropoxyphenyl)-1,2,4-oxadiazol-3-yl)-1,2,3,4-tetrahydronaphthalen-1-yl)(2-hydroxyethyl)carbamate INT-23 (15 mg, 0.03 mmol) in dioxane (1 mL) was added 4N HCl/dioxanes (116 µL, 0.116 mmol). After heating at 50° C. for 18 h, the mixture was concentrated and the resulting solid was purified by preparative HPLC to provide 9.53 mg (79%) of (R)-5-(3-(5-((2-hydroxyethyl) amino)-5,6,7,8-tetrahydronaphthalen-1-yl)-1,2,4-oxadiazol-5-yl)-2-isopropoxy benzonitrile 50. LCMS-ESI (m/z) calculated for $C_{24}H_{26}N_4O_3$: 418.5; found 419.2 [M+H]+, $t_R$=2.52 min. 1H NMR (400 MHz, CDCl3) δ 8.39 (d, J=2.2 Hz, 1H), 8.32 (dd, J=8.9, 2.2 Hz, 1H), 8.04 (d, J=7.7 Hz, 1H), 7.60 (d, J=7.6 Hz, 1H), 7.39 (t, J=7.7 Hz, 1H), 7.12 (d, J=9.1 Hz, 1H), 4.88-4.70 (m, 1H), 4.54 (s, 1H), 3.78 (d, J=12.1 Hz, 2H), 3.62 (s, 2H), 3.24 (dt, J=18.0, 5.6 Hz, 1H), 3.18-2.89 (m, 3H), 2.16 (d, J=5.2 Hz, 2H), 2.10-1.75 (m, 2H), 1.47 (d, J=6.1 Hz, 6H).

(S)-5-(3-(5-((2-hydroxyethyl)amino)-5,6,7,8-tetrahydronaphthalen-1-yl)-1,2,4-oxadiazol-5-yl)-2-isopropoxybenzonitrile 51 was prepared in an analogous fashion from (S)-tert-butyl (5-(5-(3-cyano-4-isopropoxyphenyl)-1,2,4-oxadiazol-3-yl)-1,2,3,4-tetrahydronaphthalen-1-yl)(2-hydroxyethyl)carbamate INT-22.

(S)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid (INT-24)

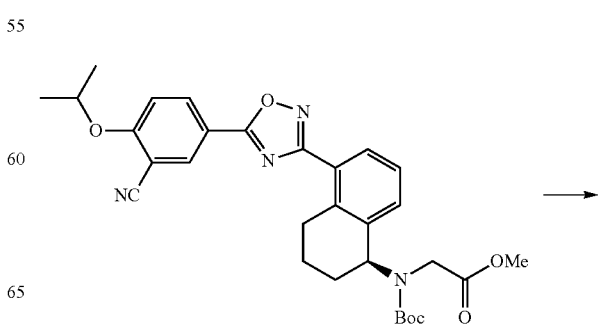

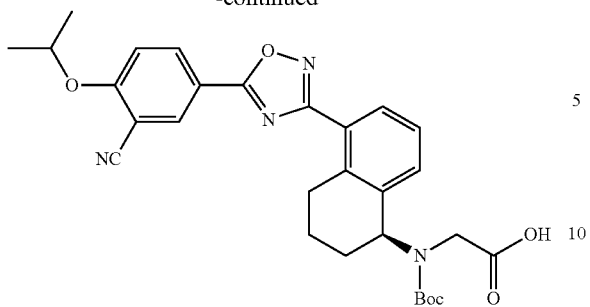

To a stirring solution of (S)-methyl 2-((5-(5-(3-cyano-4-isopropoxyphenyl)-1,2,4-oxadiazol-3-yl)-1,2,3,4-tetrahydronaphthalen-1-yl)amino)acetate INT-20 (93.2 mg, 0.17 mmol) in MeOH (2 ml) was added 10 drops of 1 N NaOH. The mixture was stirred at 50° C. for 2 h, then diluted with H$_2$O and neutralized with 1 N HCl. The aqueous solution was extracted with DCM and EA. The combined organic layers were dried over Na$_2$SO$_4$ and concentrated to provide 61 mg (67%) of (S)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-24 as a white solid. LCMS-ESI (m/z) calculated for C$_{29}$H$_{32}$N$_4$O$_6$: 532.6; found 358.1 [M−2-((tert-butoxycarbonyl)amino)acetic acid]$^+$, $t_R$=3.97 min.

(R)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-25 was prepared in an analogous fashion from (S)-methyl 2-((5-(5-(3-cyano-4-isopropoxyphenyl)-1,2,4-oxadiazol-3-yl)-1,2,3,4-tetrahydronaphthalen-1-yl)amino)acetate INT-21.

(S)-2-((5-(5-(3-cyano-4-isopropoxyphenyl)-1,2,4-oxadiazol-3-yl)-1,2,3,4-tetrahydronaphthalen-1-yl)amino)acetic acid (Compound 53)

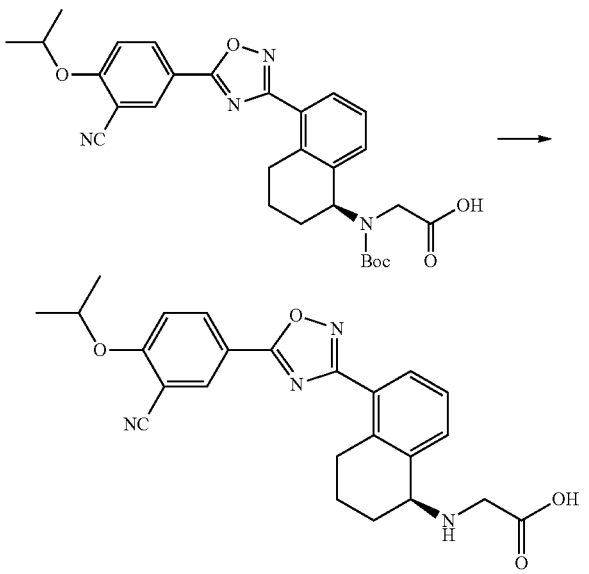

Prepared using General Procedure 11. A solution of (S)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-24 (30 mg, 0.06 mmol) in 4N HCl/dioxanes (200 µl, 50 mmol) was stirred at room temperature for 18 h. The mixture was concentrated and the residue was purified by preparative HPLC to provide 21 mg (67%) of (S)-2-((5-(5-(3-cyano-4-isopropoxyphenyl)-1,2,4-oxadiazol-3-yl)-1,2,3,4-tetrahydronaphthalen-1-yl)amino)acetic acid 53 as the TFA salt. LCMS-ESI (m/z) calculated for C$_{24}$H$_{24}$N$_4$O$_4$: 432.5; found 358.1 [M−2-aminoacetic acid], $t_R$=2.65 min.

(R)-2-((5-(5-(3-cyano-4-isopropoxyphenyl)-1,2,4-oxadiazol-3-yl)-1,2,3,4-tetrahydro naphthalen-1-yl)amino) acetic acid 52 was prepared in an analogous fashion from (R)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-25.

General Procedure 12: Preparation of Tetrahydronaphthalene Amino Amides

To the Boc-protected (R)- or (S)-tetrahydronaphthalene amino acid DMF were added N-hydroxybenzotriazole (2 eq) and EDC (2 eq). After 10 min, the appropriate amine (10 eq) was added and the reaction mixture was stirred for 18 h at room temperature. The crude reaction mixture was diluted with NaHCO$_3$ and extracted with EA. The combined organic layers were dried over Na$_2$SO$_4$ and purified by preparative HPLC.

Compounds 54 and 55 were prepared using General Procedure 12.

(S)-tert-butyl (5-(5-(3-cyano-4-isopropoxyphenyl)-1,2,4-oxadiazol-3-yl)-1,2,3,4-tetrahydronaphthalen-1-yl)(2-oxo-2-(pyrrolidin-1-yl)ethyl)carbamate (INT-26)

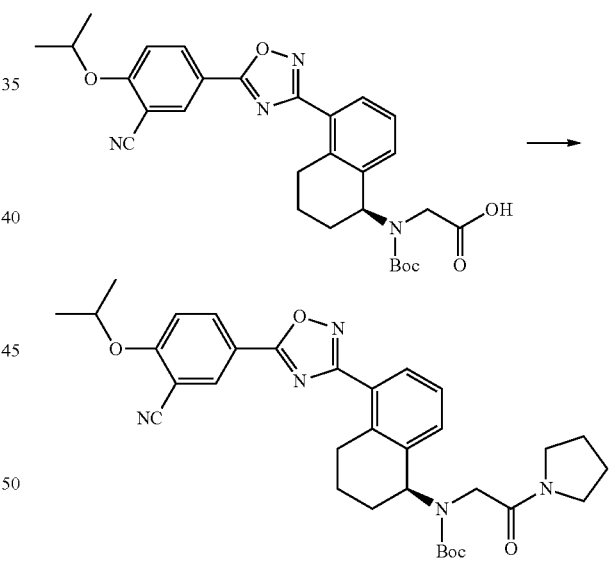

Prepared using General Procedure 12. To a stirring solution of (S)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-24 (30 mg, 0.06 mmol) in DMF (0.5 mL) were added N-hydroxybenzotriazole (15.21 mg, 0.11 mmol) and EDC (21.63 mg, 0.11 mmol). After 10 min, pyrrolidine (46 µL, 0.56 mmol) was added and the reaction mixture was stirred 18 h at room temperature. The crude reaction was diluted with sat NaHCO$_3$ added extracted with EA. The combined organic layers were dried over Na$_2$SO$_4$ and purified by preparative HPLC to give 26.9 mg (82%) of (S)-tert-butyl (5-(5-(3-cyano-4-isopropoxyphenyl)-1,2,4-oxadiazol-3-yl)-1,2,3,4-tetrahydronaphthalen-1-yl) (2-oxo-2-(pyrrolidin-1-yl)ethyl)carbamate. LCMS-ESI (m/z) calculated for $C_{33}H_{39}N_5O_5$: 585.7; found 358.1 [M−tert-butyl (2-oxo-2-(pyrrolidin-1-yl)ethyl)carbamate]$^+$, $t_R$=4.18 min.

(R)-tert-butyl (5-(5-(3-cyano-4-isopropoxyphenyl)-1,2,4-oxadiazol-3-yl)-1,2,3,4-tetrahydronaphthalen-1-yl)(2-oxo-2-(pyrrolidin-1-yl)ethyl)carbamate INT-27 was prepared in an analogous fashion from (R)-2-((tert-butoxycarbonyl)(5-(5-(3-cyano-4-isopropoxyphenyl)-1,2,4-oxadiazol-3-yl)-1,2,3,4-tetrahydronaphthalen-1-yl)amino)acetic acid INT-25.

(R)-2-isopropoxy-5-(3-(5-((2-oxo-2-(pyrrolidin-1-yl)ethyl)amino)-5,6,7,8-tetrahydronaphthalen-1-yl)-1,2,4-oxadiazol-5-yl)benzonitrile (Compound 54)

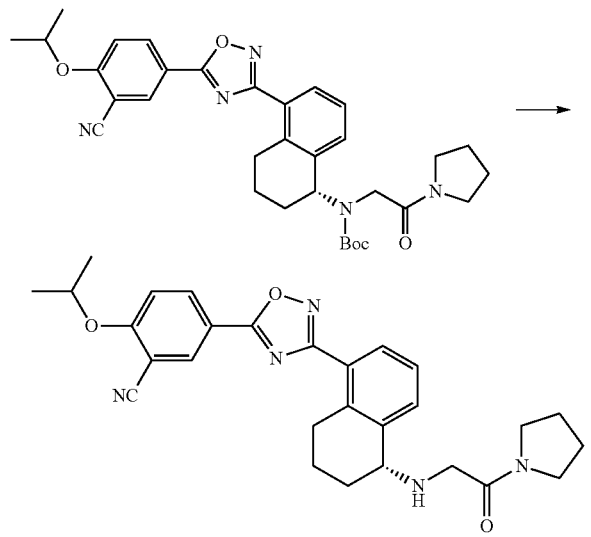

Prepared using General Procedure 11. A solution of (R)-tert-butyl (5-(5-(3-cyano-4-isopropoxyphenyl)-1,2,4-oxadiazol-3-yl)-1,2,3,4-tetrahydronaphthalen-1-yl)(2-oxo-2-(pyrrolidin-1-yl)ethyl)carbamate INT-27 (18 mg, 0.03 mmol) in 4N HCl/dioxanes (1 mL) was stirred at room temperature for 18 h. The reaction mixture was concentrated and purified by preparative HPLC to provide 12 mg (68%) of (R)-2-isopropoxy-5-(3-(5-((2-oxo-2-(pyrrolidin-1-yl)ethyl)amino)-5,6,7,8-tetrahydronaphthalen-1-yl)-1,2,4-oxadiazol-5-yl)benzonitrile 54 as the TFA salt. LCMS-ESI (m/z) calculated for $C_{28}H_{31}N_5O_3$: 485.6; found 486.2 [M+H]$^+$, $t_R$=2.60 min. $^1$H NMR (400 MHz, CDCl$_3$) δ 8.40 (d, J=2.2 Hz, 1H), 8.33 (dd, J=8.9, 2.2 Hz, 1H), 8.07 (d, J=7.6 Hz, 1H), 7.77 (d, J=7.6 Hz, 1H), 7.44 (t, J=7.7 Hz, 1H), 7.13 (d, J=9.1 Hz, 1H), 4.87-4.68 (m, 2H), 3.98-3.80 (m, 2H), 3.53-3.03 (m, 7H), 2.17 (ddd, J=17.7, 10.4, 5.5 Hz, 3H), 2.04-1.79 (m, 5H), 1.48 (d, J=6.1 Hz, 6H).

(S)-2-isopropoxy-5-(3-(5-((2-oxo-2-(pyrrolidin-1-yl)ethyl)amino)-5,6,7,8-tetrahydronaphthalen-1-yl)-1,2,4-oxadiazol-5-yl)benzonitrile 55 was prepared in an analogous fashion from (S)-tert-butyl (5-(5-(3-cyano-4-isopropoxyphenyl)-1,2,4-oxadiazol-3-yl)-1,2,3,4-tetrahydronaphthalen-1-yl)(2-oxo-2-(pyrrolidin-1-yl)ethyl)carbamate INT-26.

4-bromo-2,3-dihydro-1H-inden-1-ol (INT-28)

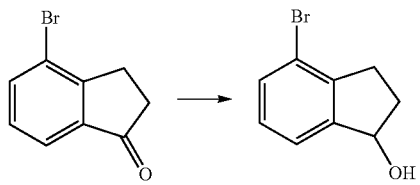 [SMILES: O=C1CCc2c(Br)cccc21 ; OC1CCc2c(Br)cccc21]

To a stirring solution of 4-bromoindanone (3 g, 14.2 mmol) in anhydrous EtOH (30 mL) were added sodium borohydride (0.36 g, 9.5 mmol) and silica gel (2 g) at 0° C. The reaction was stirred at 0° C. for 20 min and was allowed to stir at room temperature for 2 h. The reaction mixture was quenched with saturated NaHCO$_3$ and concentrated to remove EtOH. The aqueous layer was extracted with EA and the organic phase was dried over MgSO$_4$. After concentration, the crude product was purified by chromatography (EA/hexane) to yield 4-bromo-2,3-dihydro-1H-inden-1-ol INT-28 (2.56 g, 85%) as white solid. LCMS-ESI (m/z) calculated for $C_9H_9BrO$: 213.1; found 195.0 [M−H$_2$O]$^+$, $t_R$=3.07 min. $^1$H NMR (400 MHz, CDCl$_3$) δ 7.35 (d, J=7.9, 1H), 7.27 (d, J=7.4, 1H), 7.05 (t, J=7.7, 1H), 5.23 (t, J=6.2, 1H), 3.00 (ddd, J=16.6, 8.8, 4.6, 1H), 2.84-2.66 (m, 1H), 2.45 (dddd, J=13.2, 8.4, 7.0, 4.6, 1H), 1.96-1.70 (m, 2H).

(4-bromo-2,3-dihydro-1H-inden-1-yloxy)(tert-butyl)dimethylsilane (INT-29)

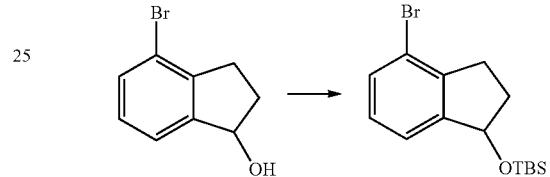

To a solution of 4-bromo-2,3-dihydro-1H-inden-1-ol INT-28 (2.56 g, 12.0 mm) in DMF (5 mL) were added TBDMSCl (2.17 g, 14.4 mmol) and imidazole (2 g, 30.0 mmol) and the reaction mixture stirred at room temperature overnight. The reaction mixture was diluted with Inter and extracted with EA. The organic layers were washed with water and brine, and dried over MgSO$_4$. The crude product was purified by chromatography (EA/hexane) to afford (4-bromo-2,3-dihydro-1H-inden-1-yloxy)(tert-butyl)dimethylsilane INT-29 (3.3 g, 84%) as a clear oil. LCMS-ESI (m/z) calculated for $C_{15}H_{23}BrOSi$: 327.3; found 195.0 [M−OTBS]$^+$, $t_R$=3.07 min. $^1$H NMR (400 MHz, CDCl$_3$) δ 7.20 (d, J=7.8 Hz, 1H), 7.06 (d, J=7.4 Hz, 1H), 6.92 (t, J=7.7 Hz, 1H), 5.13 (t, J=7.0 Hz, 1H), 2.85 (ddd, J=16.4, 9.1, 2.9 Hz, 1H), 2.57 (dt, J=16.5, 8.3 Hz, 1H), 2.36-2.17 (m, 1H), 1.76 (dtd, J=12.8, 8.8, 7.1 Hz, 1H), 0.83-0.72 (m, 9H), 0.05-0.06 (m, 6H).

tert-butyldimethyl(4-(4,4,5,5-tetramethyl-1,3,2-dioxaborolan-2-yl)-2,3-dihydro-1H-inden-1-yloxy)silane (INT-30)

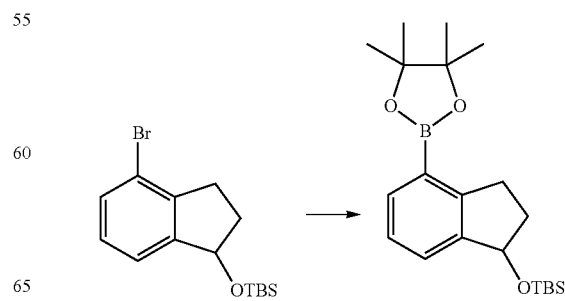

A solution of (4-bromo-2,3-dihydro-1H-inden-1-yloxy)(tert-butyl)dimethylsilane INT-29 (50 mg, 0.15 mmol), 4,4,4',4',5,5,5',5'-octamethyl-2,2'-bi(1,3,2-dioxaborolane) (42 mg, 0.16 mmol), and potassium acetate (45 mg, 0.45 mmol) in anhydrous 1,4-dioxane (2 mL) was degassed by passing $N_2$ through the solution for 5 min. $PdCl_2(dppf) \cdot CH_2Cl_2$ was then added and the reaction mixture was heated at 85° C. overnight. The solvent was removed under vacuum, the residue was diluted with EA (10 mL), and filtered through celite to remove solids. The filtrate was washed with water and brine and dried over $MgSO_4$. The crude product was purified by chromatography (EA/hexanes) to afford tert-butyldimethyl (4-(4,4,5,5-tetramethyl-1,3,2-dioxaborolan-2-yl)-2,3-dihydro-1H-inden-1-yl-oxy)silane INT-30 (26 mg, 45%) as a white semi-solid. LCMS-ESI (m/z) calculated for $C_{21}H_{35}BO_3Si$: 374.4; found 245.0 $[M-OTBS]^+$, $t_R$=3.07 min. $^1$H NMR (400 MHz, $CDCl_3$) δ 7.57-7.43 (m, 1H), 7.21 (dd, J=11.0, 4.2 Hz, 1H), 7.08-7.01 (m, 1H), 5.06 (t, J=7.0 Hz, 1H), 3.11 (ddd, J=16.8, 8.9, 3.0 Hz, 1H), 2.72 (dt, J=16.8, 8.3 Hz, 1H), 2.22 (dddd, J=12.6, 7.9, 7.1, 3.1 Hz, 1H), 1.71 (dtd, J=12.6, 8.8, 7.0 Hz, 1H), 1.21-1.10 (m, 12H), 0.81-0.71 (m, 9H), 0.03-0.07 (m, 6H).

5-(4,5-dihydrooxazol-2-yl)-2-isopropoxybenzonitrile (INT-31)

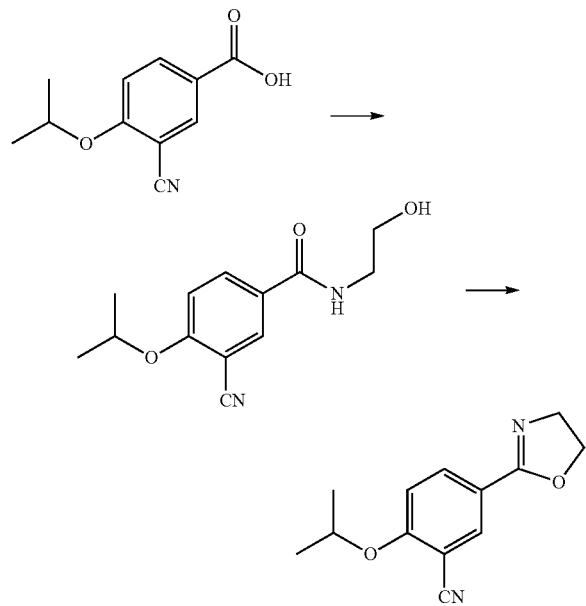

To a stirring suspension of 3-cyano-4-isopropoxybenzoic acid (1.0 g, 4.8 mmol) in DCM (20 mL) was added oxalyl chloride (3.7 g, 29.2 mmol) followed by two drops DMF. The reaction mixture was stirred at 50° C. for 2 h. The mixture was concentrated and the residue re-dissolved in DCM (10 mL). Ethanolamine (0.6 g, 9.7 mmol) and TEA (1.45 g, 14.4 mmol) were added and the reaction mixture was stirred overnight at room temperature. The resulting solid was filtered, washed with water, and dried to afford 1.0 g (83%) of 3-cyano-N-(2-hydroxyethyl)-4-isopropoxybenzamide which was used in the next step without purification. LCMS-ESI (ink) calculated for $C_{13}H_{16}N_2O_3$: 248.3; found 249.0 $[M+H]^+$, $t_R$=2.41 min. $^1$H NMR (400 MHz, $CDCl_3$) δ 8.02-7.79 (m, 2H), 6.97-6.87 (m, 1H), 6.71 (s, 1H), 4.65 (dt, J=12.1, 6.1 Hz, 1H), 3.82-3.70 (m, 2H), 3.56 (dd, J=10.2, 5.5 Hz, 2H), 1.96 (d, J=10.0 Hz, 1H), 1.40-1.29 (m, 6H).

3-cyano-N-(2-hydroxyethyl)-4-isopropoxybenzamide was dissolved in DCM (30 mL) and thionyl chloride (1.43 g, 12 mmol) was added at 0° C. The reaction mixture was stirred at room temperature for 1 h and then quenched at 0° C. with water (200 μL) and 6N NaOH solution (1 mL). The mixture was stirred for 30 min. The aqueous layers were extracted with DCM and the combined organic extracts were washed with brine and dried over $MgSO_4$ to afford 570 mg (61% for two steps) of 5-(4,5-dihydrooxazol-2-yl)-2-isopropoxybenzonitrile INT-31. LCMS-ESI (m/z) calculated for $C_{13}H_{14}N_2O_2$: 230.3; found 231.0 $[M+H]^+$, $t_R$=2.50 min. $^1$H NMR (400 MHz, $CDCl_3$) δ 8.17-7.86 (m, 2H), 6.91 (d, J=8.9 Hz, 1H), 4.65 (dt, J=12.2, 6.1 Hz, 1H), 4.37 (dd, J=14.3, 4.9 Hz, 2H), 3.98 (t, J=9.5 Hz, 2H), 1.36 (t, J=5.5 Hz, 6H).

5-(5-bromooxazol-2-yl)-2-isopropoxybenzonitrile (INT-32)

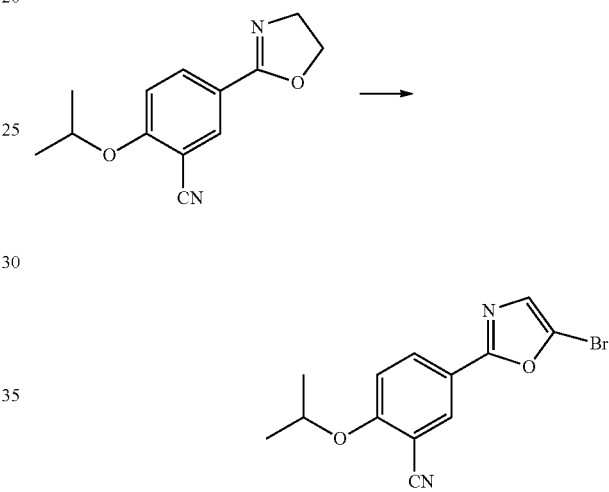

A stirring solution of 5-(4,5-dihydrooxazol-2-yl)-2-isopropoxybenzonitrile INT-31 (420 mg, 1.82 mmol), N-bromosuccinamide (990 mg, 5.56 mmol) and azoisobutyronitrile (14.9 mg, 0.09 mmol) in carbon tetrachloride (20 mL) was heated at 80° C. under $N_2$ for 18 h. The reaction mixture was cooled to room temperature and the solids were removed by filtration. The filtrate was washed with sodium thiosulfate (20 mL) and brine (20 mL), and dried over $MgSO_4$. The product was purified by chromatography (EA/hexanes) to afford 300 mg (55%) of 5-(5-bromooxazol-2-yl)-2-isopropoxybenzonitrile INT-32 as a yellow solid. LCMS-ESI (m/z) calculated for $C_{13}H_{11}BrN_2O_2$: 307.1; found 309.0 $[M+2]^+$, $t_R$=3.79 min. $^1$H NMR (400 MHz, $CDCl_3$) δ 8.19-7.93 (m, 2H), 7.08-6.85 (m, 2H), 4.81-4.47 (m, 1H), 1.38 (dd, J=6.6, 3.0 Hz, 6H).

General Procedure 13: Coupling of Heterocyclic Bromide to Indanol Boronate

A 20 mL microwave vial was charged sequentially with heterocyclic bromide (1 eq), (R)- (S)- or racemic indanol dioxaborolane (1 eq), DME/$H_2O$ (3:1, 0.05 M) and potassium carbonate (3 eq). The mixture was degassed by bubbling $N_2$ gas through the stirring solution for 10 min. $Pd(PPh_3)_4$ (0.07 eq) was added and the mixture degassed for additional 2 min. The vial was capped and subjected to microwave irradiation at 100° C. until reaction completed (40-60 min). Additional bromide was added if needed. The vial was cooled to room temperature, diluted with EA (10× volume), washed with

5-(5-(1-(tert-butyldimethylsilyloxy)-2,3-dihydro-1H-inden-4-yl)oxazol-2-yl)-2-isopropoxybenzonitrile (INT-33)

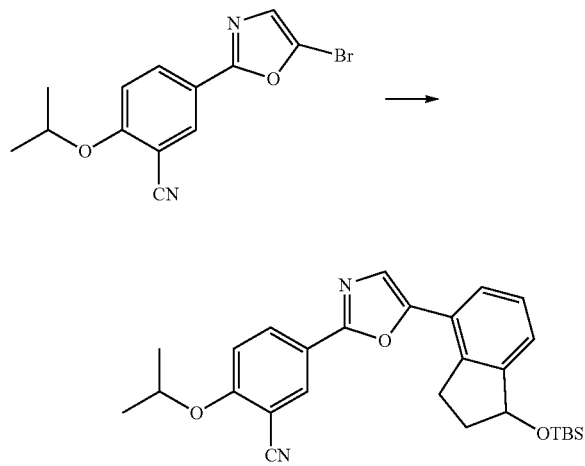 [SMILES: CC(C)Oc1ccc(-c2ncc(Br)o2)cc1C#N ; CC(C)Oc1ccc(-c2ncc(-c3cccc4c3CCC4O[Si](C)(C)C(C)(C)C)o2)cc1C#N]

Prepared using General Procedure 13. A 20 mL microwave vial was charged with 5-(5-bromooxazol-2-yl)-2-isopropoxybenzonitrile INT-32 (200 mg, 0.65 mmol), tert-butyldimethyl(4-(4,4,5,5-tetramethyl-1,3,2-dioxaborolan-2-yl)-2,3-dihydro-1H-inden-1-yloxy)silane INT-30 (243 mg, 0.65 mmol), potassium carbonate (269 mg, 1.95 mmol) and a 3:1 mixture of dimethylethylene glycol/H$_2$O (10 mL). The reaction mixture was degassed by bubbling N$_2$ gas through the stirring solution for 10 min. Pd(PPh$_3$)$_4$ was added and the solution degassed for additional 2 min. The vial was subjected to microwave irradiation at 100° C. for 40 min. The vial was cooled to 0° C. and the resulting solid obtained was collected by filtration, washed with ice water, and dried to afford 290 mg (94%) of 5-(5-(1-(tert-butyldimethylsilyloxy)-2,3-dihydro-1H-inden-4-yl)oxazol-2-yl)-2-isopropoxybenzonitrile INT-33 as a light yellow solid. LCMS-ESI (m/z) calculated for C$_{28}$H$_{34}$N$_2$O$_3$Si: 474.7; found 475.2 [M+H]$^+$, t$_R$=5.90 min (Method 1). $^1$H NMR (400 MHz, CDCl$_3$) δ 8.16-7.96 (m, 2H), 7.57-7.42 (m, 1H), 7.24-7.12 (m, 3H), 6.90 (t, J=10.4 Hz, 1H), 5.14 (t, J=7.0 Hz, 1H), 4.57 (dt, J=12.3, 6.1 Hz, 1H), 3.04 (ddd, J=16.1, 9.1, 3.1 Hz, 1H), 2.78 (dt, J=16.1, 8.1 Hz, 1H), 2.43-2.24 (m, 1H), 1.84 (ddd, J=15.8, 12.8, 8.9 Hz, 1H), 1.27 (t, J=5.8 Hz, 6H), 0.86-0.61 (m, 9H), 0.06-0.14 (m, 6H).

5-(5-(1-hydroxy-2,3-dihydro-1H-inden-4-yl)oxazol-2-yl)-2-isopropoxybenzonitrile (Compound 56)

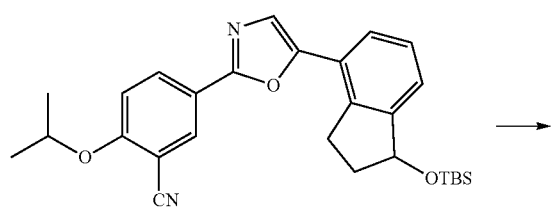

To a solution of 5-(5-(1-(tert-butyldimethylsilyloxy)-2,3-dihydro-1H-inden-4-yl)oxazol-2-yl)-2-isopropoxybenzonitrile INT-33 (350 mg, 0.737 mmol) in anhydrous THF (2 mL) was added a 1M solution of tetrabutylammonium fluoride in THF (3.6 mL, 3.6 mmol) at 0° C. The reaction mixture was allowed to stir at room temperature for 16 h before quenching with brine (5 mL). The THF was removed under vacuum, the residue was diluted with water (5 mL), and the aqueous layer was extracted with EA. The combined extracts were washed with brine, dried over MgSO$_4$, and purified by chromatography to afford 220 mg (63%) of 5-(5-(1-hydroxy-2,3-dihydro-1H-inden-4-yl)oxazol-2-yl)-2-isopropoxybenzonitrile 56 as a light yellow solid. LCMS-ESI (m/z) calculated for C$_{22}$H$_{20}$N$_2$O$_3$: 360.4; found 343.0 [M–OH]$^+$, t$_R$=2.30 min. $^1$H NMR (400 MHz, CDCl$_3$) δ 8.30 (d, J=2.2 Hz, 1H), 8.26 (dd, J=8.9, 2.2 Hz, 1H), 7.75 (d, J=7.6 Hz, 1H), 7.48 (d, J=7.3 Hz, 1H), 7.42 (t, J=7.6 Hz, 1H), 7.10 (d, J=8.9 Hz, 1H), 5.35 (d, J=4.8 Hz, 1H), 4.78 (dt, J=12.2, 6.1 Hz, 1H), 3.30 (ddd, J=16.4, 8.7, 4.8 Hz, 1H), 3.13-2.94 (m, 1H), 2.64 (dddd, J=13.3, 8.4, 7.1, 4.8 Hz, 1H), 2.17-2.08 (m, 1H), 1.86 (s, 1H), 1.60 (s, 1H), 1.46 (dd, J=13.9, 6.0 Hz, 6H).

General Procedure 14. Preparation of Indane Amines Via Chloride Displacement

To a stirring solution of indane alcohol (1 eq) in DCM (1 mL) was added thionyl chloride (2 eq.) at 0° C. The reaction mixture was stirred at room temperature for 3 h. The solvent was evaporated and the crude chloride re-dissolved in dimethyl acetamide (1 mL). Diisopropyl ethylamine (3 eq.) and the appropriate amine (3 eq.) were added and the reaction mixtures were stirred at 70° C. overnight. The reaction mixtures were quenched with water (200 μL) and purified by preparative HPLC.

Compounds 57, 58, and 61-64 were prepared using General Procedure 14.

5-(5-(1-(2-hydroxyethylamino)-2,3-dihydro-1H-inden-4-yl)oxazol-2-yl)-2-isopropoxybenzonitrile (Compound 57)

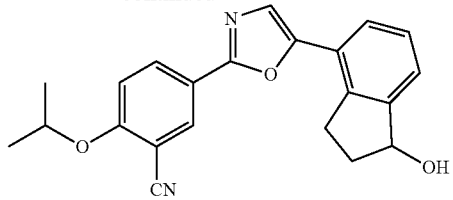

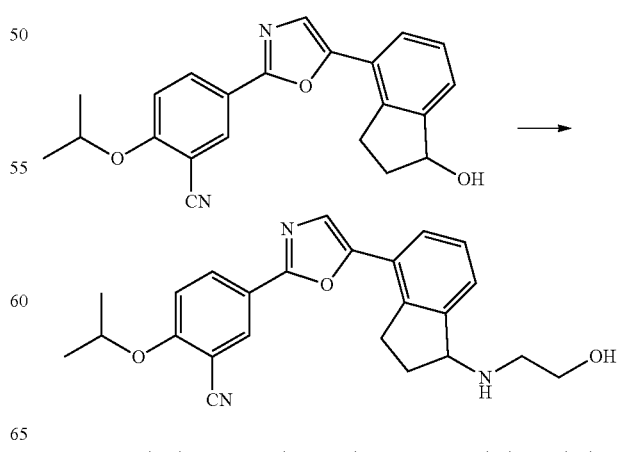

Prepared using General Procedure 14. To a stirring solution of 5-(5-(1-hydroxy-2,3-dihydro-1H-inden-4-yl)oxazol-2- yl)-2-isopropoxybenzonitrile 56 (50 mg, 0.1 mmol) in DCM (3 mL) was added thionyl chloride (25 mg, 0.21 mmol) at 0° C. The reaction mixture was stirred at room temperature for 3 h. The solvent was evaporated and the crude chloride redissolved in dimethyl acetamide (3 mL). Isopropyl ethylamine (40.8 mg, 0.316 mmol) and ethanolamine (19.3 mg, 0.31 mmol) were added and the reaction mixture heated at 70° C. overnight. The reaction mixture was quenched with NaHCO₃ and extracted with EA. The combined organic extracts were washed with brine and then dried over MgSO₄. The product was purified by chromatography (10% MeOH/DCM) to afford 25 mg (60%) of 5-(5-(1-(2-hydroxyethylamino)-2,3-dihydro-1H-inden-4-yl)oxazol-2-yl)-2-isopropoxybenzonitrile 57. LCMS-ESI (m/z) calculated for $C_{24}H_{25}N_3O_3$: 403.5; found 404.1 [M+H]⁺, $t_R$=2.41 min. ¹H NMR (400 MHz, DMSO) δ 8.18 (t, J=2.3 Hz, 1H), 8.08 (dd, J=9.0, 2.3 Hz, 1H), 7.70 (d, J=7.7 Hz, 1H), 7.44 (d, J=17.4 Hz, 1H), 7.42-7.32 (m, 1H), 7.30-7.11 (m, 2H), 4.70 (dt, J=12.2, 6.1 Hz, 2H), 4.39 (s, 1H), 3.40 (t, J=5.0 Hz, 2H), 3.18-2.95 (m, 2H), 2.93-2.75 (m, 1H), 2.73-2.54 (m, 2H), 2.38-2.16 (m, 1H), 1.98-1.78 (m, 1H), 1.15 (d, J=6.0 Hz, 61-1). ¹³C NMR (101 MHz, CDCl₃) δ 161.35, 159.17, 151.04, 146.60, 139.78, 132.16, 127.43, 125.59, 125.07, 123.99, 120.49, 116.10, 113.90, 103.77, 72.60, 62.95, 61.51, 48.70, 33.27, 31.29, 29.91, 22.02.

5-(5-(1-((R)-1-hydroxypropan-2-ylamino)-2,3-dihydro-1H-inden-4-yl)oxazol-2-yl)-2-isopropoxybenzonitrile (Compound 58)

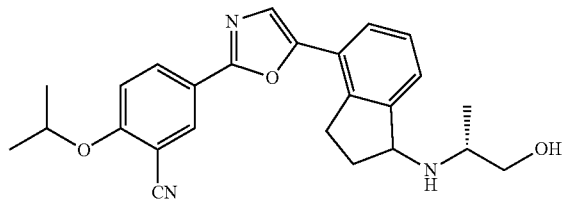 [SMILES: CC(C)Oc1ccc(-c2ncc(-c3cccc4c3CCC4N[C@H](C)CO)o2)cc1C#N]

Prepared using General Procedure 14. LCMS-ESI (m/z) calculated for: $C_{25}H_{27}N_3O_3$: 417.5; found 418.4 [M+H]⁺, $t_R$=2.49 min.

(R)-N-((R)-4-bromo-2,3-dihydro-1H-inden-1-yl)-2-methylpropane-2-sulfinamide (INT-34)

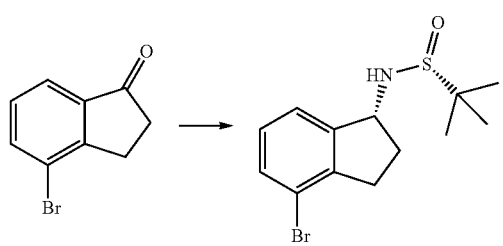 [SMILES: O=C1CCc2c(Br)cccc21 ; CC(C)(C)[S@@](=O)N[C@@H]1CCc2c(Br)cccc21]

To a stirring solution of 4-bromo-2,3-dihydro-1H-inden-1-one (5.0 g, 23.6 mmol) and (R)-2-methylpropane-2-sulfinamide (3.15 g, 26.0 mmol) in toluene (40 mL) was added titanium tetraethoxide (8.1 g, 35.5 mmol) and the reaction mixture was heated at 60° C. for 18 h under N₂. To this mixture was added THF (40 mL) and the resulting solution was cooled to −78° C. Sodium borohydride (3.5 g, 94.7 mmol) was added in one portion. The reaction mixture was stirred at −78° C. for 15 min, and then warmed to room temperature and stirred at this temperature for 2 h. The reaction mixture was cooled to 0° C. before quenching with brine and sodium potassium-tartrate. EA was added and the mixture was stirred at room temperature overnight during which time Ti salts precipitated. The organic layers were decanted, and washed successively with saturated NH₄Cl, water, and brine. The organic layers were dried over MgSO₄, filtered through a pad of MgSO₄, and concentrated to produce (R)-N-((R)-4-bromo-2,3-dihydro-1H-inden-1-yl)-2-methylpropane-2-sulfinamide INT-34 as a solid (3.14 g, 42%) which was used in the next step without purification. LCMS-ESI (m/z) calculated $C_{13}H_{18}BrNOS$: 317.3; found 318.0 [M+H]⁺, $t_R$=3.59 min. ¹H NMR (400 MHz, CDCl₃) δ 7.46 (d, J=7.5, 1H), 7.34 (d, J=7.9, 1H), 7.05 (t, J=7.7, 1H), 4.96-4.77 (m, 1H), 3.39 (d, J=6.8, 1H), 3.06-2.86 (m, 1H), 2.82-2.60 (m, 1H), 2.50-2.29 (m, 1H), 2.05-1.81 (m, 1H), 1.16 (s, 9H).

(S)-N-((S)-4-bromo-2,3-dihydro-1H-inden-1-yl)-2-methylpropane-2-sulfinamide INT-35 can be made in an analogous fashion using (S)-2-methylpropane-2-sulfinamide.

(R)-4-bromo-2,3-dihydro-1H-inden-1-amine (INT-36)

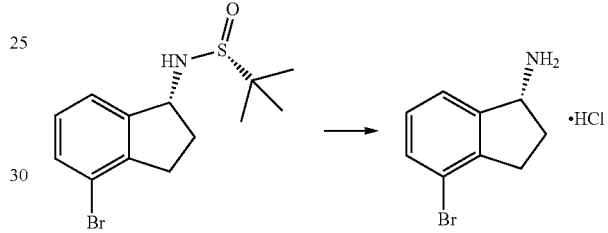

To crude (R)-N-((R)-4-bromo-2,3-dihydro-1H-inden-1-yl)-2-methylpropane-2-sulfinamide INT-34 (3.14 g, 9.9 mol) in MeOH (10 mL) was added 4N HCl in dioxane (7.5 mL, 30 mmol) and the resulting yellow suspension was stirred at room temperature for 2 h. The crude reaction mixture diluted with MeOH (5 mL), cooled to 0° C., and filtered to remove Ti by-products. The filtrate was concentrated and the resulting solid refluxed in acetonitrile (60 mL) for 30 min and then cooled to 0° C. The resulting white solid was collected to produce the HCl salt of (R)-4-bromo-2,3-dihydro-1H-inden-1-amine INT-36 (1.55 g, 63%) which was used in the next step without purification. LCMS-ESI (m/z) calculated for $C_9H_{10}BrN$: 212.1; found 197.0 [M−NH]⁺, $t_R$=0.75 min. ¹H NMR (400 MHz, DMSO) δ 8.60 (s, 1H); 7.67 (d, J=7.5 Hz, 1H), 7.57 (d, J=7.9 Hz, 1H), 7.39-7.07 (m, 1H), 4.81 (dd, J=7.9, 5.6 Hz, 1H), 3.25-2.64 (m, 3H), 2.59-2.32 (m, 1H), 2.21-1.69 (m, 1H).

(S)-4-bromo-2,3-dihydro-1H-inden-1-amine INT-37 can be made in an analogous fashion from (S)-N-((S)-4-bromo-2,3-dihydro-1H-inden-1-yl)-2-methylpropane-2-sulfinamide INT-35.

(R)-tert-butyl 4-bromo-2,3-dihydro-1H-inden-1-ylcarbamate (INT-38)

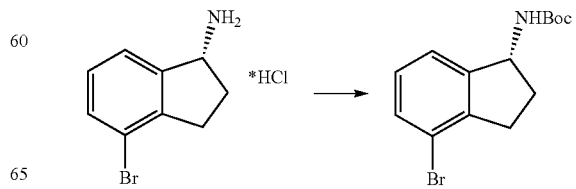

To crude (R)-4-bromo-2,3-dihydro-1H-inden-1-amine HCl INT-36 (1.55 g, 6.2 mmol) in DCM (10 mL) at 0° C. was added TEA (1.38 g, 13.7 mmol) followed by Boc anhydride (1.49 g, 6.8 mmol) and the reaction mixture stirred at room temperature overnight. The reaction mixture was washed with brine, and the organic layers were dried over MgSO$_4$ and filtered. The product was purified by chromatography (EA/hexanes) to afford (R)-tert-butyl 4-bromo-2,3-dihydro-1H-inden-1-ylcarbamate INT-38 (1.63 g, 84%) as an off-white solid. LCMS-ESI (m/z) calculated for C$_{14}$H$_{18}$BrNO$_2$: 312.20; found 197.0 [M–NHBoc]$^+$, t$_R$=3.97 min. $^1$H NMR (400 MHz, CDCl$_3$) δ 7.31 (d, J=7.9 Hz, 1H), 7.23-7.13 (m, 1H), 7.02 (t, J=7.7 Hz, 1H), 5.30-5.07 (m, 1H), 4.69 (d, J=7.5 Hz, 1H), 2.93 (ddd, J=16.5, 9.0, 3.4 Hz, 1H), 2.75 (dt, J=16.5, 8.2 Hz, 1H), 2.60-2.43 (m, 1H), 1.73 (dq, J=13.1, 8.4 Hz, 1H), 1.41 (s, 9H).

(S)-tert-butyl 4-bromo-2,3-dihydro-1H-inden-1-ylcarbamate INT-39 can be made in an analogous fashion from (S)-4-bromo-2,3-dihydro-1H-inden-1-amine INT-37.

(R)-tert-butyl 4-(4,4,5,5-tetramethyl-1,3,2-dioxaborolan-2-yl)-2,3-dihydro-1H-inden-1-ylcarbamate (INT-40)

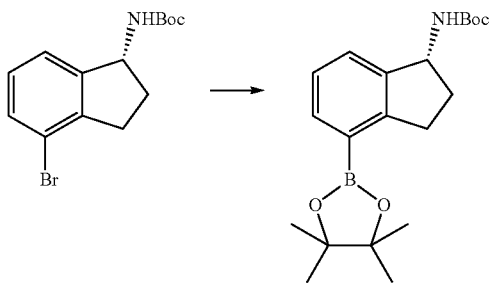 [SMILES: CC(C)(C)OC(=O)N[C@@H]1CCc2c(Br)cccc21 ; CC(C)(C)OC(=O)N[C@@H]1CCc2c(B3OC(C)(C)C(C)(C)O3)cccc21]

A solution of (R)-tert-butyl 4-bromo-2,3-dihydro-1H-inden-1-ylcarbamate INT-38 (300 mg, 0.96 mmol) and 4,4,4',4',5,5,5',5'-octamethyl-2,2'-bi(1,3,2-dioxaborolane) (268 mg, 1.0 mmol), potassium acetate (283 mg, 2.88 mmol) in anhydrous 1,4-dioxane (5 mL) was degassed by passing N$_2$ through the solution for 5 min. PdCl$_2$(dppf).DCM (157 mg, 0.19 mmol) was added and the reaction mixture was heated at 85° C. overnight. The solvent was removed under vacuum and the residue dissolved in EA (10 mL) and filtered through celite to remove the solids. The filtrate was washed with water and brine, dried over MgSO$_4$, and purified by chromatography (EA/hexanes) to afford (R)-tert-butyl 4-(4,4,5,5-tetramethyl-1,3,2-dioxaborolan-2-yl)-2,3-dihydro-1H-inden-1-ylcarbamate INT-40 (265 mg, 77%) as white semi-solid. LCMS-ESI (m/z) calculated for C$_{20}$H$_{30}$BNO$_4$: 359.3; found 383.0 [M+Na]$^+$, t$_R$=4.26 min. $^1$H NMR (400 MHz, CDCl$_3$) δ 7.71 (d, J=7.3 Hz, 1H), 7.42 (t, J=7.9 Hz, 1H), 7.24 (dd, J=9.7, 5.2 Hz, 1H), 5.19 (dd, J=15.9, 7.9 Hz, 1H), 4.72 (d, J=8.5 Hz, 1H), 3.28 (ddd, J=17.0, 8.8, 3.6 Hz, 1H), 2.99 (dt, J=16.8, 8.4 Hz, 1H), 2.69-2.44 (m, 1H), 1.77 (ddd, J=16.4, 12.8, 8.6 Hz, 1H), 1.51 (s, 9H), 1.39-1.31 (m, 12H).

(S)-tert-butyl 4-(4,4,5,5-tetramethyl-1,3,2-dioxaborolan-2-yl)-2,3-dihydro-1H-inden-1-ylcarbamate INT-41 can be made in an analogous fashion from (S)-tert-butyl 4-bromo-2,3-dihydro-1H-inden-1-ylcarbamate INT-39.

(R)-tert-butyl 4-(2-(3-cyano-4-isopropoxyphenyl)oxazol-5-yl)-2,3-dihydro-1H-inden-1-ylcarbamate (INT-42)

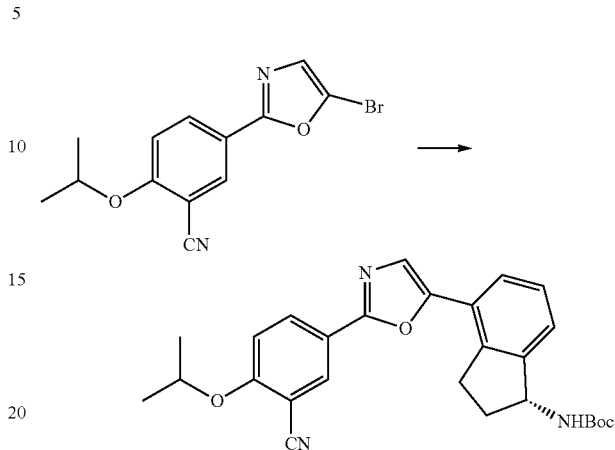

Prepared using General Procedure 13. A 20 mL microwave vial was charged with (R)-tert-butyl 4-(4,4,5,5-tetramethyl-1,3,2-dioxaborolan-2-yl)-2,3-dihydro-1H-inden-1-ylcarbamate INT-32 (58.4 mg, 0.16 mmol), 5-(5-bromooxazol-2-yl)-2-isopropoxybenzonitrile INT-40 (50 mg, 0.16 mmol), potassium carbonate (68 mg, 0.5 mmol) and a 3:1 mixture of dimethylethylene glycol/H$_2$O (2 mL). The reaction mixture was degassed by bubbling N$_2$ gas through the stirring solution for 10 min. Pd(PPh$_3$)$_4$ ((3.9 mg, 0.004 mmol) was added and the solution degassed for additional 2 min. The vial was subjected to microwave irradiation at 100° C. for 30 min. The solvent was removed and the residue dissolved in EA (10 mL), washed with brine, and then dried over MgSO$_4$. The product was purified by chromatography (EA/hexanes) to afford 50 mg (67%) of (R)-tert-butyl 4-(2-(3-cyano-4-isopropoxyphenyl)oxazol-5-yl)-2,3-dihydro-1H-inden-1-ylcarbamate INT-42 as an off-white solid. LCMS-ESI (m/z) calculated for C$_{27}$H$_{29}$N$_3$O$_4$: 459.5; found 460.2 [M+H]$^+$, t$_R$=4.1 min. $^1$H NMR (400 MHz, CDCl$_3$) δ 8.32-8.03 (m, 2H), 7.60 (dd, J=8.6, 4.1 Hz, 1H), 7.32-7.22 (m, 3H), 7.00 (d, J=8.9 Hz, 1H), 5.19 (dd, J=15.5, 7.5 Hz, 1H), 4.82-4.56 (m, 2H), 3.12 (ddd, J=16.3, 9.0, 3.5 Hz, 1H), 2.95 (dt, J=16.3, 8.1 Hz, 1H), 2.70-2.51 (m, 1H), 1.83 (dq, J=13.1, 8.2 Hz, 1H), 1.43 (s, 9H), 1.41-1.35 (m, 6H).

(S)-tert-butyl 4-(2-(3-cyano-4-isopropoxyphenyl)oxazol-5-yl)-2,3-dihydro-1H-inden-1-ylcarbamate INT-43 can be made in an analogous fashion from (S)-tert-butyl 4-(4,4,5,5-tetramethyl-1,3,2-dioxaborolan-2-yl)-2,3-dihydro-1H-inden-1-ylcarbamate INT-41.

(R)-5-(5-(1-amino-2,3-dihydro-1H-inden-4-yl)oxazol-2-yl)-2-isopropoxy-benzonitrile hydrochloride (Compound 59)

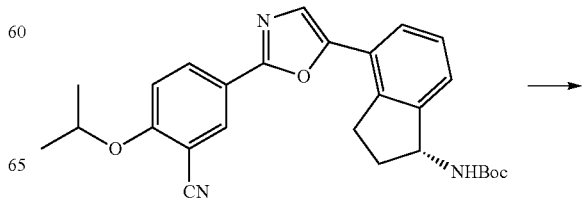

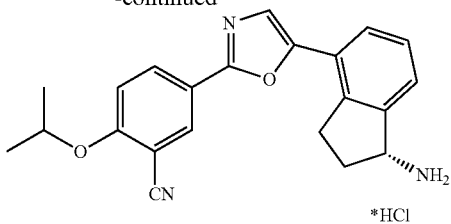

To a stirring solution of (R)-tert-butyl 4-(2-(3-cyano-4-isopropoxyphenyl)oxazol-5-yl)-2,3-dihydro-1H-inden-1-ylcarbamate INT-42 (48 mg, 0.1 mmol) in 1,4-dioxane (1 mL) was added a 4N HCl solution in 1,4-dioxane (1 mL). The reaction mixture was heated at 55-65° C. for 48 h. The cooled reaction mixture was diluted with Et$_2$O (10 mL). The resulting solid was collected and dried under high vacuum to yield 32 mg (78%) of (R)-5-(5-(1-amino-2,3-dihydro-1H-inden-4-yl)oxazol-2-yl)-2-isopropoxybenzonitrile hydrochloride 59 as a white solid. LCMS-ESI (m/z) calculated for C$_{22}$H$_{21}$N$_3$O$_2$: 359.4; found 343.1 [M–NH$_2$]$^+$, t$_R$=2.40 min. $^1$H NMR (400 MHz, DMSO) δ 8.55 (br s, 2H), 8.43 (dd, J=6.5, 2.4 Hz, 1H), 8.32 (ddd, J=6.7, 6.1, 2.9 Hz, 1H), 8.00 (t, J=13.5 Hz, 1H), 7.72 (s, 1H), 7.66 (d, J=7.5 Hz, 1H), 7.49 (dd, J=8.5, 6.3 Hz, 2H), 4.93 (dt, J=12.1, 6.0 Hz, 1H), 4.81 (s, 1H), 3.43-3.25 (m, 1H), 3.23-3.04 (m, 1H), 2.67-2.55 (m, 1H), 2.11 (ddd, J=14.2, 9.0, 5.9 Hz, 1H), 1.36 (dd, J=13.8, 7.0 Hz, 6H).

(S)-5-(5-(1-amino-2,3-dihydro-1H-inden-4-yl)oxazol-2-yl)-2-isopropoxybenzonitrile hydrochloride INT-44 can be made in an analogous fashion from (S)-tert-butyl 4-(2-(3-cyano-4-isopropoxyphenyl)oxazol-5-yl)-2,3-dihydro-1H-inden-1-ylcarbamate INT-43.

1-oxo-2,3-dihydro-1H-indene-4-carbonitrile (INT-45)

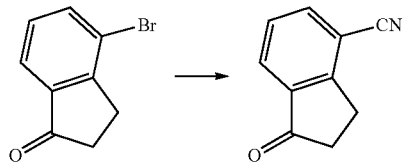 [SMILES: O=C1CCc2c(Br)cccc21 ; N#Cc1cccc2c1CCC2=O]

To a stirring solution of 4-bromo-2,3-dihydro-1H-inden-1-one (100.0 g, 0.48 mol) in 150 mL of 1-methyl-2-pyrrolidine (NMP) was added zinc cyanide (111.8 g, 0.95 mol) and tetrakis(triphenylphosphine)palladium [Pd(PPh$_3$)$_4$] (2.75 g, 0.024 mol). The solution was degassed with N$_2$ and the reaction mixture heated at 95° C. for 7 h. Upon cooling, the reaction mixture was poured onto ice water (3.5 L). The compound and inorganic Zn salts precipitated. The solid was collected and partitioned between DCM and water. The organic layers were filtered to remove the Zn salts, and the filtrate was concentrated and crystallized from a 4:1 mixture of EtOH and MeOH (400 mL) to give 45.5 g (60%) of 1-oxo-2,3-dihydro-1H-indene-4-carbonitrile INT-45 as a light yellow solid. LCMS-ESI (m/z) calculated for C$_{10}$H$_7$NO: 157.2; found 158.1 [M+H]$^+$, t$_R$=2.67 min. $^1$H NMR (400 MHz, CDCl$_3$) δ 8.00-7.90 (m, 1H), 7.86 (dd, J=7.5, 1.1, 1H), 7.50 (t, J=7.6, 1H), 3.40-3.19 (m, 2H), 2.90-2.61 (m, 2H). $^{13}$C NMR (101 MHz, CDCl$_3$) δ 204.70, 157.90, 138.38, 137.88, 128.44, 128.28, 116.31, 111.70, 36.01, 25.49.

(±)-1-hydroxy-2,3-dihydro-1H-indene-4-carbonitrile (INT-46)

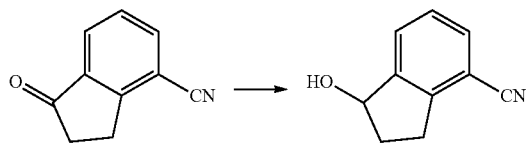 [SMILES: N#Cc1cccc2c1CCC2=O ; N#Cc1cccc2c1CCC2O]

To a stirring suspension of 1-oxo-2,3-dihydro-1H-indene-4-carbonitrile INT-45 (1.2 g, 7.64 mmol) and silica gel (catalytic) in EtOH at 0° C. was added NaBH$_4$ (237.2 mg, 7.64 mmol). The reaction was allowed to warm to room temperature and stirred for 2 h. The solvent was removed under reduced pressure, and the product was purified by chromatography (EA/hexane) to afford 1.02 g (82%) of 1-hydroxy-2,3-dihydro-1H-indene-4-carbonitrile INT-46 as a white solid. LCMS-ESI (m/z) calculated for C$_{10}$H$_9$NO; 159.2; found 160.1 [M+H]$^+$, t$_R$=2.39 min.

N,1-dihydroxy-2,3-dihydro-1H-indene-4-carboximidamide (INT-47)

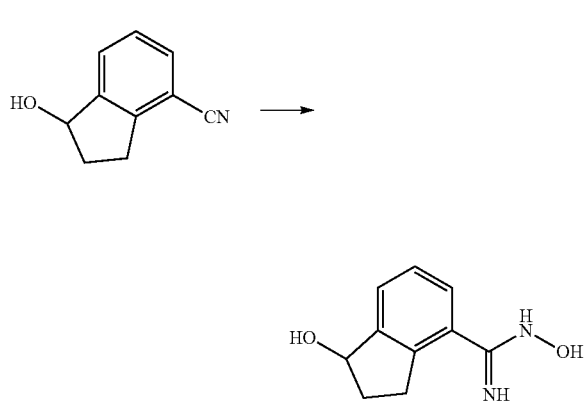

Prepared using General Procedure 1. To hydroxylamine hydrochloride (0.87 g, 12.5 mmol) and sodium carbonate (1.32 g, 12.5 mmol) in EtOH (20 mL) was added 1-hydroxy-2,3-dihydro-1H-indene-4-carbonitrile INT-46 (1.80 g, 11.3 mmol) in one portion and the solution was heated to reflux. After 16 h, the reaction was cooled and filtered to remove the solids. The EtOH was removed and the compound was purified by chromatography (MeOH/DCM) to give 1.74 g (90%) of N,1-dihydroxy-2,3-dihydro-1H-indene-4-carboximidamide INT-47 as a white foam. LCMS-ESI (m/z) calculated for C$_{10}$H$_{12}$N$_2$O$_2$: 192.1; found: 193.1 [M+H]$^+$, t$_R$=0.56 min. $^1$H NMR (400 MHz, MeOD) δ 10.30 (s, 1H), 9.97 (s, 1H), 7.72-7.58 (m, 1H), 7.46-7.37 (m, 2H), 5.22 (t, J=6.5, 1H), 3.17-3.03 (m, 1H), 2.99-2.83 (m, 1H), 2.49 (dddd, J=11.4, 8.0, 7.0, 4.4, 1H), 2.02-1.88 (m, 1H).

4-(5-(3,4-diethoxybenzyl)-1,2,4-oxadiazol-3-yl)-2,3-dihydro-1H-inden-1-ol (Compound 60)

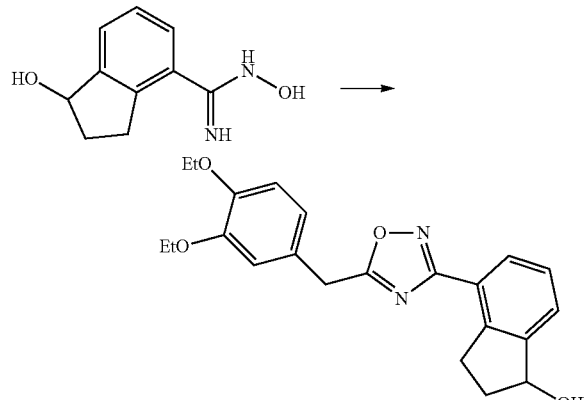

Prepared using General Procedure 2. A solution of 2-(3,4-diethoxyphenyl)acetic acid (180.0 mg, 0.80 mmol) in DMF (3 mL) was treated with HOBt (197.8 mg, 1.46 mmol) and EDC (207.3 mg, 1.08 mmol) at room temperature. The reaction was stirred for 2 h until the complete formation of the HOBt-acid complex. N-1-dihydroxy-2,3-dihydro-1H-indene-4-carboximidamide INT-47 (185.1 mg, 0.96 mmol) was added and the mixture was stirred at room temperature for 2 h and then heated to 80° C. for 16 h. The reaction mixture was diluted with NaHCO$_3$ and extracted with EA. The organic phase was dried over MgSO$_4$ and crude product was purified by chromatography (EA/hexanes) to produce 4-(5-(3,4-diethoxybenzyl)-1,2,4-oxadiazol-3-yl)-2,3-dihydro-1H-inden-1-ol 60 (190 mg, 62%) as an off-white solid. LCMS-ESI (m/z) calculated for C$_{22}$H$_{24}$N$_2$O$_4$: 380.1; found 381.1 [M+H]$^+$, t$_R$=3.45 min. $^1$H NMR (400 MHz, CDCl$_3$) δ 8.02-7.86 (m, 1H), 7.46 (d, J=7.5 Hz, 1H), 7.29 (t, J=7.6 Hz, 1H), 6.81 (ddd, J=21.0, 13.6, 5.1 Hz, 3H), 5.21 (t, J=5.6 Hz, 1H), 4.13 (s, 2H), 4.01 (dq, J=14.1, 7.0 Hz, 4H), 3.34 (ddd, J=17.5, 8.7, 4.6 Hz, 1H), 3.16-2.92 (m, 1H), 2.53-2.38 (m, 1H), 1.91 (qdd, J=8.7, 6.6, 5.5 Hz, 2H), 1.36 (td, J=7.0, 4.6 Hz, 6H).

2-((4-(5-(3,4-diethoxybenzyl)-1,2,4-oxadiazol-3-yl)-2,3-dihydro-1H-inden-1-yl)amino)ethanol (Compound 61)

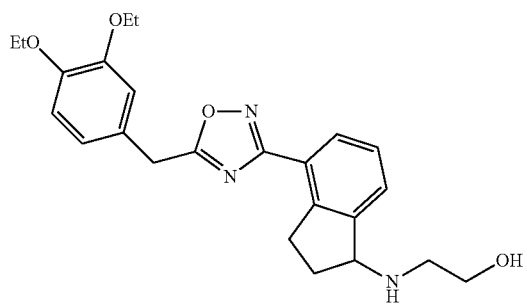 [SMILES: CCOc1ccc(Cc2nc(-c3cccc4c3CCC4NCCO)no2)cc1OCC]

Prepared using General Procedure 14 using 4-(5-(3,4-diethoxybenzyl)-1,2,4-oxadiazol-3-yl)-2,3-dihydro-1H-inden-1-ol 60 and 2-aminoethanol.

(2R)-2-((4-(5-(3,4-diethoxybenzyl)-1,2,4-oxadiazol-3-yl)-2,3-dihydro-1H-inden-1-yl)amino)propan-1-ol (Compound 62)

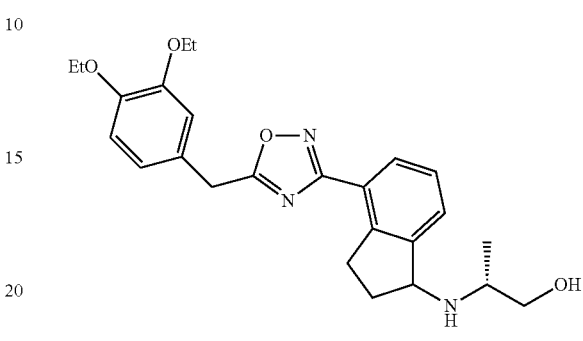

Prepared using General Procedure 14 from 4-(5-(3,4-diethoxybenzyl)-1,2,4-oxadiazol-3-yl)-2,3-dihydro-1H-inden-1-ol 60 and (R)-2-aminopropan-1-ol.

4-(5-(3,4-diethoxybenzyl)-1,2,4-oxadiazol-3-yl)-N-(2-(methylsulfonyl)ethyl)-2,3-dihydro-1H-inden-1-amine (Compound 63)

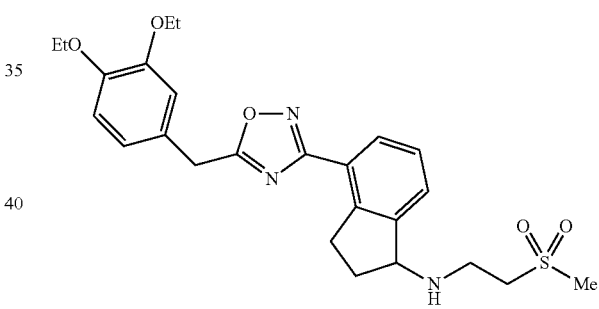

Prepared using General Procedure 14 from 4-(5-(3,4-diethoxybenzyl)-1,2,4-oxadiazol-3-yl)-2,3-dihydro-1H-inden-1-ol 60 and 2-(methylsulfonyl)ethanamine.

2-((4-(5-(3,4-diethoxybenzyl)-1,2,4-oxadiazol-3-yl)-2,3-dihydro-1H-inden-1-yl)amino)-N-methylethanesulfonamide (Compound 64)

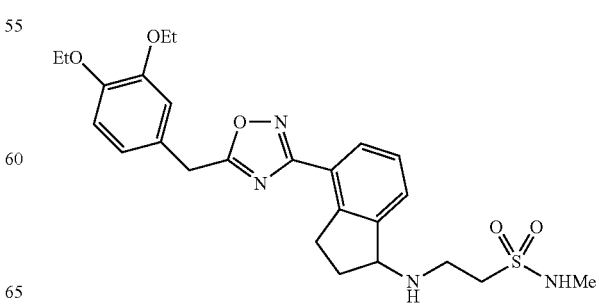

Prepared using General Procedure 14 from 4-(5-(3,4-diethoxybenzyl)-1,2,4-oxadiazol-3-yl)-2,3-dihydro-1H-inden-1-ol 60 and 2-amino-N,N-dimethylethanesulfonamide.

(R)-N-(4-cyano-2,3-dihydro-1H-indene-1-ylidene)-2-methylpropane-2-sulfinamide (INT-48)

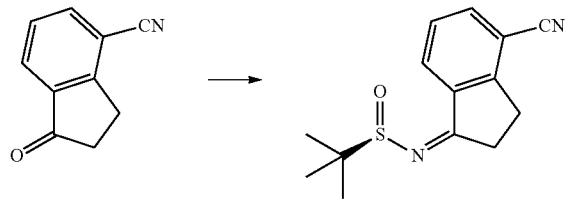 [SMILES: N#Cc1cccc2c1CCC2=O ; CC(C)(C)[S@@](=O)/N=C1/CCc2c(C#N)cccc21]

To 1-oxo-2,3-dihydro-1H-indene-4-carbonitrile INT-45 (42.5 g, 0.27 mol) and (R)-2-methylpropane-2-sulfinamide (36.0 g, 0.30 mol) in toluene (530 mL) was added titanium tetraethoxide (84.1 mL, 92.5 g, 0.40 mol) and the reaction mixture was heated at 60° C. for 12 h under $N_2$. The crude (R)-N-(4-cyano-2,3-dihydro-1H-indene-1-ylidene)-2-methylpropane-2-sulfinamide INT-48 vas used directly in the next experiment. LCMS-ESI (m/z) calculated for $C_{14}H_{16}N_2OS$: 260.3; found 261.1 [M+H]$^+$, $t_R$=3.19 min.

(R)-N-((R)-4-cyano-2,3-dihydro-1H-inden-1-yl)-2-methylpropane-2-sulfinamide (INT-49)

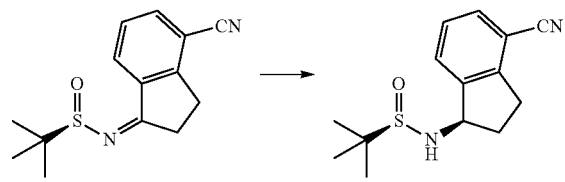 [SMILES: CC(C)(C)[S@@](=O)/N=C1/CCc2c(C#N)cccc21 ; CC(C)(C)[S@@](=O)N[C@@H]1CCc2c(C#N)cccc21]

To a flask containing the crude suspension of (R)-N-(4-cyano-2,3-dihydro-1H-indene-1-ylidene)-2-methylpropane-2-sulfinamide INT-48 under $N_2$ was added THF (1.0 L) and the reaction mixture cooled to −78° C. Sodium borohydride (40.9 g, 1.08 mol) was added portion-wise over 30 mins. (The internal temperature did not rise during the addition). The reaction mixture was stirred at −78° C. for 30 mins, half out of the bath for 30 mins, then warmed to 0° C. over 1 h. The 0° C. reaction mixture was placed in an ice bath and quenched with brine (100 mL) followed by saturated sodium potassium tartrate (420 mL) and the Ti salts precipitated. The reaction mixture was diluted with EA (1.5 L) and stirred at room temperature overnight. The organic layers were decanted and washed successively with saturated $NH_4Cl$, water, and brine. The organic layers were dried over $MgSO_4$ and filtered through a pad of $MgSO_4$. The filtrate was concentrated to produce 52.9 g of crude (R)-N-((R)-4-cyano-2,3-dihydro-1H-inden-1-yl)-2-methylpropane-2-sulfinamide INT-49 as a brown oil, which was used directly in the next step. LCMS-ESI (m/z) calculated for $C_{14}H_{18}N_2OS$: 262.3; found 263.1 [M+H]$^+$, $t_R$=2.99 min. $^1$H NMR (400 MHz, CDCl$_3$) δ 7.89 (d, J=7.7, 1H), 7.56 (t, J=6.8, 1H), 7.36 (t, J=7.7, 1H), 4.97 (q, J=7.5, 1H), 3.50 (d, J=7.6, 1H), 3.22 (ddd, J=16.9, 8.8, 3.9, 1H), 3.01 (dt, J=22.4, 6.9, 1H), 2.70-2.53 (m, 1H), 2.15-1.95 (m, 1H), 1.33-1.20 (m, 9H).

(R)-1-amino-2,3-dihydro-1H-indene-1-yl)-4-carbonitrile (INT-50)

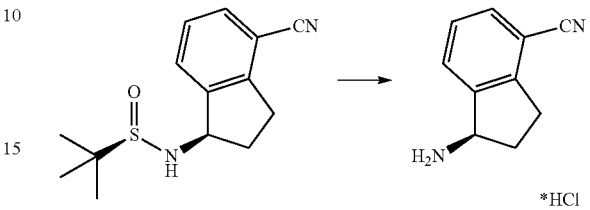

To crude (R)-N-((R)-4-cyano-2,3-dihydro-1H-inden-1-yl)-2-methylpropane-2-sulfinamide INT-49 (52.9 g, 0.20 mol) in MeOH (200 mL) was added 4N HCl in dioxane (152.0 mL, 0.60 mol) and the resulting yellow suspension was stirred at room temperature for 1.5 h. The crude reaction mixture was diluted with MeOH (500 mL) and filtered to remove some Ti by-products. The filtrate was concentrated and the resulting solid was refluxed in acetonitrile (500 mL). The resulting white solid was collected to produce 13.0 g (31% over 3 steps) of the HCl salt of (R)-1-amino-2,3-dihydro-1H-inden-1-yl)-4-carbonitrile INT-50. LCMS-ESI (m/z) calculated for $C_{10}H_{10}N_2$: 158.2; found 142.0 [M−NH$_2$]$^+$, $t_R$=0.84 min. $^1$H NMR (400 MHz, DMSO) δ 8.61 (s, 3H), 7.96 (d, J=7.7, 1H), 7.83 (d, J=7.5, 1H), 7.52 (t, J=7.7, 1H), 4.80 (s, 1H), 3.23 (ddd, J=16.6, 8.7, 5.2, 1H), 3.05 (ddd, J=16.6, 8.6, 6.3, 1H), 2.62-2.51 (m, 1H), 2.15-2.01 (m, 1H). $^{13}$C NMR (101 MHz, DMSO) δ 148.09, 141.15, 132.48, 130.32, 127.89, 117.27, 108.05, 54.36, 39.08, 29.64. The free base can be prepared by extraction with 1N $NaHCO_3$ and DCM. LCMS-ESI (m/z) calculated for $C_{10}H_{10}N_2$: 158.2; found 142.0 [M−NH$_2$]$^+$, $t_R$=0.83 min. $^1$H NMR (400 MHz, CDCl$_3$) δ 7.52-7.38 (m, 2H), 7.23 (dd, J=17.4, 9.8, 1H), 4.35 (t, J=7.6, 1H), 3.11 (ddd, J=16.8, 8.7, 3.2, 1H), 2.89 (dt, J=16.9, 8.5, 1H), 2.53 (dddd, J=12.8, 8.1, 7.3, 3.2, 1H), 1.70 (dtd, J=12.8, 8.8, 8.0, 1H). $^{13}$C NMR (101 MHz, DMSO) δ 150.16, 146.67, 130.19, 128.74, 127.38, 117.77, 107.42, 56.86, 38.86, 29.14. Chiral HPLC: (R)-1-amino-2,3-dihydro-1H-inden-1-yl)-4-carbonitrile was eluted using 5% EtOH in hexanes, plus 0.05% TEA: 95% ee, $t_R$=23.02 min.

The (S)-enantiomer INT-51 was prepared in an analogous sequence (INT-48, INT-49, and INT-50) using (S)-2-methylpropane-2-sulfinamide in the first step. $t_R$ for (S)-enantiomer=20.17 min.

(R)-tert-butyl 4-cyano-2,3-dihydro-1H-inden-1-ylcarbamate (INT-52)

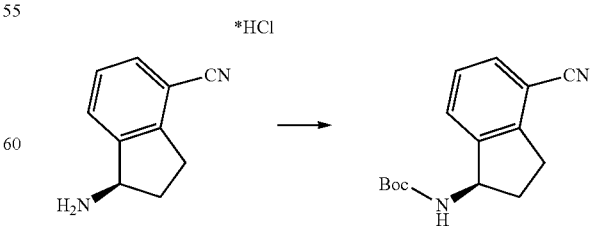

To (R)-1-amino-2,3-dihydro-1H-inden-1-yl)-4-carbonitrile HCl INT-50 (11.6 g, 59.6 mmol) in DCM (100 mL) at 0° C. was added TEA (12.0 mL, 131.0 mmol). To the resulting solution was added a solution of Boc anhydride (14.3 g, 65.6 mmol) in DCM (30 mL) and the reaction mixture stirred at room temperature for 1.5 h. The reaction mixture was washed with brine, and the organic layers were dried over MgSO$_4$ and filtered. Additional DCM was added to a total volume of 250 mL and Norit (4.5 g) was added. The product was refluxed for 15 nuns and the hot mixture filtered through a pad of celite/silica. The filtrate was concentrated and recrystallized from EA (50 mL) and hexane (150 mL) to produce 12.93 g (84%) of (R)-tert-butyl 4-cyano-2,3-dihydro-1H-inden-1-ylcarbamate INT-52 as an off-white solid. LCMS-ESI (m/z) calculated for C$_{15}$H$_{18}$N$_2$O$_2$: 258.3; found 281.1 [M+Na]$^+$, t$_R$=3.45 min. Elemental Analysis determined for C$_{15}$H$_{18}$N$_2$O$_2$; C calculated=69.74%; found=69.98%. H calculated=7.02%. found=7.14%. N calculated=10.84%; found=10.89%. $^1$H NMR (400 MHz, CDCl$_3$) δ 7.64-7.49 (m, 2H), 7.34 (dt, J=7.7, 3.8, 1H), 5.36-5.20 (m, 1H), 4.78 (d, J=6.8, 1H), 3.20 (ddd, J=16.9, 8.9, 3.3, 1H), 3.02 (dt, J=25.4, 8.4, 1H), 2.82-2.53 (m, 1H), 1.88 (dq, J=13.2, 8.6, 1H), 1.55-1.44 (m, 9H). $^{13}$C NMR (101 MHz, DMSO) δ 155.52, 146.68, 146.32, 130.89, 128.70, 127.63, 117.51, 107.76, 77.98, 55.09, 31.88, 29.11, 28.19. Chiral HPLC: (R)-tert-butyl 4-cyano-2,3-dihydro-1H-inden-1-ylcarbamate was eluted using 2.5% EtOH in hexanes: >99.9% ee, t$_R$=19.36 min.

The (S)-enantiomer INT-53 was prepared in an analogous fashion using (S)-1-amino-2,3-dihydro-1H-indene-1-yl)-4-carbonitrile HCl INT-51. t$_R$ for (S)-enantiomer=28.98 min.

(R)-tert-butyl 4-(N-hydroxycarbamimidoyl)-2,3-dihydro-1H-inden-1-ylcarbamate (INT-54)

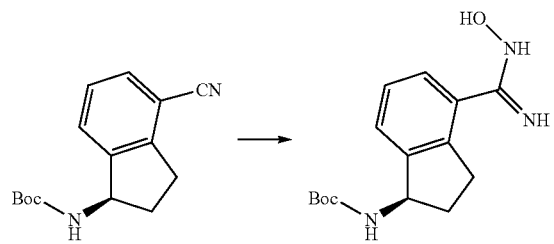 [SMILES: CC(C)(C)OC(=O)N[C@@H]1CCc2c(C#N)cccc21 ; CC(C)(C)OC(=O)N[C@@H]1CCc2c(C(=N)NO)cccc21]

Prepared using General Procedure 1. To (R)-tert-butyl 4-cyano-2,3-dihydro-1H-inden-1-ylcarbamate INT-52 (15.0 g, 58.2 mmol) in EtOH (100 mL) was added hydroxylamine hydrochloride (12.1 g, 174.2 mmol) and TEA (17.6 mL, 174.2 mmol) and the reaction mixture was heated at 85° C. for 2 h. The solvents were removed and the resulting white solid was partitioned between water and DCM. The organic layers were dried over Na$_2$SO$_4$, concentrated, and recrystallized from isopropanol (50 mL) to afford 14.4 g (85%) of (R)-tert-butyl 4-(N-hydroxycarbamimidoyl)-2,3-dihydro-1H-inden-1-ylcarbamate INT-54 as white crystalline solid. LCMS-ESI (m/z) calculated for C$_{15}$H$_{21}$N$_3$O$_3$: 291.4; found 292.1 [M+H]$^+$, t$_R$=2.04 min. $^1$H NMR (400 MHz, DMSO) δ 9.53 (s, 1H), 7.38-7.32 (m, 1H), 7.32-7.12 (m, 3H), 5.68 (s, 2H), 4.97 (q, J=8.5, 1H), 3.07 (ddd, J=16.6, 8.7, 2.6, 1H), 2.86 (dt, J=16.8, 8.4, 1H), 2.30 (ddd, J=12.6, 7.6, 3.6, 1H), 1.75 (dq, J=12.3, 9.0, 1H), 1.44 (s, 9H).

(S)-tert-butyl 4-(N-hydroxycarbamimidoyl)-2,3-dihydro-1H-inden-1-ylcarbamate INT-55 was prepared in an analogous fashion from (R)-tert-butyl 4-cyano-2,3-dihydro-1H-inden-1-ylcarbamate INT-53.

(R)-tert-butyl 4-(5-(3,4-diethoxybenzyl)-1,2,4-oxadiazol-3-yl)-2,3-dihydro-1H-inden-1-ylcarbamate (INT-56)

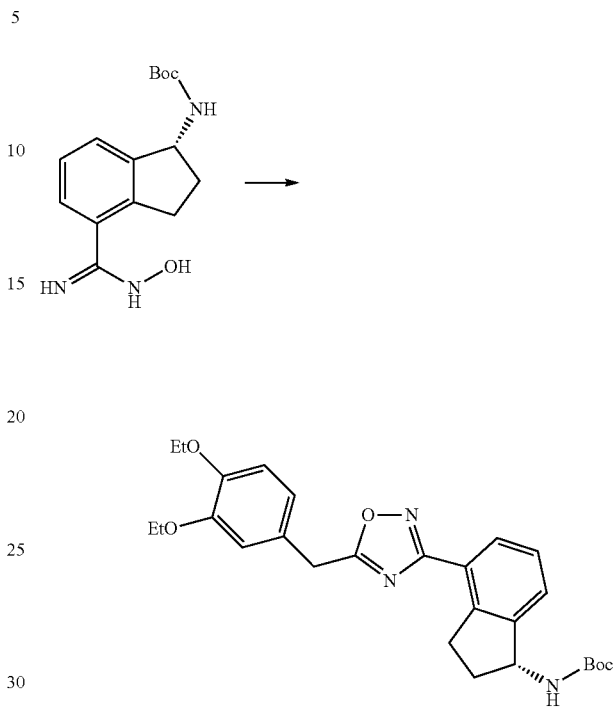

Prepared using General Procedure 2. A solution of 2-(3,4-diethoxyphenyl)acetic acid (150.0 mg, 0.67 mmol) in DMF (3 mL) was treated with HOBt (164.8 mg, 1.22 mmol) and EDC (172.7 mg, 0.9 mmol) at room temperature. The reaction was stirred for 2 h until the complete formation of the HOBt-acid complex. (R)-tert-butyl 4-(N-hydroxycarbamimidoyl)-2,3-dihydro-1H-inden-1-ylcarbamate INT-54 (233.8 mg, 0.8 mmol) was added and stirred at room temperature for 2 h and then mixture was heated to 80° C. for 16 h. The reaction was diluted with NaHCO$_3$ (10 mL) and extracted with EA (3×10 ml). The organic phase was dried over MgSO$_4$ and the crude product was purified by a chromatography (EA/hexanes) to produce (R)-tert-butyl 4-(5-(3,4-diethoxybenzyl)-1,2,4-oxadiazol-3-yl)-2,3-dihydro-1H-inden-1-ylcarbamate INT-56 (187 mg, 58%) as off-white solid and used directly in the next step. LCMS-ESI (m/z) calculated for C$_{27}$H$_{33}$N$_3$O$_5$: 479.2; found 502.2 [M+Na]$^+$, t$_R$=4.11 min. $^1$H NMR (400 MHz, CDCl$_3$) δ 7.91 (d, J=7.6 Hz, 1H), 7.39 (d, J=7.5 Hz, 1H), 7.27 (t, J=7.7 Hz, 1H), 6.81 (ddd, J=20.2, 12.8, 5.1 Hz, 3H), 5.18 (d, J=8.4 Hz, 1H), 4.69 (d, J=8.3 Hz, 1H), 4.15 (d, J=6.1 Hz, 2H), 4.06-3.93 (m, 4H), 3.32 (ddd, J=17.4, 8.8, 3.4 Hz, 1H), 3.14-2.91 (m, 1H), 2.65-2.40 (m, 1H), 1.75 (dq, J=12.9, 8.4 Hz, 1H), 1.36 (ddd, J=40.2, 26.9, 22.6 Hz, 15H).

(S)-tert-butyl 4-(5-(3,4-diethoxybenzyl)-1,2,4-oxadiazol-3-yl)-2,3-dihydro-1H-inden-1-ylcarbamate INT-57 was prepared in an analogous fashion from (R)-tert-butyl 4-(N-hydroxycarbamimidoyl)-2,3-dihydro-1H-inden-1-ylcarbamate INT-55.

(R)-4-(5-(3,4-diethoxybenzyl)-1,2,4-oxadiazol-3-yl)-2,3-dihydro-1H-inden-1-amine hydrochloride (Compound 65)

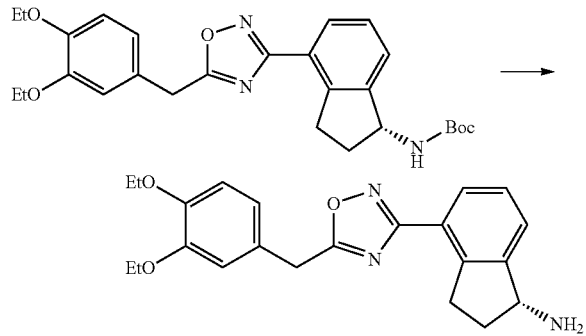

To (R)-tert-butyl 4-(5-(3,4-diethoxybenzyl)-1,2,4-oxadiazol-3-yl)-2,3-dihydro-1H-inden-1-ylcarbamate INT-56 (150 mg, 0.312 mmol) in dioxane (1 mL) was added 4N HCl in dioxane (1 mL). The mixture was stirred at room temperature for 6 h, and product precipitated. The reaction mixture was diluted with Et$_2$O and the solid collected by filtration to produce of (R)-4-(5-(3,4-diethoxybenzyl)-1,2,4-oxadiazol-3-yl)-2,3-dihydro-1H-inden-1-amine hydrochloride 65 (125 mg, 96%) as an off-white solid. LCMS-ESI (m/z): calcd for $C_{22}H_{25}N_3O_3$: 379.2; found 402.1 [M+Na]$^+$, $t_R$=2.38 min. $^1$H NMR (400 MHz, DMSO) δ 8.40 (s, 1H), 8.01 (d, J=7.6 Hz, 1H), 7.78 (d, J=7.2 Hz, 1H), 7.53 (t, J=7.7 Hz, 1H), 7.02 (d, J=2.0 Hz, 1H), 6.90 (dt, J=8.2, 5.1 Hz, 2H), 4.81 (s, 1H), 4.35 (s, 2H), 4.01 (p, J=6.9 Hz, 4H), 3.36 (s, 2H), 3.22-3.04 (m, 1H), 2.55-2.43 (m, 2H), 2.05 (dd, J=14.0, 8.4 Hz, 1H), 1.32 (td, J=7.0, 4.0 Hz, 6H).

(S)-4-(5-(3,4-diethoxybenzyl)-1,2,4-oxadiazol-3-yl)-2,3-dihydro-1H-inden-1-amine hydrochloride INT-58 can be prepared in an analogous fashion from (S)-tert-butyl 4-(5-(3,4-diethoxybenzyl)-1,2,4-oxadiazol-3-yl)-2,3-dihydro-1H-inden-1-ylcarbamate INT-57.

(R)-tert-butyl 2-(tert-butyldimethylsilyloxy)ethyl(4-cyano-2,3-dihydro-1H-inden-1-yl)carbamate (INT-59)

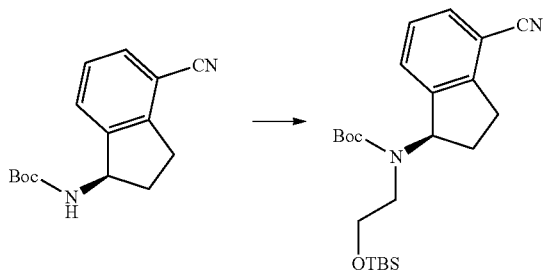 [SMILES: CC(C)(C)OC(=O)N[C@@H]1CCc2c(C#N)cccc21 ; CC(C)(C)OC(=O)N(CCO[Si](C)(C)C(C)(C)C)[C@@H]1CCc2c(C#N)cccc21]

To (R)-tert-butyl 4-cyano-2,3-dihydro-1H-inden-1-ylcarbamate INT-52 (0.700 g, 2.7 mmol) was added anhydrous DMF (10 mL) and the reaction mixture was stirred in a 0° C. ice bath under N$_2$. Sodium hydride (0.541 g, 13.5 mmol) was added and the mixture was stirred at 0° C. for 2 h. After 2 h, (2-bromoethoxy)-tert-butyldimethylsilane (1.43 g, 5.9 mmol) was added and the reaction mixture was allowed to warm to room temperature for 1 h. The reaction was cooled to 0° C. and quenched with MeOH followed by saturated NaHCO$_3$. The mixture was extracted with EA and brine. The combined organic layers were dried over MgSO$_4$, filtered, and concentrated to produce a brown oil. The crude product was purified by silica gel flash chromatography (20% EA/Hexanes) to afford 0.868 g (77%) of (R)-tert-butyl 2-(tert-butyldimethylsilyloxy)ethyl(4-cyano-2,3-dihydro-1H-inden-1-yl)carbamate INT-59 as a yellow oil. LCMS-ESI (m/z) calculated for $C_{23}H_{36}N_2O_3Si$: 416.6; found 317.1 [M+H−Boc]$^+$, $t_R$=4.05 min. $^1$H NMR (400 MHz, (CD$_3$)$_2$SO) δ 7.50 (m, 1H), 7.37 (m, 1H), 7.26 (m, 1H), 5.78 (m, 1H), 4.02 (m, 2H), 3.51 (m, 2H), 3.29 (m, 1H), 2.97 (m, 1H), 2.26 (m, 2H), 1.40 (s, 9H), 0.83 (s, 9H), 0.09 (s, 6H).

(S)-tert-butyl (4-cyano-2,3-dihydro-1H-inden-1-yl)(2-(dimethylamino)-2-oxoethyl)carbamate (INT-60)

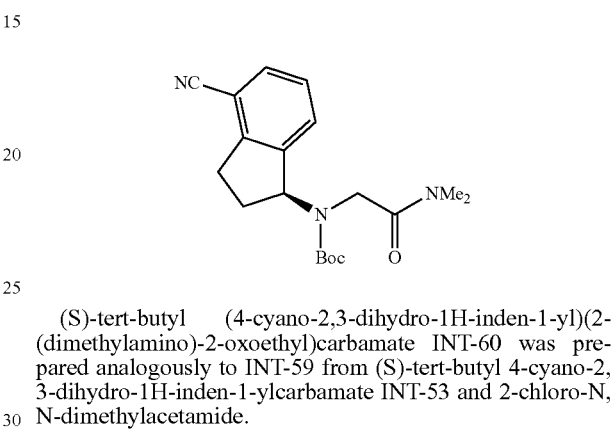

(S)-tert-butyl (4-cyano-2,3-dihydro-1H-inden-1-yl)(2-(dimethylamino)-2-oxoethyl)carbamate INT-60 was prepared analogously to INT-59 from (S)-tert-butyl 4-cyano-2,3-dihydro-1H-inden-1-ylcarbamate INT-53 and 2-chloro-N,N-dimethylacetamide.

(R)-tert-butyl 2-(tert-butyldimethylsilyloxy)ethyl(4-(N-hydroxy-carbamimidoyl)-2,3-dihydro-1H-inden-1-yl)carbamate (INT-61)

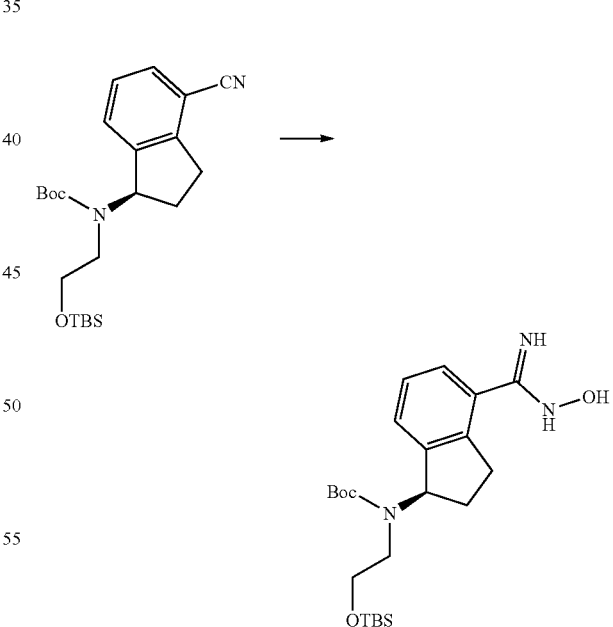

Prepared using General Procedure 1. To (R)-tert-butyl 2-(tert-butyldimethyl silyloxy)ethyl(4-cyano-2,3-dihydro-1H-inden-1-yl)carbamate INT-59 (0.800 g, 1.9 mmol) in EtOH (8 mL) was added hydroxylamine hydrochloride (0.400 g, 5.8 mmol) and Na$_2$CO$_3$ (0.610 g, 5.8) and the reaction mixture was heated at 85° C. for 12 h. Once cooled to room temperature, the reaction mixture was filtered using EtOH to rinse the filter cake. The filtrate was concentrated under reduced pressure and washed with EA and brine. The combined organic layers were dried over MgSO₄, filtered, and concentrated to produce 0.860 g (100%) of (R)-tert-butyl 2-(tert-butyldimethylsilyloxy)ethyl(4-(N-hydroxycarbamimidoyl)-2,3-dihydro-1H-inden-1-yl)carbamate INT-61 as a light yellow oil. LCMS-ESI (m/z) calculated for $C_{23}H_{39}N_3O_4Si$: 449.7; found 350.2 [M+H–Boc]⁺, $t_R$=1.97 min.

(S)-tert-butyl (2-(dimethylamino)-2-oxoethyl)(4-(N-hydroxycarbamimidoyl)-2,3-dihydro-1H-inden-1-yl)carbamate (INT-62)

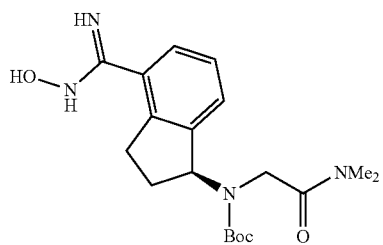 [SMILES: CN(C)C(=O)CN(C(=O)OC(C)(C)C)[C@H]1CCc2c(C(=N)NO)cccc21]

(S)-tert-butyl (2-(dimethylamino)-2-oxoethyl)(4-(N-hydroxycarbamimidoyl)-2,3-dihydro-1H-inden-1-yl)carbamate INT-62 was prepared from (S)-tert-butyl (4-cyano-2,3-dihydro-1H-inden-1-yl)(2-(dimethylamino)-2-oxoethyl)carbamate INT-60 using General Procedure 1 and in an analogous fashion to INT-61.

(R)-tert-butyl 2-(tert-butyldimethylsilyloxy)ethyl(4-(5-(4-phenyl-5-(trifluoromethyl)thiophen-2-yl)-1,2,4-oxadiazol-3-yl)-2,3-dihydro-1H-inden-1-yl)carbamate (INT-63)

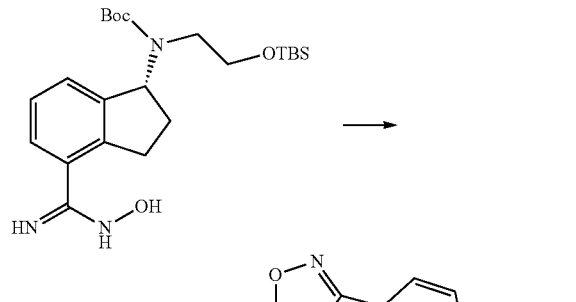

Prepared using General Procedure 2. To a solution of 4-phenyl-5-(trifluoromethyl)thiophene-2-carboxylic acid (0.109 g, 0.4 mmol) in DMF (3.0 mL) was added HOBt (0.088 g, 0.57 mmol) and EDC (0.109 g, 0.57 mmol) at room temperature. The reaction mixture was stirred for 0.5 h until the complete formation of the HOBt-acid complex. (R)-tert-butyl 2-(tert-butyldimethyl silyloxy)ethyl(4-(N-hydroxycarbamimidoyl)-2,3-dihydro-1H-inden-1-yl)carbamate INT-61 (0.200 g, 0.44 mmol) was added and the mixture was stirred at room temperature for 0.5 h until the formation of the intermediate (R)-tert-butyl 2-(tert-butyldimethylsilyloxy)ethyl(4-(N-(4-phenyl-5-(trifluoromethyl)thiophene-2-carbonyloxy)carbamimidoyl)-2,3-dihydro-1H-inden-1-yl) carbamate was observed. The reaction mixture was heated at 85° C. for 4 h. Upon cooling, the mixture was extracted with DCM and brine. The combined organic layers were dried over MgSO₄, filtered, and concentrated under reduced pressure to produce a brown oil. The crude product was purified by silica gel flash chromatography (MeOH/DCM) to yield 0.108 g (40%) of (R)-tert-butyl 2-(tert-butyldimethylsilyloxy)ethyl (4-(5-(4-phenyl-5-(trifluoromethyl)thiophen-2-yl)-1,2,4-oxa-diazol-3-yl)-2,3-dihydro-1H-inden-1-yl)carbamate INT-63 as a light yellow oil. LCMS-ESI (m/z) calculated for $C_{35}H_{42}F_3N_3O_4SSi$: 685.9; found 411.0 [M+H–tert-butyl 2-(tert-butyldimethylsilyloxy)ethylcarbamate]⁺, $t_R$=4.01 min.

(S)-tert-butyl (4-(5-(3,4-diethoxybenzyl)-1,2,4-oxadiazol-3-yl)-2,3-dihydro-1H-inden-1-yl)(2-(dimethylamino)-2-oxoethyl)carbamate (INT-64)

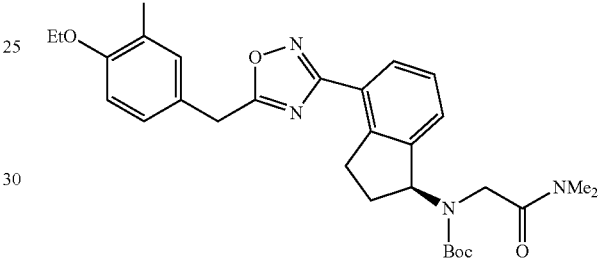

(S)-tert-butyl (4-(5-(3,4-diethoxybenzyl)-1,2,4-oxadiazol-3-yl)-2,3-dihydro-1H-inden-1-yl)(2-(dimethylamino)-2-oxoethyl)carbamate INT-64 was prepared using General Procedure 2, analogously to INT-63, from (S)-tert-butyl (2-(dimethylamino)-2-oxoethyl)(4-(N-hydroxycarbamimidoyl)-2,3-dihydro-1H-inden-1-yl)carbamate INT-62 and 2-(3,4-diethoxyphenyl)acetic acid.

(R)-2-(4-(5-(4-phenyl-5-(trifluoromethyl)thiophen-2-yl)-1,2,4-oxadiazol-3-yl)-2,3-dihydro-1H-inden-1-ylamino)ethanol (Compound 67)

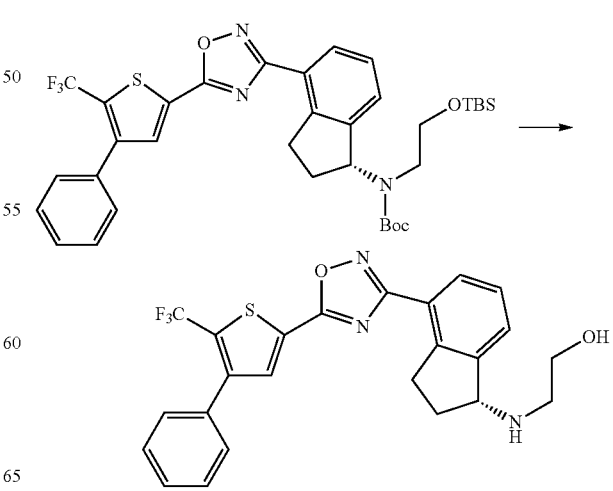

To (R)-tert-butyl 2-(tert-butyldimethylsilyloxy)ethyl(4-(5-(4-phenyl-5-(trifluoromethyl)thiophen-2-yl)-1,2,4-oxadiazol-3-yl)-2,3-dihydro-1H-inden-1-yl)carbamate INT-63 (0.108 g, 0.16 mmol) dissolved in DCM (1.5 mL) was added 2N HCl in ether (1.45 mL, 2.9 mmol). The solution was stirred at room temperature for 12 h. The solvent was removed under a stream of nitrogen and the product dried under vacuum to afford 0.052 g (65%) of (R)-2-(4-(5-(4-phenyl-5-(trifluoromethyl)thiophen-2-yl)-1,2,4-oxadiazol-3-yl)-2,3-dihydro-1H-inden-1-ylamino)ethanol 67 as the HCl salt. LCMS-ESI (m/z): calcd for $C_{24}H_{20}F_3N_3O_2S$: 471.5; found 472.1 [M+H]$^+$, $t_R$=7.43 min (Method 2). $^1$H NMR (400 MHz, CDCl$_3$) δ 9.62 (s, 1H), 8.19 (d, J=7.6, 1H), 8.03 (d, J=7.5, 1H), 7.87 (t, J=1.5, 1H), 7.53-7.40 (m, 6H), 4.86 (d, J=4.8, 1H), 3.88 (s, 2H), 3.74-3.50 (m, 1H), 3.41 (ddd, J=13.3, 9.4, 4.4, 1H), 3.06 (m, 1H), 2.98 (m, 1H), 2.67-2.42 (m, 2H). $^{13}$C NMR (100 MHz, DMSO) δ 169.22, 168.07, 145.68, 144.75, 139.39, 135.43, 132.42, 129.42, 129.37, 129.25, 128.69, 128.27, 127.62, 126.41, 123.16, 122.37, 120.47, 61.10, 56.63, 46.54; 31.66, 27.80.

(S)-2-((4-(5-(3,4-diethoxybenzyl)-1,2,4-oxadiazol-3-yl)-2,3-dihydro-1H-inden-1-yl)amino)-N,N-dimethylacetamide (Compound 66)

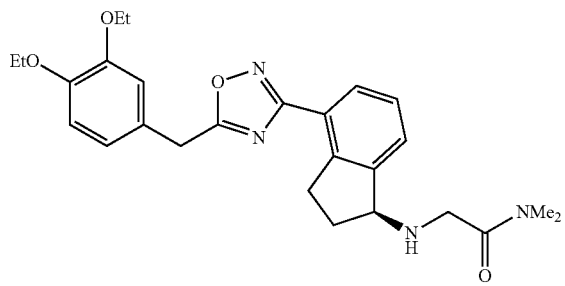 [SMILES: CCOc1ccc(Cc2nc(-c3cccc4c3CC[C@@H]4NCC(=O)N(C)C)no2)cc1OCC]

(S)-2-((4-(5-(3,4-diethoxybenzyl)-1,2,4-oxadiazol-3-yl)-2,3-dihydro-1H-inden-1-yl)amino)-N,N-dimethylacetamide 66 was prepared analogously to compound 67 from (S)-tert-butyl (4-(5-(3,4-diethoxybenzyl)-1,2,4-oxadiazol-3-yl)-2,3-dihydro-1H-inden-1-yl)(2-(dimethylamino)-2-oxoethyl)carbamate INT-64.

tert-butyl 5-cyano-1H-indole-1-carboxylate (INT-65)

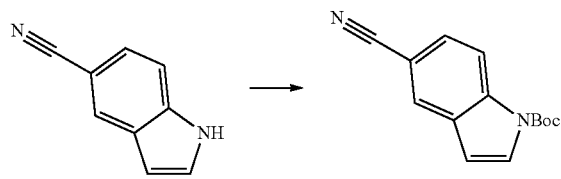 [SMILES: N#Cc1ccc2[nH]ccc2c1 ; CC(C)(C)OC(=O)n1ccc2cc(C#N)ccc21]

To a flask containing 5-cyanoindole (500 mg, 3.52 mmol) in CH$_3$CN (5 mL) was added Boc$_2$O (920 mg, 4.22 mmol) and DMAP (42 mg, 0.35 mmol) and the mixture was stirred at room temperature for 0.5 h. The mixture was concentrated, redissolved in DCM and chromatographed (EtOAc/hexanes) to provide 766 mg (90%) of tert-butyl 5-cyano-1H-indole-1-carboxylate INT-65 as a white solid. LCMS-ESI (m/z) calculated for $C_{14}H_{14}N_2O_2$: 242.27. found 243.1 [M+H]$^+$, $t_R$=3.93 min.

tert-butyl 5-(N-hydroxycarbamimidoyl)-1H-indole-1-carboxylate (INT-66)

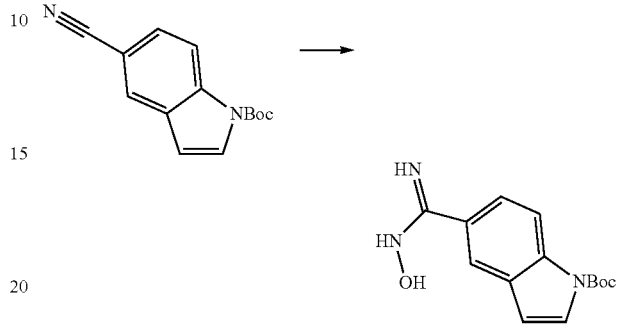

Prepared using General Procedure 1. To a flask containing tert-butyl 5-cyano-1H-indole-1-carboxylate INT-65 (200 mg, 0.73 mmol) was added EtOH (6 mL), hydroxylamine hydrochloride (177 mg, 2.54 mmol) and Na$_2$CO$_3$ (154 mg, 1.45 mmol). The mixture was stirred at 75° C. overnight then concentrated, re-dissolved in DCM and washed with NaHCO$_3$. The combined organic layers were dried over Na$_2$SO$_4$ and concentrated to provide 222 mg of crude tert-butyl 5-(N-hydroxycarbamimidoyl)-1H-indole-1-carboxylate INT-66 as a white solid which was used directly in the next experiment. LCMS-ESI (m/z) calculated for $C_{14}H_{17}N_3O_3$: 275.3; found 276.1 [M+H]$^+$, $t_R$=2.25 min.

tert-butyl 5-(5-(3-cyano-4-isopropoxyphenyl)-1,2,4-oxadiazol-3-yl)-1H-indole-1-carboxylate (INT-67)

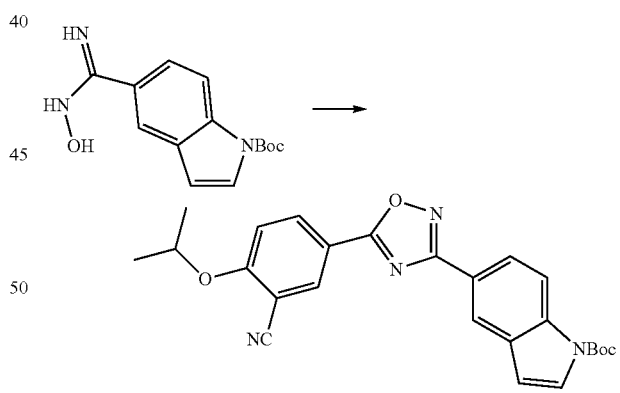

Prepared using General Procedure 2. A flask containing 3-cyano-4-isopropoxybenzoic acid (135 mg, 0.66 mmol), HOBt (130 mg, 0.85 mmol) and EDC (164 mg, 0.85 mmol) in DMF (2.5 mL) was stirred for 1.5 h at room temperature under an atmosphere of N$_2$. A solution of crude tert-butyl 5-(N-hydroxycarbamimidoyl)-1H-indole-1-carboxylate INT-66 (199 mg, 0.72 mmol) in DMF (2.5 mL) was added to the mixture. After 1 h at room temperature, the mixture was heated to 75° C. and stirred overnight. The reaction mixture was diluted with NaHCO$_3$ and extracted with EtOAc. The combined organic extracts were dried over Na$_2$SO$_4$ and concentrated. The resulting crude material was chromatographed (EtOAc/hexanes) to provide 174 mg (59%) of tert-butyl 5-(5-

(3-cyano-4-isopropoxyphenyl)-1,2,4-oxadiazol-3-yl)-1H-indole-1-carboxylate INT-67 as a white solid. LCMS-ESI (m/z) calculated for $C_{25}H_{24}N_4O_4$: 444.5; found 445.1 [M+H]$^+$, $t_R$=3.67 min (Method 1).

5-(3-(1H-indol-5-yl)-1,2,4-oxadiazol-5-yl)-2-isopropoxybenzonitrile (Compound 68)

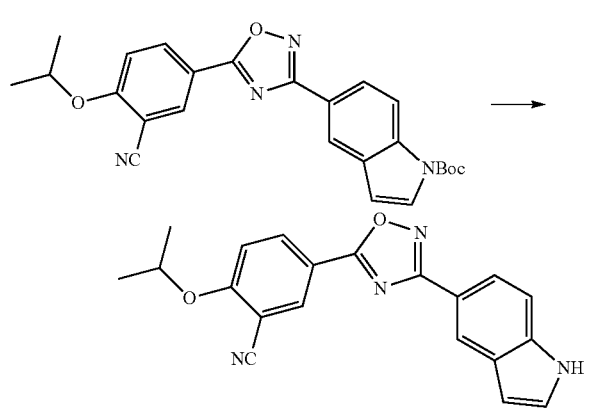

To a flask containing tert-butyl 5-(5-(3-cyano-4-isopropoxyphenyl)-1,2,4-oxadiazol-3-yl)-1H-indole-1-carboxylate INT-67 (75 mg, 0.17 mmol) was added dioxane (2 mL) followed by 4N HCl in dioxane (0.5 mL, 2 mmol). The reaction mixture was stirred overnight at room temperature then heated at 50° C. overnight. Additional 4N HCl/dioxane (0.5 mL, 2 mmol) was added and the mixture was heated at 50° C. for an additional 2 h to complete the deprotection. The reaction mixture was diluted with EtOAc and washed with NaHCO$_3$. The combined organic layers were washed with brine, dried over Na$_2$SO$_4$, and concentrated. The material was purified by chromatography (EtOAc/hexanes) to provide 17 mg (30%) of 5-(3-(1H-indol-5-yl)-1,2,4-oxadiazol-5-yl)-2-isopropoxybenzonitrile 68 as a white solid. LCMS-ESI (m/z) calculated for $C_{20}H_{16}N_4O_2$: 344.5; found 345.1 [M+H]$^+$, $t_R$=2.34 min (Method 1). $^1$H NMR (400 MHz, CDCl$_3$) δ 8.51-8.47 (m, 1H), 8.45 (d, J=2.2 Hz, 1H), 8.38 (d, J=7.2 Hz, 1H), 8.35 (dd, J=8.9, 2.2 Hz, 1H), 7.99 (dd, J=8.5, 1.6 Hz, 1H), 7.51 (d, J=8.5 Hz, 1H), 7.33-7.28 (m, 1H), 7.11 (d, J=9.0 Hz, 1H), 6.72-6.64 (m, 1H), 4.79 (dt, J=12.2, 6.1 Hz, 1H), 1.47 (t, J=5.8 Hz, 6H).

N-hydroxybenzofuran-5-carboximidamide (INT-68)

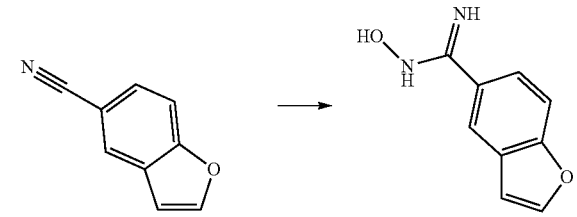 [SMILES: N#Cc1ccc2occc2c1 ; N=C(NO)c1ccc2occc2c1]

Prepared using General Procedure 1. To a flask containing benzofuran-5-carbonitrile (200 mg, 0.73 mmol) was added EtOH (6 mL), hydroxylamine hydrochloride (176.7 mg, 2.54 mmol) and Na$_2$CO$_3$ (154 mg, 1.42 mmol). The mixture was stirred at 75° C. overnight then concentrated, re-dissolved in DCM and washed with NaHCO$_3$. The combined organic layers were dried over Na$_2$SO$_4$, and concentrated to provide 222 mg of crude N-hydroxybenzofuran-5-carboximidamide INT-68 as a white solid which was used directly in the next step without purification. LCMS-ESI (m/z) calculated for $C_9H_8N_2O_2$: 176.2; found 177.1 [M+H]$^+$, $t_R$=0.83

5-(3-(benzofuran-5-yl)-1,2,4-oxadiazol-5-yl)-2-isopropoxybenzonitrile (Compound 69)

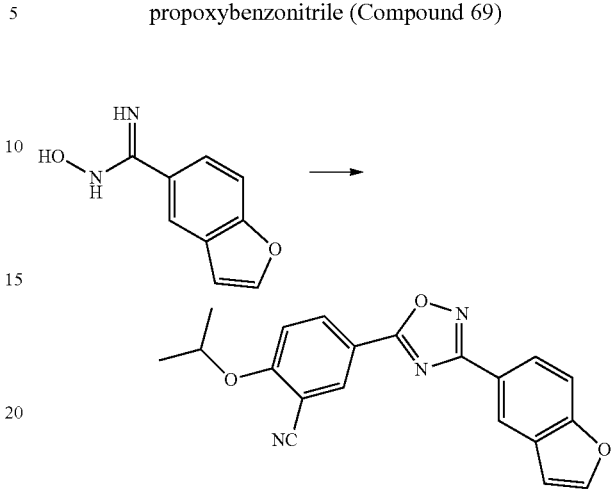

Prepared using General Procedure 2. A flask containing 3-cyano-4-isopropoxybenzoic acid (147.7 mg, 0.72 mmol), HOBt (143 mg, 0.94 mmol) and EDC (180 mg, 0.94 mmol) in DMF (2.0 mL) was stirred for 0.5 h at room temperature under an atmosphere of N$_2$. A solution of N-hydroxybenzofuran-5-carboximidamide INT-68 (218 mg, 0.79 mmol) in DMF (2.0 mL) was added to the mixture. After 1 h at room temperature, the mixture was stirred at 85° C. overnight. The reaction mixture was diluted with NaHCO$_3$ and extracted with EA. The combined organic extracts were dried over Na$_2$SO$_4$, and concentrated. The resulting crude material was chromatographed (EA/hexanes) to provide 110 mg (44%) of 5-(3-(benzofuran-5-yl)-1,2,4-oxadiazol-5-yl)-2-isopropoxybenzonitrile 69 as a white solid. LCMS-ESI (m/z) calculated for $C_{20}H_{15}N_3O_3$: 345.4; found 346.1 [M+H]$^+$, $t_R$=2.77 min (Method 1). $^1$H NMR (400 MHz, CDCl$_3$) δ 8.45 (dd, J=4.5, 1.9 Hz, 2H), 8.35 (dd, J=8.9, 2.2 Hz, 1H), 8.12 (dd, J=8.6, 1.7 Hz, 1H), 7.71 (d, J=2.2 Hz, 1H), 7.63 (d, J=8.6 Hz, 1H), 7.13 (d, J=9.0 Hz, 1H), 6.88 (dd, J=2.2, 0.8 Hz, 1H), 4.80 (s, 1H), 1.48 (d, J=6.1 Hz, 6I-1).

N-hydroxy-3-methylisonicotinimidamide (INT-69)

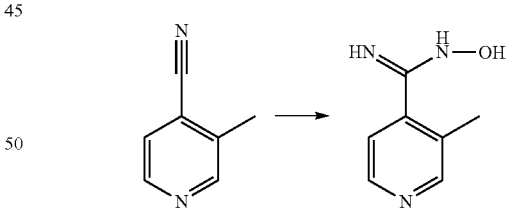

Prepared using General Procedure 1. To 3-methylisonicotinonitrile (0.500 g, 4.2 mmol) in EtOH (7 mL) was added hydroxylamine hydrochloride (0.588 g, 8.5 mmol) and Na$_2$CO$_3$ (1.34 g, 12.7 mmol) and the reaction mixture was heated at 85° C. for 4 h. Once cooled to room temperature, the reaction mixture was filtered using EtOH to rinse the filter cake. The filtrate was concentrated under reduced pressure. The resulting pale yellow solid was triturated with ice water (50 mL), filtered, and the solid was washed with ice water (5 mL). The solid was dried under reduced pressure to yield 0.47 g (74%) of N-hydroxy-3-methylisonicotinimidamide INT-69 as a white powder. LCMS-ESI (m/z) calculated for $C_7H_9N_3O$: 151.2; found 152.1 [M+H]$^+$, $t_R$=0.56 min. $^1$H NMR (400 MHz, CD$_3$OD) δ 8.43-8.32 (m, 2H), 7.34 (d, J=5.0, 1H), 2.39 (s, 3H).

2-isopropoxy-5-(3-(3-methylpyridin-4-yl)-1,2,4-oxadiazol-5-yl)benzonitrile (Compound 70)

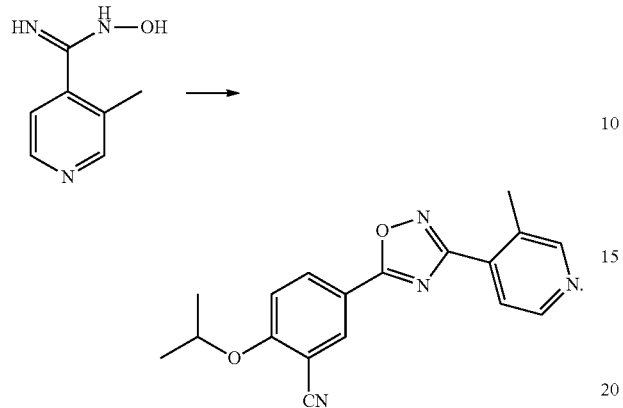

Prepared using General Procedure 2. To a solution of 3-cyano-4-isopropoxybenzoic acid (0.122 g, 0.60 mmol) in DMF (1.5 mL) was added HOBt (0.132 g, 0.86 mmol) and EDC (0.165 g, 0.86 mmol) at room temperature. The reaction was stirred for 0.5 h until the complete formation of the HOBt-acid complex. N-hydroxy-3-methylisonicotinimidamide INT-69 (0.100 g, 0.66 mmol) was added and the mixture was stirred at room temperature for 0.5 h until formation of the intermediate N-(3-cyano-4-isopropoxybenzoyloxy)-3-methylisonicotinimidamide was observed. The reaction mixture was then heated at 80° C. for 4 h. Upon cooling, the mixture was extracted with DCM and brine. The combined organic layers were dried over MgSO$_4$, filtered, and concentrated under reduced pressure to produce a brown oil. The crude product recrystallized from MeOH (3 mL) and the resulting crystals were filtered and washed with cold MeOH to yield product as a white crystalline solid. To the product was added Et$_2$O (0.5 mL) followed by 2N HCl in Et$_2$O (0.6 mL). The mixture was stirred at room temperature for 10 minutes then dried under nitrogen and subsequently under vacuum to afford 0.087 g (45%) of 2-isopropoxy-5-(3-(3-methylpyridin-4-yl)-1,2,4-oxadiazol-5-yl)benzonitrile 70 as the HCl salt. LCMS-ESI (m/z) calculated for C$_{18}$H$_{16}$N$_4$O$_2$: 320.3; found 321.1 [M+H]$^+$, t$_R$=8.82 min (Method 2). $^1$H NMR (400 MHz, CDCl$_3$) δ 8.80 (d, J=17.5, 2H), 8.70 (d, J=5.7, 1H), 8.44 (d, J=2.2, 1H), 8.36 (dd, J=8.9, 2.2, 1H), 7.18 (d, J=9.1, 1H), 4.83 (dt, J=12.2, 6.1, 1H), 2.95 (s, 3H), 1.49 (d, J=6.1, 6H). $^{13}$C NMR (101 MHz, DMSO) δ 173.90, 166.58, 162.81, 147.11, 142.99, 137.55, 135.01, 134.79, 134.06, 125.00, 115.42, 115.17, 115.00, 102.57, 72.66, 21.48, 18.69.

4-bromo-2-((tert-butyldimethylsilyloxy)methyl)pyridine (INT-70)

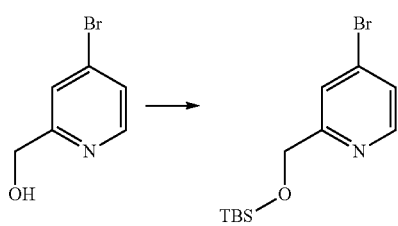

To a stirring solution of (4-bromopyridin-2-yl)methanol (1.50 g, 8.0 mmol) in DCM (4 mL) was added tert-butylchlorodimethylsilane (1.20 g, 8.0 mmol) following by TEA (1.60 g, 12.0 mmol). The reaction mixture was stirred at room temperature for 12 h then washed with brine and EA. The combined organic layers were dried over MgSO$_4$, filtered, and concentrated to yield an amber liquid. The crude product was purified by chromatography (EA/Hexanes) to produce 1.67 g (70%) of 4-bromo-2-((tert-butyldimethylsilyloxy)methyl)pyridine INT-70 as a light yellow liquid. LCMS-ESI (m/z) calculated for C$_{12}$H$_{20}$BrNOSi: 302.3; found 303.0 [M+H]$^+$, t$_R$=4.87 min (Method 1). $^1$H NMR (400 MHz, CDCl$_3$) δ 8.30 (d, J=5.3, 1H), 7.68 (dd, J=1.9, 0.7, 1H), 7.35-7.24 (m, 1H), 4.80 (s, 2H), 0.99-0.86 (m, 9H), 0.16-0.06 (m, 6H).

2-((tert-butyldimethylsilyloxy)methyl)isonicotinonitrile (INT-71)

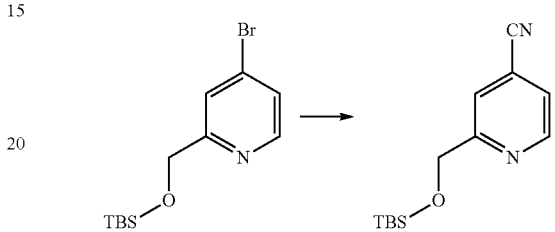

To a stirring solution of 4-bromo-2-((tert-butyldimethylsilyloxy)methyl)pyridine INT-70 (0.800 g, 2.6 mmol) in 3 mL of 1-methyl-2-pyrrolidine (NMP) was added zinc cyanide (0.610 g, 5.2 mmol) and tetrakis(triphenylphosphine)palladium(0) (0.060 g, 0.052 mmol). The solution was degassed with N$_2$ and the reaction mixture heated at 95° C. for 12 h. Upon cooling, the reaction mixture was diluted with saturated NaHCO$_3$ and extracted with DCM. The combined organic layers were dried over MgSO$_4$, filtered, and concentrated. The crude product was purified by chromatography (MeOH/DCM) to produce 0.170 g (26%) of 2-((tert-butyldimethylsilyloxy)methyl)isonicotinonitrile INT-71 as a light yellow solid. LCMS-ESI (m/z) calculated for C$_{13}$H$_{20}$N$_2$OSi: 248.4; found 249.1 [M+H]$^+$, t$_R$=4.21 min (Method 1).

2-((tert-butyldimethylsilyloxy)methyl)-N-hydroxyisonicatinimidamide (INT-72)

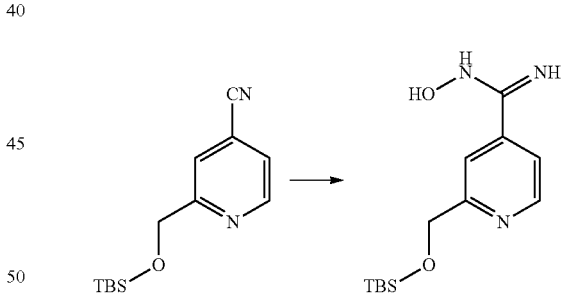

Prepared using General Procedure 1. To 2-((tert-butyldimethylsilyloxy)methyl)isonicotinonitrile INT-71 (0.169 g, 0.68 mmol) in EtOH (8 mL) was added hydroxylamine hydrochloride (0.142 g, 2.0 mmol) and Na$_2$CO$_3$ (0.216 g, 2.0 mmol) and the reaction mixture was heated at 85° C. for 12 h. Once cooled to room temperature, the reaction mixture was filtered using EtOH to rinse the filter cake. The filtrate was concentrated under reduced pressure and washed with EA and brine. The combined organic layers were dried over MgSO$_4$, filtered, and concentrated to produce 0.191 g (100%) of 2-((tert-butyldimethylsilyloxy)methyl)-N-hydroxyisonicotinimidamide INT-72 as a light yellow oil. LCMS-ESI (m/z) calculated for C$_{13}$H$_{23}$N$_3$O$_2$Si: 281.4; found 282.1 [M+H]$^+$, t$_R$=2.76 min (Method 1). $^1$H NMR (400 MHz, (CD$_3$)$_2$SO) δ 8.50 (dd, J=5.2, 0.7, 1H), 7.74 (dd, J=1.6, 0.7, 1H), 7.51 (dd, J=5.2, 1.7, 1H), 5.98 (s, 2H), 0.96-0.89 (m, 9H), 0.14-0.07 (m, 6H).

5-(3-(2-(hydroxymethyl)pyridin-4-yl)-1,2,4-oxadiazol-5-yl)-2-isopropoxy-benzonitrile (Compound 71)

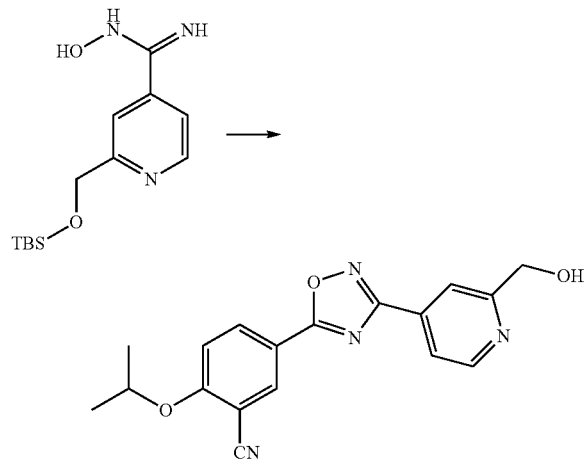

Prepared using General Procedure 2. To a solution of 3-cyano-4-isopropoxybenzoic acid (0.033 g, 0.16 mmol) in DMF (1.0 mL) was added HOBt (0.036 g, 0.23 mmol) and EDC (0.045 g, 0.23 mmol) at room temperature. The reaction was stirred for 0.5 h until the complete formation of the HOBt-acid complex. 2-((Tert-butyldimethylsilyloxy)methyl)-N-hydroxyisonicotinimidamide INT-72 (0.050 g, 0.18 mmol) was added and the mixture was stirred at room temperature for 0.5 h until the formation of the intermediate 2-((tert-butyldimethylsilyloxy)methyl)-N-(3-cyano-4-isopropoxybenzoyloxy)isonicotinimidamide was observed. The reaction mixture was then heated at 85° C. for 4 h. To the cooled reaction mixture MeOH (1.0 mL) was added, and the solution was filtered. The resulting filtrate was purified by preparative HPLC to produce 5.6 mg (8%) of 5-(3-(2-(hydroxymethyl)pyridin-4-yl)-1,2,4-oxadiazol-5-yl)-2-isopropoxybenzonitrile 71 as the TFA salt. LCMS-ESI (m/z) calculated for $C_{18}H_{16}N_4O_3$: 336.3; found 337.1 [M+H]$^+$, $t_R$=7.45 min (Method 2). NMR (400 CD$_3$OD) δ 8.78 (d, J=5.5, 1H), 8.48 (dd, J=10.6, 8.3, 1.4, 3H), 8.23 (dd, J=5.5, 1.6, 1H), 7.48 (d, J=9.0, 1H), 4.93 (s, 2H), 4.89 (m, 1H), 1.48 (d, J=6.1, 6H).

Selected compounds and their corresponding analytical data is shown in Table 1, where the LCMS data was collected using Method 2 (see General Methods). The enantiomeric purity was determined for key intermediates and selected final compounds and is presumed from the synthesis for the remaining compounds.

TABLE 1

| STRUCTURE | COMPOUND NUMBER | LCMS RETENTION TIME (min) |
|---|---|---|
| 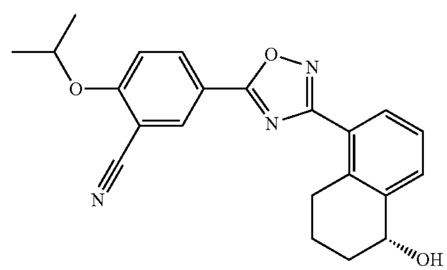 [SMILES: CC(C)Oc1ccc(-c2nc(-c3cccc4c3CCC[C@H]4O)no2)cc1C#N] | 1 | 9.32 |
| 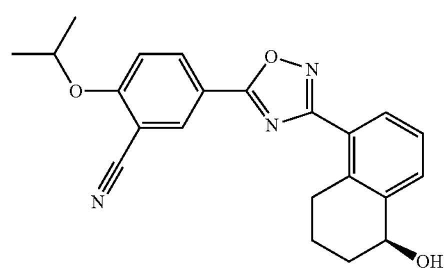 [SMILES: CC(C)Oc1ccc(-c2nc(-c3cccc4c3CCC[C@@H]4O)no2)cc1C#N] | 2 | 9.32 |
| 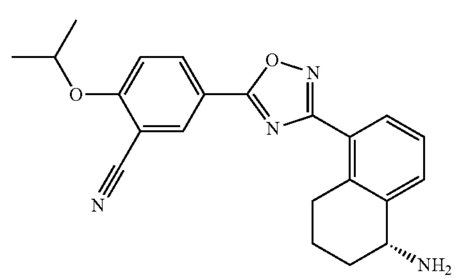 [SMILES: CC(C)Oc1ccc(-c2nc(-c3cccc4c3CCC[C@H]4N)no2)cc1C#N] | 3 | 6.35 |

TABLE 1-continued
| STRUCTURE | COMPOUND NUMBER | LCMS RETENTION TIME (min) |
|---|---|---|
| 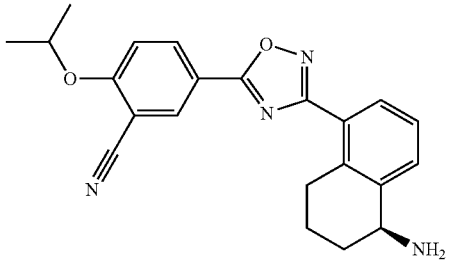 [SMILES: CC(C)Oc1ccc(-c2nc(-c3cccc4c3CCC[C@@H]4N)no2)cc1C#N] | 4 | 6.34 |
| 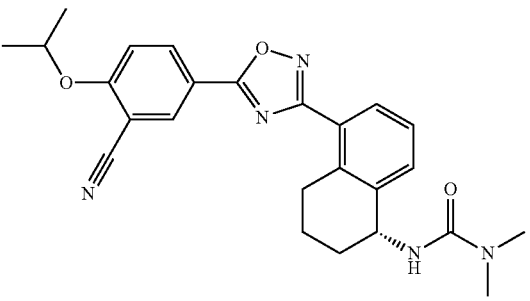 [SMILES: CC(C)Oc1ccc(-c2nc(-c3cccc4c3CCC[C@H]4NC(=O)N(C)C)no2)cc1C#N] | 5 | 9.21 |
| 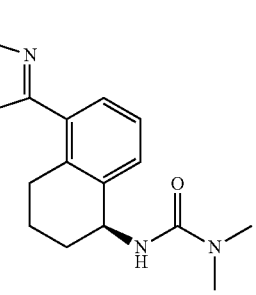 | 6 | 9.20 |
| 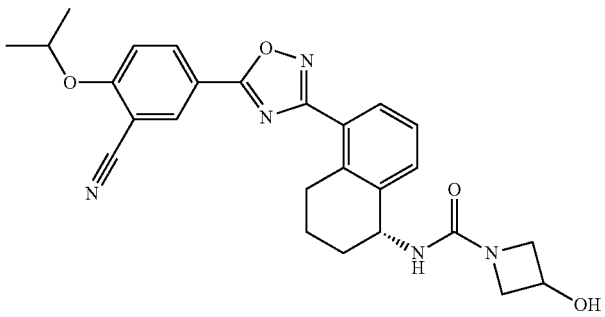 [SMILES: CC(C)Oc1ccc(-c2nc(-c3cccc4c3CCC[C@H]4NC(=O)N3CC(O)C3)no2)cc1C#N] | 7 | 8.09 |
| 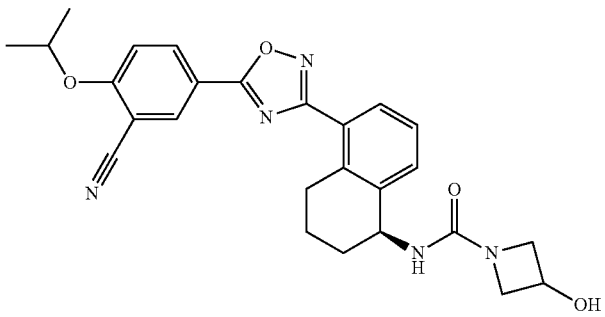 [SMILES: CC(C)Oc1ccc(-c2nc(-c3cccc4c3CCC[C@@H]4NC(=O)N3CC(O)C3)no2)cc1C#N] | 8 | 8.08 |

TABLE 1-continued
| STRUCTURE | COMPOUND NUMBER | LCMS RETENTION TIME (min) |
|---|---|---|
| 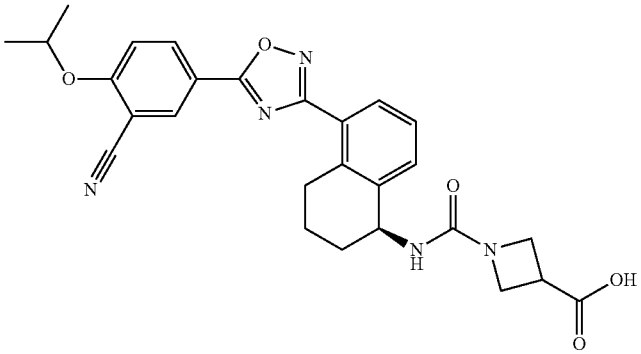 [SMILES: CC(C)Oc1ccc(-c2nc(-c3cccc4c3CCC[C@@H]4NC(=O)N3CC(C(=O)O)C3)no2)cc1C#N] | 9 | 8.25 |
| 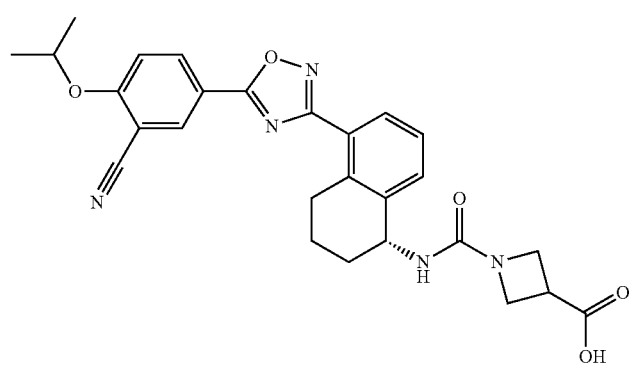 [SMILES: CC(C)Oc1ccc(-c2nc(-c3cccc4c3CCC[C@H]4NC(=O)N3CC(C(=O)O)C3)no2)cc1C#N] | 10 | 8.26 |
| 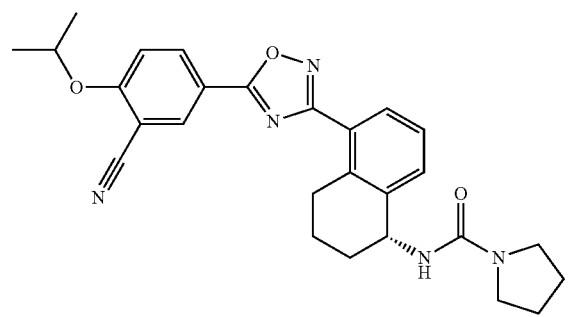 [SMILES: CC(C)Oc1ccc(-c2nc(-c3cccc4c3CCC[C@H]4NC(=O)N3CCCC3)no2)cc1C#N] | 11 | 9.53 |
| 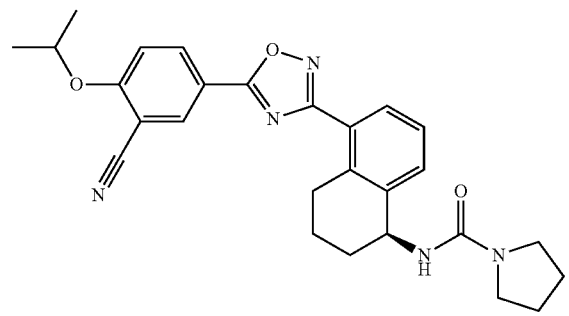 [SMILES: CC(C)Oc1ccc(-c2nc(-c3cccc4c3CCC[C@@H]4NC(=O)N3CCCC3)no2)cc1C#N] | 12 | 9.53 |

TABLE 1-continued

| STRUCTURE | COMPOUND NUMBER | LCMS RETENTION TIME (min) |
|---|---|---|
| 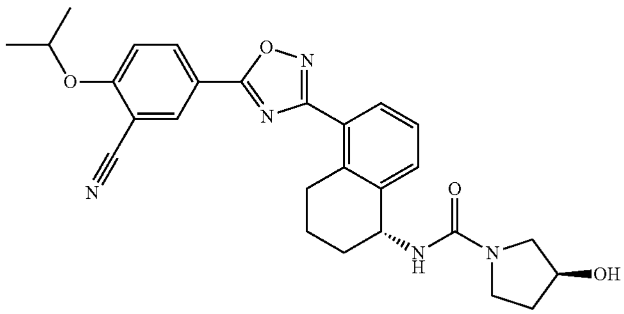 [SMILES: CC(C)Oc1ccc(-c2nc(-c3cccc4c3CCC[C@H]4NC(=O)N3CC[C@H](O)C3)no2)cc1C#N] | 13 | 8.16 |
| 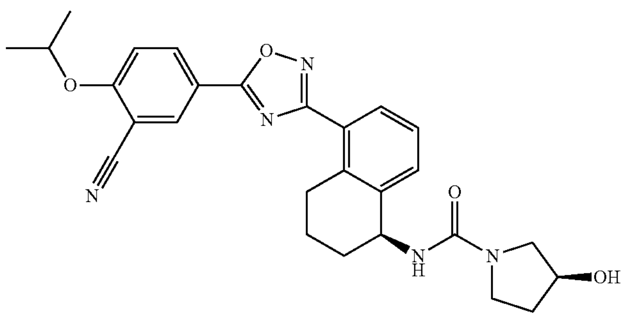 [SMILES: CC(C)Oc1ccc(-c2nc(-c3cccc4c3CCC[C@@H]4NC(=O)N3CC[C@H](O)C3)no2)cc1C#N] | 14 | 8.16 |
| 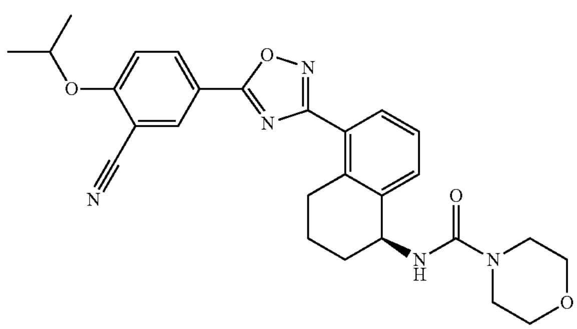 [SMILES: CC(C)Oc1ccc(-c2nc(-c3cccc4c3CCC[C@@H]4NC(=O)N3CCOCC3)no2)cc1C#N] | 15 | 9.01 |
| 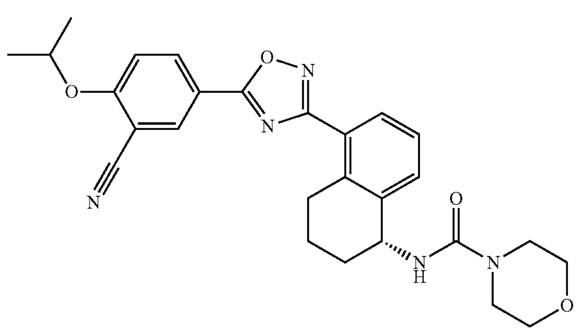 [SMILES: CC(C)Oc1ccc(-c2nc(-c3cccc4c3CCC[C@H]4NC(=O)N3CCOCC3)no2)cc1C#N] | 16 | 9.03 |

TABLE 1-continued

| STRUCTURE | COMPOUND NUMBER | LCMS RETENTION TIME (min) |
|---|---|---|
| 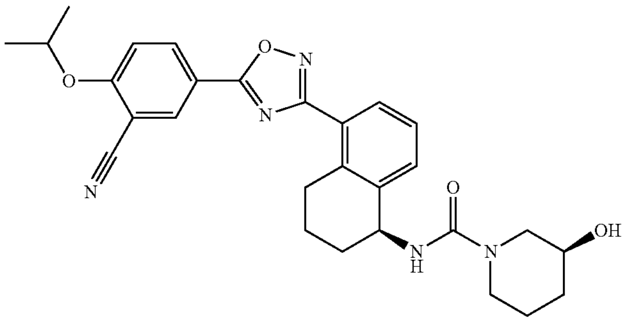 [SMILES: CC(C)Oc1ccc(-c2nc(-c3cccc4c3CCC[C@@H]4NC(=O)N3CCC[C@H](O)C3)no2)cc1C#N] | 17 | 8.55 |
| 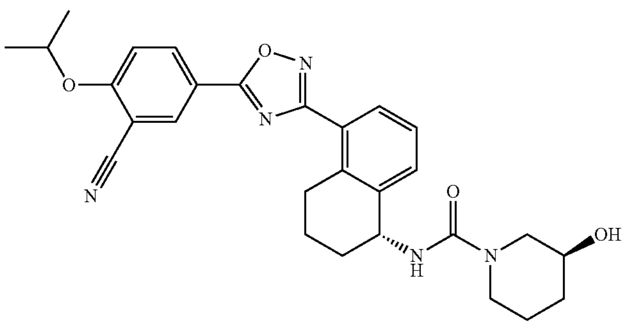 [SMILES: CC(C)Oc1ccc(-c2nc(-c3cccc4c3CCC[C@H]4NC(=O)N3CCC[C@H](O)C3)no2)cc1C#N] | 18 | 8.56 |
| 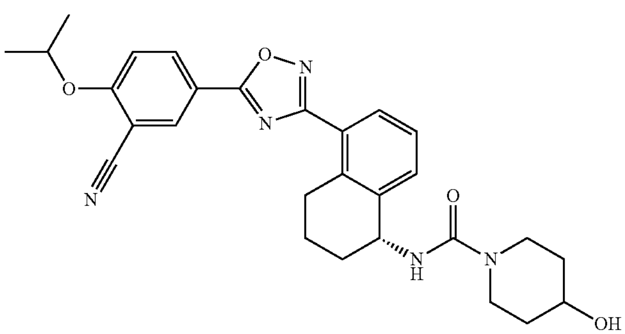 [SMILES: CC(C)Oc1ccc(-c2nc(-c3cccc4c3CCC[C@H]4NC(=O)N3CCC(O)CC3)no2)cc1C#N] | 19 | 8.31 |
| 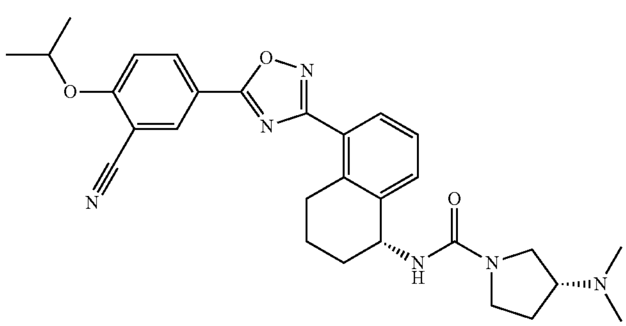 [SMILES: CC(C)Oc1ccc(-c2nc(-c3cccc4c3CCC[C@H]4NC(=O)N3CC[C@@H](N(C)C)C3)no2)cc1C#N] | 20 | 6.45 |

TABLE 1-continued

| STRUCTURE | COMPOUND NUMBER | LCMS RETENTION TIME (min) |
|---|---|---|
| 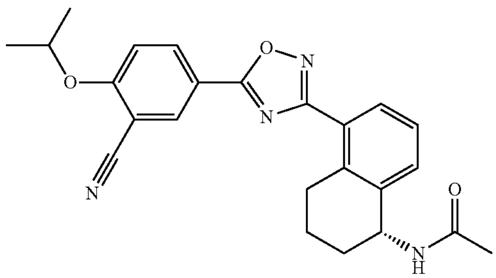 [SMILES: CC(=O)N[C@@H]1CCCc2c(-c3noc(-c4ccc(OC(C)C)c(C#N)c4)n3)cccc21] | 21 | 8.90 |
| 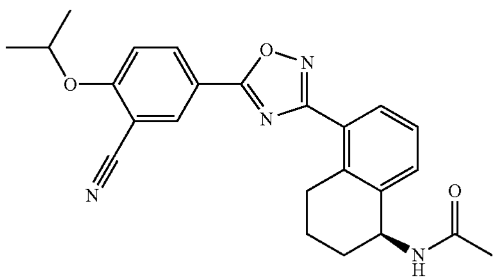 [SMILES: CC(=O)N[C@H]1CCCc2c(-c3noc(-c4ccc(OC(C)C)c(C#N)c4)n3)cccc21] | 22 | 8.89 |
| 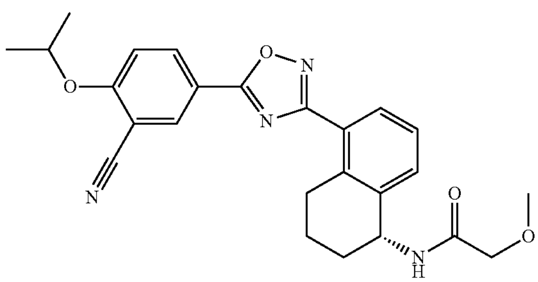 [SMILES: COCC(=O)N[C@@H]1CCCc2c(-c3noc(-c4ccc(OC(C)C)c(C#N)c4)n3)cccc21] | 23 | 9.37 |
| 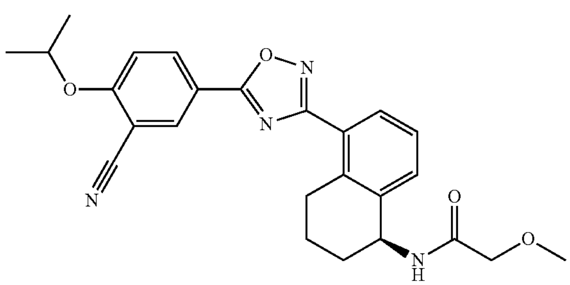 [SMILES: COCC(=O)N[C@H]1CCCc2c(-c3noc(-c4ccc(OC(C)C)c(C#N)c4)n3)cccc21] | 24 | 9.36 |
| 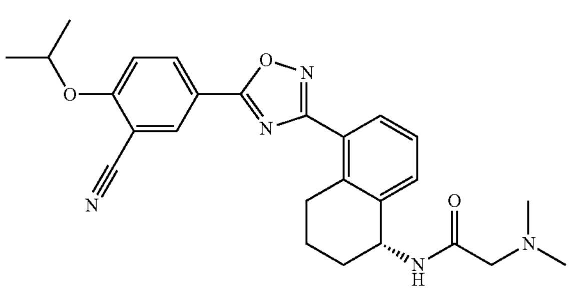 [SMILES: CC(C)Oc1ccc(-c2nc(-c3cccc4c3CCC[C@H]4NC(=O)CN(C)C)no2)cc1C#N] | 25 | 6.56 |

TABLE 1-continued

| STRUCTURE | COMPOUND NUMBER | LCMS RETENTION TIME (min) |
|---|---|---|
| 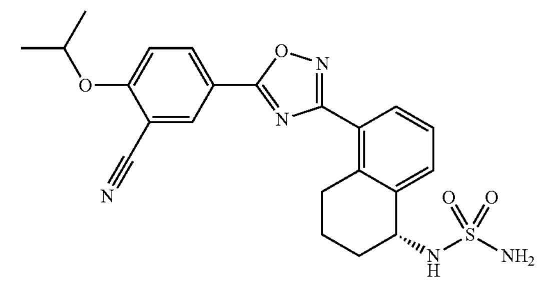 [SMILES: CC(C)Oc1ccc(-c2nc(-c3cccc4c3CCC[C@H]4NS(N)(=O)=O)no2)cc1C#N] | 26 | 8.82 |
| 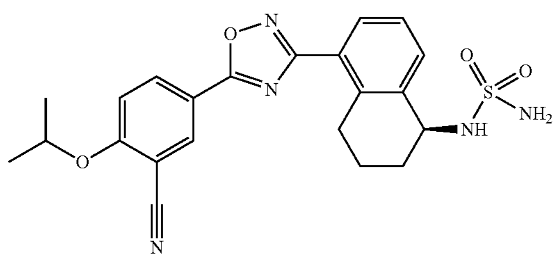 [SMILES: CC(C)Oc1ccc(-c2nc(-c3cccc4c3CCC[C@@H]4NS(N)(=O)=O)no2)cc1C#N] | 27 | 8.8 |
| 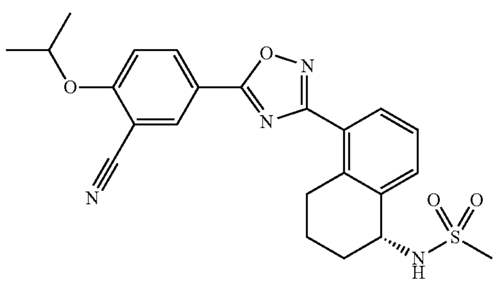 [SMILES: CC(C)Oc1ccc(-c2nc(-c3cccc4c3CCC[C@H]4NS(C)(=O)=O)no2)cc1C#N] | 28 | 9.41 |
| 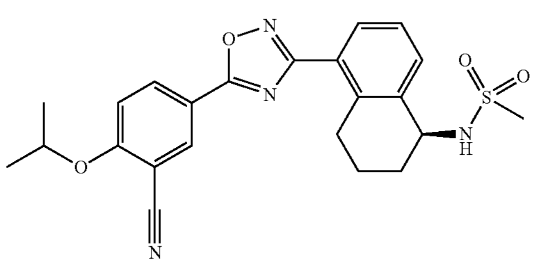 [SMILES: CC(C)Oc1ccc(-c2nc(-c3cccc4c3CCC[C@@H]4NS(C)(=O)=O)no2)cc1C#N] | 29 | 9.36 |
| 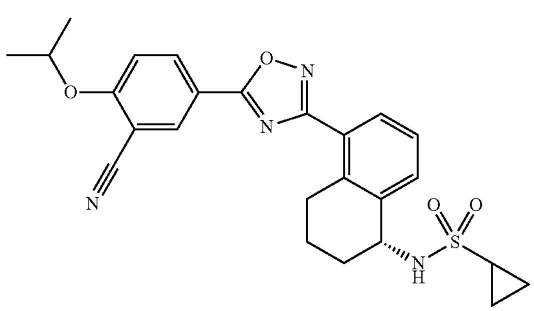 [SMILES: CC(C)Oc1ccc(-c2nc(-c3cccc4c3CCC[C@H]4NS(=O)(=O)C3CC3)no2)cc1C#N] | 30 | 9.87 |

TABLE 1-continued
| STRUCTURE | COMPOUND NUMBER | LCMS RETENTION TIME (min) |
|---|---|---|
| 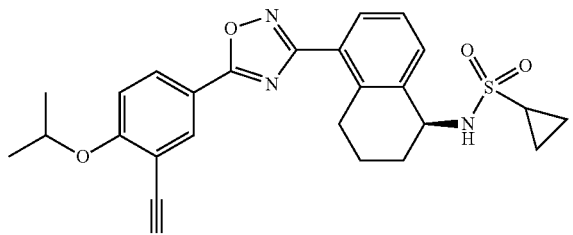 | 31 | 9.83 |
| 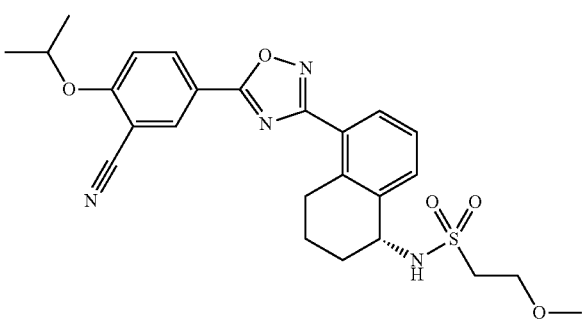 [SMILES: COCCS(=O)(=O)N[C@@H]1CCCc2c(-c3noc(-c4ccc(OC(C)C)c(C#N)c4)n3)cccc21] | 32 | 9.68 |
| 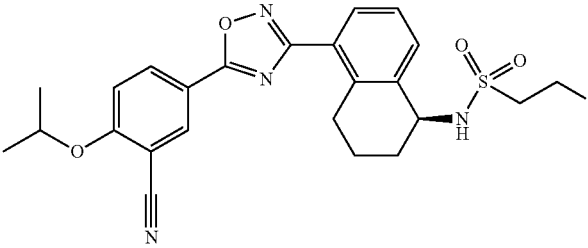 | 33 | 9.66 |
| 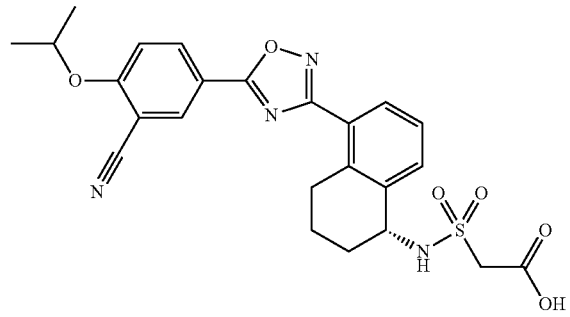 [SMILES: CC(C)Oc1ccc(-c2nc(-c3cccc4c3CCC[C@H]4NS(=O)(=O)CC(=O)O)no2)cc1C#N] | 34 | 8.83 |
| 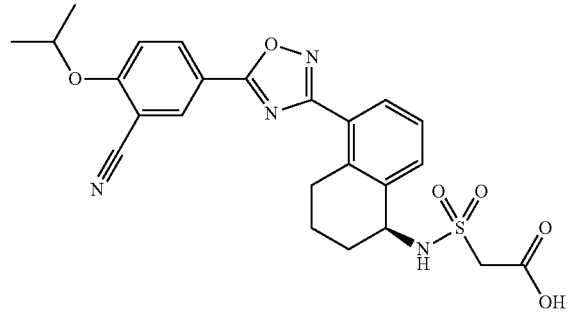 [SMILES: CC(C)Oc1ccc(-c2nc(-c3cccc4c3CCC[C@@H]4NS(=O)(=O)CC(=O)O)no2)cc1C#N] | 35 | 8.84 |

TABLE 1-continued

| STRUCTURE | COMPOUND NUMBER | LCMS RETENTION TIME (min) |
|---|---|---|
| [structure] | 36 | 8.73 |
| [structure] | 37 | 8.76 |
| [structure] | 38 | 8.47 |
| [structure] | 39 | 8.49 |

TABLE 1-continued

| STRUCTURE | COMPOUND NUMBER | LCMS RETENTION TIME (min) |
|---|---|---|
| 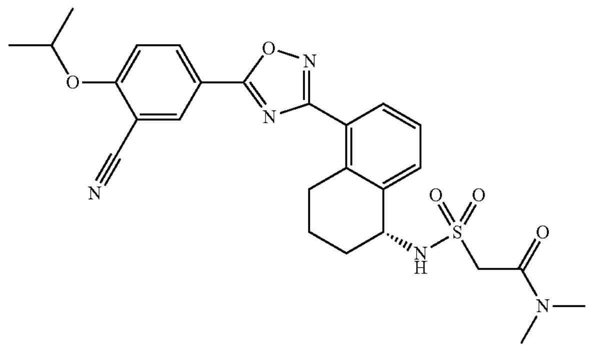 [SMILES: CC(C)Oc1ccc(-c2nc(-c3cccc4c3CCC[C@H]4NS(=O)(=O)CC(=O)N(C)C)no2)cc1C#N] | 40 | 9.09 |
| 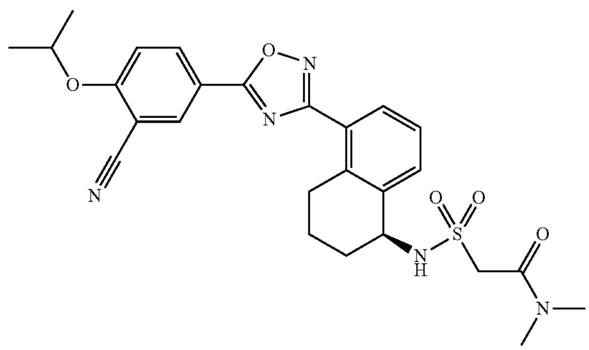 [SMILES: CC(C)Oc1ccc(-c2nc(-c3cccc4c3CCC[C@@H]4NS(=O)(=O)CC(=O)N(C)C)no2)cc1C#N] | 41 | 9.07 |
| 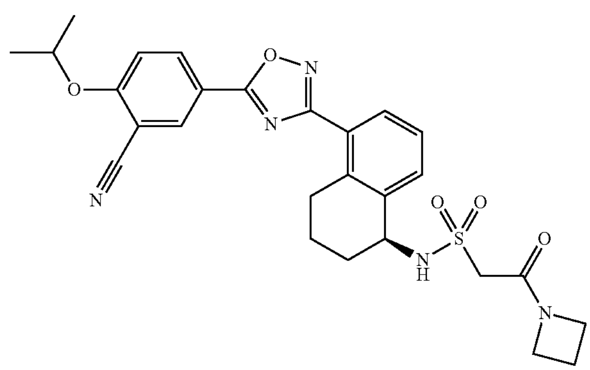 [SMILES: CC(C)Oc1ccc(-c2nc(-c3cccc4c3CCC[C@@H]4NS(=O)(=O)CC(=O)N3CCC3)no2)cc1C#N] | 42 | 9.00 |
| 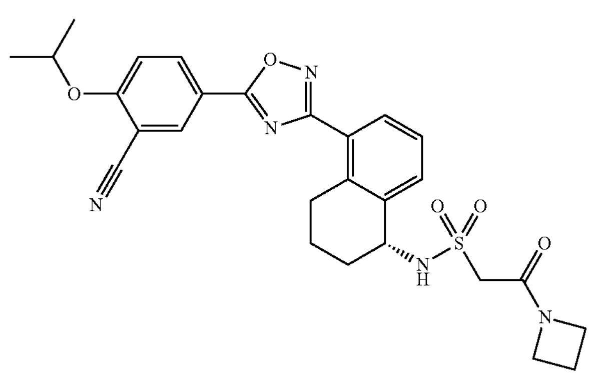 [SMILES: CC(C)Oc1ccc(-c2nc(-c3cccc4c3CCC[C@H]4NS(=O)(=O)CC(=O)N3CCC3)no2)cc1C#N] | 43 | 9.02 |

TABLE 1-continued

| STRUCTURE | COMPOUND NUMBER | LCMS RETENTION TIME (min) |
|---|---|---|
| 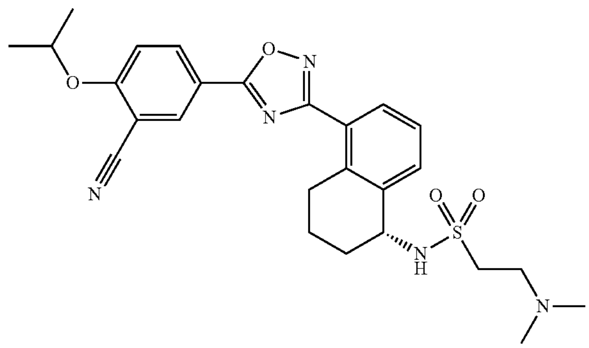 [SMILES: CC(C)Oc1ccc(-c2nc(-c3cccc4c3CCC[C@H]4NS(=O)(=O)CCN(C)C)no2)cc1C#N] | 44 | 6.74 |
| 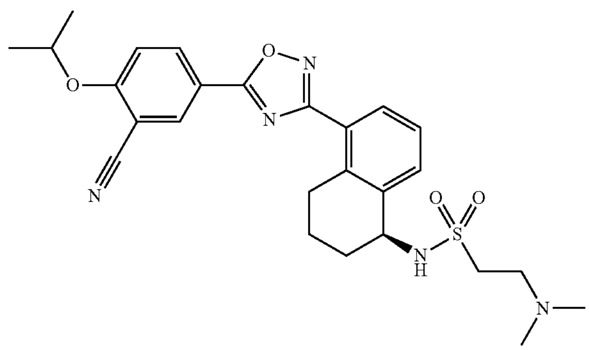 [SMILES: CC(C)Oc1ccc(-c2nc(-c3cccc4c3CCC[C@@H]4NS(=O)(=O)CCN(C)C)no2)cc1C#N] | 45 | 6.82 |
| 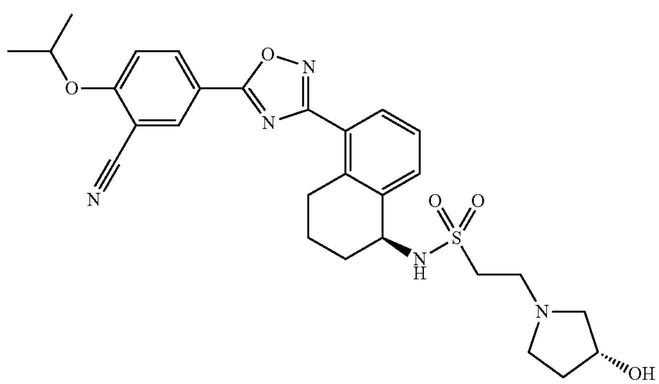 [SMILES: CC(C)Oc1ccc(-c2nc(-c3cccc4c3CCC[C@@H]4NS(=O)(=O)CCN3CC[C@@H](O)C3)no2)cc1C#N] | 46 | 6.69 |
| 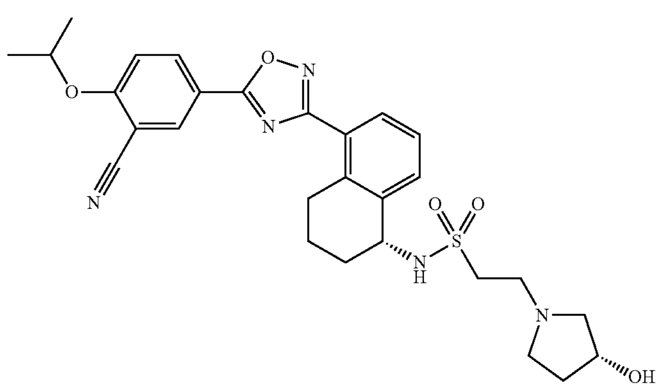 [SMILES: CC(C)Oc1ccc(-c2nc(-c3cccc4c3CCC[C@H]4NS(=O)(=O)CCN3CC[C@@H](O)C3)no2)cc1C#N] | 47 | 6.58 |

TABLE 1-continued

| STRUCTURE | COMPOUND NUMBER | LCMS RETENTION TIME (min) |
|---|---|---|
| *(structure)* | 48 | 6.55 |
| *(structure)* | 49 | 6.54 |
| *(structure)* | 50 | 6.36 |
| *(structure)* | 51 | 6.40 |
| *(structure)* | 52 | 6.13 |

TABLE 1-continued

| STRUCTURE | COMPOUND NUMBER | LCMS RETENTION TIME (min) |
|---|---|---|
| 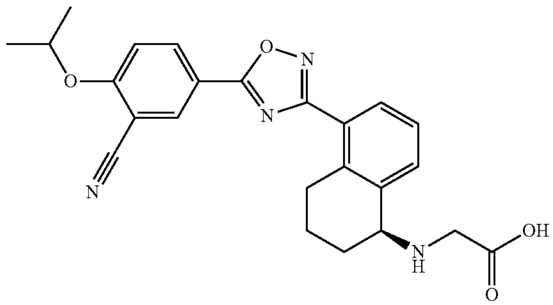 [SMILES: CC(C)Oc1ccc(-c2nc(-c3cccc4c3CCC[C@@H]4NCC(=O)O)no2)cc1C#N] | 53 | 6.52 |
| 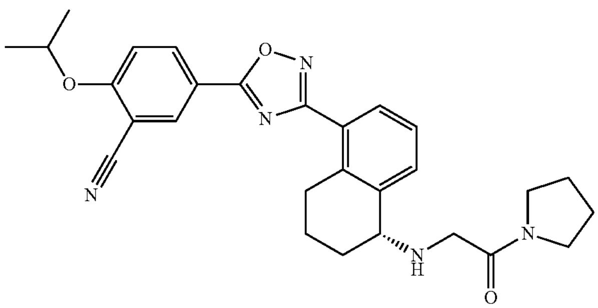 [SMILES: CC(C)Oc1ccc(-c2nc(-c3cccc4c3CCC[C@H]4NCC(=O)N3CCCC3)no2)cc1C#N] | 54 | 6.71 |
| 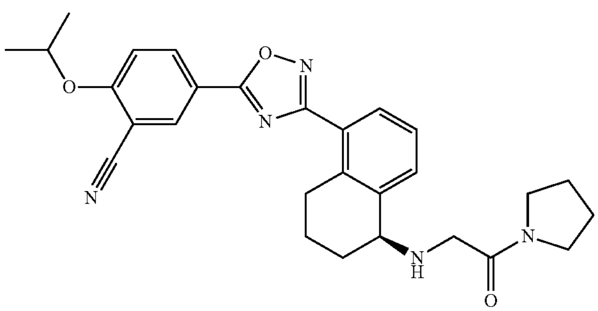 [SMILES: CC(C)Oc1ccc(-c2nc(-c3cccc4c3CCC[C@@H]4NCC(=O)N3CCCC3)no2)cc1C#N] | 55 | 6.76 |
| 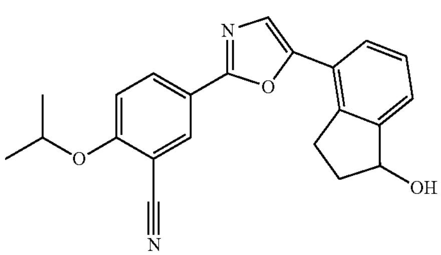 [SMILES: CC(C)Oc1ccc(-c2ncc(-c3cccc4c3CCC4O)o2)cc1C#N] | 56 | 8.63 |
| 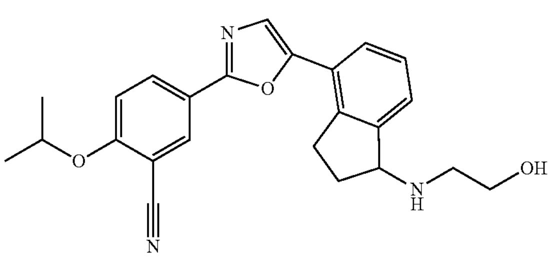 [SMILES: CC(C)Oc1ccc(-c2ncc(-c3cccc4c3CCC4NCCO)o2)cc1C#N] | 57 | 6.16 |

TABLE 1-continued

| STRUCTURE | COMPOUND NUMBER | LCMS RETENTION TIME (min) |
|---|---|---|
| 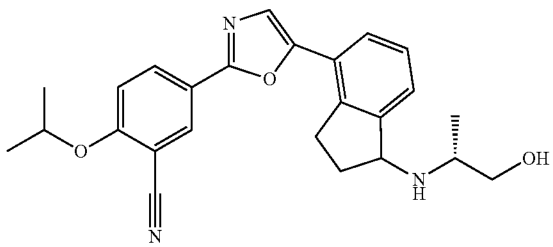 [SMILES: CC(C)Oc1ccc(-c2ncc(-c3cccc4c3CCC4N[C@H](C)CO)o2)cc1C#N] | 58 | 6.34 |
| 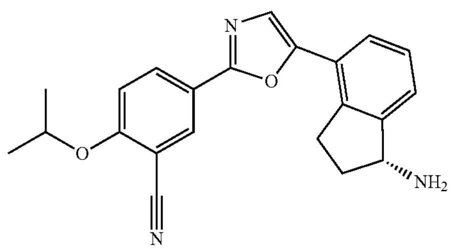 [SMILES: CC(C)Oc1ccc(-c2ncc(-c3cccc4c3CC[C@H]4N)o2)cc1C#N] | 59 | 5.85 |
| 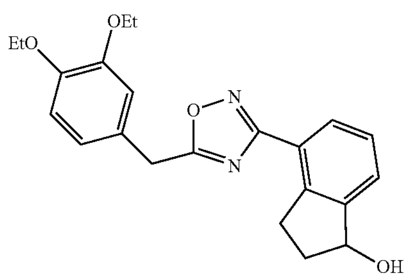 [SMILES: CCOc1ccc(Cc2nc(-c3cccc4c3CCC4O)no2)cc1OCC] | 60 | 8.56 |
| 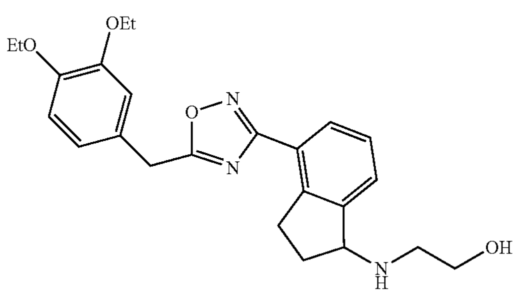 [SMILES: CCOc1ccc(Cc2nc(-c3cccc4c3CCC4NCCO)no2)cc1OCC] | 61 | 6.07 |
| 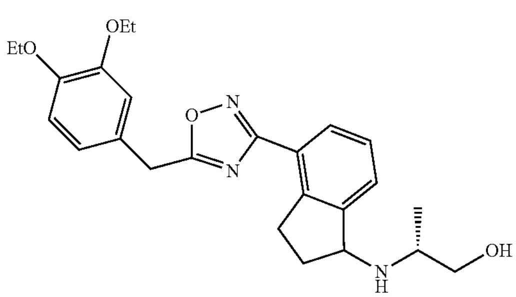 [SMILES: CCOc1ccc(Cc2nc(-c3cccc4c3CCC4N[C@H](C)CO)no2)cc1OCC] | 62 | 6.22 |

TABLE 1-continued

| STRUCTURE | COMPOUND NUMBER | LCMS RETENTION TIME (min) |
|---|---|---|
| 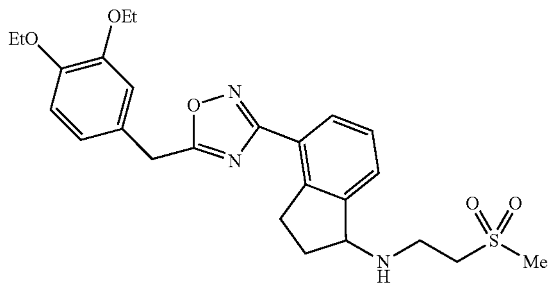 [SMILES: CCOc1ccc(Cc2nc(-c3cccc4c3CCC4NCCS(C)(=O)=O)no2)cc1OCC] | 63 | 6.33 |
| 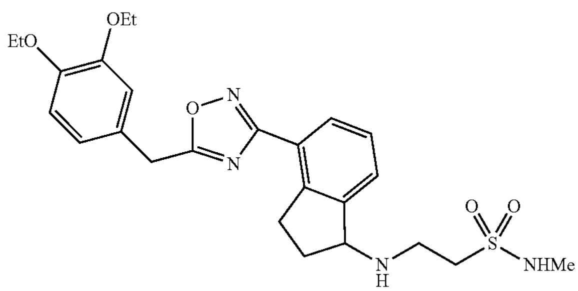 [SMILES: CCOc1ccc(Cc2nc(-c3cccc4c3CCC4NCCS(=O)(=O)NC)no2)cc1OCC] | 64 | 6.43 |
| 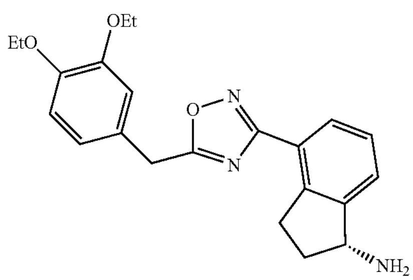 [SMILES: CCOc1ccc(Cc2nc(-c3cccc4c3CC[C@H]4N)no2)cc1OCC] | 65 | 6.00 |
| 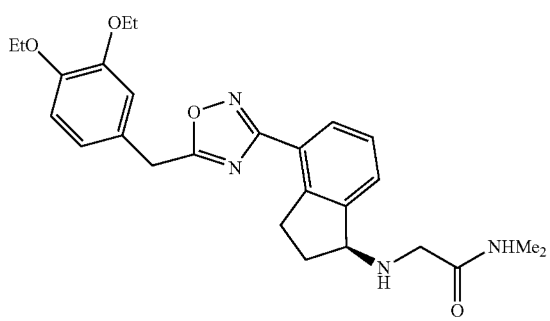 | 66 | 6.23 |
| 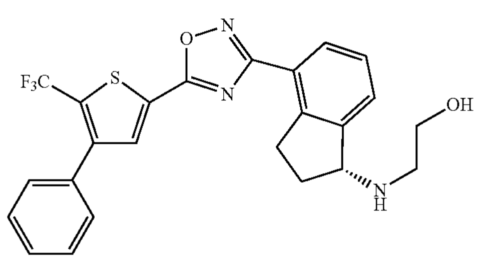 [SMILES: OCCN[C@@H]1CCc2c(-c3noc(-c4cc(-c5ccccc5)c(C(F)(F)F)s4)n3)cccc21] | 67 | 7.40 |

TABLE 1-continued

| STRUCTURE | COMPOUND NUMBER | LCMS RETENTION TIME (min) |
|---|---|---|
| 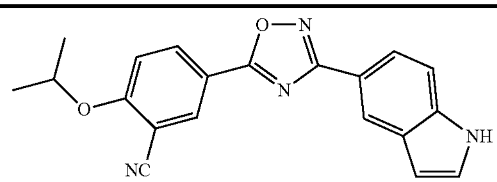 | 68 | 9.66 |
| 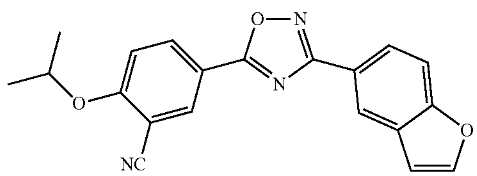 [SMILES: CC(C)Oc1ccc(-c2nc(-c3ccc4occc4c3)no2)cc1C#N] | 69 | 10.74 |
| 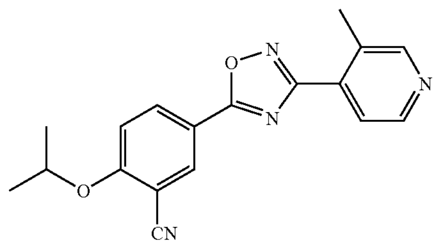 [SMILES: Cc1cnccc1-c1noc(-c2ccc(OC(C)C)c(C#N)c2)n1] | 70 | 8.81 |
| 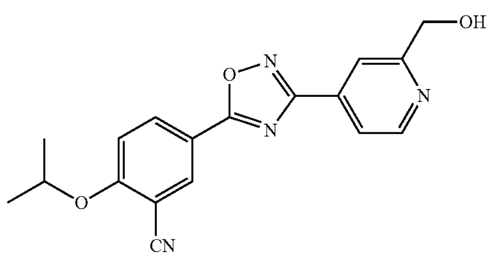 [SMILES: CC(C)Oc1ccc(-c2nc(-c3ccnc(CO)c3)no2)cc1C#N] | 71 | 7.44 |

Biological Assays

Assay Procedures
Generation of $S1P_1$-Mediated Inhibition of cAMP Reporter Assay A mammalian expression plasmid containing $S1P_1$/EDG1 cloned into pcDNA3.1 was purchased from Missouri S&T cDNA Resource Centre. The nucleotide and amino acid sequence of human $S1P_1$/EDG1 are published in Hla and Maciag (J Biol Chem, 265 (1990), 9308-9313). $S1P_1$/pcDNA3.1 was transfected into the CRE-bla CHO K1 (Invitrogen) cell line, and stable single cell clones were selected using standard techniques. Expression of functional $S1P_1$/EDG1 receptor was confirmed by cell surface FACS with a $S1P_1$ antibody (R&D Systems, clone 218713) and S1P-mediated inhibition of Forskolin induced cAMP.

$S1P_1$ CRE-bla CHOK1 Reporter Assay—Characterization of $S1P_1$ Agonists

Cells were seeded into 384-well black wall/clear bottom plates at $10^4$ cells/well/19.5 μl assay media (DMEM-phenol free, 0.5% charcoal/dextran stripped serum, 2 mM glutamine, 0.1 mM NEAA, 1 mM Na-Pyruvate, 25 mM Hepes) and incubated for 18 hrs at 37° C. in 5% $CO_2$. Dose response curves (10-point) were generated in 10 mM Hepes, 0.1% Pluronic F127, in the presence of Forskolin. Cells were treated with 0.5 μl compound in the presence of 2 μM Forskolin for 4 hrs at 37° C. The FRET-based β-lactamase fluorescent substrate (LiveBLAzer™-FRET B/G Loading Kit CC4-AM; Invitrogen) was prepared according to manufacturer's directions, and incubated with cells for 2 hrs at room temperature. Plates were read at Ex:410/Em:458 and Ex:410/Em:522, and the response ratio determined. Data was analyzed by non-linear regression to determine the EC50 for inhibition of Forskolin induced cAMP.

Specificity Over Other SIP Receptors

To assess compound specificity on other S1P receptors the following cell lines were used: $S1P_2$ CRE-bla CHOK1, $S1P_3$-Gα15 NFAT-bla HEK293T (Invitrogen), $S1P_4$-bla TANGO U2OS (Invitrogen), $S1P_5$-bla TANGO U2OS (Invitrogen). The same assay set up for $S1P_i$ was used but without Forskolin. $S1P_4$ and $S1P_5$ assays were performed in FreeStyle Expression medium (Invitrogen). $S1P_5$ cells were incubated for 48 hrs in prior to treatment with compound.

Reported $S1P_1$ Activity

Activity data for selected $S1P_1$ agonists is displayed in Table 2. The activity range is denoted as follows: ++++ denotes agonist activity<0.05 nM. +++ denotes agonist activity between 0.05 to 0.50 nM, and ++ denotes agonist activity between 0.50-5.00 nM, and + denotes agonist activity>5.00 nM. N/A denotes not available.

TABLE 2

| COMPOUND NUMBER | S1P$_1$ ACTIVITY |
|---|---|
| 1 | +++ |
| 2 | ++++ |
| 3 | ++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | ++ |
| 17 | ++ |
| 18 | ++ |
| 19 | ++ |
| 20 | ++ |
| 21 | +++ |
| 22 | +++ |
| 23 | ++ |
| 24 | +++ |
| 25 | ++ |
| 26 | +++ |
| 27 | ++++ |
| 28 | +++ |
| 29 | +++ |
| 30 | +++ |
| 31 | ++ |
| 32 | +++ |
| 33 | +++ |
| 34 | ++++ |
| 35 | ++++ |
| 36 | ++++ |
| 37 | ++++ |
| 38 | ++++ |
| 39 | ++++ |
| 40 | ++++ |
| 41 | ++++ |
| 42 | ++++ |
| 43 | ++++ |
| 44 | +++ |
| 45 | ++ |
| 46 | ++ |
| 47 | +++ |
| 48 | +++ |
| 49 | +++ |
| 50 | +++ |
| 51 | +++ |
| 52 | ++++ |
| 53 | +++ |
| 54 | ++ |
| 55 | +++ |
| 56 | ++ |
| 57 | ++ |
| 58 | + |
| 59 | + |
| 60 | + |
| 61 | + |
| 62 | + |
| 63 | + |
| 64 | + |
| 65 | + |
| 66 | + |
| 67 | + |
| 68 | ++ |
| 69 | ++ |
| 70 | ++++ |
| 71 | +++ |

S1P$_1$-S1P$_5$ data for specific compounds is presented in Table 3. The agonist values (EC$_{50}$) are reported in nM.

TABLE 3

| COMPOUND NUMBER | S1P$_1$ | S1P$_2$ | S1P$_3$ | S1P$_4$ | S1P$_5$ |
|---|---|---|---|---|---|
| 8 | 0.143 | >10000 | >10000 | >10000 | 108.9 |
| 13 | 0.100 | >10000 | >10000 | >10000 | 77.0 |
| 29 | 0.065 | >10000 | >10000 | >10000 | 37.8 |
| 33 | 0.192 | >10000 | >10000 | 616.7 | 260.1 |
| 37 | 0.024 | 1437 | >10000 | 879.4 | 3.5 |
| 49 | 0.104 | >10000 | >10000 | >10000 | 94.6 |

In Vivo Assays

Determination of Absolute Oral Bioavailability in Rats.

Pharmacokinetic studies are conducted in non-fasted female Sprague-Dawely rats (Simonsen Laboratories or Harlan Laboratories). Rats are housed in an ALAAC accredited facility and the research is approved by the facilities Institutional Animal Care and Use Committee (IACUC). The animals are acclimated to the laboratory for at least 48 h prior to initiation of experiments.

Compounds are formulated in 5% DMSO/5% Tween20 and 90% purified water (intravenous infusion) or 5% DMSO/5% Tween20 and 90% 0.1N HCL (oral gavage). The concentration of the dosing solutions is verified by HPLC-UV. For intravenous dosing, compounds are administered by an infusion pump into the jugular vein over one minute to manually restrained animals (n=4 rats/compound). Oral dosing is by gavage using a standard stainless steel gavage needle (n=2-4 rats/compound). For both routes of administration, blood is collected at eight time-points after dosing with the final sample drawn 24 h post dose. Aliquots of the blood samples are transferred to polypropylene 96-well plate and frozen at −20° C. until analysis.

After thawing the blood samples at room temperature, 5 µL of DMSO is added to each well. Proteins are precipitated by adding 150 µL acetonitrile containing 200 nM internal standard (4-hydroxy-3-(alpha-iminobenzyl)-1-methyl-6-phenylpyrindin-2-(1H)-one) and 0.1% formic acid. Plates are mixed for 1 min on a plate shaker to facilitate protein precipitation and then centrifuged at 3,000 rpm for 10 min to pellet protein. The supernatant is transferred to a clean plate and centrifuged at 3,000 rpm for 10 min to pellet any remaining solid material prior to LC/MS/MS analysis. Calibration curve standards are prepared by spiking 5 µL compound stock in DMSO into freshly collected EDTA rat blood. An eight point standard curve spanning a range of 5 nM to 10,000 nM is included with each bio-analytical run. The standards are processed identically to the rat pharmacokinetic samples.

Concentrations in the rat pharmacokinetic samples are determined using a standardized HPLC-LC/MS/MS method relative to the eight point standard curve. The system consists of a Leap CTC Pal injector, Agilent 1200 HPLC with binary pump coupled with an Applied Biosystems 3200 QTrap. Compounds are chromatographed on a Phenomenex Synergy Fusion RP 20×2 mm 2 um Mercury Cartridge with Security Guard. A gradient method is used with mobile phase A consisting of 0.1% formic acid in water and mobile phase B consisting of 0.1% formic acid in acetonitrile at flow rates varying from 0.7 to 0.8 mL/min. Ions are generated in positive ionization mode using an electrospray ionization (ESI) interface. Multiple reaction monitoring (MRM) methods are developed specific to each compound. The heated nebulizer is set at 325° C. with a nebulizer current of 4.8 µA. Collision energies used to generate daughter ions range between 29 and 39 V. Peak area ratios obtained from MRM of the mass transitions specific for each compound are used for quantification. The limit of quantification of the method is typically 5 nM. Data are collected and analyzed using Analyst software version 1.4.2.

Blood and/or plasma concentration versus time data are analyzed using non-compartmental methods (WinNonlin version 5.2; model 200 for oral dosing and model 202 for intravenous infusion). Absolute oral bioavailability (%) is calculated using the following expression: (Oral AUC×IV Dose)/(IV AUC×Oral Dose)×100.

Lymphopenia

In mice: Female C57BL6 mice (Simonsen Laboratories, Gilroy Calif.) are housed in an ALAAC accredited facility and the research is approved by the facilities Institutional Animal Care and Use Committee (IACUC). The animals are acclimated to the laboratory for at least 5 days prior to initiation of experiments. Mice (n=3/compound/time-point) are dosed by oral gavage with 1 mg/kg compound formulated in a vehicle consisting of 5% DMSO/5% Tween 20 and 90% 0.1N HCl. Control mice are dosed PO with the vehicle. Terminal whole blood samples are collected from isoflurane anesthetized mice by cardiac puncture into EDTA. Whole blood is incubated with rat anti-mouse CD16/CD32 (Mouse BD Fc Block, #553141), PE-Rat anti-mouse CD45R/B220 (BD #553089), APC-Cy7-Rat anti-mouse CD8a (BD #557654), and Alexa Fluor647-Rat anti-mouse CD4 (BD #557681) for 30 min on ice. Red blood cells are lysed using BD Pharm Lyse Lysing buffer (#555899) and white blood cells are analyzed by FACS. Lymphopenia is expressed as the % of white blood cells that are CD4 or CD8 positive T cells. The overall lymphopenia response over 24 h is estimated by calculating the area under the effect curve (AUEC) using the linear trapezoidal rule.

In rats: Female rats (Simonsen Laboratories, Gilroy Calif.) are housed in an ALAAC accredited facility and the research is approved by the facilities Institutional Animal Care and Use Committee (IACUC). The animals are acclimated to the laboratory for at least 5 days prior to initiation of experiments. Rats (n=3/compound/time-point) are dosed by oral gavage with 1 mg/kg compound formulated in a vehicle consisting of 5% DMSO/5% Tween 20 and 90% 0.1N HCL. Control rats are dosed PO with the vehicle. Whole blood is collected from isoflurane anesthetized rats via the retro-orbital sinus and terminal samples are collected by cardiac puncture into EDTA. Whole blood is incubated with mouse anti-rat CD32 (BD #550271), PE-mouse anti-rat CD45R/B220 (BD #554881), PECy5-mouse anti-rat CD4 (BD #554839), and APC-mouse anti-rat CD8a (eBioscience #17-0084) for 30 minutes on ice. Red blood cells are lysed using BD Pharm Lyse Lysing buffer (#555899) and white blood cells are analyzed with a BD FACSArray. Lymphopenia is expressed as the % of white blood cells that are CD4 or CD8 positive T cells. The overall lymphopenia response over 24 h is estimated by calculating the area under the effect curve (AUEC) using the linear trapezoidal rule. In some experiments, total lymphocyte counts are determined using a standard impedance based veterinary hematology analyzer (IDEXX Preclinical Research Services, Sacramento, Calif.).

Evaluation of Therapeutic Index in Rats

Studies may be conducted in non-fasted male and female Sprague-Dawely rats (Simonsen Laboratories). Rats may be housed in an AAALAC accredited facility and the research can be approved by the facilities Institutional Animal Care and Use Committee (IACUC). The animals should be acclimated to the laboratory for at least 5 days prior to initiation of experiments.

The compounds may be formulated as suspensions in a vehicle consisting of 0.5% carboxymethyl cellulose (Acros Organics) in purified water (pH adjusted to ~2.2 with hydrochloric acid). The same formulation is used in the rat lymphopenia and toxicology studies described below. The concentration of each compound in suspension should be verified to be within ±10% of the target concentration by HPLC-UV.

Prior to the conduct of toxicology studies, the effect of three to five daily doses of each compound on peripheral T-cell counts of female rats may be determined (see lymphopenia measurements in rats above). In these lymphopenia studies, blood samples are collected onto EDTA at intervals after the final study dose. The collection times need not be identical for each study, however, all studies may include a sample collected 24 hours after the final dose. The lymphopenia data is used as a biomarker to select equally pharmacologically active doses for the subsequent toxicology study. The low dose for the toxicology study is the dose of each compound that resulted in a 50% reduction of T-cell count 24 h after the final dose in the lymphopenia study relative to vehicle treated rats.

In the toxicology studies, three male and three female rats per group are assigned to dosing groups using body weight based randomization. A control group in each study receives vehicle. All animals are dosed orally by gavage on 5 or 14-consecutive days at a dose volume of 5 mL/kg/day. The animals are observed daily for any manifestations of adverse effect. Twenty-four hours after the final study dose, the rats are anesthetized with isoflurane and a terminal blood sample is taken by intra-cardiac puncture for hematology and clinical chemistry evaluation (IDEXX Laboratories, Sacramento, Calif.). The lungs with trachea are collected, weighed, and then prepared for histology by perfusion with 10% neutral buffered formalin via the trachea. The internally fixed lungs are then preserved in 10% neutral buffered formalin and submitted for histological examination (IDEXX).

The dose of each compound resulting in a 10% increase in the lung to terminal body weight ratio can be estimated for each compound by linear interpolation. The therapeutic index can then be estimated as the ratio of the dose producing 10% lung weight increase to the dose producing 50% T-Cell depletion.

Description of the TNBS Crohn's Colitis Model in Rats

Male Sprague-Dawley rats (180-200 g) are acclimatized for seven days and then assigned to 8 rats per group so that each group has approximately the same mean weight. Twenty-four hours prior to disease initiation, rats are deprived of food. Rats are anaesthetized and weighed, then 80 mg/kg TNBS solution (50% TNBS: 50% 200 proof ethanol) is instilled into colon via a 20 g feeding needle inserted into the anus. The rats are maintained in head down position until recovery from anesthesia. Daily oral dosing is initiated 2 h post TNBS-instillation for six days. Prednisolone serves as a positive control and is administered orally daily at 10 mg/kg. Body weights are monitored daily and 24 h after the last dose, all groups are terminated. The colon is removed, flushed of fecal matter and examined for gross changes including strictures, adhesions and ulcers. The colon length, weight of the distal 2 cm, and wall thickness is recorded.

Description of Influenza A H1N1 Model in Mice

Male C57Bl/6 (6-8 weeks of age) may be acclimatized for seven days and then assigned to 5-8 mice per group so that each group has approximately the same mean weight. Mice may be infected with $10^4$ PFUs mouse-adapted influenza A virus (A/WSN/33) via the intra-tracheal route. Mice may then be treated with 0.2-1.5 mg/kg compound p.o. 1 hr post-infection. Forty eight hours after infection mice may be euthanized by cervical dislocation and bronchoalveolar lavage fluid can be collected. Quantitative cytokine analysis may be performed via ELISA. In some experiments whole body perfusion can be performed and lungs can be collected for cellular enumeration of inflammatory cells. Longevity studies may be performed by infection with 3-10×10⁴ PFUs mouse-adapted influenza A virus over 14 days.

We claim:

1. A compound having the structure of Formula I-R or I-S or a pharmaceutically acceptable salt, ester, hydrate or solvate thereof:

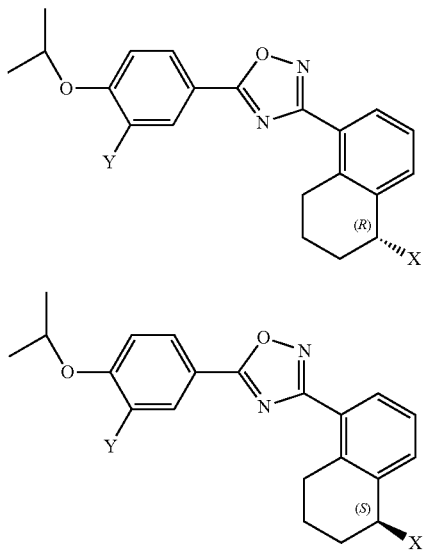

wherein
X is —NR'R" or —OR'";
Y is —CN, —Cl, or —CF$_3$;
R' is H, C$_{1-4}$ alkyl, n-hydroxy C$_{1-4}$ alkyl, —SO$_2$—R$^1$, or —CO—R$^1$;
R" is H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, thiazolyl, pyrazolyl, pyrrolidinyl, imidazolyl, or phenyl;
or R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from the group consisting of —OH, oxo, —NH$_2$, n-hydroxy-C$_{1-4}$ alkyl, —COOH, —(CH$_2$)$_m$—COOH, —(CH$_2$)$_m$—COOR$^1$, —N(R$^1$R$^1$), and —(CH$_2$)$_m$—CO—N(R$^5$R$^5$);
R'" is H, C$_{1-4}$ alkyl, or —CO—R$^1$;
each R$^1$ is independently C$_{1-4}$ alkyl or H;
each R$^2$ is independently H, halo, OH, oxo, =NH, NH$_2$, —COOH, F, —NHR$^1$, —N(R$^5$R$^5$), —SO$_2$—R$^1$, —SO$_2$—N(R$^5$R$^5$), —N(R$^1$)—SO$_2$—R$^1$, —COOR$^1$, —OCO—R$^1$, —CO—N(R$^5$R$^5$), —N(R$^1$)—COR$^1$, C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl;
each R$^3$ is independently R$^2$, C$_{1-4}$ alkyl, C$_{3-6}$ cycloalkyl, or C$_{1-4}$ alkyl optionally substituted with 1 or more R$^2$;
each R$^4$ is independently halo, OH, —NH$_2$, —NHR$^1$, —N(R$^1$R$^1$), —COOH, —COOR$^1$, —NHCO—R$^1$; each R$^5$ is independently C$_{1-4}$ alkyl or H, or two R$^5$ taken together with the nitrogen atom to which they are bound form a 4, 5, or 6 membered saturated heterocyclic ring containing 0 or 1 additional heteroatoms where such additional heteroatom is O or N wherein such heterocycle is optionally substituted with —OH, —NH$_2$, —N(R$^1$R$^1$), n-hydroxy C$_{1-4}$ alkyl, —(CH$_2$)$_m$—COOH, —(CH$_2$)$_m$—COOR$^1$; and
each m is independently 0, 1, 2, or 3.

2. The compound of claim 1 wherein the compound has the structure of Formula I-R or a pharmaceutically acceptable salt, ester, hydrate or solvate thereof.

3. The compound of claim 1 wherein the compound has the structure of Formula I-S or a pharmaceutically acceptable salt, ester, hydrate or solvate thereof.

4. The compound of claim 1 wherein the compound is substantially enantiomerically pure.

5. The compound of claim 1 wherein Y is Cl.

6. The compound of claim 1 wherein Y is CF$_3$.

7. The compound of claim 1 wherein Y is CN.

8. The compound of claim 1 wherein X is —NR'R".

9. The compound of claim 1 wherein X is —OR'".

10. The compound of claim 9 wherein X is —OH.

11. The compound of claim 9 wherein X is —OCO—R$^1$.

12. The compound of claim 11 wherein R$^1$ is C$_{1-3}$ alkyl.

13. The compound of claim 8 wherein R' is H.

14. The compound of claim 8 wherein R' is —COR$^1$.

15. The compound of claim 8 wherein R' is —SO$_2$—R$^1$.

16. The compound of claim 8 wherein R" is H.

17. The compound of claim 8 wherein R" is —SO$_2$—R$^3$.

18. The compound of claim 8 wherein R" is C$_{1-4}$ alkyl optionally substituted with 1 or more R$^2$.

19. The compound of claim 8 wherein R" is —(CR$^a$R$^b$)$_n$—R$^2$; each R$^a$ and each R$^b$ is independently selected from the group consisting of H, hydroxyl and methyl or R$^a$ and R$^b$ bound to the same carbon taken together are oxo; and n is 0, 1, 2, or 3.

20. The compound of claim 19 wherein n is 2.

21. The compound of claim 20 wherein R$^2$ is —OH, —NH$_2$, —NHR$^1$, —N(R$^5$R$^5$), or —COOH.

22. The compound of claim 17 wherein R$^3$ is C$_{1-4}$ alkyl optionally substituted with 1 or more R$^2$.

23. The compound of claim 17 wherein Y is CN.

24. The compound of claim 22 wherein R$^3$ is —C$_2$H$_5$—N ((R$^5$R$^5$) or —CH$_2$—CO—N(R$^5$R$^5$).

25. The compound of claim 23 wherein R$^3$ is C$_2$H$_5$—O—R$^1$.

26. The compound of claim 7 wherein X is —NH—CO—N(R$^5$R$^5$).

27. The compound of claim 1 wherein the compound is selected from the group consisting of:

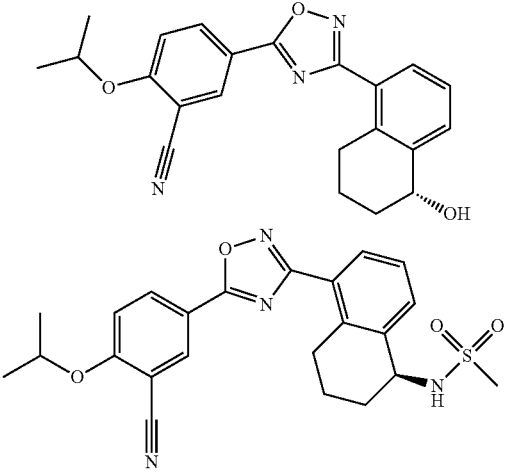

145
-continued
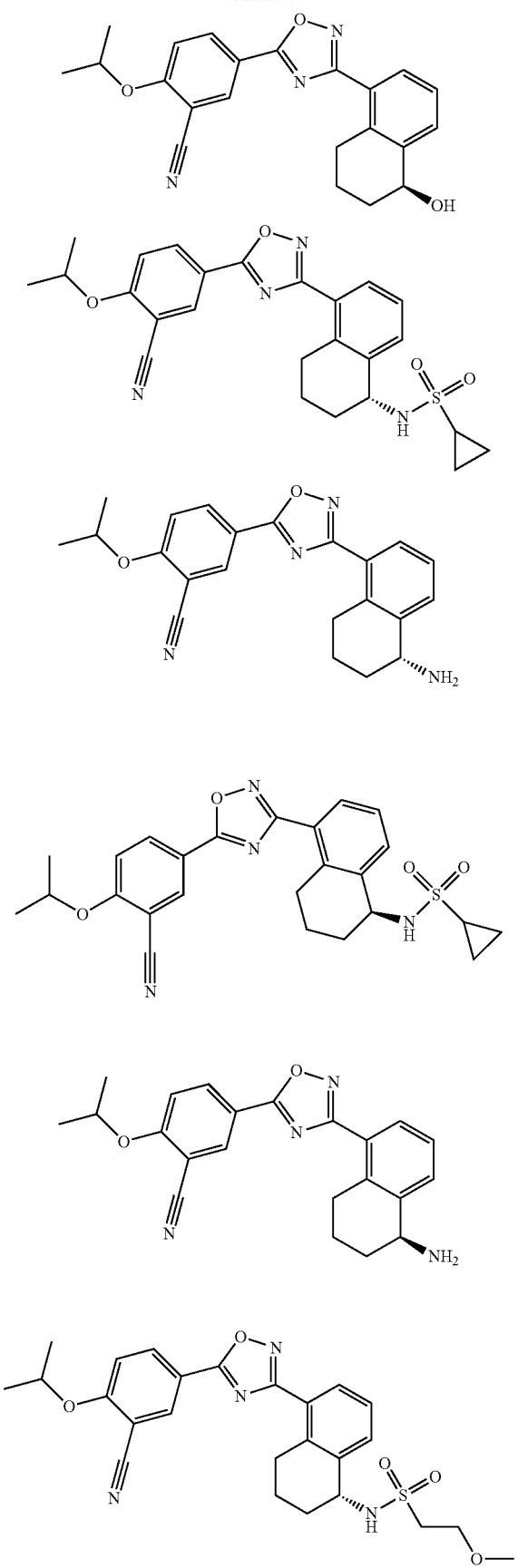
146
-continued
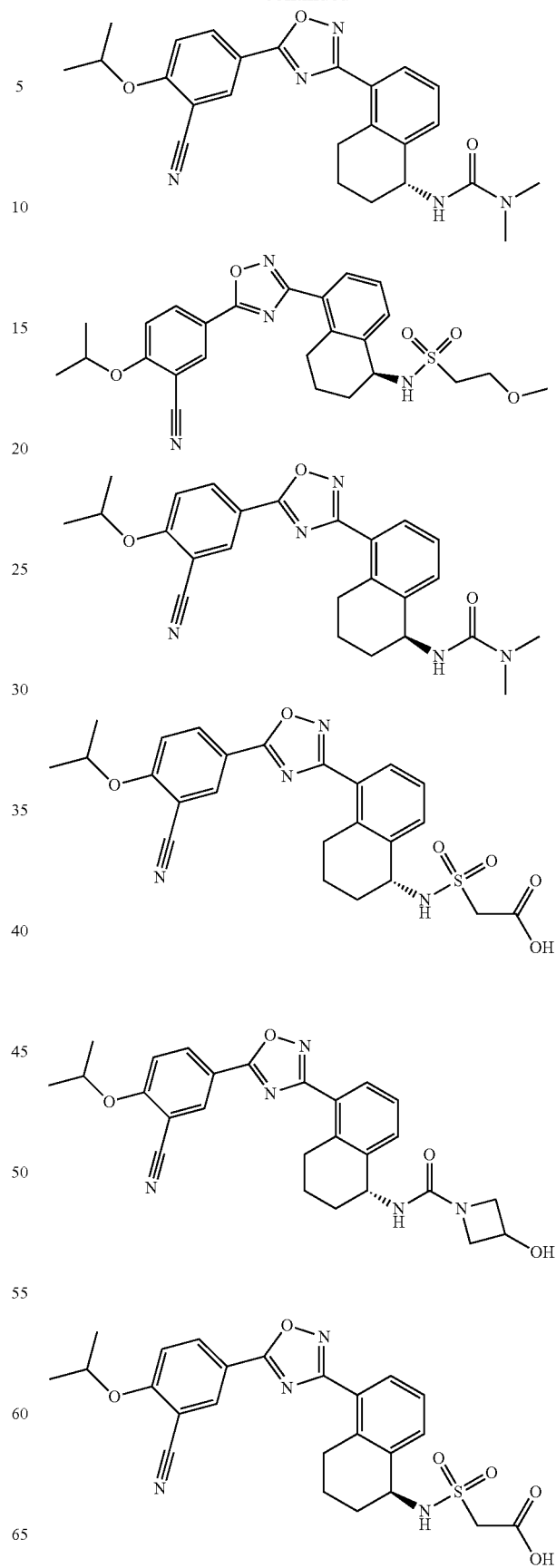

147
-continued
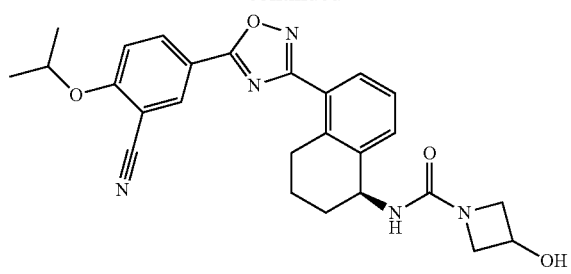
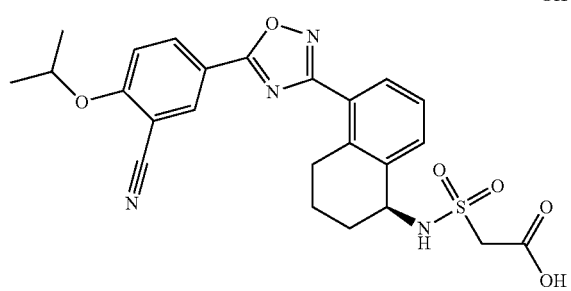
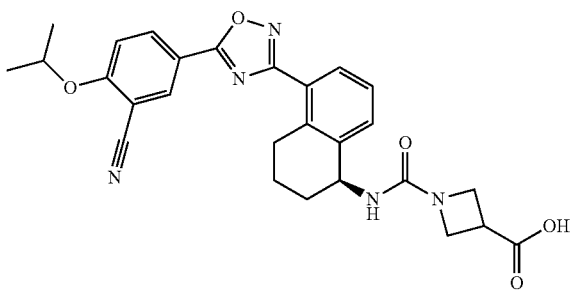
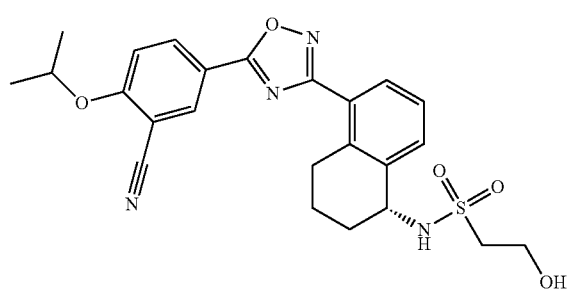
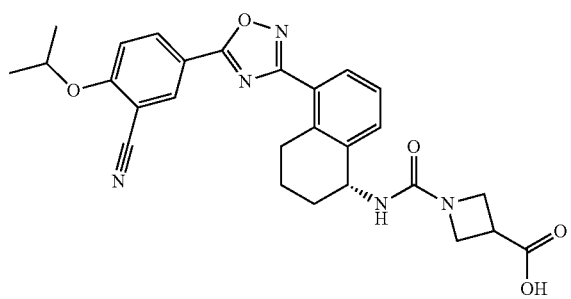
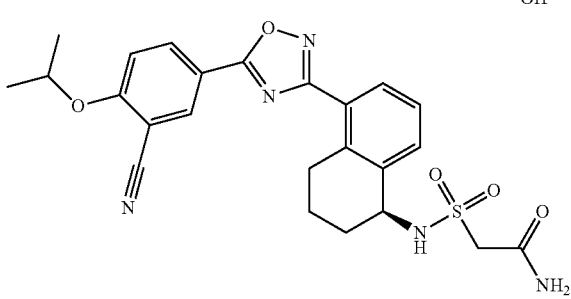
148
-continued
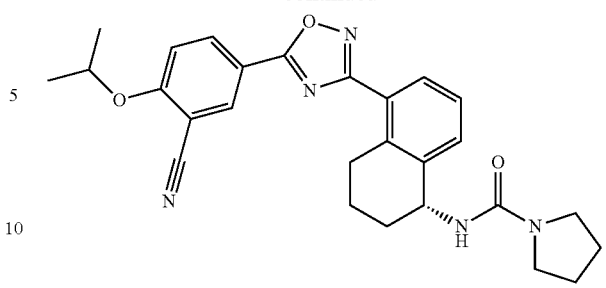
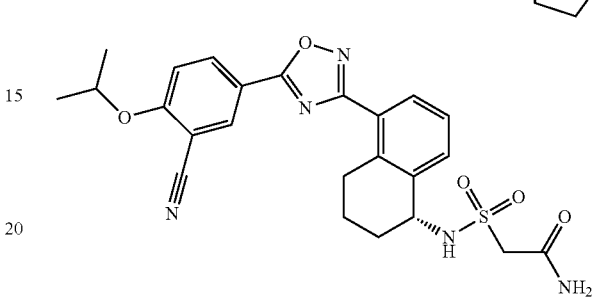
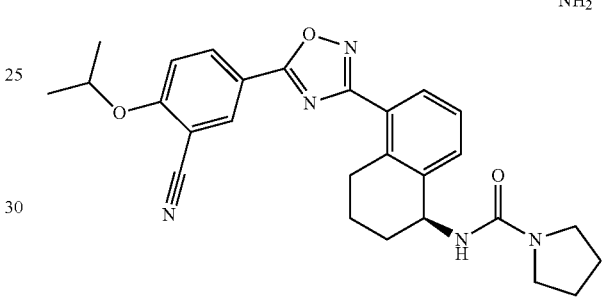
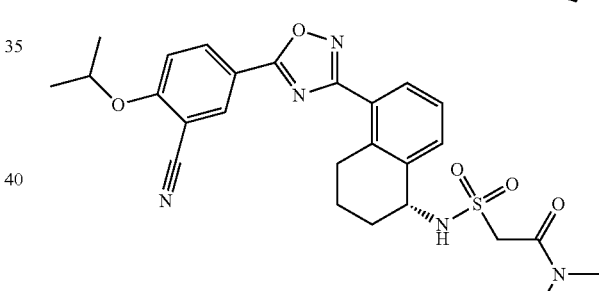
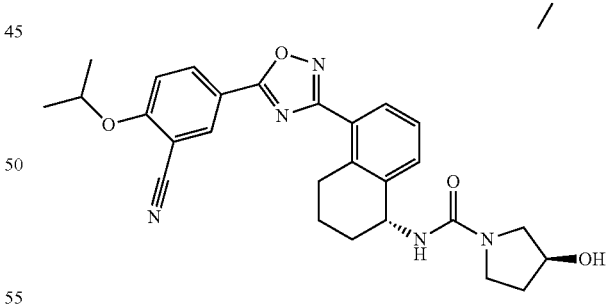
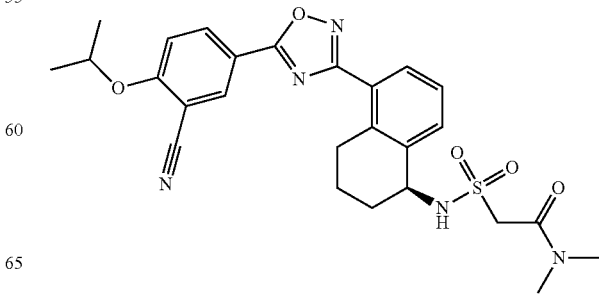

149
-continued
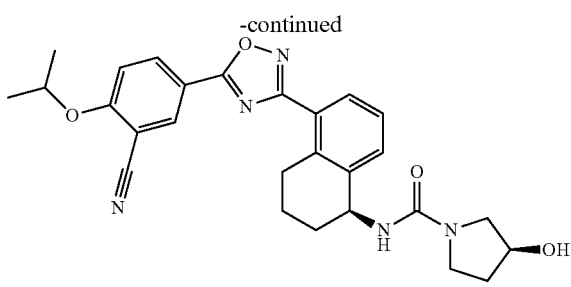
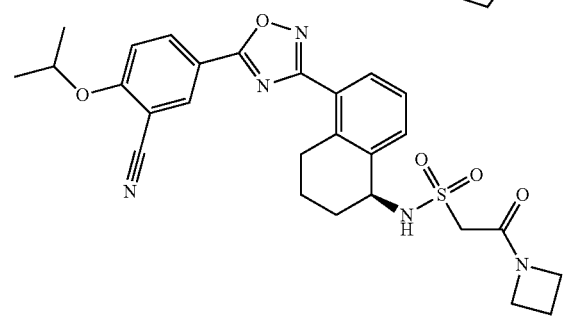
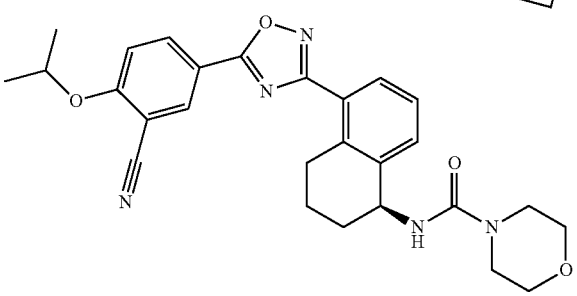
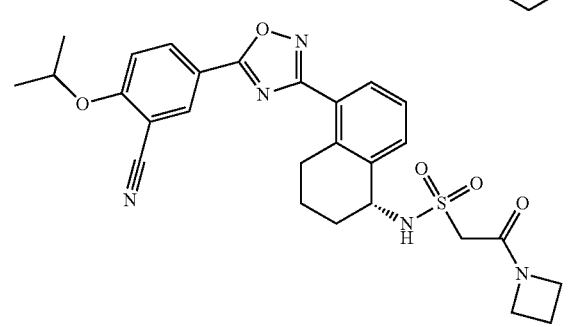
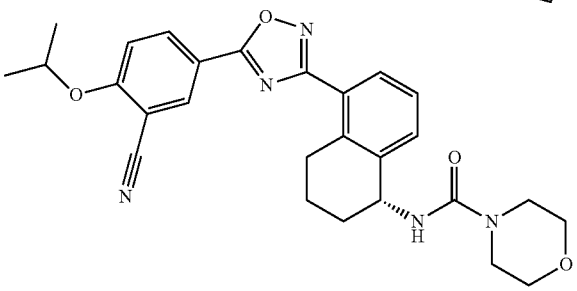
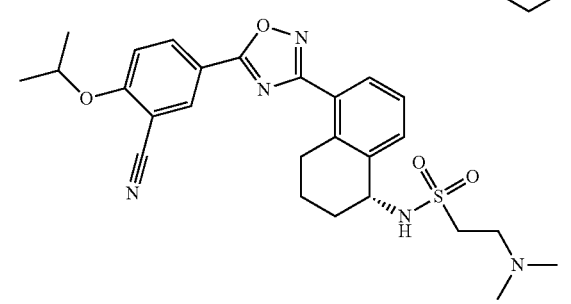
150
-continued
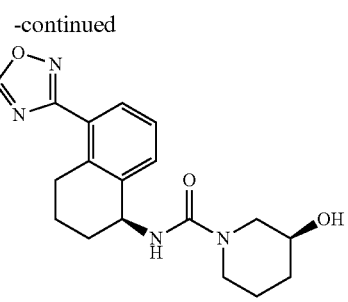
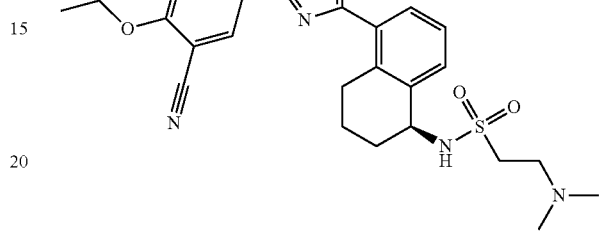
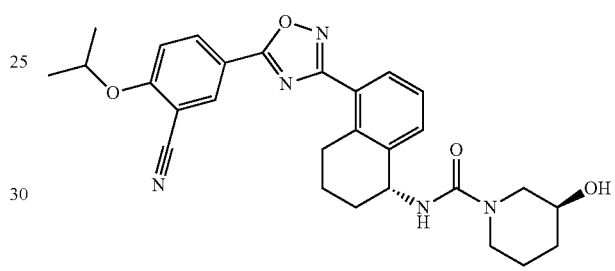
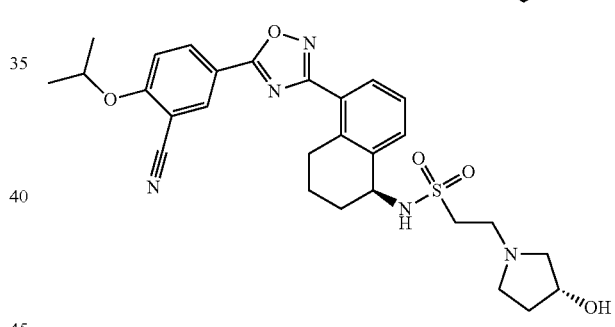
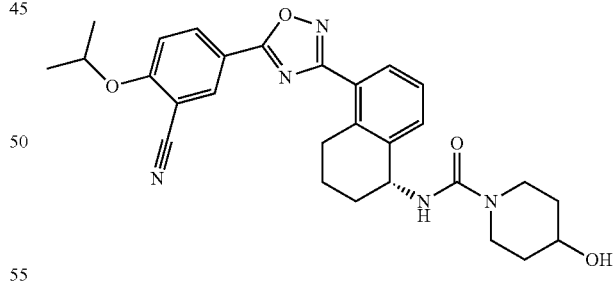
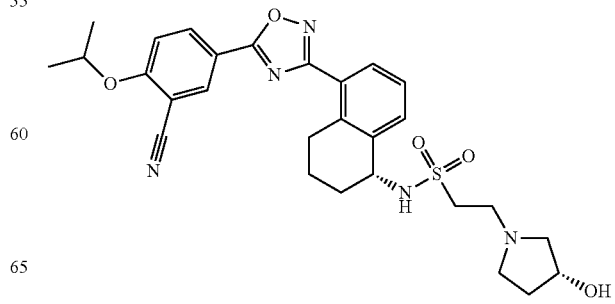

151
-continued
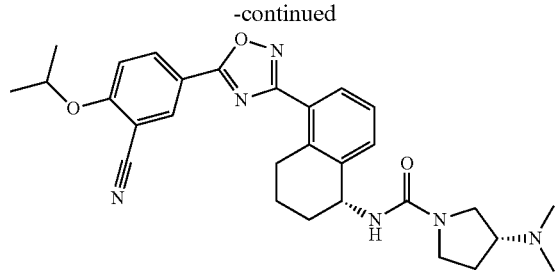
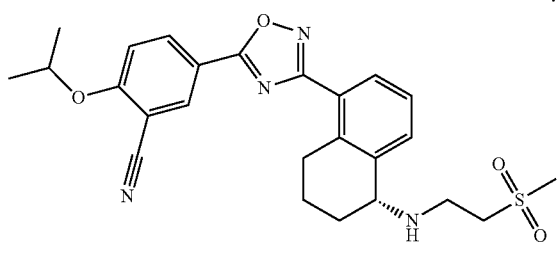
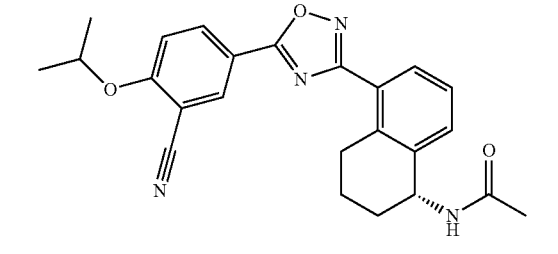
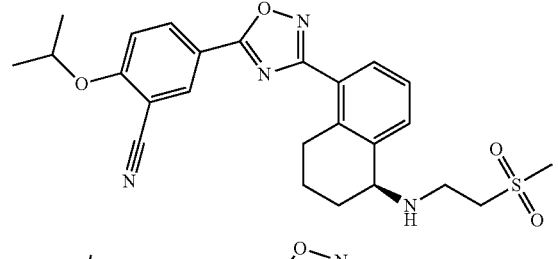
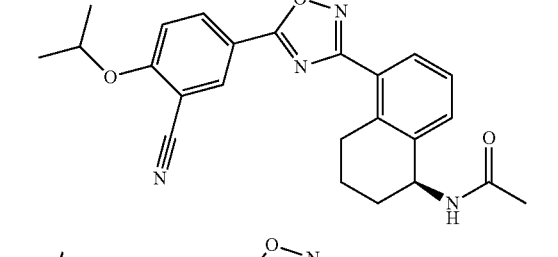
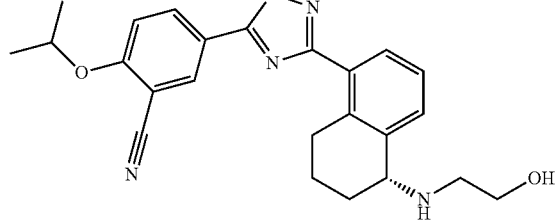
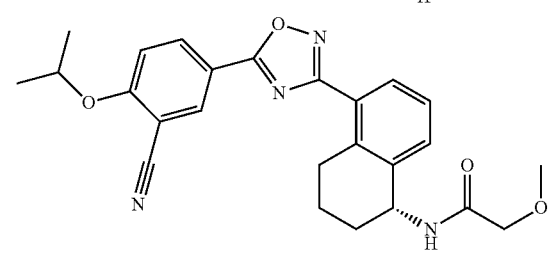
152
-continued
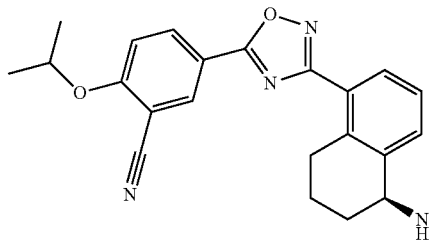
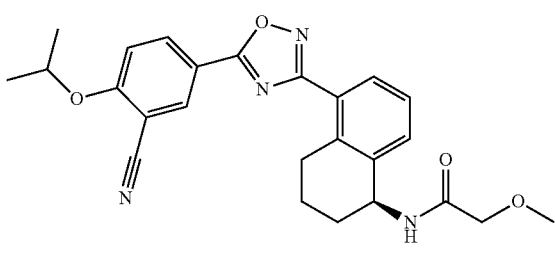
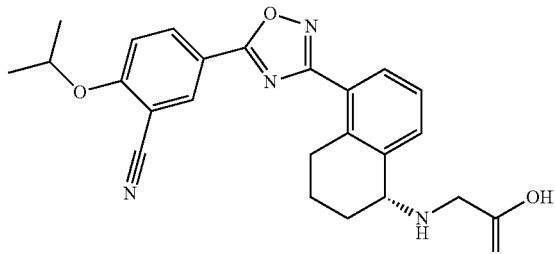
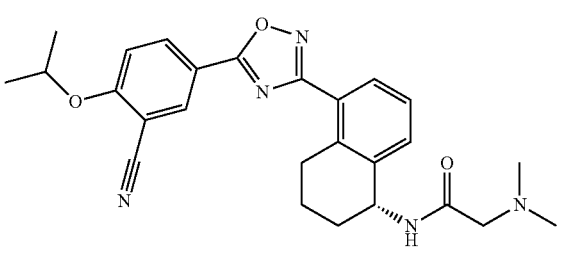
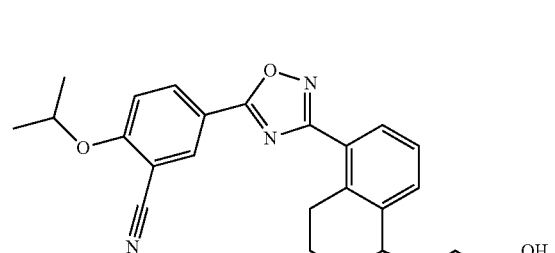
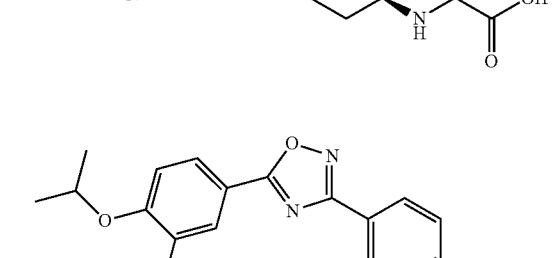
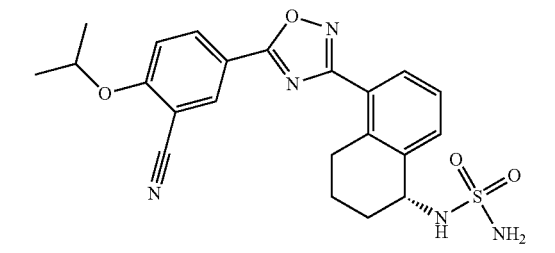

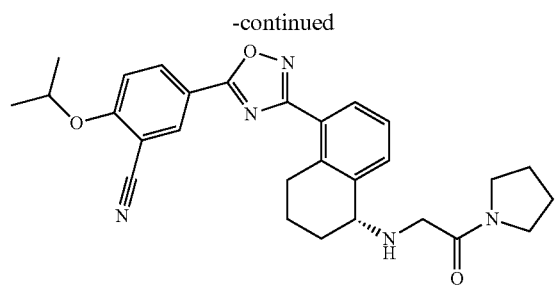

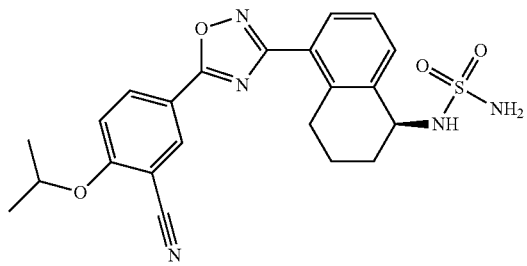

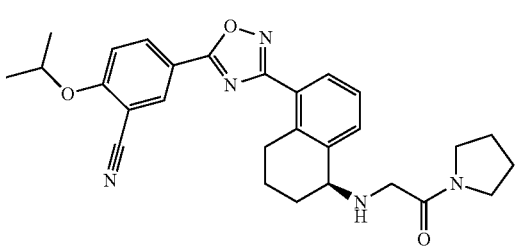

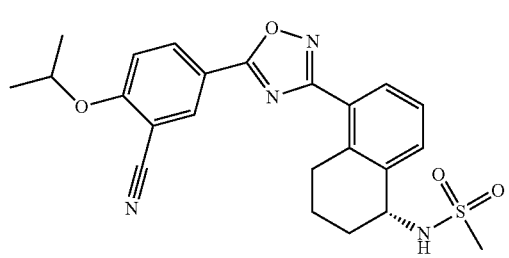

or a pharmaceutically acceptable salt, ester, hydrate or solvate thereof.

28. The compound of claim 27 selected from the group consisting of:

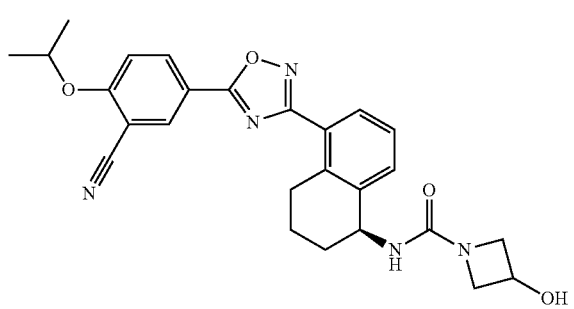

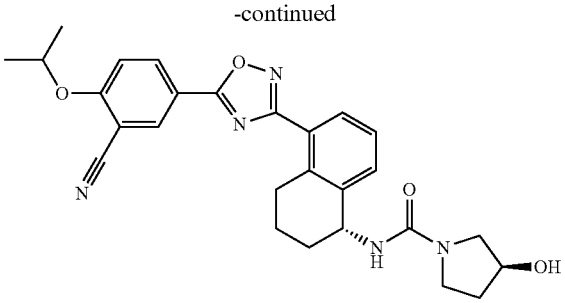

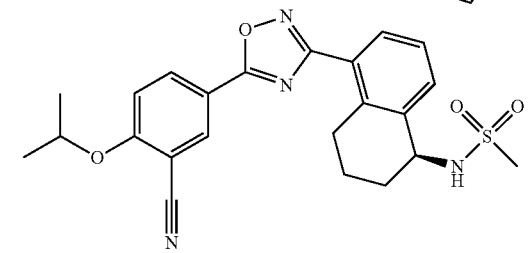

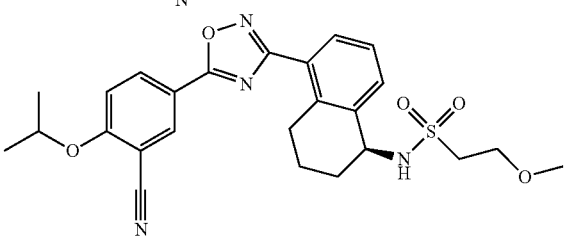

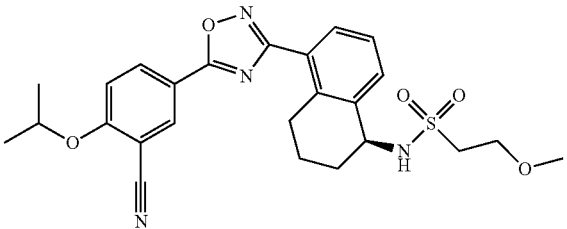

and

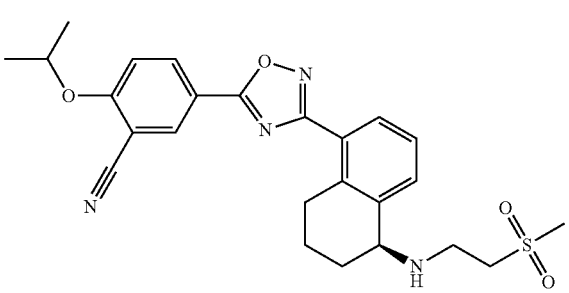

or a pharmaceutically acceptable salt, ester, hydrate or solvate thereof.

29. A pharmaceutical composition comprising a compound of claims 1-4 and 5-28 and a suitable excipient.

30. A pharmaceutical combination comprising the compound of claims 1-4 and 5-28 and a second medicament.

31. The combination of claim 30 wherein the second medicament is medically indicated for the treatment of multiple sclerosis, transplant rejection, or acute respiratory distress syndrome.

* * * * *